United States Patent
Munigeti et al.

(10) Patent No.: US 10,273,219 B2
(45) Date of Patent: *Apr. 30, 2019

(54) CRYSTALLINE FORMS OF NEUROTROPHIN MIMETIC COMPOUNDS AND THEIR SALTS

(71) Applicant: PharmatrophiX, Inc., Menlo Park, CA (US)

(72) Inventors: Rajgopal Munigeti, Reminderville, OH (US); Frank M. Longo, Menlo Park, CA (US)

(73) Assignee: PharmatrophiX, Inc., Menlo Park, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/687,311

(22) Filed: Aug. 25, 2017

(65) Prior Publication Data

US 2018/0037560 A1 Feb. 8, 2018

Related U.S. Application Data

(63) Continuation-in-part of application No. 15/682,389, filed on Aug. 21, 2017, which is a continuation of application No. 14/972,506, filed on Dec. 17, 2015, which is a continuation of application No. 13/509,470, filed as application No. PCT/US2010/056537 on Nov. 12, 2010, now Pat. No. 9,271,986.

(60) Provisional application No. 61/350,797, filed on Jun. 2, 2010, provisional application No. 61/294,279, filed on Jan. 12, 2010, provisional application No. 61/260,671, filed on Nov. 12, 2009.

(51) Int. Cl.
| | | |
|---|---|---|
| C07D 295/15 | (2006.01) | |
| A61K 31/535 | (2006.01) | |
| C07D 295/145 | (2006.01) | |
| C07C 309/04 | (2006.01) | |
| C07C 309/30 | (2006.01) | |

(52) U.S. Cl.
CPC .......... C07D 295/15 (2013.01); A61K 31/535 (2013.01); C07C 309/04 (2013.01); C07C 309/30 (2013.01); C07D 295/145 (2013.01); C07B 2200/13 (2013.01)

(58) Field of Classification Search
CPC .......... C07D 295/15; C07D 295/145; C07C 309/30; C07C 309/04; A61K 31/535; H05K 999/99; C07B 2200/13
See application file for complete search history.

(56) References Cited

U.S. PATENT DOCUMENTS

| | | |
|---|---|---|
| 4,039,685 A | 8/1977 | Koppe et al. |
| 4,743,607 A | 5/1988 | Jones et al. |
| 5,028,622 A | 7/1991 | Plaitakis |
| 5,321,029 A | 6/1994 | Maschler et al. |
| 5,439,806 A | 8/1995 | Kunz et al. |
| 5,608,067 A | 3/1997 | Afonso et al. |
| 5,958,875 A | 9/1999 | Longo et al. |
| 6,017,878 A | 1/2000 | Saragovi et al. |
| 6,029,114 A | 2/2000 | Shamovsky et al. |
| 6,462,058 B1 | 10/2002 | Fujishima et al. |
| 6,583,148 B1 | 6/2003 | Kelley et al. |
| 6,699,989 B1 | 3/2004 | Shetty |
| 6,747,735 B2 | 6/2004 | Chen et al. |
| 6,881,719 B2 | 4/2005 | Saragovi et al. |
| 7,723,328 B2 | 5/2010 | Longo et al. |
| 8,916,556 B2 | 12/2014 | Longo et al. |
| 9,271,986 B2 | 3/2016 | Munigeti et al. |
| 9,464,066 B2 | 10/2016 | Damodara |
| 2002/0028827 A1 | 3/2002 | Naicker et al. |
| 2002/0051988 A1 | 5/2002 | Gilchrest et al. |
| 2003/0232815 A1 | 12/2003 | Hamilton et al. |
| 2004/0167183 A1 | 8/2004 | Klopfenstein et al. |
| 2004/0186044 A1 | 9/2004 | Cosgaya et al. |
| 2004/0208862 A1 | 10/2004 | Brady-Kalnay et al. |
| 2004/0220138 A1 | 11/2004 | Gervais et al. |
| 2004/0248984 A1 | 12/2004 | Krieglstein et al. |
| 2006/0014790 A1 | 1/2006 | John et al. |
| 2006/0052406 A1 | 3/2006 | Fisher et al. |
| 2006/0246072 A1 | 11/2006 | Longo et al. |
| 2007/0060526 A1 | 3/2007 | Longo et al. |
| 2008/0221147 A1 | 9/2008 | Ross et al. |
| 2010/0267727 A1 | 10/2010 | Longo et al. |
| 2011/0003819 A1 | 1/2011 | Longo et al. |
| 2011/0230479 A1 | 9/2011 | Longo et al. |
| 2012/0322799 A1 | 12/2012 | Damodara |
| 2013/0005731 A1 | 1/2013 | Munigeti et al. |

(Continued)

FOREIGN PATENT DOCUMENTS

| | | |
|---|---|---|
| CN | 102740856 A | 10/2012 |
| DE | 19939910 A1 | 3/2001 |

(Continued)

OTHER PUBLICATIONS

Advisory Action dated Jul. 8, 2013 for U.S. Appl. No. 12/762,947.
Azaryan, et al. Synthesis and anticonvulsant activity of aminoalkyl derivatives of 5-(p-alkoxyphenyl)-5-methylhydantoins. Pharmaceutical Chemistry Journal 18.5 (1984): 318-322. Translated from Khimiko-farmatsevticheskii Zhurnal, vol. 18, No. 5, pp. 568-572, May 1984. DOI:10.1007/BF00766664.
Beattie, et al. ProNGF induces p75-mediated death of oligodendrocytes following spinal cord injury. Neuron. Oct. 24, 2002;36(3):375-86.
Bronfman, et al. Ligand-induced internalization of the p75 neurotrophin receptor: a slow route to the signaling endosome. J Neurosci. Apr. 15, 2003;23(8):3209-20.
Cacace et al. Derivati degli acidi teofillin-7-carbonico, teofillin-7-acetico e teofillin-7-propionico. Annali di Chimica, vol. 45, (1955), pp. 983-999 (English abstract).

(Continued)

*Primary Examiner* — Sarah Pihonak
*Assistant Examiner* — Jason Deck
(74) *Attorney, Agent, or Firm* — Wilson Sonsini Goodrich & Rosati

(57) ABSTRACT

The present invention includes crystalline forms of (2S,3S)-2-amino-3-methyl-N-(2-morpholinoethyl)-pentanamide and salts thereof. Furthermore, the present invention provides compositions comprising the crystalline forms and therapeutic uses of the crystalline forms.

3 Claims, 78 Drawing Sheets

(56) References Cited

U.S. PATENT DOCUMENTS

| | | |
|---|---|---|
| 2014/0100224 A1 | 4/2014 | Longo et al. |
| 2015/0111903 A1 | 4/2015 | Longo et al. |
| 2015/0259278 A1 | 9/2015 | Munigeti |
| 2016/0176832 A1 | 6/2016 | Munigeti et al. |
| 2016/0229823 A1 | 8/2016 | Gopal |
| 2017/0157127 A1 | 6/2017 | Longo et al. |
| 2017/0158653 A1 | 6/2017 | Munigeti et al. |
| 2018/0037559 A1 | 2/2018 | Munigeti et al. |

FOREIGN PATENT DOCUMENTS

| | | |
|---|---|---|
| EP | 0386611 A2 | 9/1990 |
| EP | 0400290 A1 | 12/1990 |
| EP | 1238970 A1 | 9/2002 |
| JP | 42005231 B | 3/1967 |
| JP | H08119922 A | 5/1996 |
| JP | H1081661 A | 3/1998 |
| JP | 2008536844 A | 9/2008 |
| WO | WO-8910744 A1 | 11/1989 |
| WO | WO-9616980 A1 | 6/1996 |
| WO | WO-9742168 A1 | 11/1997 |
| WO | WO-9749674 A1 | 12/1997 |
| WO | WO-9807742 A1 | 2/1998 |
| WO | WO-9837079 A1 | 8/1998 |
| WO | WO-9847863 A1 | 10/1998 |
| WO | WO-9854123 A1 | 12/1998 |
| WO | WO-9950264 A1 | 10/1999 |
| WO | WO-0017190 A2 | 3/2000 |
| WO | WO-0027378 A2 | 5/2000 |
| WO | WO-0037462 A1 | 6/2000 |
| WO | WO-0100657 A2 | 1/2001 |
| WO | WO-0114320 A1 | 3/2001 |
| WO | WO-0190047 A1 | 11/2001 |
| WO | WO-03006423 A1 | 1/2003 |
| WO | WO-03040096 A2 | 5/2003 |
| WO | WO-03104226 A1 | 12/2003 |
| WO | WO-2004028466 A2 | 4/2004 |
| WO | WO-2004031145 A2 | 4/2004 |
| WO | WO-2004077061 A1 | 9/2004 |
| WO | WO-2005044810 A1 | 5/2005 |
| WO | WO-2005051919 A1 | 6/2005 |
| WO | WO-2006005941 A1 | 1/2006 |
| WO | WO-2006113097 A2 | 10/2006 |
| WO | WO-2007073505 A2 | 6/2007 |
| WO | WO-2008107365 A1 | 9/2008 |
| WO | WO-2010102212 A2 | 9/2010 |
| WO | WO-2011060262 A1 | 5/2011 |
| WO | WO-2011066544 A2 | 6/2011 |
| WO | WO-2014052659 A1 | 4/2014 |

OTHER PUBLICATIONS

Canadian office action dated Feb. 3, 2016 for CA Application No. 2754570.
Carlson, et al. Developing a dynamic pharmacophore model for HIV-1 integrase. J Med Chem. Jun. 1, 2000;43(11):2100-14.
Carter, et al. Selective activation of NF-kappa B by nerve growth factor through the neurotrophin receptor p75. Science. Apr. 26, 1996;272(5261):542-5.
Casaccia-Bonnefil, et al. Death of oligodendrocytes mediated by the interaction of nerve growth factor with its receptor p75. Nature. Oct. 24, 1996;383(6602):716-9.
Chapter 13 Spectroscopy, Organic Chemistry 4e Carey, 2000, The McGraw-Hill Companies available online at: http://www.mhhe.com/physsci/chemistry/carey/student/olc/ch13nmr.html.
Co-pending U.S. Appl. No. 12/718,675, filed Mar. 5, 2010.
Co-pending U.S. Appl. No. 15/687,311, filed Aug. 25, 2017.
Culp, et al. Determination of synthetic components in flavors by deuterium/hydrogen isotopic ratios. Journal of Agricultural and Food Chemistry 40.10 (1992): 1892-1897. DOI: 10.1021/jf00022a033.
Dawson, T.M. and Dawson, V.L., Molecular pathways of neurodegeneration in Parkinson's disease. Science, 2003. vol. 302. pp. 819-822.
Dechant, et al. The neurotrophin receptor p75(NTR): novel functions and implications for diseases of the nervous system. Nat Neurosci. Nov. 2002;5(11):1131-6. Review.
Domeniconi, et al. Pro-NGF secreted by astrocytes promotes motor neuron cell death. Mol Cell Neurosci. Feb. 2007;34(2):271-9. Epub Dec. 26, 2006.
European office action dated Jul. 13, 2015 for EP Application No. 10749395.9.
European search report and opinion dated Apr. 2, 2013 for EP Application No. 12191674.6.
European search report and opinion dated Aug. 24, 2011 for EP Application No. 06 758242.9.
European Search report dated Apr. 19, 2017 for EP Application No. 10830787.7.
European Search Report dated Aug. 19, 2016 for EP Application No. 13840840.6.
European office action dated Jan. 8, 2016 for EP Application No. 12191674.6.
European office action dated Jan. 13, 2016 for EP Application No. 12191676.1.
European office action dated Mar. 18, 2014 for EP Application No. 12191674.6.
European office action dated Mar. 19, 2014 for EP Application No. 12191676.1.
European office action dated Jul. 9, 2012 for EP Application No. 06758242.9.
European office action dated Aug. 24, 2011 for EP Application No. 06758242.9.
European search report and opinion dated Feb. 10, 2014 for EP Application No. 10830787.7.
European search report and opinion dated Apr. 19, 2013 for EP Application No. 12191676.1.
European search report and opinion dated Apr. 28, 2014 for EP Application No. 10749395.9.
Fahnestock, et al. The precursor pro-nerve growth factor is the predominant form of nerve growth factor in brain and is increased in Alzheimer's disease. Mol Cell Neurosci. Aug. 2001;18(2):210-20.
Foehr, et al. NF-kappa B signaling promotes both cell survival and neurite process formation in nerve growth factor-stimulated PC12 cells. J Neurosci. Oct. 15, 2000;20(20):7556-63.
Freedman, et al., Treatment optimization in multiple sclerosis. The Canadian Journal of Neurological sciences, 2004. vol. 31. pp. 157-168.
Gavezzotti. Are crystal structures predictable? Accounts of chemical research 27.10 (1994): 309-314.
Gentry, et al. Nerve growth factor activation of nuclear factor kappaB through its p75 receptor is an anti-apoptotic signal in RN22 schwannoma cells. J Biol Chem. Mar. 17, 2000;275(11):7558-65.
Gould. Salt selection for basic drugs. International Journal of Pharmaceutics 33.1 (1986): 201-217.
Guillory J Ked- Brittain H G: "Generation of Polymorphs, Hydrates, Solvates, and Amorphous Solids", Jan. 1, 1999 (Jan. 1, 1999), Polymorphism in Pharmaceutical Solids; [Drugs and the Pharmaceutical Sciences ; 95], Marcel Dekker Inc, New York* Basel, pp. I-11,183, XP002350313, ISBN: 978-0-8247-0237-3.
Harrington, et al. Activation of Rac GTPase by p75 is necessary for c-jun N-terminal kinase-mediated apoptosis. J Neurosci. Jan. 1, 2002;22(1):156-66.
Harrington, et al. Secreted proNGF is a pathophysiological death-inducing ligand after adult CNS injury. Proc Natl Acad Sci U S A. Apr. 20, 2004;101(16):6226-30. Epub Mar. 16, 2004.
He, et al. Structure of nerve growth factor complexed with the shared neurotrophin receptor p75. Science. May 7, 2004;304(5672):870-5.
Henze, et al., Screening of Beta-2 agonists and confirmation of fenoterol, orciprenaline, reproterol and terbutaline with gas chromatographymass spectrometry as tetrahydroisoquinoline derivatives. Journal of Chromatography B, 751 (2001) 93-105.
Hirayama, Noriaki (ed.) Yuuki kagoubutsu kessho sakusei hando bukku- genri to nouhau—(Handbook of production of crystals of organic compounds—principles and knowhow), Maruzen Publishing CO. Ltd, Jul. 25, 2008, p. 57-84.

(56) References Cited

OTHER PUBLICATIONS

Holscher, et al., Development of Beta-Amyloid-Induced Neurodegeneration in Alzheimer'S Disease and Novel Neuroprotective Strategies. Reviews in the Neurosciences, 2005, Freund & Pettman, U.K., vol. 16, pp. 181-212.

Huang, et al. Nerve growth factor signaling in caveolae-like domains at the plasma membrane. J Biol Chem. Dec. 17, 1999;274(51):36707-14.

International preliminary report on patentability dated Mar. 31, 2015 for PCT/US2013/062025.

International preliminary report on patentability dated May 4, 2011 for PCT/US2010/058345.

International preliminary report on patentability dated May 15, 2012 for PCT/US2010/056537.

International Preliminary Report on Patentability dated Sep. 15, 2011 for PCT/US2010/026372.

International Preliminary Report on Patentability dated Oct. 25, 2007 for PCT/US2006/011985.

International search report and written opinion dated Jan. 10, 2014 for PCT/US2013/062025.

International search report and written opinion dated Jan. 16, 2011 for PCT/US2010/056537.

International search report and written opinion dated Jan. 31, 2011 for PCT/US2010/026372.

International search report and written opinion dated May 19, 2011 for PCT/US2010/058345.

International search report and written opinion dated Dec. 28, 2006 for PCT/US2006/011985.

Interview Summary dated Jun. 6, 2014 for U.S. Appl. No. 12/762,947.

Interview Summary dated Aug. 25, 2009 for U.S. Appl. No. 11/396,936.

Jaen, et al. Kynurenic acid derivatives inhibit the binding of nerve growth factor (NGF) to the low-affinity p75 NGF receptor. J Med Chem. Oct. 27, 1995;38(22):4439-45.

Jain, A. et al.: "Estimation of Melting Points of Organic Compounds", Industrial & Engineering Chemistry Research., val. 43, No. 23, Nov. 1, 2004 (Nov. 1, 2004), pp. 7618-7621, XP055363537, US, ISSN: 0888-5885, DOI: 10.1021/ ie049378m.

Kawaguchi, Yoko, et al., Drug and crystal polymorphism. Journal Human environment engineering. 2002; 4(2): 310-17.

Klosa. Synthesis of alkylenediamino amides of theophyline-7-acetic acid. Journal fusr Praktische Chemie (Leipzig). vol. 12 pp. 212-214 (1961).

Kojima, Takashi. Iyakuhin kaihatsu niokeru kesshosei sentaku no kouritsuka wo mezashite (Aiming at efficient selection of crystallinity in the development of pharmaceutical products). Journal of Pharmaceutical science and technology. Japan Sep. 1, 2008; 68(5): p. 344-349.

Lachyankar, et al. Novel functional interactions between Trk kinase and p75 neurotrophin receptor in neuroblastoma cells. J Neurosci Res. Jan. 15, 2003;71(2):157-72.

Lad, et al. Activation of the mitogen-activated protein kinase pathway through p75NTR: a common mechanism for the neurotrophin family. J Neurosci Res. Sep. 1, 2003;73(5):614-26.

Lee, et al. Regulation of cell survival by secreted proneurotrophins. Science. Nov. 30, 2001;294(5548):1945-8.

Lee, et al. Targeted mutation of the gene encoding the low affinity NGF receptor p75 leads to deficits in the peripheral sensory nervous system. Cell. May 29, 1992;69(5):737-49.

Lesauteur, et al. Small peptide mimics of nerve growth factor bind TrkA receptors and affect biological responses. J Biol Chem. Mar. 24, 1995;270(12):6564-9.

Lin, et al. Inhibition of nuclear translocation of transcription factor NF-kappa B by a synthetic peptide containing a cell membrane-permeable motif and nuclear localization sequence. J Biol Chem. Jun. 16, 1995 ;270(24):14255-8.

Longo, et al. Electromagnetic fields influence NGF activity and levels following sciatic nerve transection. J Neurosci Res. Jan. 15, 1999;55(2):230-7.

Longo, et al. Neurotrophin Small Molecule Mimetics: Candidate Therapeutic Agents for Neurological Disorders. Current Medicinal Chemistry—Central Nervous System Agents, vol. 5, No. 1, Mar. 2005, pp. 29-41(13). DOI:10.2174/1568015053202769.

Longo, et al. Neuroprotective strategies in Alzheimer's disease. NeuroRx. Jan. 2004 ;1(1):117-27. Review.

Longo, et al. Neurotrophin-based strategies for neuroprotection. J Alzheimers Dis. Dec. 2004;6(6 Suppl):S13-7.

Longo, et al. Small molecule modulation of p75 neurotrophin receptor functions. CNS Neurol Disord Drug Targets. Feb. 2008;7(1):63-70.

Longo, et al. Synthetic NGF peptide derivatives prevent neuronal death via a p75 receptor-dependent mechanism. J Neurosci Res. Apr. 1, 1997;48(1):1-17.

Longo, et al. The in vitro biological effect of nerve growth factor is inhibited by synthetic peptides. Cell Regul. Jan. 1990;1(2):189-95.

Maliartchouk, et al. Genuine monovalent ligands of TrkA nerve growth factor receptors reveal a novel pharmacological mechanism of action. J Biol Chem. Apr. 7, 2000;275(14):9946-56.

Mamidipudi, et al. Identification of interleukin 1 receptor-associated kinase as a conserved component in the p75-neurotrophin receptor activation of nuclear factor-kappa B. J Biol Chem. Aug. 2, 2002;277(31):28010-8. Epub May 28, 2002.

Massa, et al. Alzheimer's therapeutics: neurotrophin domain small molecule mimetics. J Mol Neurosci. 2003;20(3):323-6.

Massa, et al. Alzheimer's therapeutics: neurotrophin small molecule mimetics. J Mol Neurosci. Aug.-Oct. 2002;19(1-2):107-11.

Massa, et al. Small, nonpeptide p75NTR ligands induce survival signaling and inhibit proNGF-induced death. J Neurosci. May 17, 2006;26(20):5288-300.

Michaelis, et al. {beta}-Amyloid-induced neurodegeneration and protection by structurally diverse microtubule-stabilizing agents. J Pharmacol Exp Ther. Feb. 2005;312(2):659-68. Epub Sep. 16, 2004.

Mufson, et al. Cortical neurons express nerve growth factor receptors in advanced age and Alzheimer disease. Proc Natl Acad Sci U S A. Jan. 15, 1992;89(2):569-73.

Notice of allowance dated Jan. 7, 2010 for U.S. Appl. No. 11/396,936.

Notice of allowance dated Jun. 20, 2016 for U.S. Appl. No. 14/230,833.

Notice of Allowance dated Aug. 1, 2017 for U.S. Appl. No. 15/264,425.

Notice of allowance dated Sep. 17, 2015 for U.S. Appl. No. 13/509,470.

Notice of Allowance dated Dec. 1, 2017 for U.S. Appl. No. 15/264,425.

Notice of allowance dated Aug. 18, 2014 for U.S. Appl. No. 12/762,947.

Nykjaer. Sortilin is essential for proNGF-induced neuronal cell death. Nature. Feb. 26, 2004;427(6977):843-8.

Nykjaer. p75NTR—live or let die. Curr Opin Neurobiol. Feb. 2005;15(1):49-57.

Oelssner, W. Zur pharmakologie neuartiger Methylxanthinderivate. Pharmazie, vol. 16, (1961), pp. 84-89 (English abstract).

Office Action dated Feb. 8, 2017 for Australian Application No. 2013323416.

Office Action dated Feb. 22, 2017 for U.S. Appl. No. 14/972,506.
Office action dated Mar. 13, 2013 for U.S. Appl. No. 12/762,947.
Office action dated Mar. 15, 2016 for U.S. Appl. No. 14/432,183.
Office action dated May 6, 2013 for U.S. Appl. No. 13/512,839.
Office action dated Jul. 2, 2015 for U.S. Appl. No. 13/509,470.
Office action dated Jul. 25, 2016 for U.S. Appl. No. 14/529,807.
Office action dated Jul. 30, 2014 for U.S. Appl. No. 13/509,470.
Office Action dated Aug. 29, 2017 for U.S. Appl. No. 15/380,635.
Office action dated Sep. 21, 2012 for U.S. Appl. No. 12/762,947.
Office action dated Oct. 10, 2013 for U.S. Appl. No. 13/512,839.
Office action dated Mar. 6, 2014 for U.S. Appl. No. 12/762,947.
Office action dated Apr. 8, 2016 for U.S. Appl. No. 13/927,302.
Office action dated May 27, 2009 for U.S. Appl. No. 11/396,936.
Office action dated Jul. 23, 2015 for U.S. Appl. No. 13/927,302.
Office action dated Aug. 23, 2012 for U.S. Appl. No. 12/910,349.
Office action dated Oct. 25, 2012 for U.S. Appl. No. 12/762,940.
Office action dated Dec. 30, 2015 for U.S. Appl. No. 14/529,807.
Official action dated Dec. 27, 2012 for U.S. Appl. No. 12/910,349.

(56) References Cited

OTHER PUBLICATIONS

Orazi, et al. Substitution in the hydrantoin ring—I: Aminomethylation. Tetrahedron. 1961; 15(1-4):93-99.doi:10.1016/0040-4020(61)80012-4.

Pardridge, W.M. Blood-brain barrier drug targeting enables neuroprotection in brain ischemia following delayed intravenous administration of neurotrophins. Adv Exp Med Biol. 2002;513:397-430.

Patani, et al. Bioisosterism: a rational approach in drug design. Chemical Reviews. American Chemical Society. 1996; 96:3147-3176. DOI: 10.1021/cr950066q.

Pehar, et al. Modulation of p75-dependent motor neuron death by a small non-peptidyl mimetic of the neurotrophin loop 1 domain. Eur J Neurosci. Sep. 2006;24(6):1575-80.

Podulso, et al. Permeability at the blood-brain and blood-nerve barriers of the neurotrophic factors: NGF, CNTF, NT-3, BDNF. Brain Res Mol Brain Res. Mar. 1996;36(2):280-6.

Restriction Requirement dated Oct. 7, 2015 for U.S. Appl. No. 14/529,807.

Rodriquez-Spong et al. General principles of pharmaceutical solid polymorphism: a supramolecular perspective. Adv Drug Deliv Rev. Feb. 23, 2004;56(3):241-74.

Roux, et al. The p75 neurotrophin receptor activates Akt (protein kinase B) through a phosphatidylinositol 3-kinase-dependent pathway. J Biol Chem. Jun. 22, 2001;276(25):23097-104. Epub Apr. 18, 2001.

Sakurai, et al. IkappaB kinases phosphorylate NF-kappaB p65 subunit on serine 536 in the transactivation domain. J Biol Chem. Oct. 22, 1999;274(43):30353-6.

Salehi, et al. Nrage, a novel MAGE protein, interacts with the p75 neurotrophin receptor and facilitates nerve growth factor-dependent apoptosis. Neuron. Aug. 2000;27(2):279-88.

Saltzman, et al. Intracranial delivery of recombinant nerve growth factor: release kinetics and protein distribution for three delivery systems. Pharm Res. Feb. 1999;16(2):232-40.

Saragovi, et al. Small molecule and protein-based neurotrophic ligands: agonists and antagonists as therapeutic agents. Expert Opinion on Therapeutic Patents 9.6 (1999): 737-751. DOI:10.1517/13543776.9.6.737.

Simonovic, et al. Crystal structure of human PEDF, a potent anti-angiogenic and neurite growth-promoting factor. Proc Natl Acad Sci U S A. Sep. 25, 2001;98(20):11131-5. Epub Sep. 18, 2001.

Singhal, et al. Drug polymorphism and dosage form design: a practical perspective. Adv Drug Deliv Rev. Feb. 23, 2004;56(3):335-47.

Soltoff, et al. Nerve growth factor promotes the activation of phosphatidylinositol 3-kinase and its association with the trk tyrosine kinase. J Biol Chem. Aug. 25, 1992;267(24):17472-7.

Thoenen, et al. Neurotrophins: from enthusiastic expectations through sobering experiences to rational therapeutic approaches. Nat Neurosci. Nov. 2002;5 Suppl:1046-50.

Vetter, et al. Nerve growth factor rapidly stimulates tyrosine phosphorylation of phospholipase C-gamma 1 by a kinase activity associated with the product of the trk protooncogene. Proc Natl Acad Sci U S A. Jul. 1, 1991;88(13):5650-4.

Walsh, et al. Absence of the p75 neurotrophin receptor alters the pattern of sympathosensory sprouting in the trigeminal ganglia of mice overexpressing nerve growth factor. J Neurosci. Jan. 1, 1999;19(1):258-73.

Wang, et al. Dimerization-dependent block of the proapoptotic effect of p75(NTR). J Neurosci Res. Jun. 1, 2000;60(5):587-93.

Wong, et al. A p75(NTR) and Nogo receptor complex mediates repulsive signaling by myelin-associated glycoprotein. Nat Neurosci. Dec. 2002;5(12):1302-8.

Yang, et al. Leukocyte antigen-related protein tyrosine phosphatase receptor: a small ectodomain isoform functions as a homophilic ligand and promotes neurite outgrowth. J Neurosci. Apr. 15, 2003;23(8):3353-63.

Yankner, et al. Nerve growth factor potentiates the neurotoxicity of beta amyloid. Proc Natl Acad Sci U S A. Nov. 1990;87(22):9020-3.

Yoon, et al. Competitive signaling between TrkA and p75 nerve growth factor receptors determines cell survival. J Neurosci. May 1, 1998;18(9):3273-81.

Zhang, et al. p75 neurotrophin receptor protects primary cultures of human neurons against extracellular amyloid beta peptide cytotoxicity. J Neurosci. Aug. 13, 2003;23(19):7385-94.

Zhang, et al. Neuroprotection in transient focal brain ischemia after delayed intravenous administration of brain-derived neurotrophic factor conjugated to a blood-brain barrier drug targeting system. Stroke. Jun. 2001;32(6):1378-84.

Zhou, et al. Multiple levels for regulation of TrkA in PC12 cells by nerve growth factor. J Neurochem. Sep. 1995;65(3):1146-56.

Zhou, et al. Expression of TrkA confers neuron-like responsiveness to nerve growth factor on an immortalized hypothalamic cell line. Proc Natl Acad Sci U S A. Apr. 26, 1994;91(9):3824-8.

Balbach, et al. Pharmaceutical evaluation of early development candidates "the 100 mg-approach". Int J Pharm. May 4, 2004;275(1-2):1-12.

Bastin, et al. Salt selection and optimisation procedures for pharmaceutical new chemical entities. Organic Process Research & Development 4.5 (2000): 427-435.

Jelesarov, et al. Isothermal titration calorimetry and differential scanning calorimetry as complementary tools to investigate the energetics of biomolecular recognition. Journal of molecular recognition 12.1 (1999): 3-18.

Matsumoto, M. (ed.), Yakuzaigaku Manual, Nankodo Co., Ltd., First Edition, pp. 28 and 76 (1989).

Office Action dated Feb. 12, 2014 for Chinese Application No. 201080060921.7.

Office Action dated Mar. 26, 2013 for Chinese Application No. 201080060921.7.

Office Action dated Oct. 2, 2013 for Australian Application No. 2010319349.

Office action dated Oct. 31, 2014 for Japanese Application No. 2012-539022.

Pattarawarapan, et al. Molecular basis of neurotrophin-receptor interactions. J Med Chem. Dec. 4, 2003;46(25):5277-91.

Co-pending U.S. Appl. No. 15/853,480, filed Dec. 22, 2017.

Lopez et al., Acetylcholinesterase inhibitory activity of some amaryllidaceae alkaloids and narcissus extracts. Life Science, 2002;71: 2521-2529.

U.S. Appl. No. 15/380,635 Office Action dated Feb. 9, 2018.

Co-pending U.S. Appl. No. 16/125,496, filed Sep. 7, 2018.

EP12191674.6 Office Action dated Feb. 12, 2018.

EP12191676.1 Office Action dated Feb. 12, 2018.

U.S. Appl. No. 15/380,635 Office Action dated Sep. 17, 2018.

U.S. Appl. No. 15/682,389 Office Action dated Aug. 3, 2018.

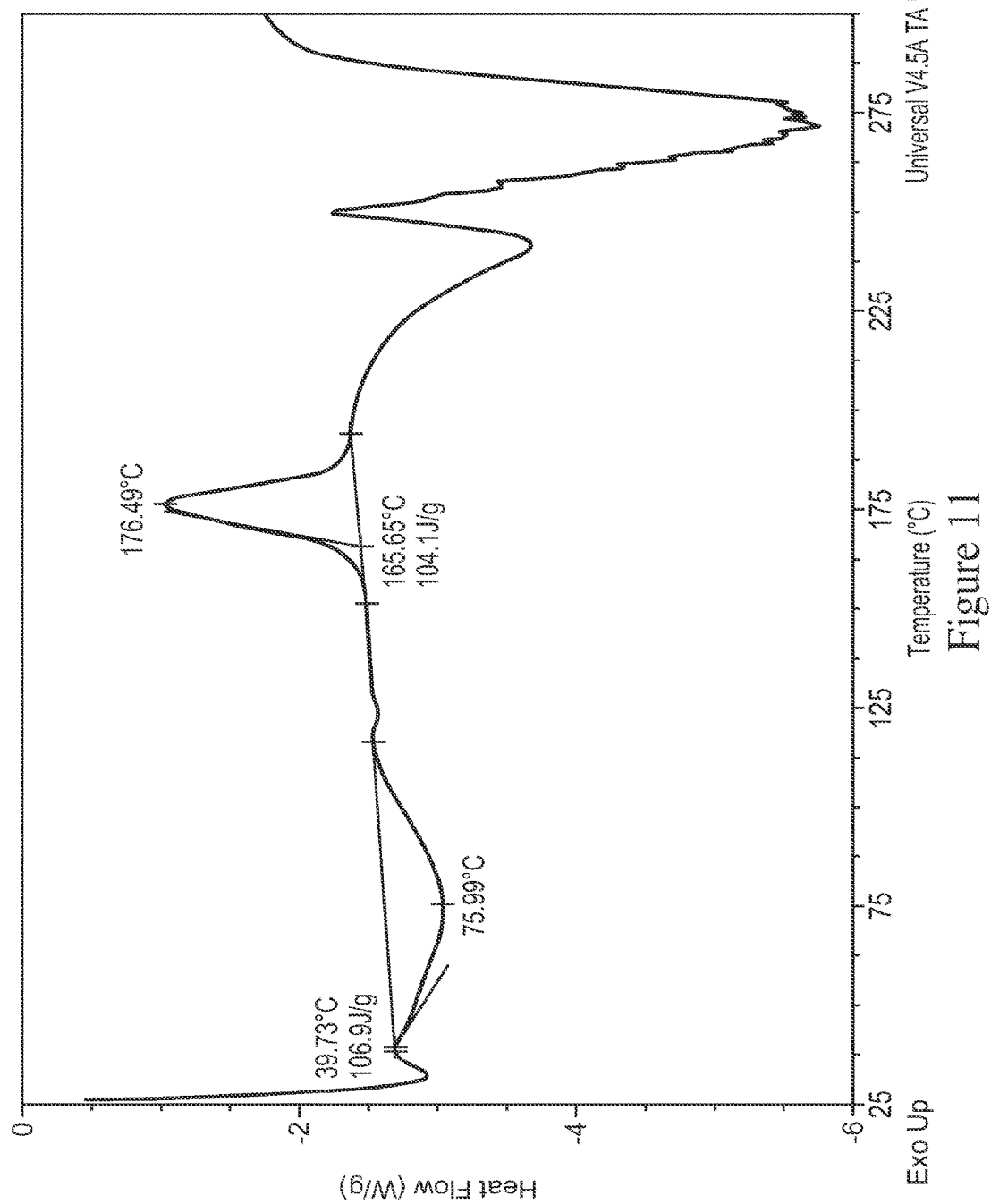

CRYSTALLINE FORMS OF NEUROTROPHIN MIMETIC COMPOUNDS AND THEIR SALTS

CROSS-REFERENCE

The present application is a continuation-in-part of U.S. application Ser. No. 15/682,389, entitled "CRYSTALLINE FORMS OF NEUROTROPHIN MIMETIC COMPOUNDS AND THEIR SALTS," filed Aug. 21, 2017 which is a continuation of U.S. application Ser. No. 14/972,506, entitled "CRYSTALLINE FORMS OF NEUROTROPHIN MIMETIC COMPOUNDS AND THEIR SALTS," filed Dec. 17, 2015 which is a continuation of U.S. application Ser. No. 13/509,470, entitled "CRYSTALLINE FORMS OF NEUROTROPHIN MIMETIC COMPOUNDS AND THEIR SALTS," filed Aug. 29, 2012, now U.S. Pat. No. 9,271,986, which is a National Stage Entry of PCT/US2010/056537, filed on Nov. 12, 2010 and entitled "CRYSTALLINE FORMS OF NEUROTROPHIN MIMETIC COMPOUNDS AND THEIR SALTS" which claims the benefit of U.S. Provisional Application No. 61/260,671, filed on Nov. 12, 2009 and entitled "THERAPEUTIC COMPOUNDS USEFUL FOR TREATING P75 RELATED CONDITIONS INCLUDING NEURODEGENERATIVE DISORDERS"; U.S. Provisional Application No. 61/294,279, filed on Jan. 12, 2010 and entitled "CRYSTALLINE FORMS OF NEUROTROPHIN MIMETIC COMPOUNDS AND THEIR SALTS"; and U.S. Provisional Application No. 61/350,797, filed on Jun. 2, 2010 and entitled "CRYSTALLINE FORMS OF NEUROTROPHIN MIMETIC COMPOUNDS AND THEIR SALTS"; the contents of each of which are hereby incorporated by reference in their entireties for all purposes.

FIELD OF THE INVENTION

The present invention relates to crystalline forms of neurotrophin mimetic compounds and crystalline forms of the salts and/or solvates of neurotrophin mimetic compounds, processes of preparing the crystalline forms, and methods of using them.

BACKGROUND OF THE INVENTION

Neurotrophins are polypeptides that play a role in the development, function, and/or survival of certain cells, including neurons, oligodendrocytes, Schwann cells, hair follicle cells, and other cells. The death or dysfunction of neurons and other cell types has been directly implicated in a number of neurodegenerative disorders. It has been suggested that alterations in neurotrophin localization, expression levels of neurotrophins, and/or expression levels of the receptors that bind neurotrophins are therefore linked to neuronal degeneration. Degeneration occurs in the neurodegenerative disorders Alzheimer's, Parkinson's and ALS, among others. Degeneration of oligodendrocytes can occur in central nervous system injury, multiple sclerosis, and other pathological states.

A variety of neurotrophins have been identified, including Nerve Growth Factor (NGF), Neurotrophin-3 (NT-3), Neurotrophin-4/5 (NT-4/5), Neurotrophin 6 (NT-6) and Brain Derived Neurotrophic Factor (BDNF). Neurotrophins are found in both precursor form, known as pro-neurotrophins, and in mature form. The mature forms are proteins of about 120 amino acids in length that exist in physiological states as stable, non-covalent approximately 25 kDa homodimers. Each neurotrophin monomer includes three solvent-exposed β-hairpin loops, referred to as loops 1, 2, and 4 that exhibit relatively high degrees of amino acid conservation across the neurotrophin family.

Mature neurotrophins bind preferentially to the receptors Trk and $p75^{NTR}$ (p75 neurotrophin receptor, also called the Low Affinity Nerve Growth Factor Receptor or LNGFR) while pro-neurotrophins, which contain an N-terminal domain proteolytically removed in mature forms, interact principally with $p75^{NTR}$ and through their N-terminal domains, with the sorting receptor sortilin (Fahnestock, M., et al. (2001) Mol Cell Neurosci 18, 210-220; Harrington, A. W. et al. (2004) Proc Natl Acad Sci USA 101, 6226-6230; Nykiaer. A. et al., (2004) Nature 427, 843-848). $p75^{NTR}$ interacts with Trks and modulates Trk signaling, but is also independently coupled to several signaling systems, including pro-survival signals, IRAK/TRAF6/NF.kappa.B, PI3/AKT, and proapoptotic signals, NRAGE/JNK (Mamidipudi, V., et al. (2002) J Biol Chem 277, 28010-28018; Roux, P. P., et al. (2001) J Biol Chem 276, 23097-23104; Salehi, A. H., et al. (2000) Neuron 27, 279-288).

When administered for therapeutic use, neurotrophins exhibit suboptimal pharmacological properties, including poor stability with low serum half lives, likely poor oral bioavailability, and restricted central nervous system penetration (Podulso, J. F., Curran, G. L. (1996) Brain Res Mol Brain Res 36, 280-286; Saltzman, W. M., et al (1999) Pharm Res 16, 232-240; Partridge, W. M. (2002) Adv Exp Med Bio 513, 397-430). Additionally, the highly pleiotropic effects of neurotrophins achieved through action of the dual receptor signaling network increases the chances of adverse effects.

It has been suggested that the unliganded form of $p75^{NTR}$ is proapoptotic, and that homodimerization induced by neurotrophin binding eliminates the effect (Wang, J. J., et al (2000) J Neurosci Res 60, 587-593), consistent with studies showing no effects on survival of monomeric $p75^{NTR}$ ligands, including monovalent Fabs (Maliartchouk, S., et al (2000) J Biol Chem 275, 9946-9956) and monomeric cyclic peptides (Longo, F. M., (1997) J Neurosci Res 48, 1-17), while related bivalent forms in each study promote cell survival. However, these monomeric ligands may not engage the receptor in the same way as the natural ligands. Though active NGF is a homodimers containing 2 potential $p75^{NTR}$ binding sites, recent structural evidence suggests that it engages only one $p75^{NTR}$ molecule, disallowing the binding of another (He, X. L., (2004) Science 304, 870-875).

Unfortunately, technical and ethical considerations have thus far hampered the development of therapeutic agents based upon neurotrophins. For example, it is technically difficult to produce sufficient quantities of pure neurotrophins using recombinant DNA techniques. Additionally, although it is possible to utilize human fetal cells to produce neurotrophins, the ethical ramifications raised by the use of such cells (typically obtained from an aborted fetus) have all but prevented the utilization of this approach. Accordingly, there is an unmet need in the art for the development of small molecule agents with favorable drug-like features based upon neurotrophins, i.e., neurotrophin mimetics, that are capable of targeting specific neurotrophin receptors for use in the treatment of disorders or diseases. U.S. Patent Application Publication Nos. 2006/024072 and 2007/0060526 describe certain neurotrophin mimetics, and the contents of these two publications are herein incorporated by reference in their entirety for all purposes.

Those skilled in the pharmaceutical arts understand that crystallization of an active pharmaceutical ingredient offers the best method for controlling important physiochemical qualities, such as stability, solubility, bioavailability, particle size, bulk density, flow properties, polymorphic content, and other properties. Thus, there is a need for crystalline forms of neurotrophin mimetics and processes to produce such forms. These crystalline forms should be suitable for pharmaceutical use.

SUMMARY OF THE INVENTION

In certain embodiments, the disclosure provides a crystalline form of (2S,3S)-2-amino-3-methyl-N-(2-morpholinoethyl)-pentanamide tetra(monohydrogensulfate), monosulfate that exhibits an X-ray powder diffraction pattern comprising peaks at about 8.01±0.3; 9.85±0.3; 21.30±0.3; and 21.99±0.3 degrees two-theta. The crystalline form may further comprise peaks at about 15.01±0.3; 18.06±0.3; 18.88±0.3; 24.27±0.3 and 15.499±0.3 degrees two-theta.

The disclosure provides a pharmaceutical composition comprising the crystalline form of (2S,3S)-2-amino-3-methyl-N-(2-morpholinoethyl)-pentanamide tetra(monohydrogensulfate), monosulfate described herein.

In certain aspects, the disclosure provides a method for treating a disorder involving degeneration or dysfunction of cells expressing p75, comprising administering to a patient in need of such treatment a therapeutically effective amount of the pharmaceutical composition of (2S,3S)-2-amino-3-methyl-N-(2-morpholinoethyl)-pentanamide tetra(monohydrogensulfate), monosulfate described herein. In certain embodiments, the disorder is a neurodegenerative disorder. In certain embodiments, the disorder is selected from the group consisting of Alzheimer's disease, Huntington's disease, Pick's disease, amyotrophic lateral sclerosis, epilepsy, Parkinson's disease, spinal cord injury, stroke, hypoxia, ischemia, brain injury, diabetic neuropathy, peripheral neuropathy, nerve transplantation, multiple sclerosis, peripheral nerve injury, and hair loss.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 11 is a DSC thermogram of (2S,3S)-2-amino-3-methyl-N-(2-morpholinoethyl)-pentanamide monosulfate.

DETAILED DESCRIPTION OF THE INVENTION

Figure 1:
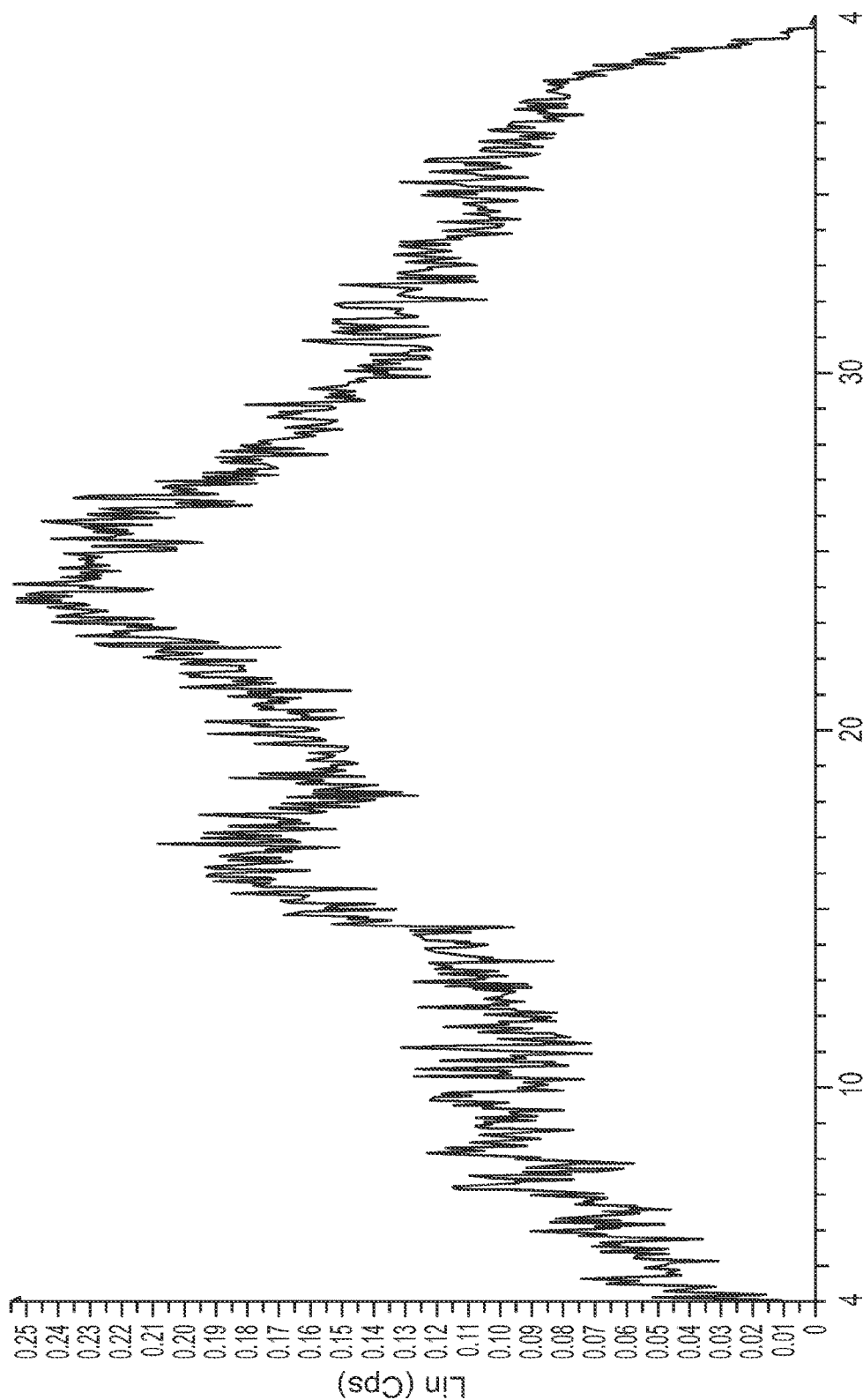
FIG. 1 is a graph of a x-ray powder diffraction (XRD) pattern of the amorphous di-HCl salt of (2S,3S)-2-amino-3-methyl-N-(2-morpholinoethyl)-pentanamide.

In patients with disorders related to degeneration or dysfunction of cells expressing p75, such as neurodegenerative disorders, alterations in neurotrophin localization, expression levels of neurotrophins, expression levels of the receptors that bind neurotrophins, and/or receptor signaling and functional outcomes can occur. Accordingly, by providing patients suffering from such disorders with a corresponding neurotrophic factor or mimetic thereof that modulates $p75^{NTR}$ function or proNGF/NGF binding to prevent cellular degeneration or dysfunction, such neural degeneration can be alleviated or prevented.

The present invention relates to crystalline forms of neurotrophin mimetic compounds as well as crystalline forms of salts and/or solvates of neurotrophin mimetic compounds. These crystalline materials can be formulated into pharmaceutical compositions and used for treating disorders involving degeneration or dysfunction of cells expressing p75.

Definitions

It is to be understood that the terminology used herein is for the purpose of describing particular embodiments only and is not intended to be limiting.

Unless defined otherwise, all technical and scientific terms used herein have the same meaning as commonly understood to one of ordinary skill in the art to which the present application belongs. Although any methods and materials similar or equivalent to those described herein can be used in the practice or testing of the present application, representative methods and materials are herein described.

Following long-standing patent law convention, the terms "a", "an", and "the" refer to "one or more" when used in this application, including the claims. Thus, for example, reference to "a carrier" includes mixtures of one or more carriers, two or more carriers, and the like.

Unless otherwise indicated, all numbers expressing quantities of ingredients, reaction conditions, and so forth used in the specification and claims are to be understood as being modified in all instances by the term "about". Accordingly, unless indicated to the contrary, the numerical parameters set forth in the present specification and attached claims are approximations that can vary depending upon the desired properties sought to be obtained by the present application. Generally the term "about", as used herein when referring to a measurable value such as an amount of weight, time, dose, etc. is meant to encompass in one example variations of ±20% or ±10%, in another example ±5%, in another example ±1%, and in yet another example±0.1% from the specified amount, as such variations are appropriate to perform the disclosed method.

The term "compound(s) of the present invention", "present compound(s)", or "2-amino-3-methyl-N-(2-morpholinoethyl)-pentanamide" refers to the crystalline forms of 2-amino-3-methyl-N-(2-morpholinoethyl)-pentanamide described throughout the application including a crystalline form of any single enantiomer of 2-amino-3-methyl-N-(2-morpholinoethyl)-pentanamide, a mixture of any two enantiomers of 2-amino-3-methyl-N-(2-morpholinoethyl)-pentanamide, a mixture of any three enantiomers of 2-amino-3-methyl-N-(2-morpholinoethyl)-pentanamide, and a mixture of any four enantiomers of 2-amino-3-methyl-N-(2-morpholinoethyl)-pentanamide.

Polymorphism can be characterized as the ability of a compound to crystallize into different crystal forms, while maintaining the same chemical formula. A crystalline polymorph of a given drug substance is chemically identical to any other crystalline polymorph of that drug substance in containing the same atoms bonded to one another in the same way, but differs in its crystal forms, which can affect one or more physical properties, such as stability, solubility, melting point, bulk density, flow properties, bioavailability, etc.

The term "composition" denotes one or more substance in a physical form, such as solid, liquid, gas, or a mixture thereof. One example of composition is a pharmaceutical composition, i.e., a composition related to, prepared for, or used in medical treatment.

The term "carboxylic acid" refers to an organic acid characterized by one or more carboxyl groups, such as acetic acid and oxalic acid. "Sulfonic acid" refers to an organic acid with the general formula of R—$(S(O)_2$—$OH)_n$, wherein R is an organic moiety and n is an integer above zero, such as 1, 2, and 3. The term "polyhydroxy acid" refers to a carboxylic acid containing two or more hydroxyl groups. Examples of polyhydroxy acid include, but are not limited to, lactobionic acid, gluconic acid, and galactose.

"Neurotrophin mimetic compound" denotes an organic compound that resembles the biological function or activity of neurotrophin.

As used herein, "pharmaceutically acceptable" means suitable for use in contact with the tissues of humans and animals without undue toxicity, irritation, allergic response, and the like, commensurate with a reasonable benefit/risk ratio, and effective for their intended use within the scope of sound medical judgment.

"Salts" include derivatives of an active agent, wherein the active agent is modified by making acid or base addition salts thereof. Preferably, the salts are pharmaceutically acceptable salts. Such salts include, but are not limited to, pharmaceutically acceptable acid addition salts, pharmaceutically acceptable base addition salts, pharmaceutically acceptable metal salts, ammonium and alkylated ammonium salts. Acid addition salts include salts of inorganic acids as well as organic acids. Representative examples of suitable inorganic acids include hydrochloric, hydrobromic, hydroiodic, phosphoric, sulfuric, nitric acids and the like. Representative examples of suitable organic acids include formic, acetic, trichloroacetic, trifluoroacetic, propionic, benzoic, cinnamic, citric, fumaric, glycolic, lactic, maleic, malic, malonic, mandelic, oxalic, picric, pyruvic, salicylic, succinic, methanesulfonic, ethanesulfonic, tartaric, ascorbic, pamoic, bismethylene salicylic, ethanedisulfonic, gluconic, citraconic, aspartic, stearic, palmitic, EDTA, glycolic, p-aminobenzoic, glutamic, benzenesulfonic, p-toluenesulfonic acids, sulphates, nitrates, phosphates, perchlorates, borates, acetates, benzoates, hydroxynaphthoates, glycerophosphates, ketoglutarates and the like. Base addition salts include but are not limited to, ethylenediamine, N-methylglucamine, lysine, arginine, ornithine, choline, N,N'-dibenzylethylenediamine, chloroprocaine, diethanolamine, procaine, N-benzylphenethylamine, diethylamine, piperazine, tris-(hydroxymethyl)-aminomethane, tetramethylammonium hydroxide, triethylamine, dibenzylamine, ephenamine, dehydroabietylamine, N-ethylpiperidine, benzylamine, tetramethylammonium, tetraethylammonium, methylamine, dimethylamine, trimethylamine, ethylamine, basic amino acids, e.g., lysine and arginine dicyclohexylamine and the like. Examples of metal salts include lithium, sodium, potassium, magnesium salts and the like. Examples of ammonium and alkylated ammonium salts include ammonium, methylammonium, dimethylammonium, trimethylammonium, ethylammonium, hydroxyethylammonium, diethylammonium, butylammonium, tetramethylammonium salts and the like. Examples of organic bases include lysine, arginine, guanidine, diethanolamine, choline and the like. Standard methods for the preparation of pharmaceutically acceptable salts and their formulations are well known in the art, and are disclosed in various references, including for example, "Remington: The Science and Practice of Pharmacy", A. Gennaro, ed., 20th edition, Lippincott, Williams & Wilkins, Philadelphia, Pa.

As used herein, "solvate" means a complex formed by solvation (the combination of solvent molecules with molecules or ions of the active agent of the present invention), or an aggregate that consists of a solute ion or molecule (the active agent of the present invention) with one or more solvent molecules. In the present invention, the preferred solvate is hydrate. Examples of hydrate include, but are not limited to, hemihydrate, monohydrate, dihydrate, trihydrate, hexahydrate, etc. It should be understood by one of ordinary skill in the art that the pharmaceutically acceptable salt of the present compound may also exist in a solvate form. The solvate is typically formed via hydration which is either part of the preparation of the present compound or through natural absorption of moisture by the anhydrous compound of the present invention. Solvates including hydrates may be consisting in stoichiometric ratios, for example, with two, three, four salt molecules per solvate or per hydrate molecule. Another possibility, for example, that two salt molecules are stoichiometric related to three, five, seven solvent or hydrate molecules. Solvents used for crystallization, such as alcohols, especially methanol and ethanol; aldehydes; ketones, especially acetone; esters, e.g. ethyl acetate; may be embedded in the crystal grating. Preferred are pharmaceutically acceptable solvents.

The term "substantially similar" as used herein means an analytical spectrum, such as XRD pattern, Raman spectroscopy, and etc., which resembles the reference spectrum to a great degree in both the peak locations and their intensity.

The terms "excipient", "carrier", and "vehicle" are used interexchangeably throughout this application and denote a substance with which a compound of the present invention is administered.

"Therapeutically effective amount" means the amount of a crystalline form that, when administered to a patient for treating a disease or other undesirable medical condition, is sufficient to have a beneficial effect with respect to that disease or condition. The therapeutically effective amount will vary depending on the crystalline form, the disease or condition and its severity, and the age, weight, etc. of the patient to be treated. Determining the therapeutically effective amount of a given crystalline form is within the ordinary skill of the art and requires no more than routine experimentation.

As used herein, the phrase "a disorder involving degeneration or dysfunction of cells expressing p75" includes, but is not limited to, disorders related to upregulation of p75. Such disorders include neurodegenerative disorders, as well as conditions involving degeneration of $p75^{NTR}$-expressing cells, such as hair loss. Within the nervous system, the p75 receptor is expressed by various cell types including neurons, oligodendrocytes, astrocytes. Compounds targeting p75 receptors expressed by neurons can be used to prevent loss of function, degeneration and/or death of neurons in a number of nervous system disorders including (but not limited to) Alzheimer's disease, Parkinson's disease, Huntington's disease, stroke, traumatic brain injury, spinal cord injury, epilepsy, multiple sclerosis, amyotrophic lateral sclerosis, neuropathies, myopathies and various forms of retinal degeneration. In each of these disorders, neurons expressing p75 are affected.

Crystalline Materials

In one embodiment, the present invention provides a crystalline form of 2-amino-3-methyl-N-(2-morpholinoethyl)-pentanamide (free base). In another embodiment, the present invention provides a crystalline form of a salt and/or solvate of (2S,3S)-2-amino-3-methyl-N-(2-morpholinoethyl)-pentanamide. In one embodiment, the salt is a sulfuric acid addition salt. In one embodiment, the salt is a sulfonic acid addition salt. In one embodiment, the salt is a carboxylic acid addition salt. In one embodiment, the salt is a polyhydroxy acid addition salt. Examples of the crystalline salt include, but are not limited to, monosulfate, tetra(monohydrogensulfate), monosulfate, digluconate, dimesylate, ditosylate, dinapsylate, monoedisylate, and monooxalate. The naphthalenesulfonic acid, which forms dinapsylate salt with 2-amino-3-methyl-N-(2-morpholinoethyl)-pentanamide, can be 1-naphthalenesulfonic acid, 2-naphthalenesulfonic acid, or 3-naphthalenesulfonic acid. In one embodiment, the naphthalenesulfonic acid is 2-naphthalenesulfonic acid. The compound of 2-amino-3-methyl-N-(2-morpholinoethyl)-pentanamide is selected from the group consisting of: (2S,3S)-2-amino-3-methyl-N-(2-morpholinoethyl)-pentanamide; (2R,3R)-2-amino-3-methyl-N-(2-morpholinoethyl)-pentanamide; (2R,3 S)-2-amino-3-methyl-N-(2-morpholinoethyl)-pentanamide; (2S,3R)-2-amino-3-methyl-N-(2-morpholinoethyl)-pentanamide; and a mixture thereof. Scheme A shows the chemical structures of the present compounds.

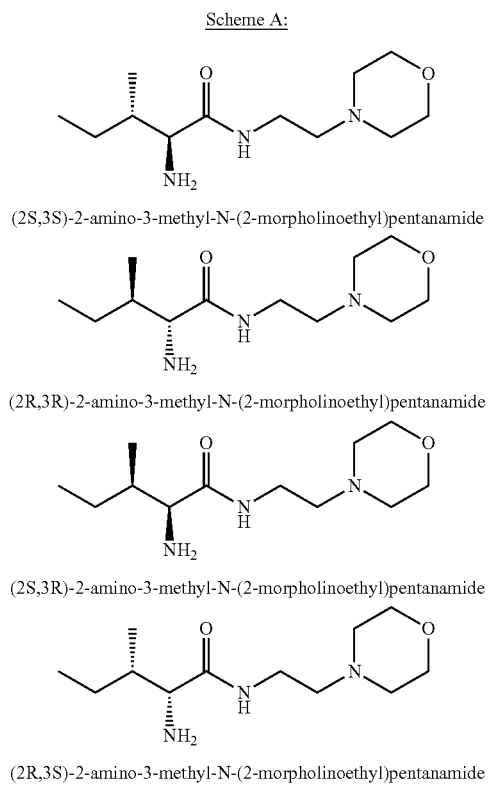

Scheme A:

(2S,3S)-2-amino-3-methyl-N-(2-morpholinoethyl)pentanamide (2R,3R)-2-amino-3-methyl-N-(2-morpholinoethyl)pentanamide (2S,3R)-2-amino-3-methyl-N-(2-morpholinoethyl)pentanamide (2R,3S)-2-amino-3-methyl-N-(2-morpholinoethyl)pentanamide In one embodiment, the crystalline forms are characterized by the interlattice plane intervals determined by a X-ray powder diffraction pattern (XRDP). The spectrum of XRDP is typically represented by a diagram plotting the intensity of the peaks versus the location of the peaks, i.e., diffraction angle 2θ (two-theta) in degrees. The intensities are often given in parenthesis with the following abbreviations: very strong=vst; strong=st; medium=m; weak=w; and very weak=vw. The characteristic peaks of a given XRDP can be selected according to the peak locations and their relative intensity to conveniently distinguish this crystalline structure from others.

Those skilled in the art recognize that the measurements of the XRDP peak locations and/or intensity for a given crystalline form of the same compound will vary within a margin of error. The values of degree 2θ allow appropriate error margins. Typically, the error margins are represented by "±". For example, the degree 2θ of about "8.716±0.3" denotes a range from about 8.716+0.3, i.e., about 9.016, to about 8.716−0.3, i.e., about 8.416. Depending on the sample preparation techniques, the calibration techniques applied to the instruments, human operational variation, and etc, those skilled in the art recognize that the appropriate error of margins for a XRDP can be ±0.5; ±0.4; ±0.3; ±0.2; ±0.1; ±0.05; or less.

Additional details of the methods and equipment used for the XRDP analysis are described in the Examples section.

In one embodiment, the crystalline form of (2S,3S)-2-amino-3-methyl-N-(2-morpholinoethyl)-pentanamide exhibits an XRDP comprising peaks at about 8.716; 15.438; and 19.198 degrees two-theta with the margin of error of about ±0.5; about ±0.4; about ±0.3; about ±0.2; about ±0.1; about ±0.05; or less. In another embodiment, the XRDP of the crystalline form further comprises peaks at about 20.912 and 20.599 degrees two-theta with the margin of error of about ±0.5; about ±0.4; about ±0.3; about ±0.2; about ±0.1; about ±0.05; or less. In yet another embodiment, the crystalline form of (2S,3S)-2-amino-3-methyl-N-(2-morpholinoethyl)-pentanamide exhibits an XRDP comprising peaks shown in the table below:

TABLE 1

XRDP Table of (2S,3S)-2-amino-3-methyl-N-(2-morpholinoethyl)-pentanamide.

| Angle 2 Theta ° | d value Angstrom | Intensity % |
| --- | --- | --- |
| 8.716 | 10.13693 | 53.2 (vst) |
| 15.438 | 5.73486 | 100.0 (vst) |
| 16.554 | 5.35074 | 7.0 (w) |
| 17.514 | 5.05977 | 15.3 (m) |
| 18.358 | 4.82894 | 8.6 (w) |
| 19.198 | 4.61948 | 30.4 (vst) |
| 19.773 | 4.48646 | 17.8 (m) |
| 20.126 | 4.40854 | 9.0 (w) |
| 20.599 | 4.30831 | 20.8 (st) |
| 20.912 | 4.24452 | 27.7 (st) |
| 22.391 | 3.96741 | 5.6 (w) |
| 23.200 | 3.83088 | 11.5 (m) |
| 23.867 | 3.72529 | 7.4 (w) |
| 24.390 | 3.64661 | 11.4 (m) |
| 25.709 | 3.46243 | 14.3 (m) |
| 26.387 | 3.37497 | 13.0 (m) |
| 29.629 | 3.01264 | 4.9 (vw) |
| 30.822 | 2.89872 | 4.8 (vw) |
| 31.270 | 2.85819 | 4.9 (vw) |

Figure 5:
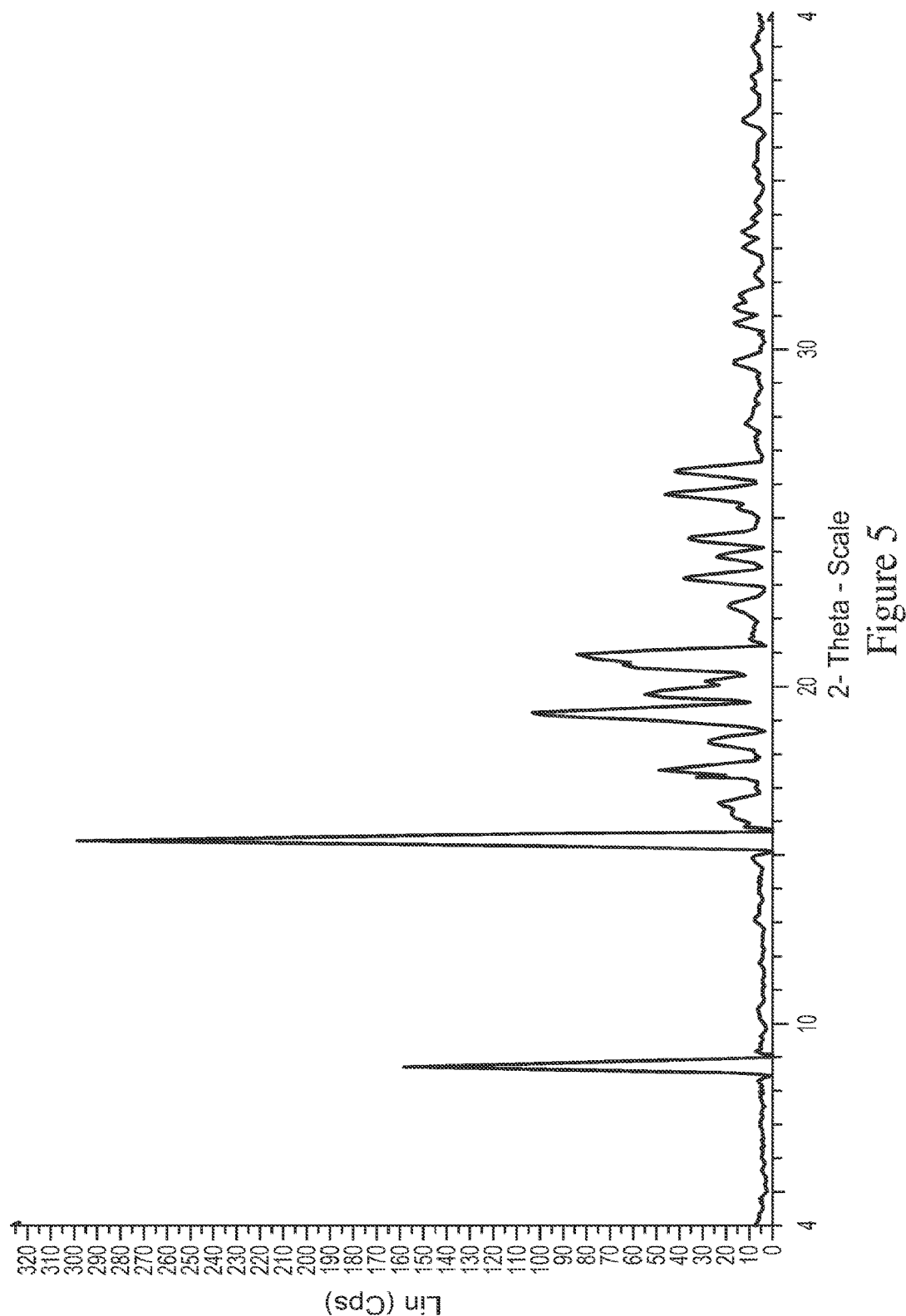
FIG. 5 is a graph of a x-ray powder diffraction (XRD) pattern of (2S,3S)-2-amino-3-methyl-N-(2-morpholinoethyl)-pentanamide (free base).

In one specific embodiment, the crystalline form of (2S,3S)-2-amino-3-methyl-N-(2-morpholinoethyl)-pentanamide exhibits an XRDP that is substantially similar to FIG. 5.

In one embodiment, the crystalline form of (2S,3S)-2-amino-3-methyl-N-(2-morpholinoethyl)-pentanamide monosulfate exhibits an XRDP comprising peaks at about 25.306 and about 27.027 degrees two-theta with the margin of error of about ±0.5; about ±0.4; about ±0.3; about ±0.2; about ±0.1; about ±0.05; or less. In another embodiment, the XRDP of the crystalline form further comprises a peak at about 17.449 degrees two-theta with the margin of error of about ±0.5; about ±0.4; about ±0.3; about ±0.2; about ±0.1; about ±0.05; or less. In yet another embodiment, the crystalline form of (2S,3S)-2-amino-3-methyl-N-(2-morpholinoethyl)-pentanamide monosulfate exhibits an XRDP comprising peaks shown in the table below:

TABLE 2

XRDP Table of (2S,3S)-2-amino-3-methyl-N-(2-morpholinoethyl)-pentanamide monosulfate.

| Angle 2 Theta ° | d value Angstrom | Intensity % |
| --- | --- | --- |
| 17.449 | 5.07811 | 43.3 (vst) |
| 25.306 | 3.51657 | 100.0 (vst) |
| 27.027 | 3.29634 | 72.7 (vst) |

Figure 10:
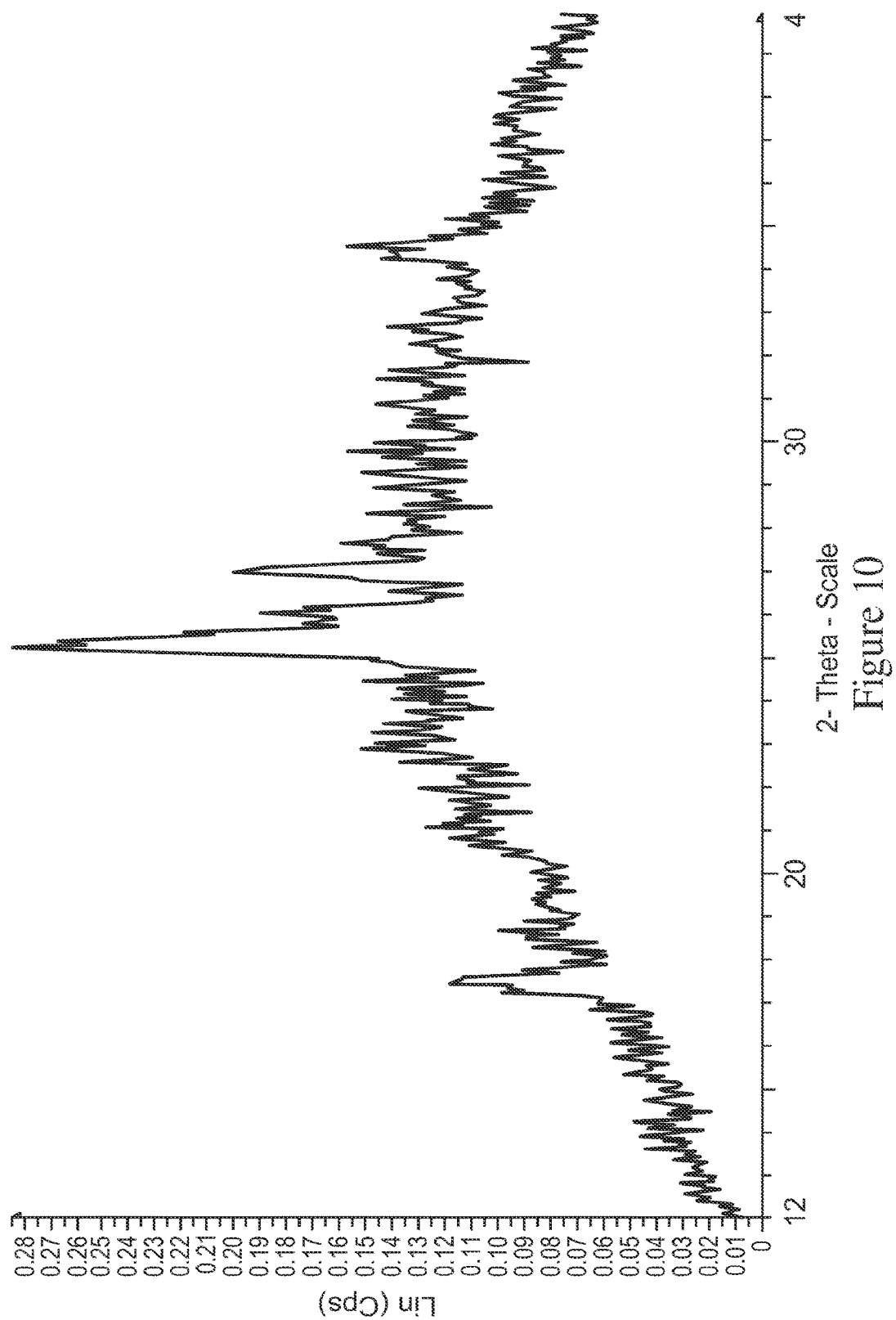
FIG. 10 is a graph of a x-ray powder diffraction (XRD) pattern of (2S,3S)-2-amino-3-methyl-N-(2-morpholinoethyl)-pentanamide monosulfate.
Figure 55:
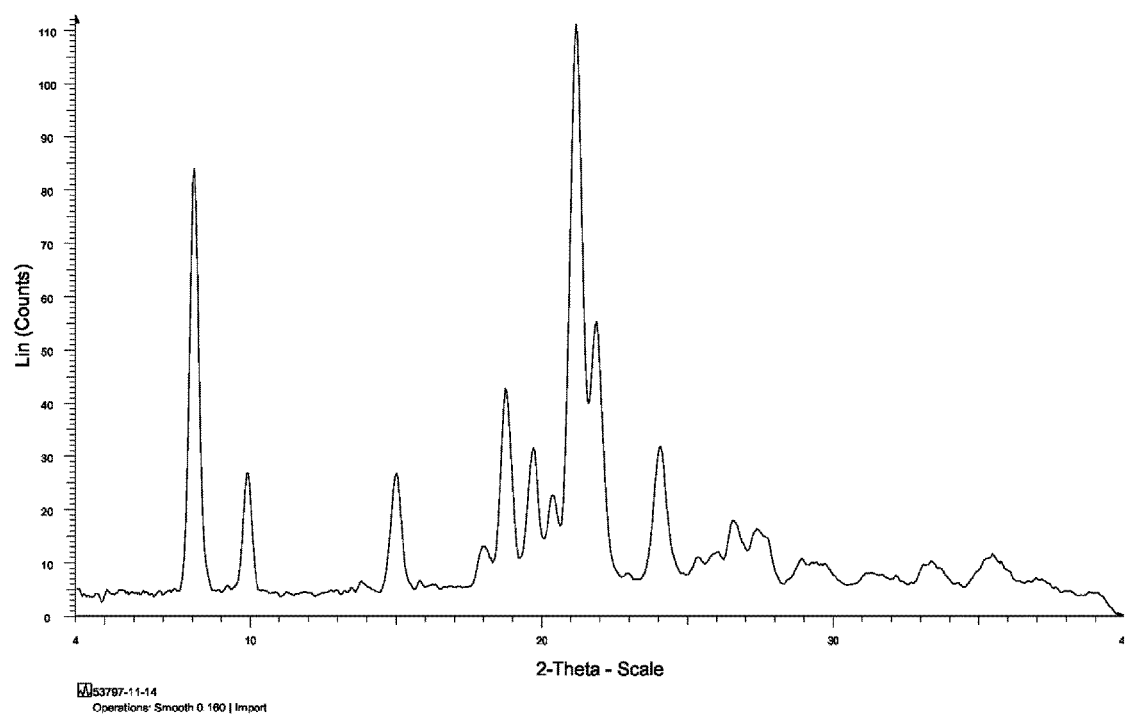
FIG. 55 is a graph of a x-ray powder diffraction (XRD) pattern of (2S,3S)-2-amino-3-methyl-N-(2-morpholinoethyl)-pentanamide tetra(monohydrogensulfate), monosulfate from the large scale preparation in Example 12.

In one specific embodiment, the crystalline form of (2S,3S)-2-amino-3-methyl-N-(2-morpholinoethyl)-pentanamide monosulfate exhibits an XRDP that is substantially similar to FIG. 10 or substantially similar to FIG. 55.

In one embodiment, the crystalline form of (2S,3S)-2-amino-3-methyl-N-(2-morpholinoethyl)-pentanamide tetra(monohydrogensulfate), monosulfate, represented by the following formula:

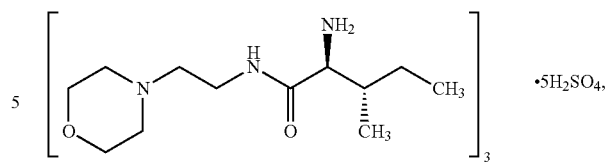

exhibits an XRDP comprising peaks at about 21.784; 22.468; and 19.277 degrees two-theta with the margin of error of about ±0.5; about ±0.4; about ±0.3; about ±0.2; about ±0.1; about ±0.05; or less. In another embodiment, the XRDP of the crystalline form further comprises peaks at about 24.618 and 15.499 degrees two-theta with the margin of error of about ±0.5; about ±0.4; about ±0.3; about ±0.2; about ±0.1; about ±0.05; or less. In yet another embodiment, the crystalline form of (2S,3S)-2-amino-3-methyl-N-(2-morpholinoethyl)-pentanamide tetra(monohydrogensulfate), monosulfate exhibits an XRDP comprising peaks shown in the tables below:

TABLE 3A

XRDP Table of (2S,3S)-2-amino-3-methyl-N-(2-morpholinoethyl)-pentanamide tetra(monohydrogensulfate), monosulfate (from the small scale preparation in Example 4)

| Angle 2 Theta ° | d value Angstrom | Intensity % |
| --- | --- | --- |
| 8.572 | 10.30642 | 7.9 (w) |
| 10.390 | 8.50740 | 5.5 (w) |
| 15.499 | 5.71227 | 16.6 (m) |
| 18.550 | 4.77929 | 9.7 (w) |
| 19.277 | 4.60050 | 32.6 (vst) |
| 20.208 | 4.39062 | 19.9 (m) |
| 21.784 | 4.07644 | 100.0 (vst) |
| 22.468 | 3.95387 | 44.7 (vst) |
| 24.618 | 3.61327 | 23.5 (st) |
| 26.472 | 3.36417 | 12.1 (m) |
| 27.178 | 3.27837 | 12.3 (m) |
| 28.107 | 3.17216 | 9.6 (w) |

TABLE 3B

XRDP Table of (2S,3S)-2-amino-3-methyl-N-(2-morpholinoethyl)-pentanamide tetra(monohydrogensulfate), monosulfate (from the large scale preparation in Example 12)

| Angle 2 Theta ° | d value Angstrom | Intensity % |
| --- | --- | --- |
| 8.01 | 11.03 | 78.7 (vst) |
| 9.85 | 8.89 | 56.9 (st) |
| 15.01 | 5.90 | 20.0 (st) |
| 18.06 | 4.91 | 22.5 (st) |
| 18.88 | 4.70 | 39.2 (st) |
| 19.79 | 4.48 | 13.0 (st) |
| 20.51 | 4.33 | 18.2 (m) |
| 21.30 | 4.17 | 100.0 (vst) |
| 21.99 | 4.04 | 59.1 (vst) |
| 24.27 | 3.66 | 33.6 (st) |
| 26.11 | 3.66 | 8.4 (w) |
| 26.88 | 3.41 | 21.2 (m) |

Figure 13:
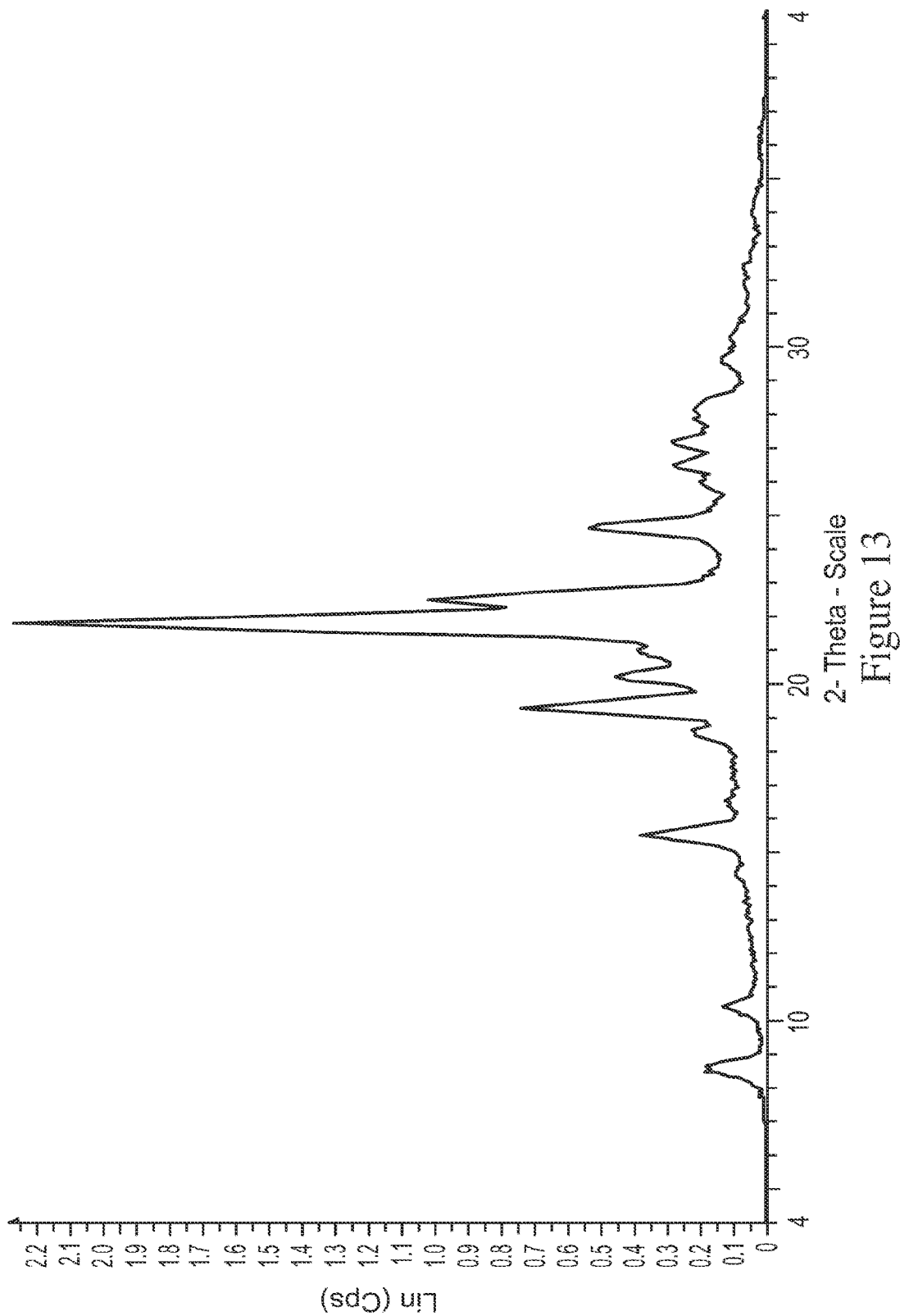
FIG. 13 is a graph of a x-ray powder diffraction (XRD) pattern of (2S,3S)-2-amino-3-methyl-N-(2-morpholinoethyl)-pentanamide tetra(monohydrogensulfate), monosulfate.

In one specific embodiment, the crystalline form of (2S,3S)-2-amino-3-methyl-N-(2-morpholinoethyl)-pentanamide tetra(monohydrogensulfate), monosulfate exhibits an XRDP that is substantially similar to FIG. 13.

In one embodiment, the crystalline form of (2S,3S)-2-amino-3-methyl-N-(2-morpholinoethyl)-pentanamide digluconate exhibits an XRDP comprising peaks at about 19.447; 24.377; and 22.637 degrees two-theta with the margin of error of about ±0.5; about ±0.4; about ±0.3; about ±0.2; about ±0.1; about ±0.05; or less. In another embodiment, the XRDP of the crystalline form further comprises peaks at about 15.730 and 7.768 degrees two-theta with the margin of error of about ±0.5; about ±0.4; about ±0.3; about ±0.2; about ±0.1; about ±0.05; or less. In yet another embodiment, the crystalline form of (2S,3S)-2-amino-3-methyl-N-(2-morpholinoethyl)-pentanamide digluconate exhibits an XRDP comprising peaks shown in the table below:

TABLE 4

XRDP Table of (2S,3S)-2-amino-3-methyl-N-(2-morpholinoethyl)-pentanamide digluconate.

| Angle 2 Theta ° | d value Angstrom | Intensity % |
|---|---|---|
| 7.768 | 11.37097 | 60.9 (vst) |
| 9.071 | 9.74106 | 23.1 (st) |
| 15.730 | 5.62923 | 88.8 (vst) |
| 19.447 | 4.56067 | 100.0 (vst) |
| 21.198 | 4.18776 | 57.3 (vst) |
| 22.637 | 3.92466 | 93.3 (vst) |
| 24.377 | 3.64838 | 99.1 (vst) |
| 25.981 | 3.42667 | 59.4 (vst) |
| 28.856 | 3.09148 | 25.8 (st) |
| 31.182 | 2.86600 | 45.3 (vst) |

Figure 19:
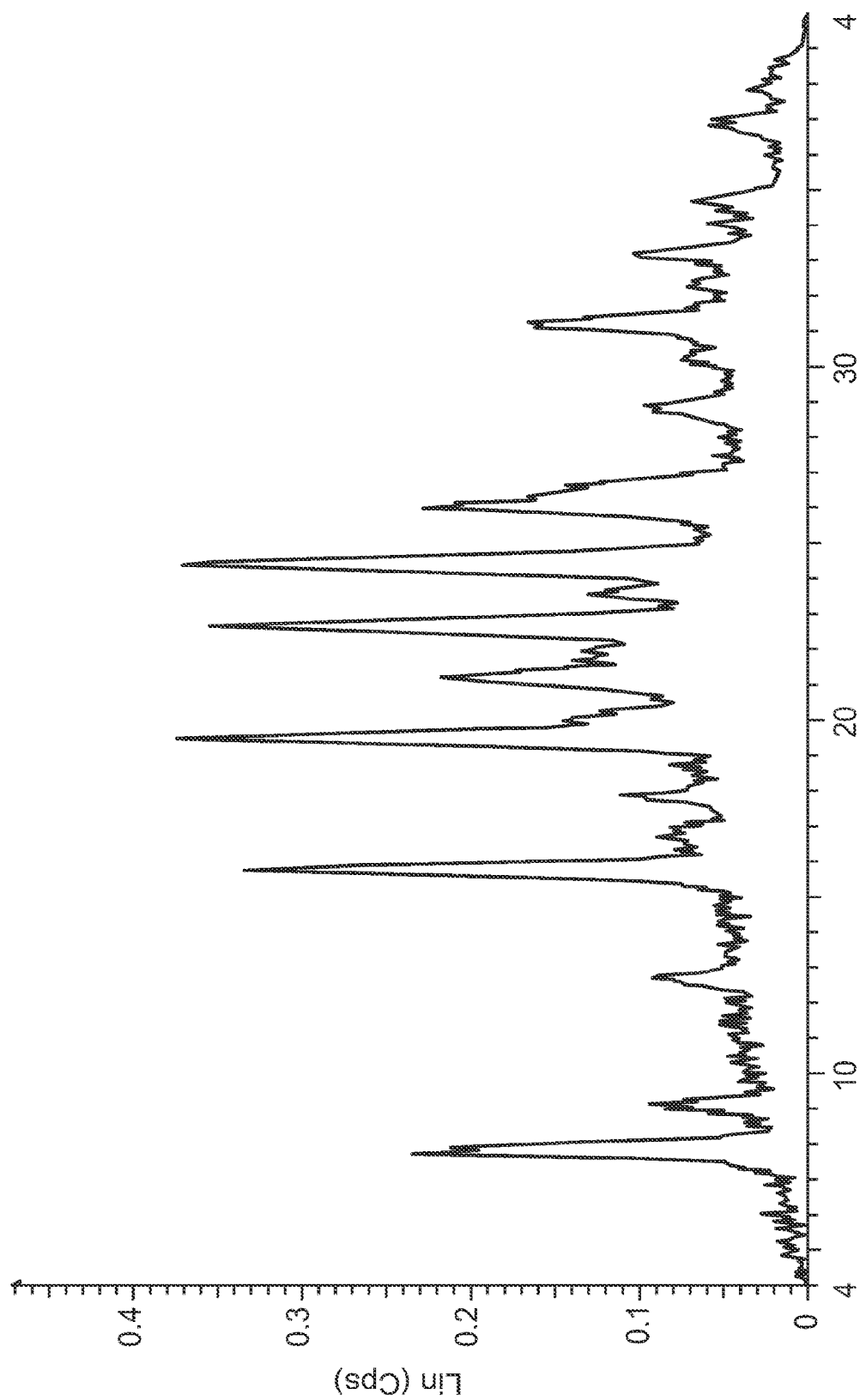
FIG. 19 is a graph of a x-ray powder diffraction (XRD) pattern of (2S,3S)-2-amino-3-methyl-N-(2-morpholinoethyl)-pentanamide digluconate.

In one specific embodiment, the crystalline form of (2S,3S)-2-amino-3-methyl-N-(2-morpholinoethyl)-pentanamide digluconate exhibits an XRDP that is substantially similar to FIG. 19.

In one embodiment, the crystalline form of (2S,3S)-2-amino-3-methyl-N-(2-morpholinoethyl)-pentanamide dimesylate exhibits an XRDP comprising peaks at about 8.499, 21.162, and 22.292 degrees two-theta with the margin of error of about ±0.5; about ±0.4; about ±0.3; about ±0.2; about ±0.1; about ±0.05; or less. In another embodiment, the XRDP of the crystalline form further comprises peaks at about 9.421, 16.543, and 18.912 degrees two-theta with the margin of error of about ±0.5; about ±0.4; about ±0.3; about ±0.2; about ±0.1; about ±0.05; or less. In yet another embodiment, the crystalline form of (2S,3S)-2-amino-3-methyl-N-(2-morpholinoethyl)-pentanamide dimesylate exhibits an XRDP comprising peaks shown in the table below:

TABLE 5

XRDP Table of (2S,3S)-2-amino-3-methyl-N-(2-morpholinoethyl)-pentanamide dimesylate.

| Angle 2 Theta ° | d value Angstrom | Intensity Count | Intensity % |
|---|---|---|---|
| 8.499 | 10.395 | 37.3 | 100 |
| 9.421 | 9.37978 | 27.3 | 87.7 |
| 12.837 | 6.89036 | 12.3 | 39.5 |
| 13.412 | 6.59644 | 8.87 | 28.5 |
| 15.812 | 5.60013 | 15.3 | 49.1 |
| 16.543 | 5.35436 | 21.4 | 68.8 |
| 17.093 | 5.18306 | 14 | 45 |
| 18.912 | 4.68856 | 19.8 | 63.6 |
| 21.162 | 4.19476 | 29.3 | 93.9 |
| 22.292 | 3.98469 | 31.2 | 100 |
| 24.884 | 3.5752 | 11.5 | 36.9 |
| 25.767 | 3.45468 | 14.2 | 45.5 |
| 29.585 | 3.01697 | 7.6 | 24.4 |

Figure 25:
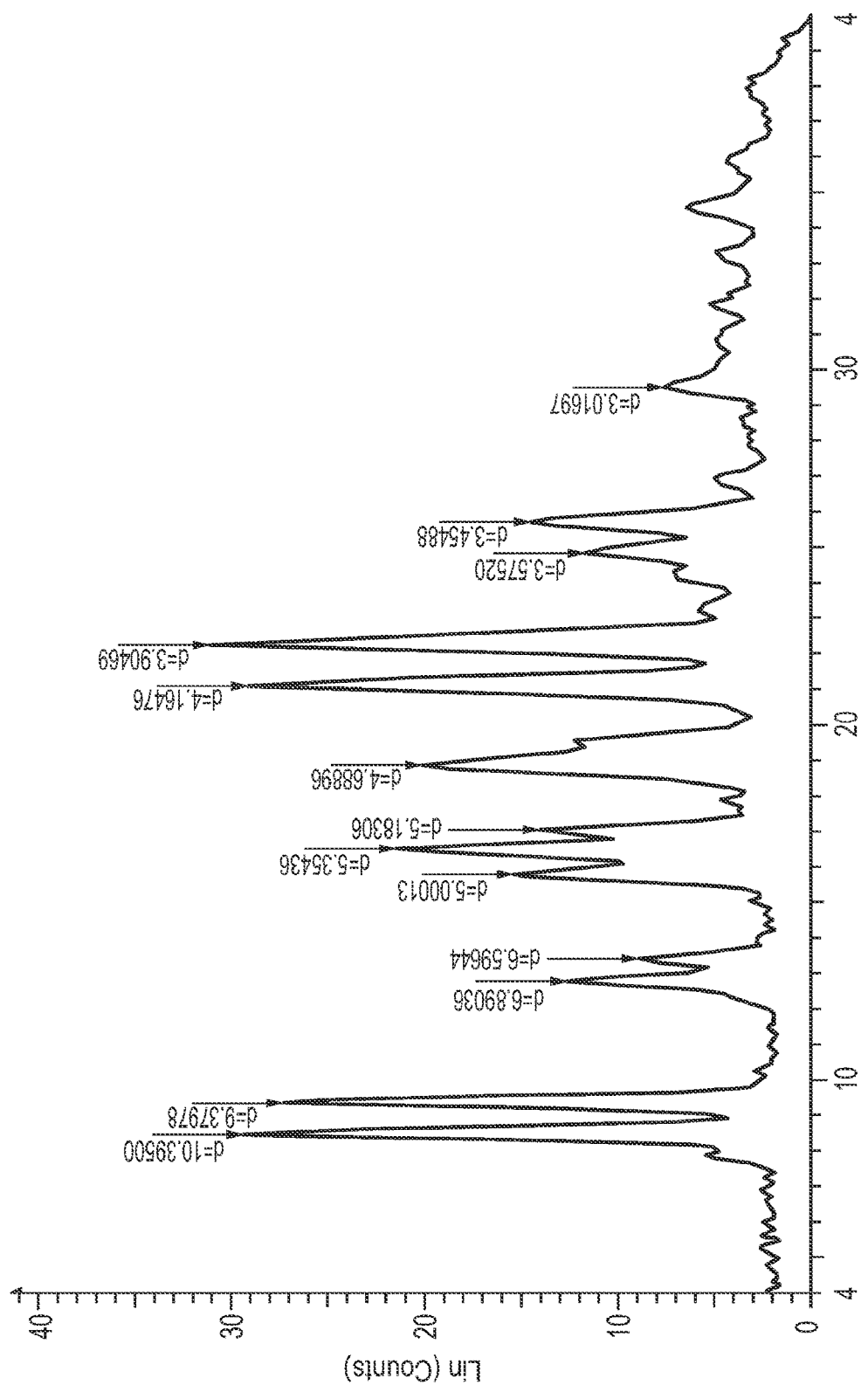
FIG. 25 is a graph of a x-ray powder diffraction (XRD) pattern of (2S,3S)-2-amino-3-methyl-N-(2-morpholinoethyl)-pentanamide dimesylate.

In one specific embodiment, the crystalline form of (2S,3S)-2-amino-3-methyl-N-(2-morpholinoethyl)-pentanamide dimesylate exhibits an XRDP that is substantially similar to FIG. 25.

In one embodiment, the crystalline form of (2S,3S)-2-amino-3-methyl-N-(2-morpholinoethyl)-pentanamide ditosylate exhibits an XRDP comprising peaks at about 6.021 and 18.078 degrees two-theta with the margin of error of about ±0.5; about ±0.4; about ±0.3; about ±0.2; about ±0.1; about ±0.05; or less. In another embodiment, the XRDP of the crystalline form further comprises peaks at about 17.557, 20.475, and 11.029 degrees two-theta with the margin of error of about ±0.5; about ±0.4; about ±0.3; about ±0.2; about ±0.1; about ±0.05; or less. In yet another embodiment, the crystalline form of (2S,3S)-2-amino-3-methyl-N-(2-morpholinoethyl)-pentanamide ditosylate exhibits an XRDP comprising peaks shown in the table below:

TABLE 6

XRDP Table of (2S,3S)-2-amino-3-methyl-N-(2-morpholinoethyl)-pentanamide ditosylate.

| Angle 2 Theta ° | d value Angstrom | Intensity Count | Intensity % |
|---|---|---|---|
| 6.021 | 14.66728 | 96.1 | 100 |
| 11.029 | 8.01566 | 23.2 | 24.2 |
| 12.76 | 6.9319 | 11.9 | 12.4 |
| 14.281 | 6.1967 | 10.4 | 10.9 |
| 15.738 | 5.62628 | 12.3 | 12.8 |
| 17.557 | 5.04708 | 32.3 | 33.6 |
| 18.078 | 4.90303 | 40.9 | 42.6 |
| 20.475 | 4.33393 | 34.2 | 35.6 |
| 24.332 | 3.65501 | 13.7 | 14.2 |
| 25.504 | 3.48965 | 13.8 | 14.4 |

Figure 30:
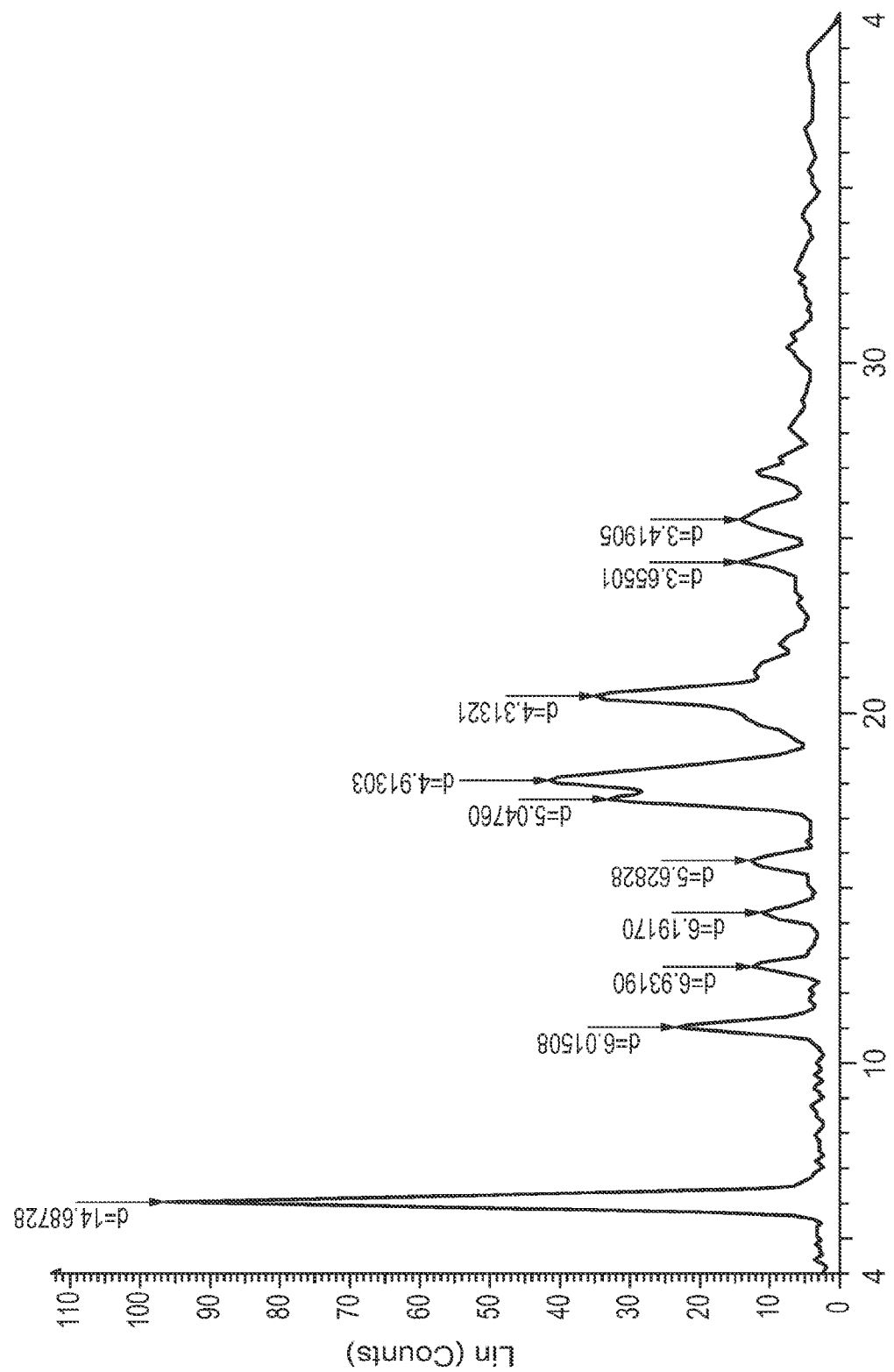
FIG. 30 is a graph of a x-ray powder diffraction (XRD) pattern of (2S,3S)-2-amino-3-methyl-N-(2-morpholinoethyl)-pentanamide ditosylate.

In one specific embodiment, the crystalline form of (2S,3S)-2-amino-3-methyl-N-(2-morpholinoethyl)-pentanamide ditosylate exhibits an XRDP that is substantially similar to FIG. 30.

In one embodiment, the crystalline form of (2S,3S)-2-amino-3-methyl-N-(2-morpholinoethyl)-pentanamide dinapsylate exhibits an XRDP comprising peaks at about 5.943, 15.872, and 18.515 degrees two-theta with the margin of error of about ±0.5; about ±0.4; about ±0.3; about ±0.2; about ±0.1; about ±0.05; or less. In another embodiment, the XRDP of the crystalline form further comprises peaks at about 22.046 degree two-theta with the margin of error of about ±0.5; about ±0.4; about ±0.3; about ±0.2; about ±0.1; about ±0.05; or less. In yet another embodiment, the crystalline form of (2S,3S)-2-amino-3-methyl-N-(2-morpholinoethyl)-pentanamide dinapsylate exhibits an XRDP comprising peaks shown in the table below:

TABLE 7

XRDP Table of (2S,3S)-2-amino-3-methyl-N-(2-morpholinoethyl)-pentanamide dinapsylate.

| Angle 2 Theta ° | d value Angstrom | Intensity Count | Intensity % |
|---|---|---|---|
| 5.943 | 14.85943 | 56.2 | 100 |
| 8.018 | 11.0176 | 5.25 | 9.3 |
| 11.005 | 8.03299 | 12.2 | 21.8 |
| 14.985 | 5.90739 | 8.89 | 15.8 |
| 15.872 | 5.57894 | 29.5 | 52.5 |
| 18.515 | 4.78809 | 28.9 | 51.5 |
| 19.454 | 4.5592 | 12.1 | 21.5 |
| 22.046 | 4.02857 | 18.8 | 33.5 |
| 24.35 | 3.65239 | 14 | 24.9 |

TABLE 7-continued

XRDP Table of (2S,3S)-2-amino-3-methyl-N-(2-morpholinoethyl)-pentanamide dinapsylate.

| Angle 2 Theta ° | d value Angstrom | Intensity Count | Intensity % |
|---|---|---|---|
| 27.8 | 3.20642 | 8.75 | 15.6 |
| 29.279 | 3.04776 | 9.91 | 17.6 |

Figure 35:
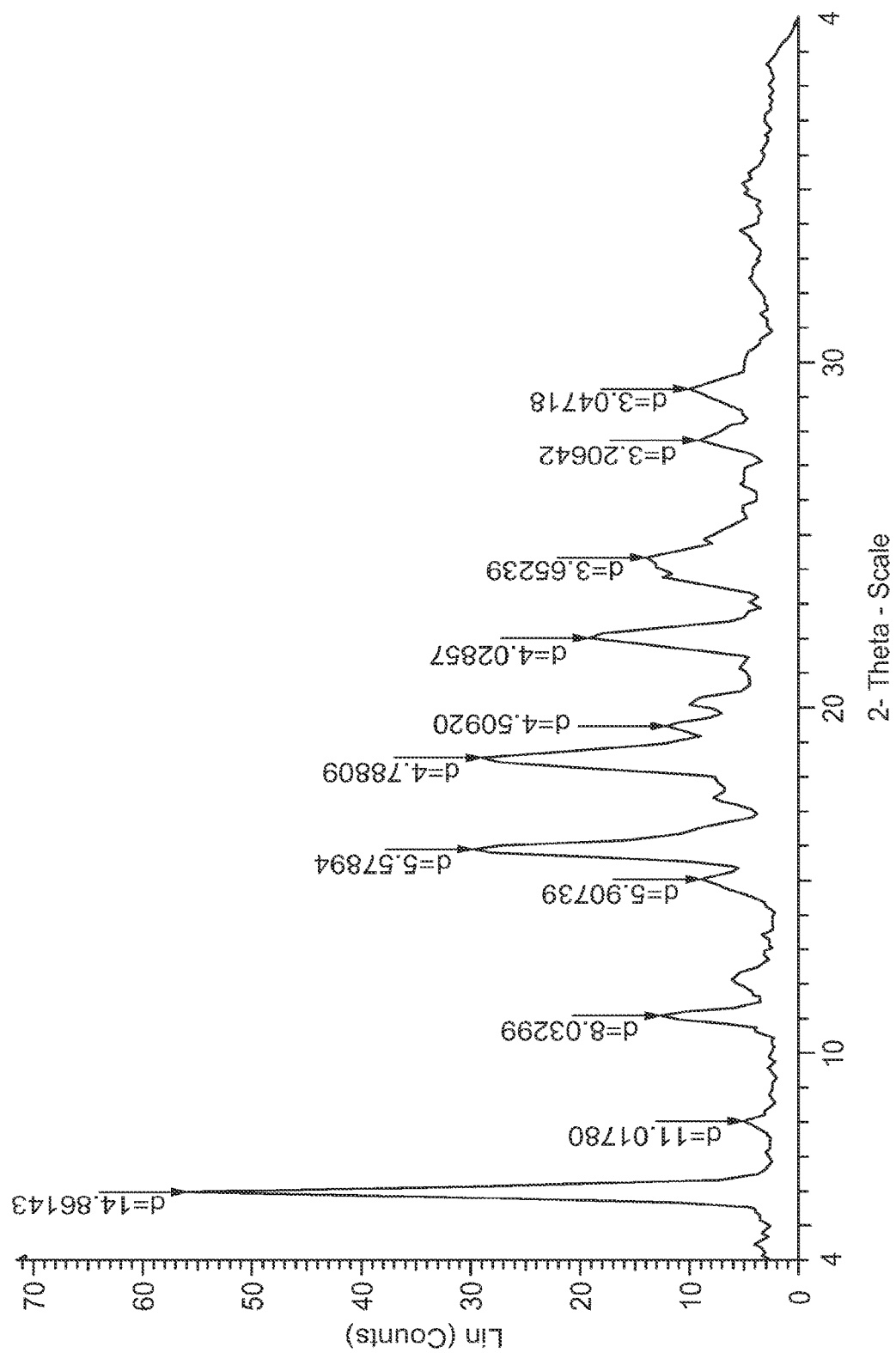
FIG. 35 is a graph of a x-ray powder diffraction (XRD) pattern of (2S,3S)-2-amino-3-methyl-N-(2-morpholinoethyl)-pentanamide dinapsylate.

In one specific embodiment, the crystalline form of (2S,3S)-2-amino-3-methyl-N-(2-morpholinoethyl)-pentanamide dinapsylate exhibits an XRDP that is substantially similar to FIG. 35.

In one embodiment, the crystalline form of (2S,3S)-2-amino-3-methyl-N-(2-morpholinoethyl)-pentanamide monoedisylate exhibits an XRDP comprising peaks at about 7.447 and 20.406 degrees two-theta with the margin of error of about ±0.5; about ±0.4; about ±0.3; about ±0.2; about ±0.1; about ±0.05; or less. In another embodiment, the XRDP of the crystalline form further comprises peaks at about 23.443 and 22.244 degrees two-theta with the margin of error of about ±0.5; about ±0.4; about ±0.3; about ±0.2; about ±0.1; about ±0.05; or less. In yet another embodiment, the crystalline form of (2S,3S)-2-amino-3-methyl-N-(2-morpholinoethyl)-pentanamide monoedisylate exhibits an XRDP comprising peaks shown in the table below:

TABLE 8

XRDP Table of (2S,3S)-2-amino-3-methyl-N-(2-morpholinoethyl)-pentanamide monoedisylate.

| Angle 2 Theta ° | d value Angstrom | Intensity Count | Intensity % |
|---|---|---|---|
| 7.447 | 11.86098 | 42.9 | 100 |
| 12.023 | 7.3552 | 7.88 | 18.4 |
| 13.971 | 6.33368 | 5.58 | 13 |
| 14.812 | 5.9759 | 14.7 | 34.3 |
| 15.933 | 5.55777 | 10.5 | 24.5 |
| 17.624 | 5.02816 | 10.3 | 24 |
| 19.273 | 4.60157 | 11 | 25.5 |
| 20.406 | 4.34846 | 40.5 | 94.5 |
| 22.244 | 3.99321 | 23.5 | 54.8 |
| 23.443 | 3.79165 | 28.8 | 67.2 |
| 24.161 | 3.68047 | 14.4 | 33.6 |
| 27.481 | 3.2429 | 8.72 | 20.3 |
| 29.684 | 3.0071 | 6.98 | 16.3 |

Figure 40:
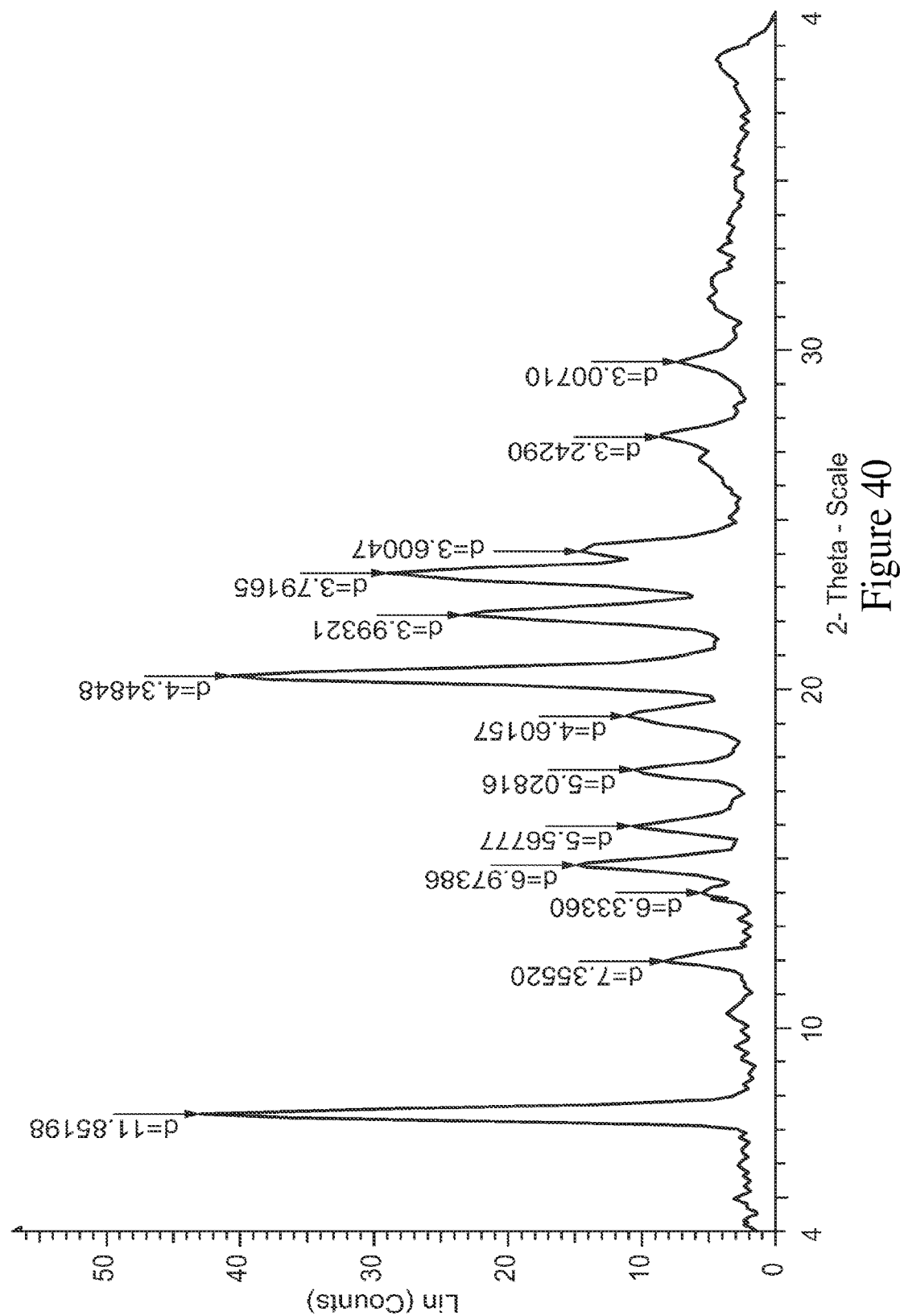
FIG. 40 is a graph of a x-ray powder diffraction (XRD) pattern of (2S,3S)-2-amino-3-methyl-N-(2-morpholinoethyl)-pentanamide monoedisylate.

In one specific embodiment, the crystalline form of (2S,3S)-2-amino-3-methyl-N-(2-morpholinoethyl)-pentanamide monoedisylate exhibits an XRDP that is substantially similar to FIG. 40.

In one embodiment, the crystalline form of (2S,3S)-2-amino-3-methyl-N-(2-morpholinoethyl)-pentanamide monooxalate exhibits an XRDP comprising peaks at about 7.260 and 19.671 degrees two-theta with the margin of error of about ±0.5; about ±0.4; about ±0.3; about ±0.2; about ±0.1; about ±0.05; or less. In another embodiment, the XRDP of the crystalline form further comprises peaks at about 18.917 and 16.024 degrees two-theta with the margin of error of about ±0.5; about ±0.4; about ±0.3; about ±0.2; about ±0.1; about ±0.05; or less. In yet another embodiment, the crystalline form of (2S,3S)-2-amino-3-methyl-N-(2-morpholinoethyl)-pentanamide monooxalate exhibits an XRDP comprising peaks shown in the table below:

TABLE 9

XRDP Table of (2S,3S)-2-amino-3-methyl-N-(2-morpholinoethyl)-pentanamide monooxalate.

| Angle 2 Theta ° | d value Angstrom | Intensity Count | Intensity % |
|---|---|---|---|
| 7.26 | 12.16562 | 33.4 | 100 |
| 10.872 | 8.13099 | 14.5 | 43.3 |
| 12.594 | 7.0227 | 8.34 | 24.9 |
| 13.844 | 6.39151 | 12.9 | 38.5 |
| 14.436 | 6.13074 | 10.5 | 31.3 |
| 16.024 | 5.52652 | 21.4 | 64.1 |
| 18.116 | 4.89273 | 15.3 | 45.6 |
| 18.917 | 4.6874 | 26.5 | 79.2 |
| 19.671 | 4.50923 | 30.3 | 90.6 |
| 20.782 | 4.27066 | 15.9 | 47.7 |
| 22.52 | 3.94483 | 16.7 | 50 |
| 25.221 | 3.52813 | 8.81 | 26.3 |

Figure 45:
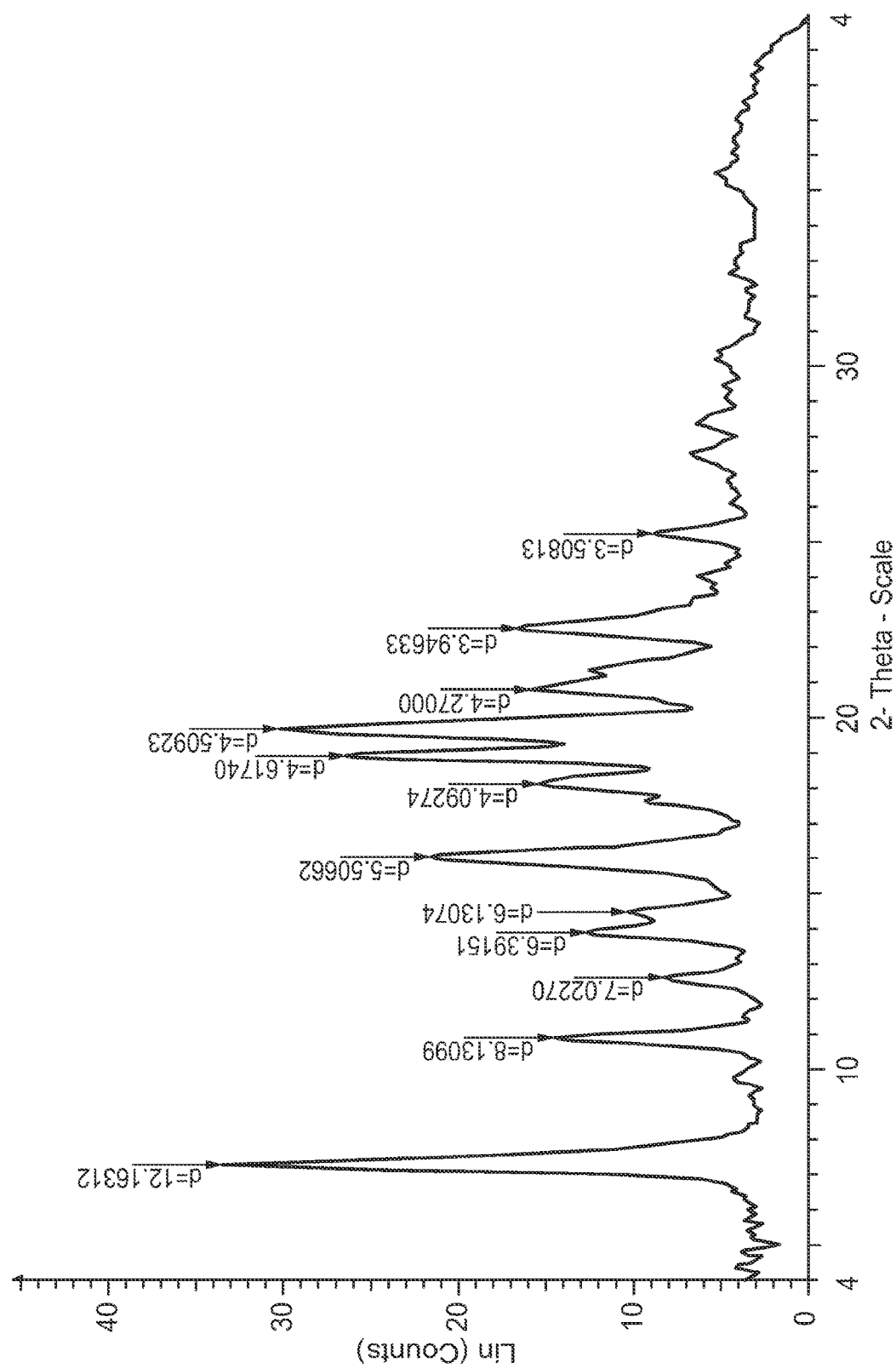
FIG. 45 is a graph of a x-ray powder diffraction (XRD) pattern of (2S,3S)-2-amino-3-methyl-N-(2-morpholinoethyl)-pentanamide monooxalate.

In one specific embodiment, the crystalline form of (2S,3S)-2-amino-3-methyl-N-(2-morpholinoethyl)-pentanamide monooxalate exhibits an XRDP that is substantially similar to FIG. 45.

In one embodiment, the crystalline forms are characterized by Raman spectroscopy. The Raman spectrum is typically represented by a diagram plotting the Raman intensity of the peaks versus the Raman shift of the peaks. The "peaks" of Raman spectroscopy are also known as "absorption bands". The intensities are often given in parenthesis with the following abbreviations: strong=st; medium=m; and weak=w. The characteristic peaks of a given Raman spectrum can be selected according to the peak locations and their relative intensity to conveniently distinguish this crystalline structure from others.

Those skilled in the art recognize that the measurements of the Raman peak shifts and/or intensity for a given crystalline form of the same compound will vary within a margin of error. The values of peak shift, expressed in reciprocal wave numbers ($cm^{-1}$), allow appropriate error margins. Typically, the error margins are represented by "±". For example, the Raman shift of about "1310±10" denotes a range from about 1310+10, i.e., about 1320, to about 1310−10, i.e., about 1300. Depending on the sample preparation techniques, the calibration techniques applied to the instruments, human operational variations, and etc, those skilled in the art recognize that the appropriate error of margins for a Raman shift can be ±12; ±10; ±8; ±5; ±3; ±1; or less.

Additional details of the methods and equipment used for the Raman spectroscopy analysis are described in the Examples section.

Figure 12A:
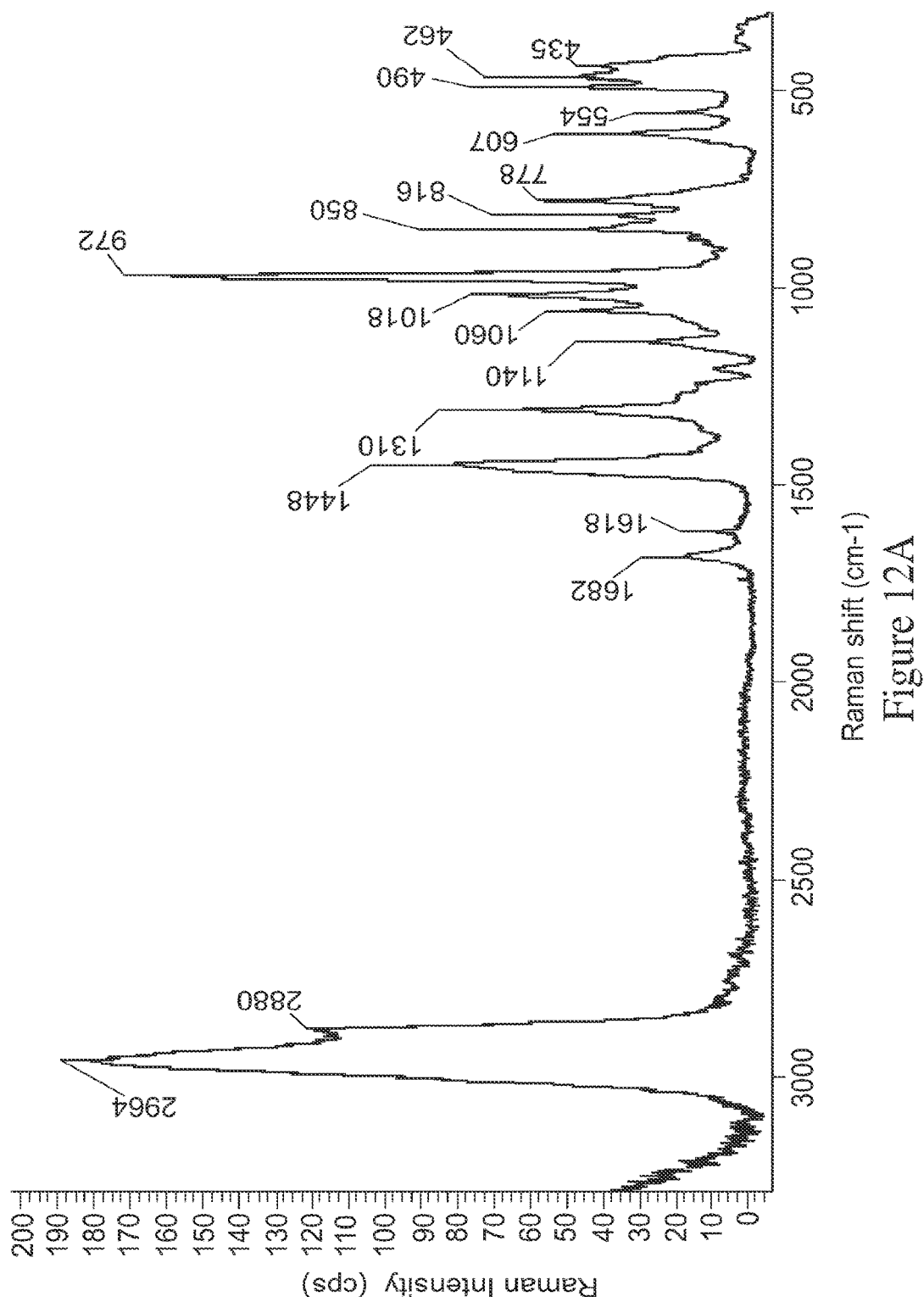
FIGS. 12A and 12B are Raman spectrum of (2S,3S)-2-amino-3-methyl-N-(2-morpholinoethyl)-pentanamide monosulfate.
Figure 12B:
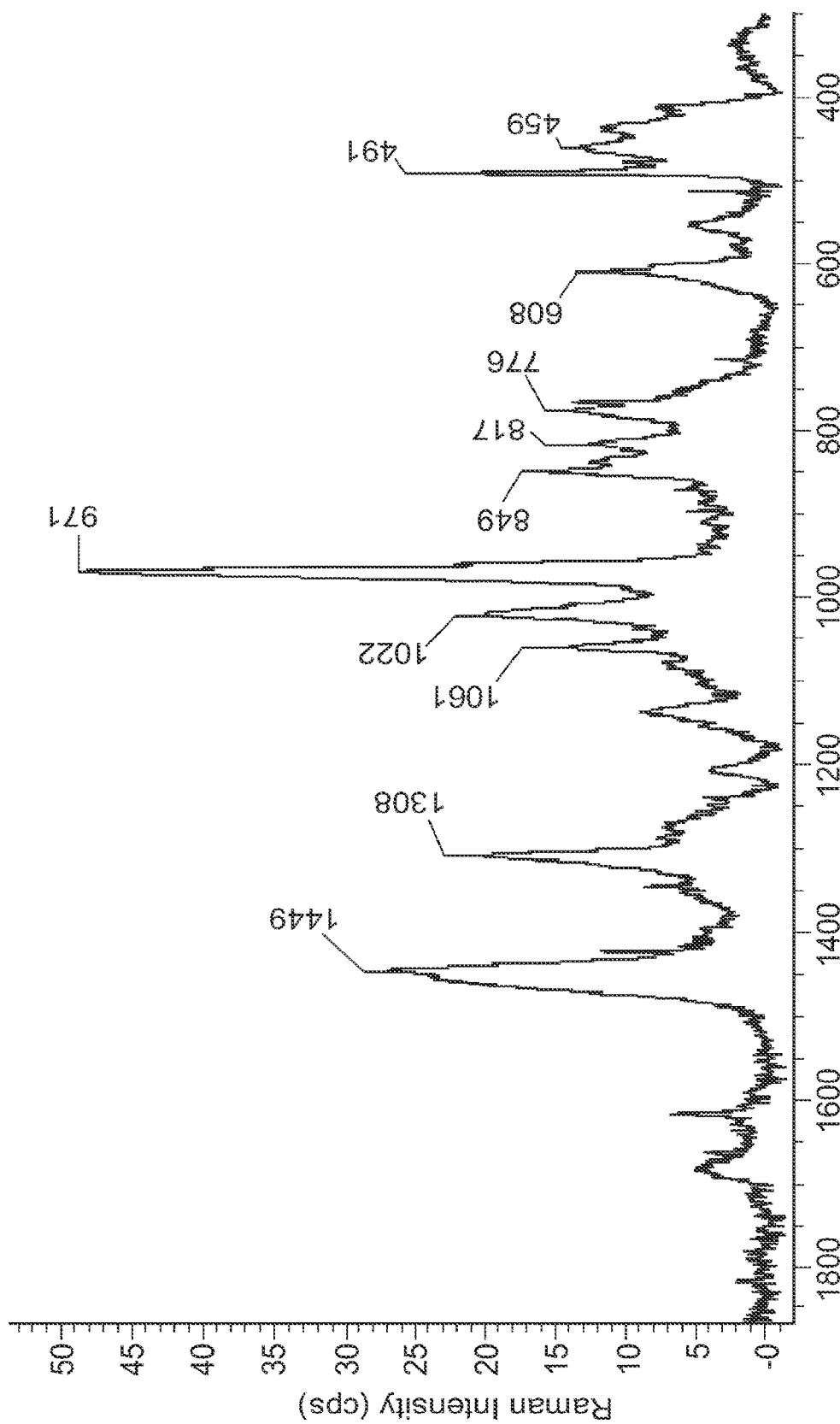

In one embodiment, the crystalline form of (2S,3S)-2-amino-3-methyl-N-(2-morpholinoethyl)-pentanamide exhibits an Raman spectrum comprising peaks at about 2964 (s); about 2873 (s); and about 1451 (s) $cm^{-1}$ with the error of margin of about ±12; about ±10; about ±8; about ±5; about ±3; about ±1; or less. In another embodiment, the Raman spectrum further comprises peaks at about 1310 (m) and about 805 (m) $cm^{-1}$ with the error of margin of about ±12; about ±10; about ±8; about ±5; about ±3; about ±1; or less. In one specific embodiment, the crystalline form of (2S,3S)-2-amino-3-methyl-N-(2-morpholinoethyl)-pentanamide exhibits a Raman spectrum that is substantially similar to FIGS. 8A and 8B. In one embodiment, the crystalline form of (2S,3S)-2-amino-3-methyl-N-(2-morpholinoethyl)-pentanamide monosulfate exhibits an Raman spectrum comprising peaks at about 2964 (s); about 2880 (s); and about 972 (s) $cm^{-1}$ with the error of margin of about ±12; about ±10; about ±8; about ±5; about ±3; about ±1; or less. In another embodiment, the Raman spectrum further comprises peaks at about 1448 (m) and about 1310 (m) cm$^{-1}$ with the error of margin of about ±12; about ±10; about ±8; about ±5; about ±3; about ±1; or less. In one specific embodiment, the crystalline form of (2S,3S)-2-amino-3-methyl-N-(2-morpholinoethyl)-pentanamide monosulfate exhibits a Raman spectrum that is substantially similar to FIGS. 12A and 12B.

Figure 18A:
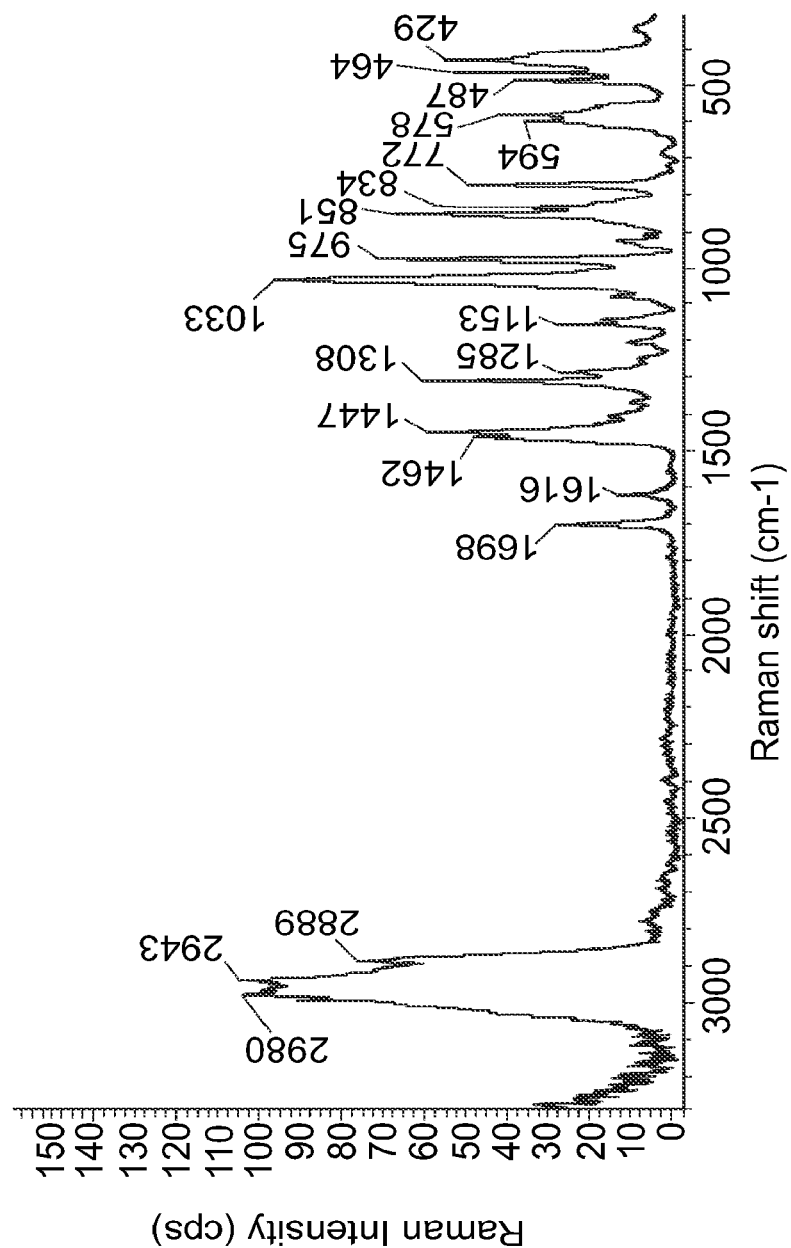
FIGS. 18A and 18B are Raman spectrum of (2S,3S)-2-amino-3-methyl-N-(2-morpholinoethyl)-pentanamide tetra (monohydrogensulfate), monosulfate.
Figure 18B:
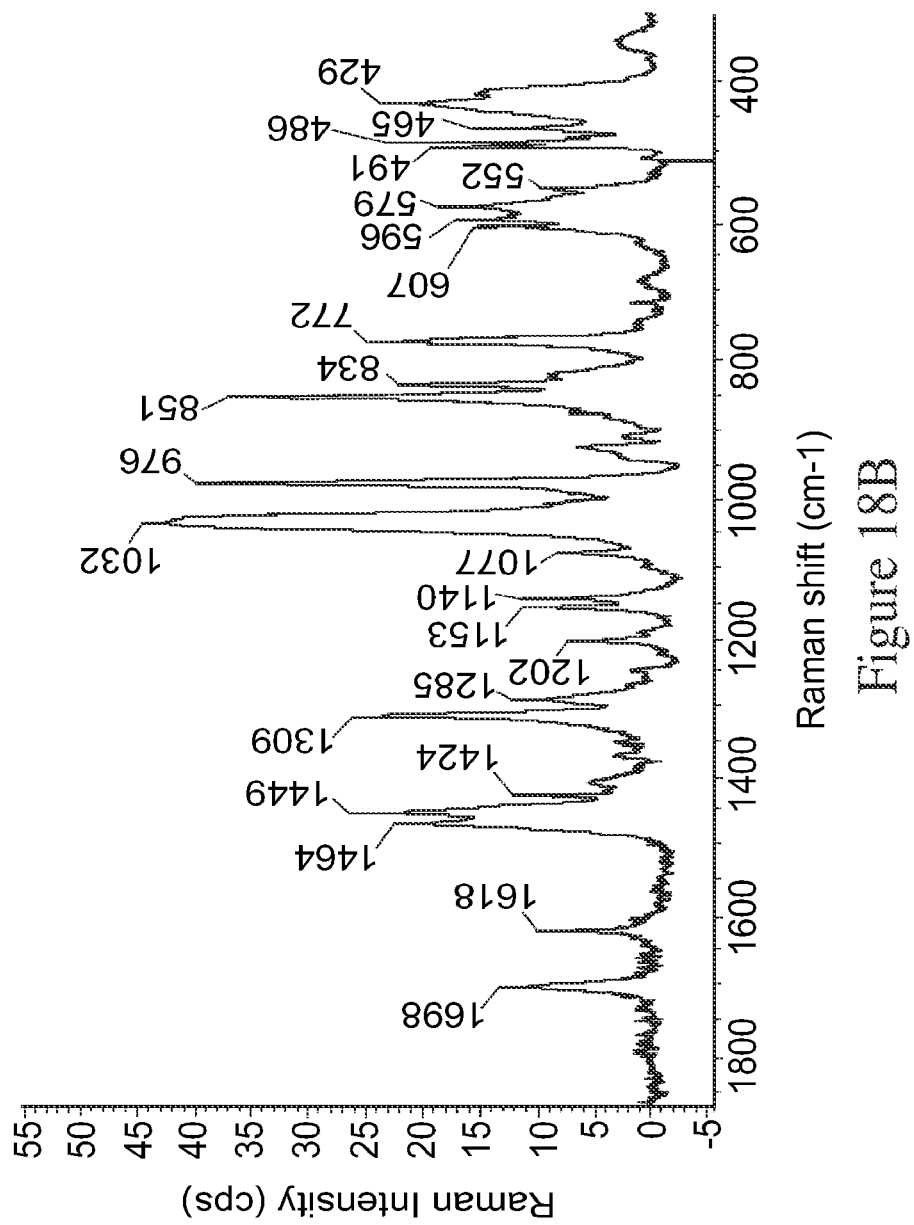

In one embodiment, the crystalline form of (2S,3S)-2-amino-3-methyl-N-(2-morpholinoethyl)-pentanamide tetra(monohydrogensulfate), monosulfate exhibits an Raman spectrum comprising peaks at about 2980 (s); about 2943 (s); about 2889 (s); and about 1033 (s) cm$^{-1}$ with the error of margin of about ±12; about ±10; about ±8; about ±5; about ±3; about ±1; or less. In another embodiment, the Raman spectrum further comprises peaks at about 975 (m) and about 851 (m) cm$^{-1}$ with the error of margin of about ±12; about ±10; about ±8; about ±5; about ±3; about ±1; or less. In one specific embodiment, the crystalline form of (2S,3S)-2-amino-3-methyl-N-(2-morpholinoethyl)-pentanamide tetra(monohydrogensulfate), monosulfate exhibits a Raman spectrum that is substantially similar to FIGS. 18A and 18B.

In one embodiment, the crystalline form of (2S,3S)-2-amino-3-methyl-N-(2-morpholinoethyl)-pentanamide digluconate exhibits an Raman spectrum comprising peaks at about 2957 (s); about 2928 (s); and about 910 (s) cm$^{-1}$ with the error of margin of about ±12; about ±10; about ±8; about ±5; about ±3; about ±1; or less. In another embodiment, the Raman spectrum further comprises peaks at about 1450 (m); about 1139 (m); and about 883 (m) cm$^{-1}$ with the error of margin of about ±12; about ±10; about ±8; about ±5; about ±3; about ±1; or less. In one specific embodiment, the crystalline form of (2S,3S)-2-amino-3-methyl-N-(2-morpholinoethyl)-pentanamide digluconate exhibits a Raman spectrum that is substantially similar to FIGS. 24A and 24B. In one embodiment, the crystalline form of (2S,3S)-2-amino-3-methyl-N-(2-morpholinoethyl)-pentanamide dimesylate exhibits an Raman spectrum comprising peaks at about 2935 (s); about 1040 (s); and about 778 (s) cm$^{-1}$ with the error of margin of about ±12; about ±10; about ±8; about ±5; about ±3; about ±1; or less. In another embodiment, the Raman spectrum further comprises peaks at about 1444 (m) and about 557 (m) cm$^{-1}$ with the error of margin of about ±12; about ±10; about ±8; about ±5; about ±3; about ±1; or less. In one specific embodiment, the crystalline form of (2S,3S)-2-amino-3-methyl-N-(2-morpholinoethyl)-pentanamide dimesylate exhibits a Raman spectrum that is substantially similar to FIG. 29.

In one embodiment, the crystalline form of (2S,3S)-2-amino-3-methyl-N-(2-morpholinoethyl)-pentanamide ditosylate exhibits an Raman spectrum comprising peaks at about 2980 (s); about 1123 (s); and about 800 (s) cm$^{-1}$ with the error of margin of about ±12; about ±10; about ±8; about ±5; about ±3; about ±1; or less. In another embodiment, the Raman spectrum further comprises peaks at about 2922 (m), about 1599 (m), and about 637 (m) cm$^{-1}$ with the error of margin of about ±12; about ±10; about ±8; about ±5; about ±3; about ±1; or less. In one specific embodiment, the crystalline form of (2S,3S)-2-amino-3-methyl-N-(2-morpholinoethyl)-pentanamide ditosylate exhibits a Raman spectrum that is substantially similar to FIG. 34. In one embodiment, the crystalline form of (2S,3S)-2-amino-3-methyl-N-(2-morpholinoethyl)-pentanamide dinapsylate exhibits an Raman spectrum comprising peaks at about 3053 (w); about 1380 (s); and about 766 (s) cm$^{-1}$ with the error of margin of about ±12; about ±10; about ±8; about ±5; about ±3; about ±1; or less. In another embodiment, the Raman spectrum further comprises peaks at about 2974 (w) and about 514 (m) cm$^{-1}$ with the error of margin of about ±12; about ±10; about ±8; about ±5; about ±3; about ±1; or less. In one specific embodiment, the crystalline form of (2S,3S)-2-amino-3-methyl-N-(2-morpholinoethyl)-pentanamide dinapsylate exhibits a Raman spectrum that is substantially similar to FIG. 39.

In one embodiment, the crystalline form of (2S,3S)-2-amino-3-methyl-N-(2-morpholinoethyl)-pentanamide monoedisylate exhibits an Raman spectrum comprising peaks at about 2954 (s); about 1058 (s); and about 825 (s) cm$^{-1}$ with the error of margin of about ±12; about ±10; about ±8; about ±5; about ±3; about ±1; or less. In another embodiment, the Raman spectrum further comprises peaks at about 3003 (s) and about 521 (s) cm$^{-1}$ with the error of margin of about ±12; about ±10; about ±8; about ±5; about ±3; about ±1; or less. In one specific embodiment, the crystalline form of (2S,3S)-2-amino-3-methyl-N-(2-morpholinoethyl)-pentanamide monoedisylate exhibits a Raman spectrum that is substantially similar to FIG. 44. In one embodiment, the crystalline form of (2S,3S)-2-amino-3-methyl-N-(2-morpholinoethyl)-pentanamide monooxalate exhibits an Raman spectrum comprising peaks at about 2897 (s); about 1692 (s); and about 491 (m) cm$^{-1}$ with the error of margin of about ±12; about ±10; about ±8; about ±5; about ±3; about ±1; or less. In another embodiment, the Raman spectrum further comprises peaks at about 2955 (s), about 1443 (s), and about 1252 (s) cm$^{-1}$ with the error of margin of about ±12; about ±10; about ±8; about ±5; about ±3; about ±1; or less. In one specific embodiment, the crystalline form of (2S,3S)-2-amino-3-methyl-N-(2-morpholinoethyl)-pentanamide monooxalate exhibits a Raman spectrum that is substantially similar to FIG. 49. In one embodiment, the crystalline forms are characterized by Differential Scanning calorimetry (DSC). The DSC thermogram is typically expressed by a diagram plotting the normalized heat flow in units of Watts/gram ("W/g") versus the measured sample temperature in degree C. The DSC thermogram is usually evaluated for extrapolated onset and end (outset) temperatures, peak temperature, and heat of fusion. The single maximum value of a DSV thermogram is often used as the characteristic peak to distinguish this crystalline structure from others.

Those skilled in the art recognize that the measurements of the DSC thermogram for a given crystalline form of the same compound will vary within a margin of error. The values of a single maximum value, expressed in degree C., allow appropriate error margins. Typically, the error margins are represented by "±". For example, the single maximum value of about "53.09±2.0" denotes a range from about 53.09+2, i.e., about 55.09, to about 53.09−2, i.e., about 51.09. Depending on the sample preparation techniques, the calibration techniques applied to the instruments, human operational variations, and etc, those skilled in the art recognize that the appropriate error of margins for a single maximum value can be ±2.5; ±2; ±1.5; ±1; ±0.5; or less.

Additional details of the methods and equipment used for the DSC thermogram analysis are described in the Examples section.

Figure 6:
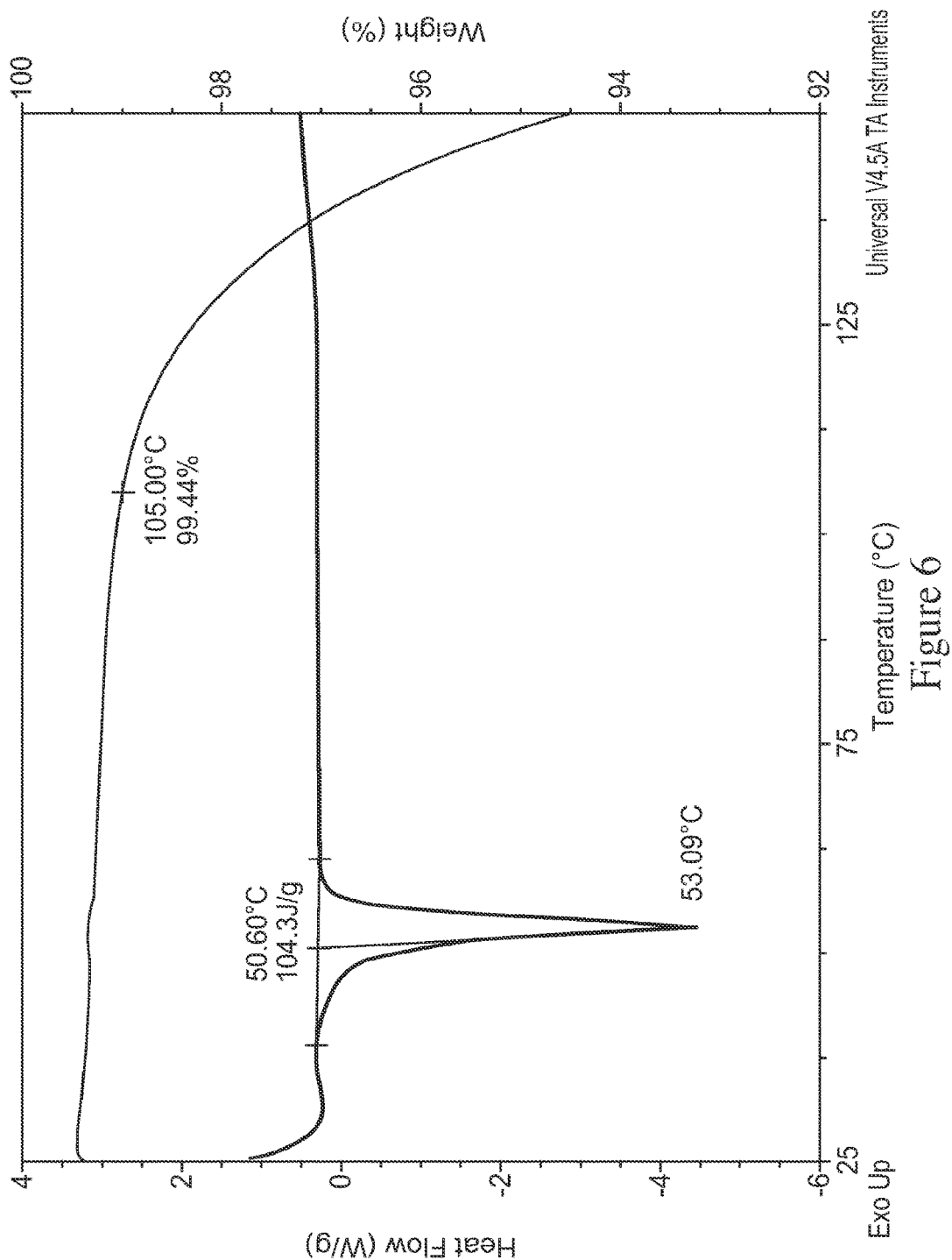
FIG. 6 is an overlay of DSC and TGA thermograms of (2S,3S)-2-amino-3-methyl-N-(2-morpholinoethyl)-pentanamide (free base).

In one embodiment, the crystalline form of (2S,3S)-2-amino-3-methyl-N-(2-morpholinoethyl)-pentanamide exhibits a DSC thermogram comprising a single maximum value at about 53.09±2.0° C. with the error of margin of about ±2.5; about ±2; about ±1.5; about ±1; about ±0.5; or less. In one specific embodiment, the crystalline form of (2S,3S)-2-amino-3-methyl-N-(2-morpholinoethyl)-pentanamide exhibits a DSC thermogram that is substantially similar to FIG. 6. In one embodiment, the crystalline form of (2S,3S)-2-amino-3-methyl-N-(2-morpholinoethyl)-pentanamide monosulfate exhibits a DSC thermogram comprising a single maximum value at about 176.49±2.0° C. with the error of margin of about ±2.5; about ±2; about ±1.5; about ±1; about ±0.5; or less. In one specific embodiment, the crystalline form of (2S,3S)-2-amino-3-methyl-N-(2-morpholinoethyl)-pentanamide monosulfate exhibits a DSC thermogram that is substantially similar to FIG. 11.

Figure 14:
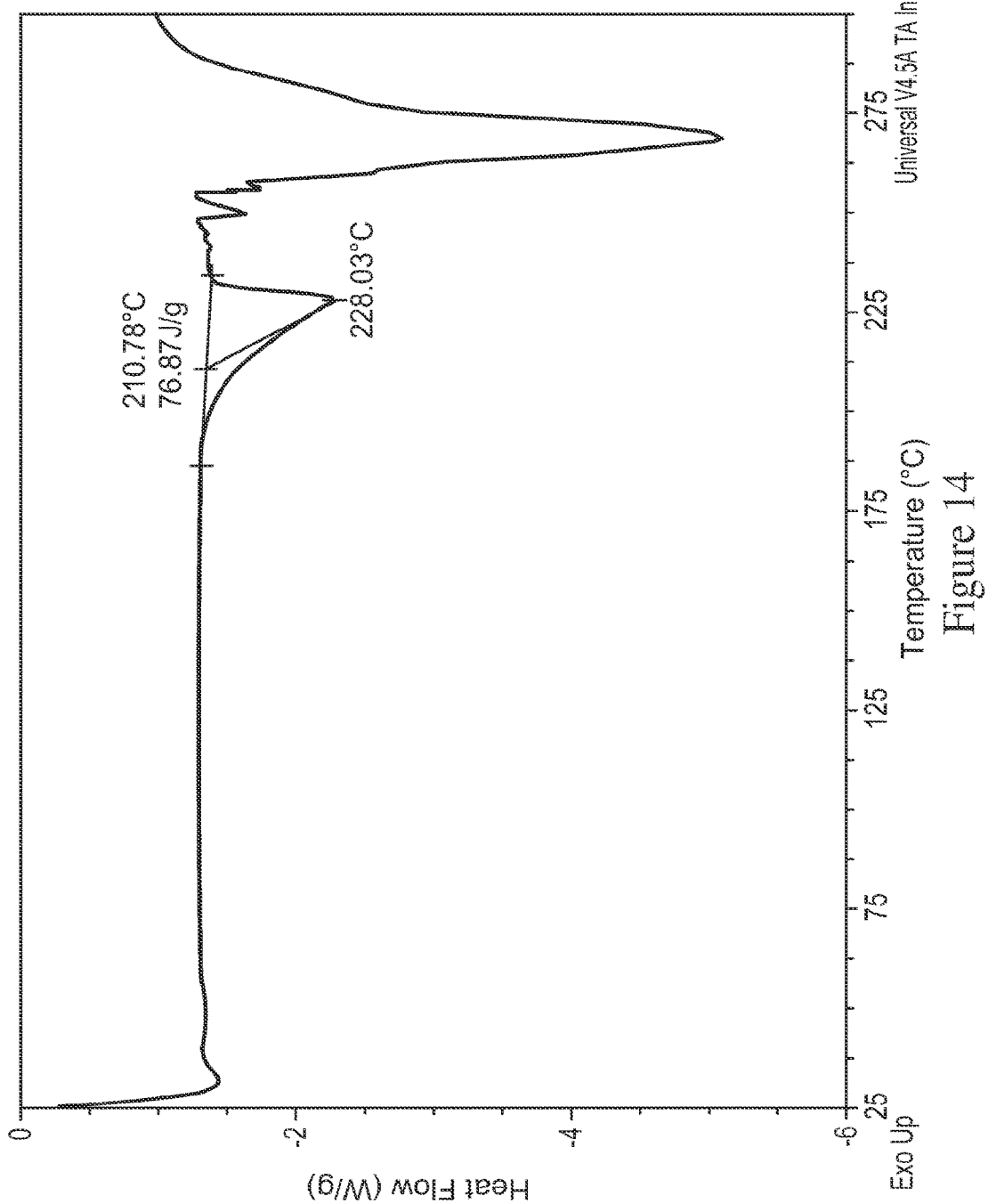
FIG. 14 is a DSC thermogram of (2S,3S)-2-amino-3-methyl-N-(2-morpholinoethyl)-pentanamide tetra(monohydrogensulfate), monosulfate.
Figure 56:
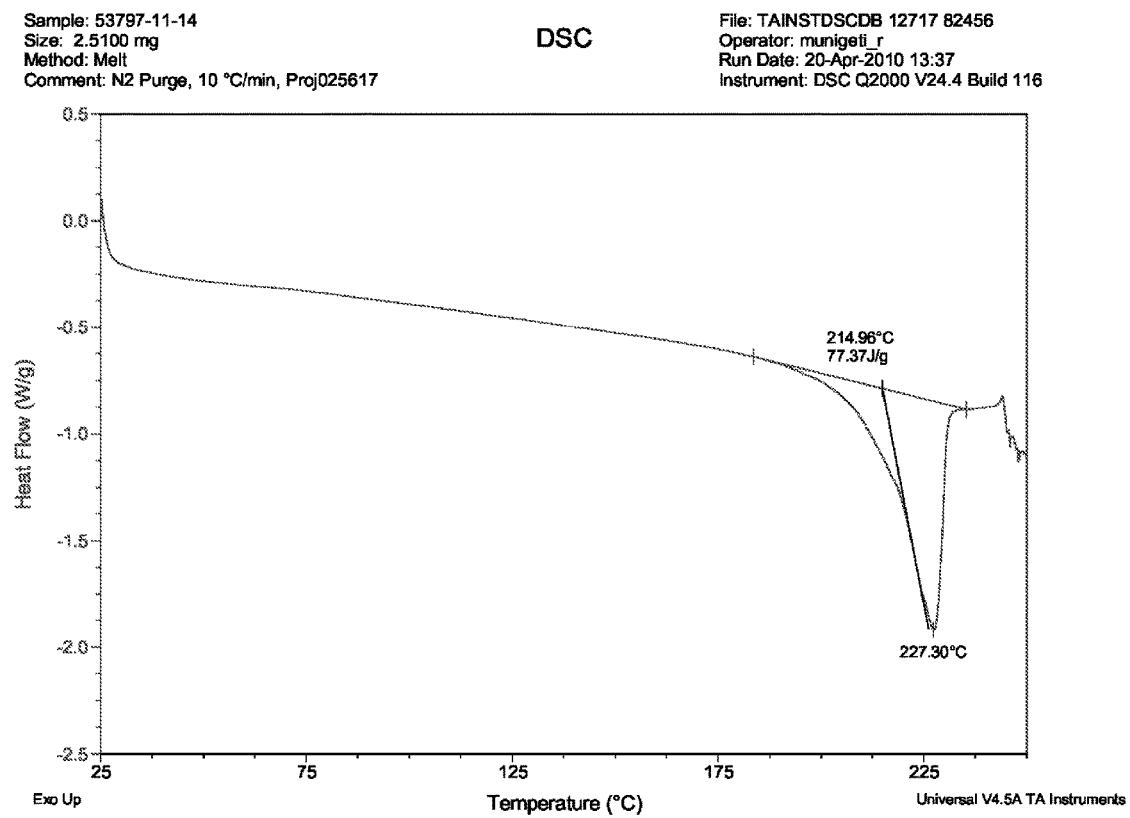
FIG. 56 is a DSC thermogram of (2S,3S)-2-amino-3-methyl-N-(2-morpholinoethyl)-pentanamide tetra(monohydrogensulfate), monosulfate from the large scale preparation in Example 12.
Figure 57:
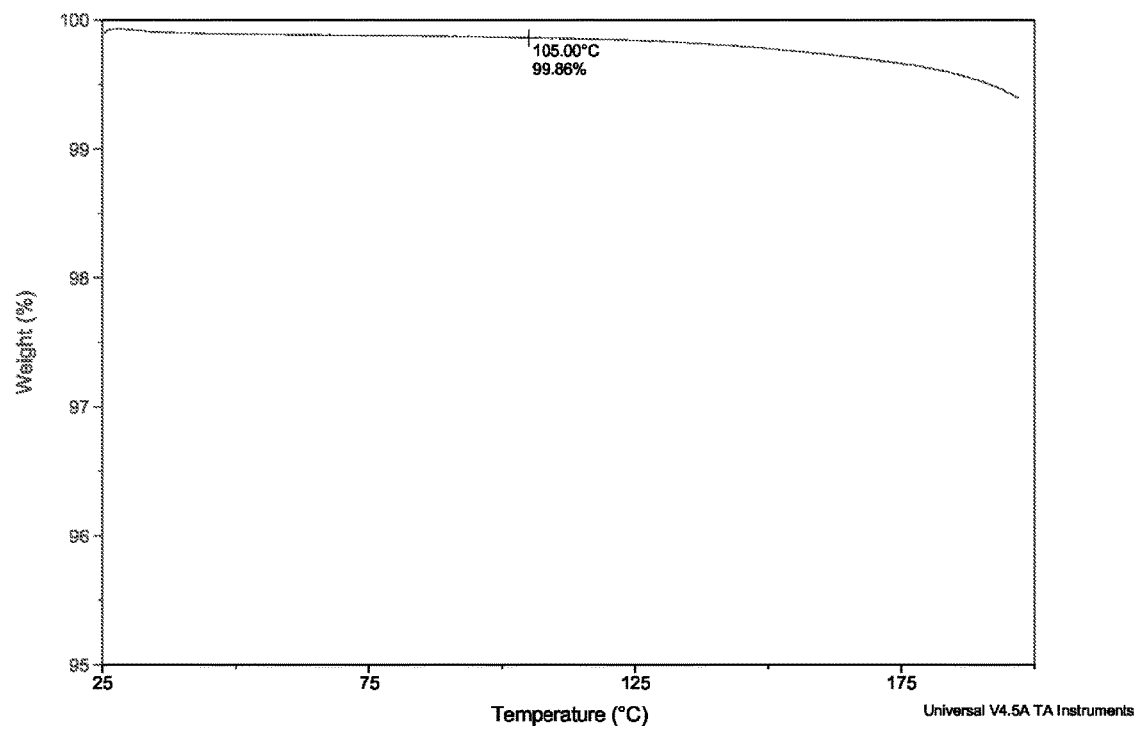
FIG. 57 is a TGA thermogram of (2S,3S)-2-amino-3-methyl-N-(2-morpholinoethyl)-pentanamide tetra(monohydrogensulfate), monosulfate from the large scale preparation in Example 12.
Figure 58A:
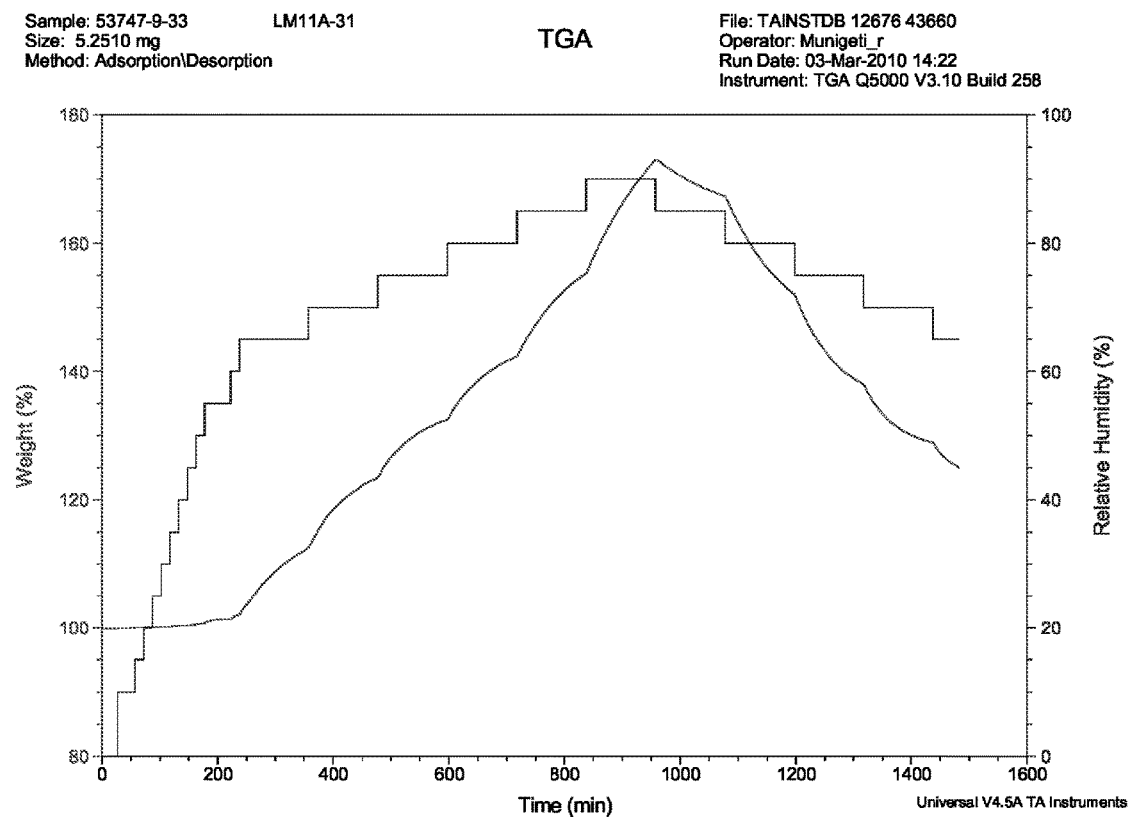
FIGS. 58A and 58B are DVS plots of (2S,3S)-2-amino-3-methyl-N-(2-morpholinoethyl)-pentanamide tetra(monohydrogensulfate), monosulfate from the large scale preparation in Example 12.
Figure 58B:
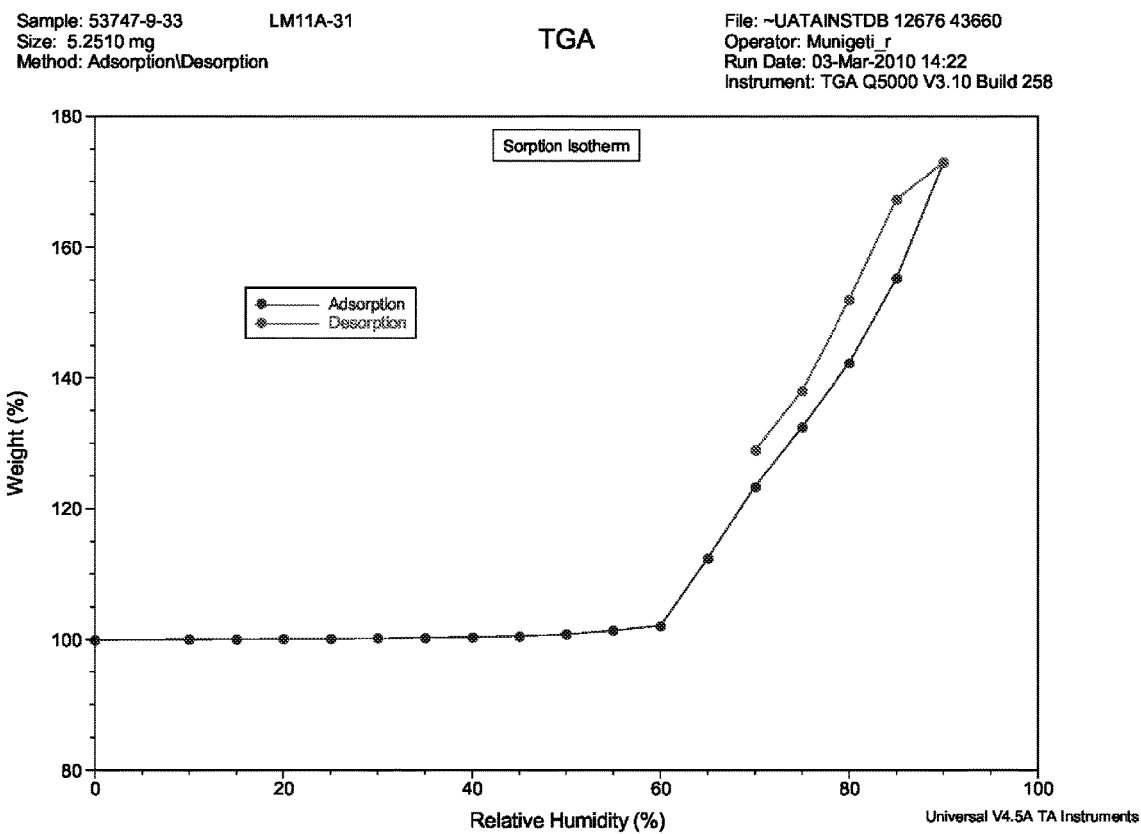
Figure 59:
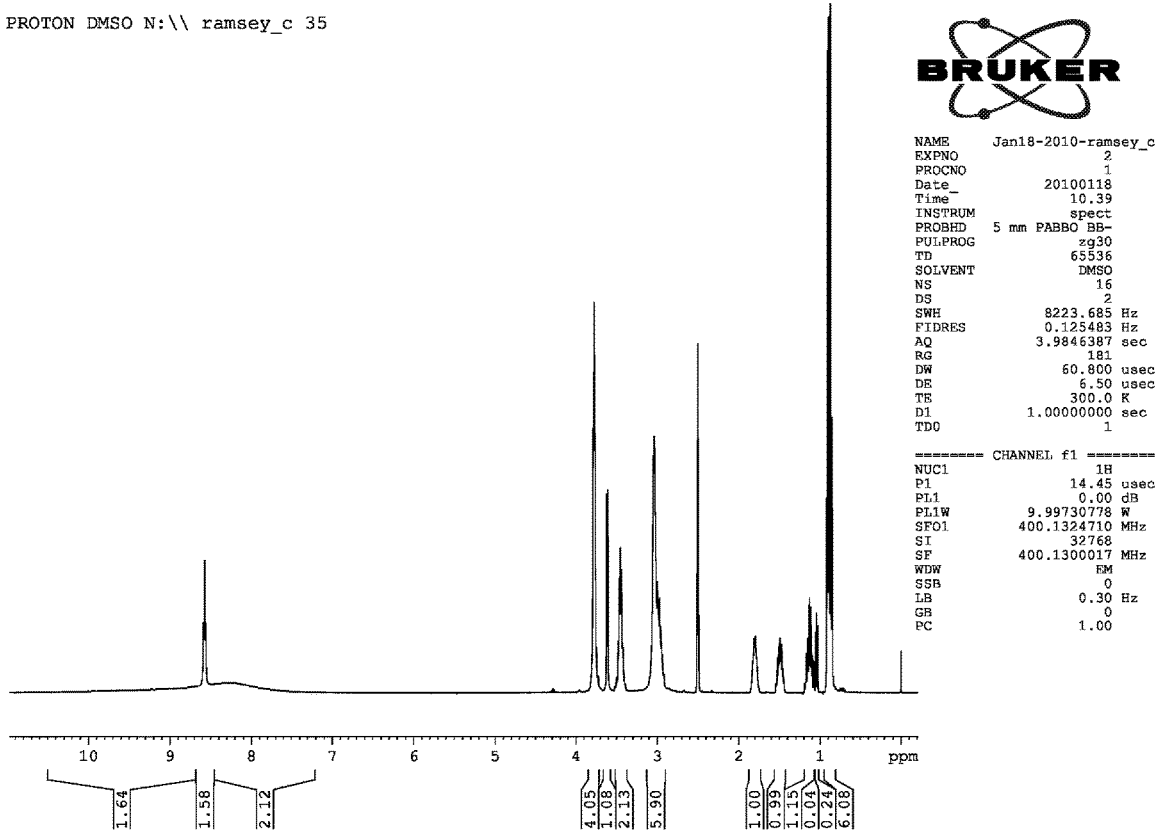
FIG. 59 is a H-NMR spectrum of (2S,3S)-2-amino-3-methyl-N-(2-morpholinoethyl)-pentanamide tetra(monohydrogensulfate), monosulfate from the large scale preparation in Example 12.

In one embodiment, the crystalline form of (2S,3S)-2-amino-3-methyl-N-(2-morpholinoethyl)-pentanamide tetra(monohydrogensulfate), monosulfate exhibits a DSC thermogram comprising a single maximum value at about 228.03±2.0° C. with the error of margin of about ±4; about ±3; about ±2.5; about ±2; about ±1.5; about ±1; about ±0.5; or less. In one specific embodiment, the crystalline form of (2S,3S)-2-amino-3-methyl-N-(2-morpholinoethyl)-pentanamide tetra(monohydrogensulfate), monosulfate exhibits a DSC thermogram that is substantially similar to FIG. 14 or FIG. 56.

Figure 20:
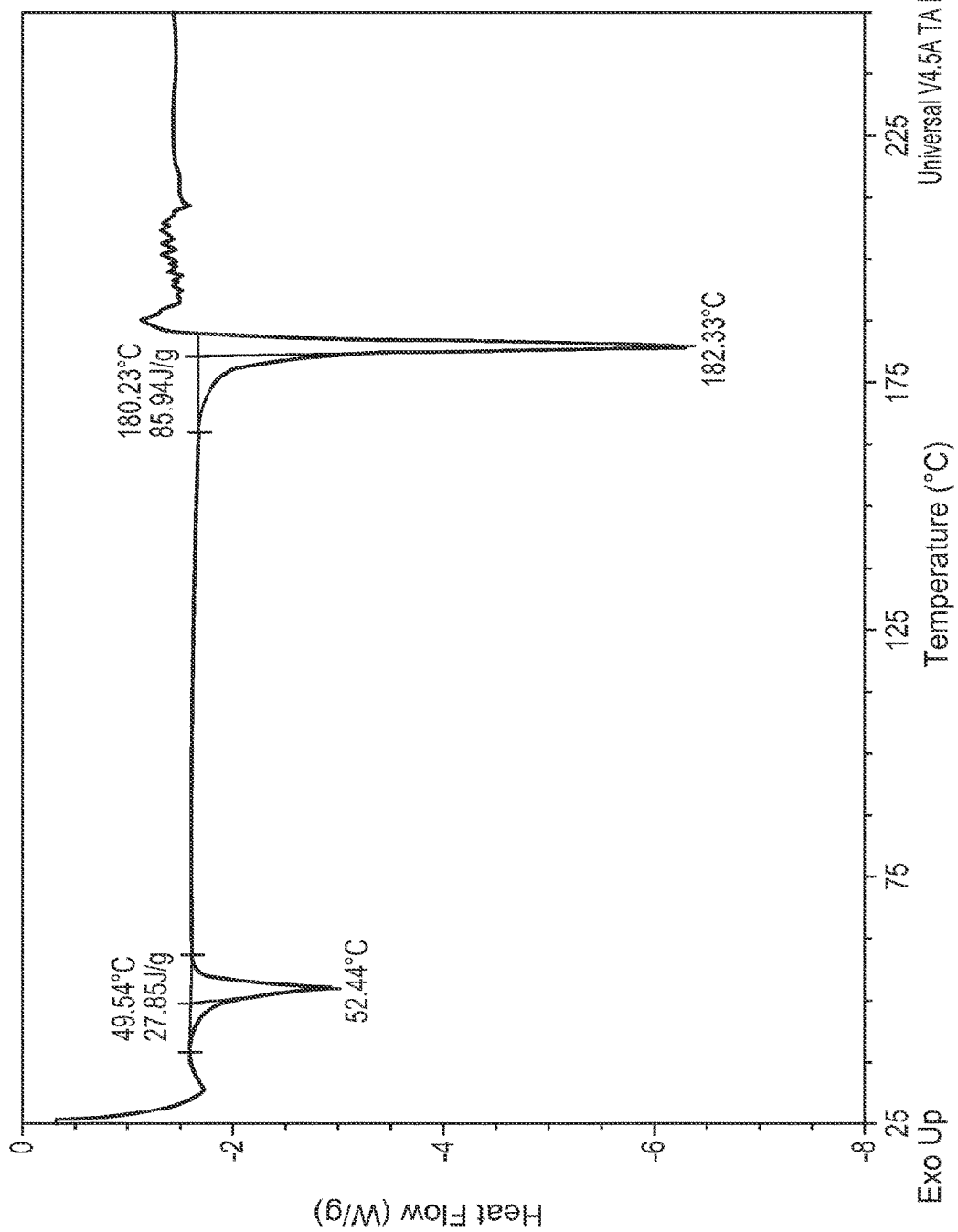
FIG. 20 is a DSC thermogram of (2S,3S)-2-amino-3-methyl-N-(2-morpholinoethyl)-pentanamide digluconate.
Figure 26A:
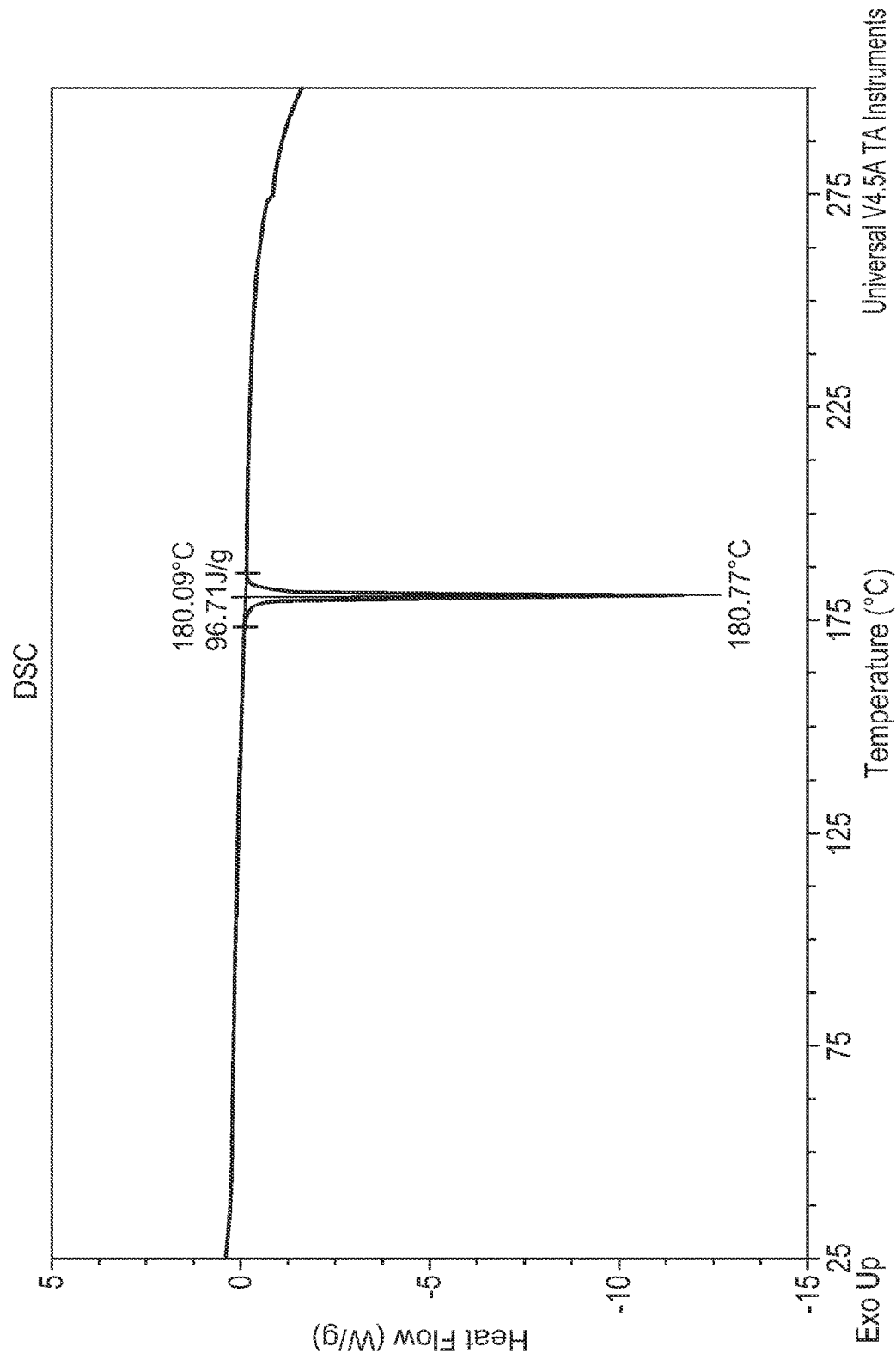
FIG. 26A is a DSC thermogram of (2S,3S)-2-amino-3-methyl-N-(2-morpholinoethyl)-pentanamide dimesylate.

In one embodiment, the crystalline form of (2S,3S)-2-amino-3-methyl-N-(2-morpholinoethyl)-pentanamide digluconate exhibits a DSC thermogram comprising a single maximum value at about 182.33±2.0° C. with the error of margin of about ±2.5; about ±2; about ±1.5; about ±1; about ±0.5; or less. In one specific embodiment, the crystalline form of (2S,3S)-2-amino-3-methyl-N-(2-morpholinoethyl)-pentanamide digluconate exhibits a DSC thermogram that is substantially similar to FIG. 20. In one embodiment, the crystalline form of (2S,3S)-2-amino-3-methyl-N-(2-morpholinoethyl)-pentanamide dimesylate exhibits a DSC thermogram comprising a single maximum value at about 180.77±2.0° C. with the error of margin of about ±2.5; about ±2; about ±1.5; about ±1; about ±0.5; or less. In one specific embodiment, the crystalline form of (2S,3S)-2-amino-3-methyl-N-(2-morpholinoethyl)-pentanamide dimesylate exhibits a DSC thermogram that is substantially similar to FIG. 26A.

Figure 31A:
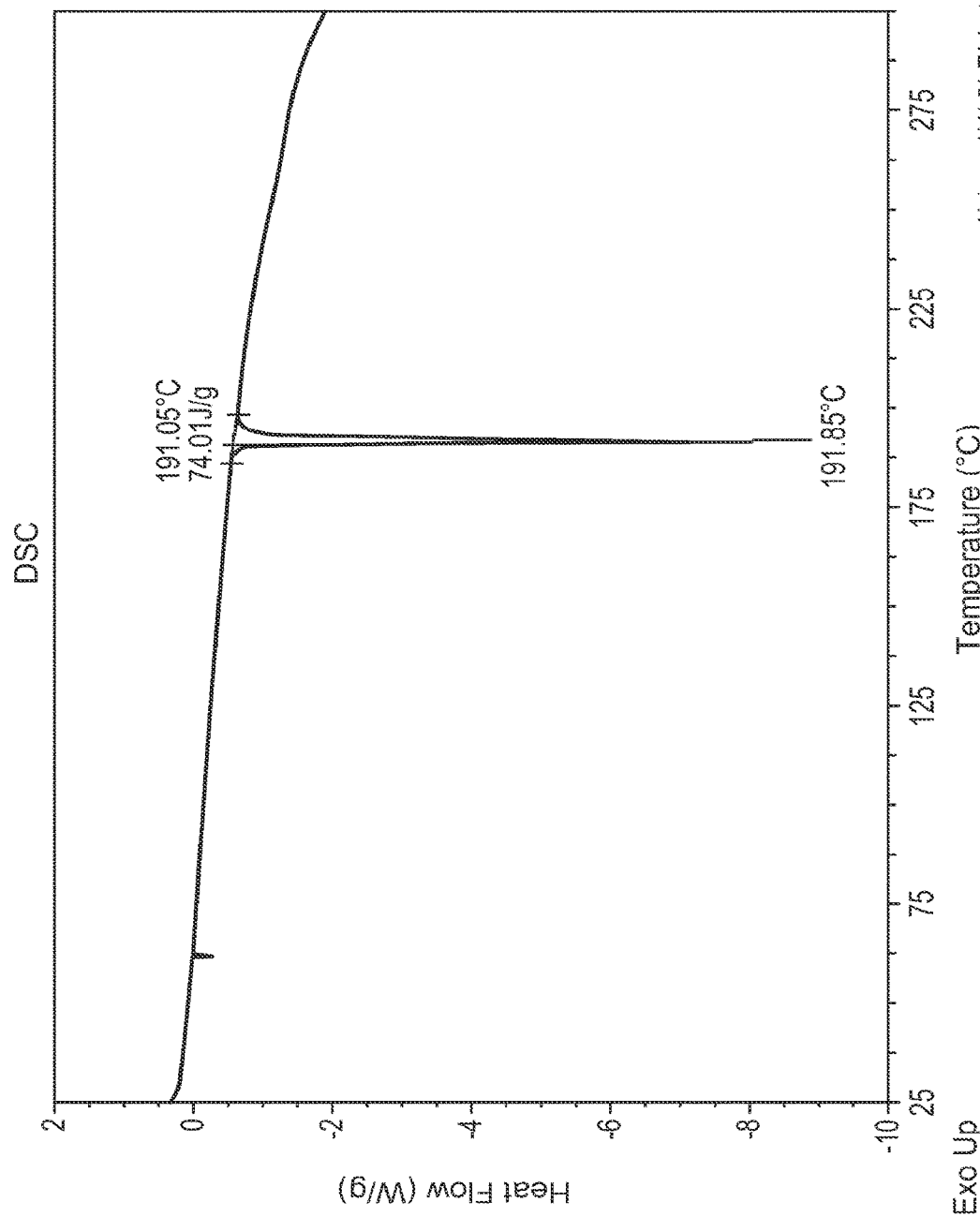
FIG. 31A is a DSC thermogram of (2S,3S)-2-amino-3-methyl-N-(2-morpholinoethyl)-pentanamide ditosylate.

In one embodiment, the crystalline form of (2S,3S)-2-amino-3-methyl-N-(2-morpholinoethyl)-pentanamide ditosylate exhibits a DSC thermogram comprising a single maximum value at about 191.85±2.0° C. with the error of margin of about ±2.5; about ±2; about ±1.5; about ±1; about ±0.5; or less. In one specific embodiment, the crystalline form of (2S,3S)-2-amino-3-methyl-N-(2-morpholinoethyl)-pentanamide ditosylate exhibits a DSC thermogram that is substantially similar to FIG. 31A.

Figure 36A:
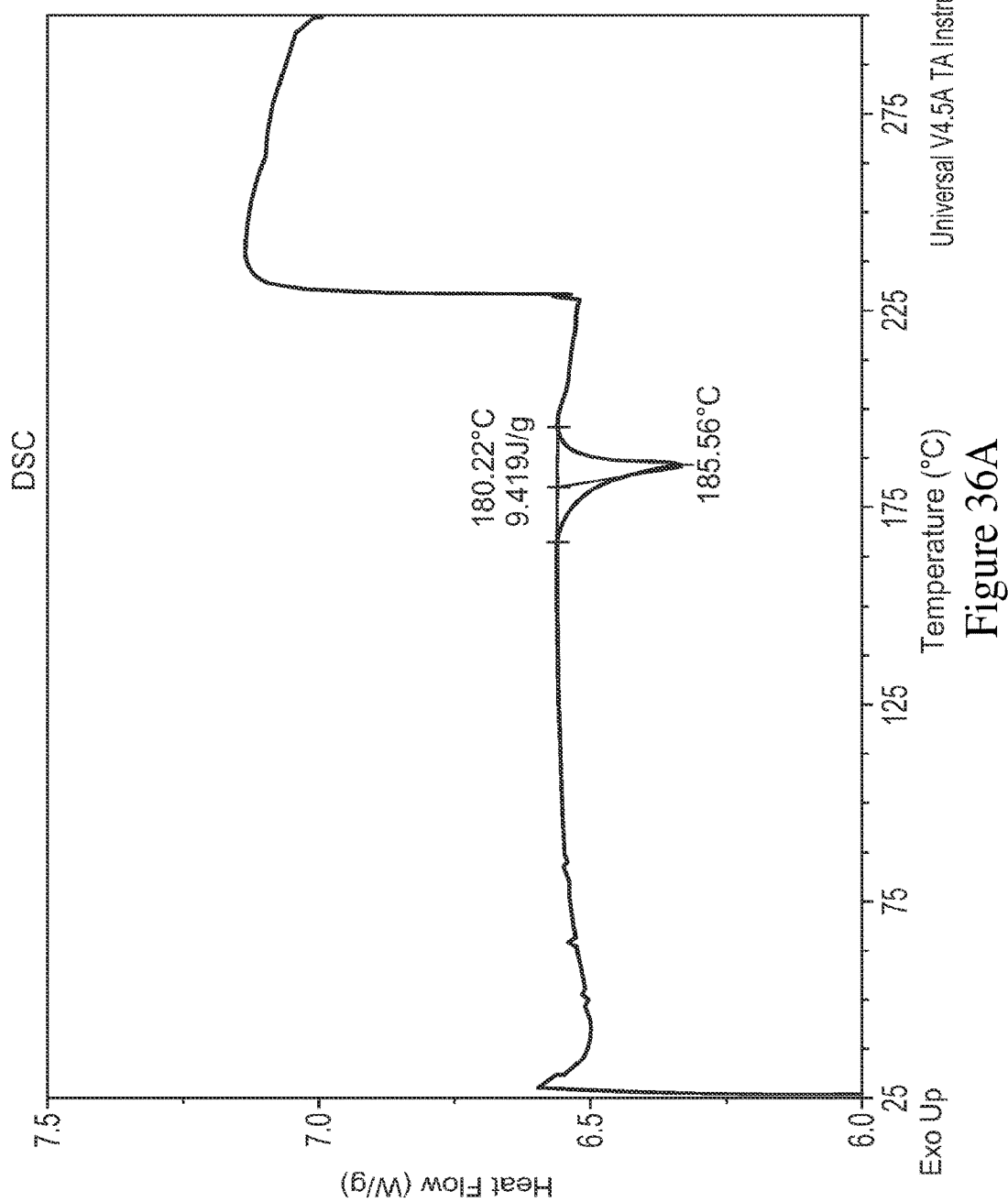
FIG. 36A is a DSC thermogram of (2S,3S)-2-amino-3-methyl-N-(2-morpholinoethyl)-pentanamide dinapsylate.

In one embodiment, the crystalline form of (2S,3S)-2-amino-3-methyl-N-(2-morpholinoethyl)-pentanamide dinapsylate exhibits a DSC thermogram comprising a single maximum value at about 185.56±2.0° C. with the error of margin of about ±2.5; about ±2; about ±1.5; about ±1; about ±0.5; or less. In one specific embodiment, the crystalline form of (2S,3S)-2-amino-3-methyl-N-(2-morpholinoethyl)-pentanamide dinapsylate exhibits a DSC thermogram that is substantially similar to FIG. 36A.

Figure 41A:
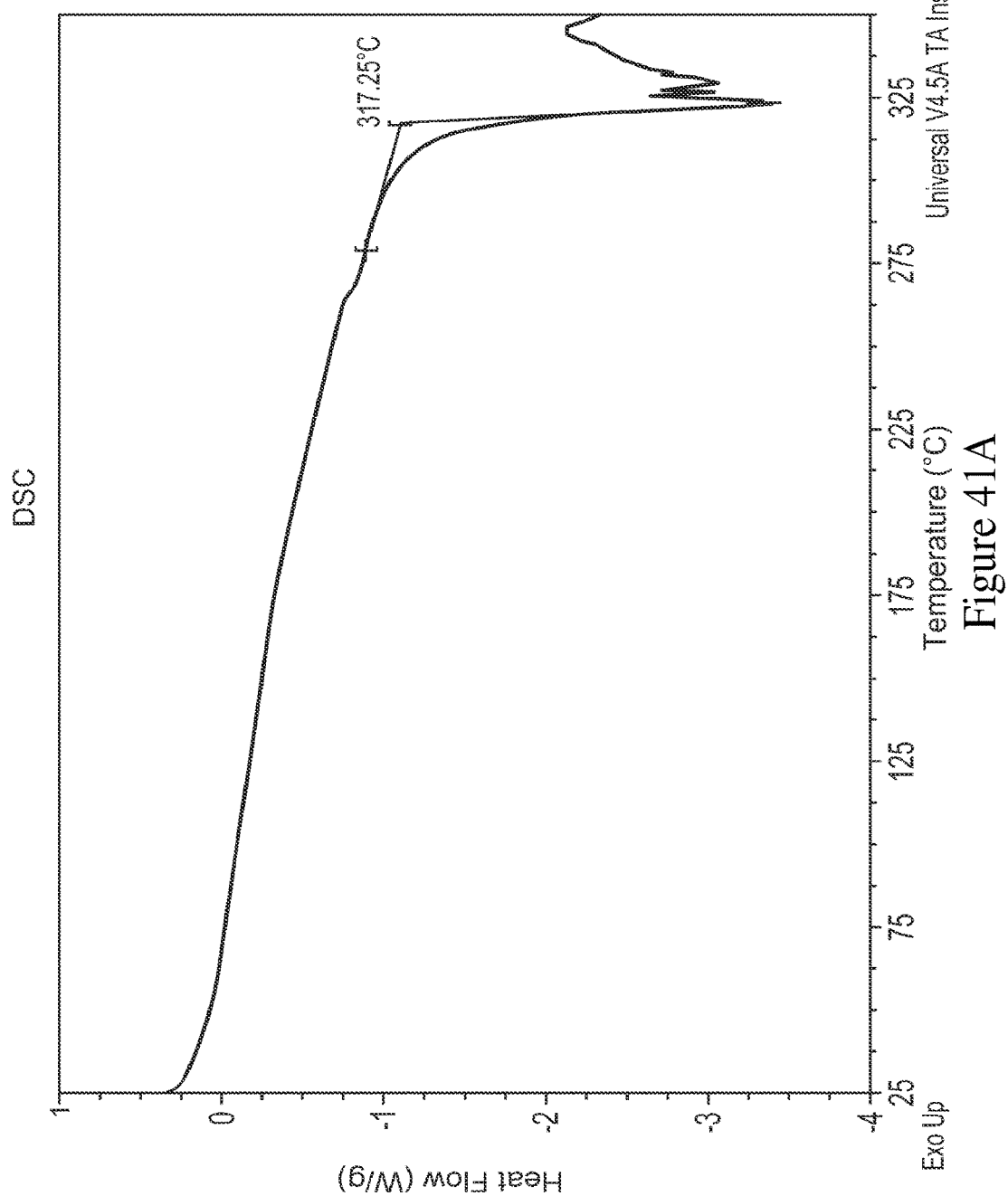
FIG. 41A is a DSC thermogram of (2S,3S)-2-amino-3-methyl-N-(2-morpholinoethyl)-pentanamide monoedisylate.

In one embodiment, the crystalline form of (2S,3S)-2-amino-3-methyl-N-(2-morpholinoethyl)-pentanamide monoedisylate exhibits a DSC thermogram comprising a single maximum value at about 317.25±2.0° C. with the error of margin of about ±2.5; about ±2; about ±1.5; about ±1; about ±0.5; or less. In one specific embodiment, the crystalline form of (2S,3S)-2-amino-3-methyl-N-(2-morpholinoethyl)-pentanamide monoedisylate exhibits a DSC thermogram that is substantially similar to FIG. 41A.

Figure 46A:
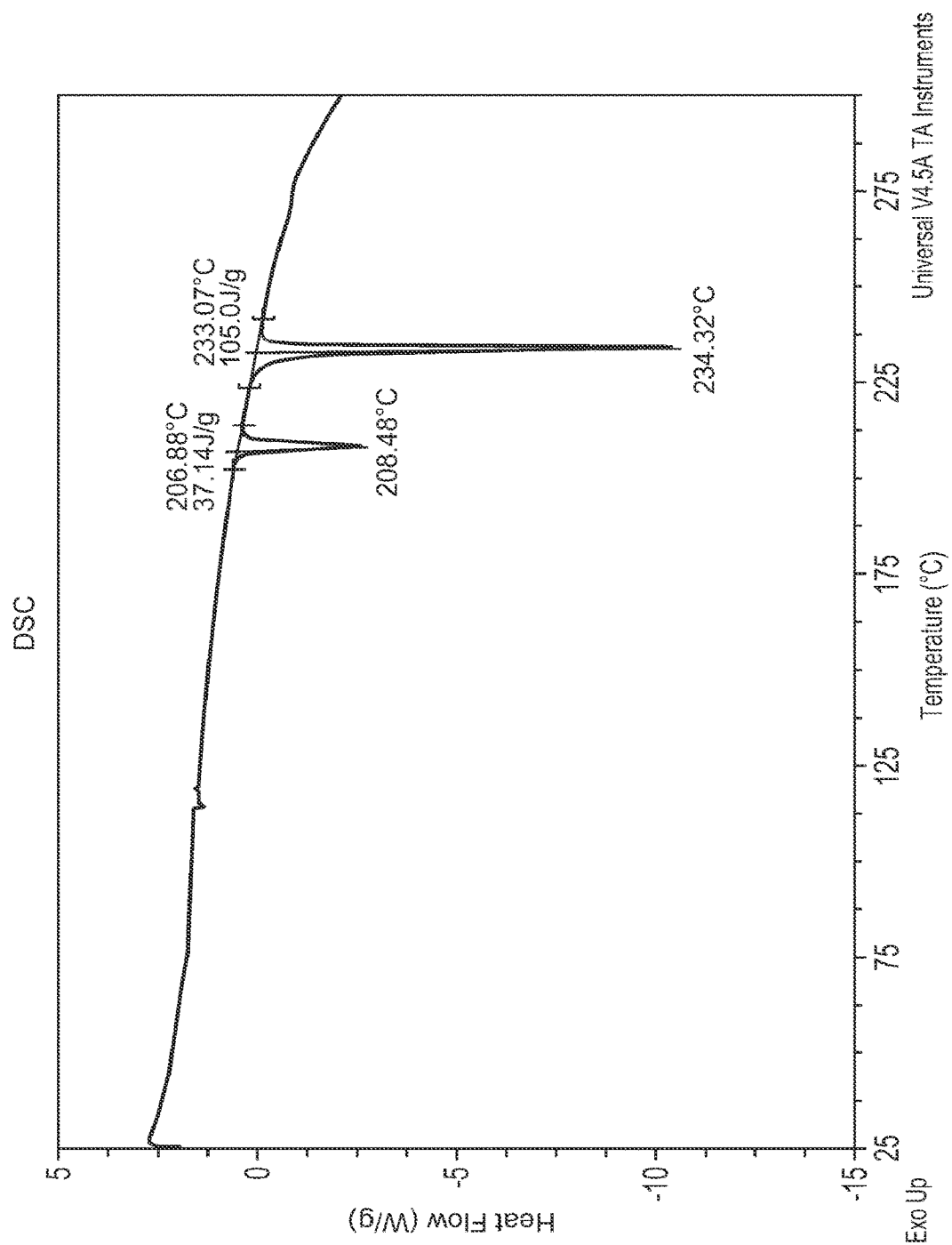
FIG. 46A is a DSC thermogram of (2S,3S)-2-amino-3-methyl-N-(2-morpholinoethyl)-pentanamide monooxalate.

In one embodiment, the crystalline form of (2S,3S)-2-amino-3-methyl-N-(2-morpholinoethyl)-pentanamide monooxalate exhibits a DSC thermogram comprising a single maximum value at about 234.32±2.0° C. with the error of margin of about ±2.5; about ±2; about ±1.5; about ±1; about ±0.5; or less. In one specific embodiment, the crystalline form of (2S,3S)-2-amino-3-methyl-N-(2-morpholinoethyl)-pentanamide monooxalate exhibits a DSC thermogram that is substantially similar to FIG. 46A.

Additional methods of characterize the present crystalline forms are described in the Example section of this application.

Pharmaceutical Formulations

In another embodiment, the present invention provides a pharmaceutical composition comprising a therapeutically effective amount of a crystalline form of the present invention as the active ingredient, combined with a pharmaceutically acceptable excipient or carrier. The excipients are added to the formulation for a variety of purposes.

Diluents may be added to the formulations of the present invention. Diluents increase the bulk of a solid pharmaceutical composition, and may make a pharmaceutical dosage form containing the composition easier for the patient and care giver to handle. Diluents for solid compositions include, for example, microcrystalline cellulose (e.g., AVICEL), microfine cellulose, lactose, starch, pregelatinized starch, calcium carbonate, calcium sulfate, sugar, dextrates, dextrin, dextrose, dibasic calcium phosphate dihydrate, tribasic calcium phosphate, kaolin, magnesium carbonate, magnesium oxide, maltodextrin, mannitol, polymethacrylates (e.g., EUDRAGIT), potassium chloride, powdered cellulose, sodium chloride, sorbitol, and talc.

Solid pharmaceutical compositions that are compacted into a dosage form, such as a tablet, may include excipients whose functions include helping to bind the active ingredient and other excipients together after compression. Binders for solid pharmaceutical compositions include acacia, alginic acid, carbomer (e.g., carbopol), carboxymethylcellulose sodium, dextrin, ethyl cellulose, gelatin, guar gum, hydrogenated vegetable oil, hydroxyethyl cellulose, hydroxypropyl cellulose (e.g., KLUCEL), hydroxypropyl methyl cellulose (e.g., METHOCEL), liquid glucose, magnesium aluminum silicate, maltodextrin, methylcellulose, polymethacrylates, povidone (e.g., KOLLIDON, PLASDONE), pregelatinized starch, sodium alginate, and starch.

The dissolution rate of a compacted solid pharmaceutical composition in the patient's stomach may be increased by the addition of a disintegrant to the composition. Disintegrants include alginic acid, carboxymethylcellulose calcium, carboxymethylcellulose sodium (e.g., AC-DI-SOL and PRIMELLOSE), colloidal silicon dioxide, croscarmellose sodium, crospovidone (e.g., KOLLIDON and POLYPLASDONE), guar gum, magnesium aluminum silicate, methyl cellulose, microcrystalline cellulose, polacrilin potassium, powdered cellulose, pregelatinized starch, sodium alginate, sodium starch glycolate (e.g., EXPLOTAB), and starch.

Glidants can be added to improve the flowability of a non-compacted solid composition and to improve the accuracy of dosing. Excipients that may function as glidants include colloidal silicon dioxide, magnesium trisilicate, powdered cellulose, starch, talc, and tribasic calcium phosphate.

When a dosage form such as a tablet is made by the compaction of a powdered composition, the composition is subjected to pressure from a punch and dye. Some excipients and active ingredients have a tendency to adhere to the surfaces of the punch and dye, which can cause the product to have pitting and other surface irregularities. A lubricant can be added to the composition to reduce adhesion and ease the release of the product from the dye. Lubricants include magnesium stearate, calcium stearate, glyceryl monostearate, glyceryl palmitostearate, hydrogenated castor oil, hydrogenated vegetable oil, mineral oil, polyethylene glycol, sodium benzoate, sodium lauryl sulfate, sodium stearyl fumarate, stearic acid, talc, and zinc stearate.

Flavoring agents and flavor enhancers make the dosage form more palatable to the patient. Common flavoring agents and flavor enhancers for pharmaceutical products that may be included in the composition of the present invention include maltol, vanillin, ethyl vanillin, menthol, citric acid, fumaric acid, ethyl maltol, and tartaric acid.

Solid and liquid compositions may also be dyed using any pharmaceutically acceptable colorant to improve their appearance and/or facilitate patient identification of the product and unit dosage level.

The present invention is not intended to encompass true solutions of atomoxetine hydrochloride whereupon the crystal structure of the novel crystalline forms and the properties that characterize the novel crystalline forms of atomoxetine hydrochloride of the present invention are lost. However, the use of the novel forms to prepare such solutions (e.g., so as to deliver atomoxetine hydrochloride in a liquid pharmaceutical formulation) is considered to be within the contemplation of the invention.

In liquid pharmaceutical compositions prepared using the crystalline forms of the present invention, atomoxetine hydrochloride and any other solid excipients are dissolved or suspended in a liquid carrier such as water, vegetable oil, alcohol, polyethylene glycol, propylene glycol, or glycerin.

Liquid pharmaceutical compositions may contain emulsifying agents to disperse uniformly throughout the composition an active ingredient or other excipient that is not soluble in the liquid carrier. Emulsifying agents that may be useful in liquid compositions of the present invention include, for example, gelatin, egg yolk, casein, cholesterol, acacia, tragacanth, chondrus, pectin, methyl cellulose, carbomer, cetostearyl alcohol, and cetyl alcohol.

Liquid pharmaceutical compositions may also contain a viscosity enhancing agent to improve the mouth-feel of the product and/or coat the lining of the gastrointestinal tract. Such agents include acacia, alginic acid bentonite, carbomer, carboxymethylcellulose calcium or sodium, cetostearyl alcohol, methyl cellulose, ethylcellulose, gelatin guar gum, hydroxyethyl cellulose, hydroxypropyl cellulose, hydroxypropyl methyl cellulose, maltodextrin, polyvinyl alcohol, povidone, propylene carbonate, propylene glycol alginate, sodium alginate, sodium starch glycolate, starch tragacanth, and xanthan gum.

Sweetening agents such as sorbitol, saccharin, sodium saccharin, sucrose, aspartame, fructose, mannitol, and invert sugar may be added to improve the taste.

Preservatives and chelating agents such as alcohol, sodium benzoate, butylated hydroxyl toluene, butylated hydroxyanisole, and ethylenediamine tetraacetic acid may be added at levels safe for ingestion to improve storage stability.

A liquid composition may also contain a buffer such as gluconic acid, lactic acid, citric acid or acetic acid, sodium gluconate, sodium lactate, sodium citrate, or sodium acetate. Selection of excipients and the amounts used may be readily determined by the formulation scientist based upon experience and consideration of standard procedures and reference works in the field.

The solid compositions of the present invention include powders, granulates, aggregates and compacted compositions. The dosages include dosages suitable for oral, buccal, rectal, parenteral (including subcutaneous, intramuscular, and intravenous), inhalant and ophthalmic administration. Although the most suitable administration in any given case will depend on the nature and severity of the condition being treated, the most preferred route of the present invention is oral. The dosages may be conveniently presented in unit dosage form and prepared by any of the methods well-known in the pharmaceutical arts.

Dosage forms include solid dosage forms like tablets, powders, capsules, suppositories, sachets, troches and lozenges, as well as liquid syrups, suspensions and elixirs.

The dosage of STRATTERA may be used as guidance. The oral dosage form of the present invention is preferably in the form of an oral capsule or tablet having a dosage of about 5 mg to about 160 mg in total weight including the active ingredient and other excipients, more preferably from about 20 mg to about 80 mg, and most preferably capsules or tablets of 10, 18, 20, 25, 40, 60 and 80 mg. Daily dosages may include 1, 2, or more capsules per day.

The dosage form of the present invention may be a capsule containing the composition, preferably a powdered or granulated solid composition of the invention, within either a hard or soft shell. The shell may be made from gelatin and optionally contain a plasticizer such as glycerin and sorbitol, and an opacifying agent or colorant.

A composition for tableting or capsule filling may be prepared by wet granulation. In wet granulation, some or all of the active ingredients and excipients in powder form are blended and then further mixed in the presence of a liquid, typically water, that causes the powders to clump into granules. The granulate is screened and/or milled, dried and then screened and/or milled to the desired particle size. The granulate may then be tableted, or other excipients may be added prior to tableting, such as a glidant and/or a lubricant.

A tableting composition may be prepared conventionally by dry blending. For example, the blended composition of the actives and excipients may be compacted into a slug or a sheet and then comminuted into compacted granules. The compacted granules may subsequently be compressed into a tablet.

As an alternative to dry granulation, a blended composition may be compressed directly into a compacted dosage form using direct compression techniques. Direct compression produces a more uniform tablet without granules. Excipients that are particularly well suited for direct compression tableting include microcrystalline cellulose, spray dried lactose, dicalcium phosphate dihydrate and colloidal silica. The proper use of these and other excipients in direct compression tableting is known to those in the art with experience and skill in particular formulation challenges of direct compression tableting.

A capsule filling of the present invention may comprise any of the aforementioned blends and granulates that were described with reference to tableting, however, they are not subjected to a final tableting step.

The active ingredient and excipients may be formulated into compositions and dosage forms according to methods known in the art.

It is not necessary that the formulations of the present invention contain only one crystalline form of atomoxetine hydrochloride. The crystalline forms of the present invention may be used in pharmaceutical formulations or compositions as single components or mixtures together with other crystalline forms of atomoxetine hydrochloride or with amorphous atomoxetine hydrochloride. However, it is preferred that the pharmaceutical formulations or compositions of the present invention contain 25-100% by weight, especially 50-100% by weight, of at least one of the novel forms, based on the total amount of atomoxetine hydrochloride in the formulation or composition. Preferably, such an amount of the novel crystalline form of atomoxetine hydrochloride is 75-100% by weight, especially 90100% by weight. Highly preferred is an amount of 95-100% by weight.

Therapeutic Use

The present invention also provides treatment of disorders involving degradation or dysfunction of cells expressing p75.

In one aspect, there is provided a method for activating p75 receptors comprising contacting a cell containing a p75 receptor with the present crystalline form. Additionally disclosed are methods for treating nervous system disorders including (but not limited to) Alzheimer's disease, Parkinson's disease, Huntington's disease, stroke, traumatic brain injury, spinal cord injury, epilepsy, multiple sclerosis, amyotrophic lateral sclerosis, neuropathies, myopathies and various forms of retinal degeneration, based on the ability of the crystalline forms of the present invention to target p75 receptors expressed by neurons.

Additionally disclosed are methods for treating nervous system disorders including (and not limited to) multiple sclerosis, spinal cord injury and perinatal anoxia, based on the ability of the crystalline forms of the present application to target p75 receptors expressed by oligodendrocytes.

Further disclosed are methods for treating diseases other than those of the nervous system, particularly preventing loss of hair follicle cells and thereby preventing hair loss; preventing hepatic cirrhosis and promote liver regeneration; to regulate angiogenesis and promote neovascularization in the setting of diabetic wounds or other ischemic settings; to prevent cardiomyopathy by preventing myocardial cell loss or by stimulating growth of new cardiomyocytes either in the setting of ischemia or after myocardial infarction; and to inhibit tumor cell growth. In addition p75 is expressed by stem cells and is known to regulate stem cell growth; therefore, p75 ligands can be used to promote stem cell growth as part of a strategy to promote tissue and organ regeneration.

The present invention also provides methods of treating neurodegenerative and other disorders or conditions in a subject. More particularly, the methods of the present invention involve administration of a crystalline form in a subject to treat a neurodegenerative disorder or other disorder or condition. The crystalline form can be administered in an amount effective to induce survival signaling and/or inhibit proNGF-induced cell death, which has been determined to be associated with neurodegenerative and other disorders. The terms "subject" and "patient" are used interchangeably throughout the present application.

The condition to be treated can be any condition which is mediated, at least in part, by binding of neurotrophins to $p75^{NTR}$ Such conditions include, but are not limited to, Alzheimer's disease, Huntington's disease, Pick's disease, amyotrophic lateral sclerosis, epilepsy, Parkinson's disease, spinal cord injury, stroke, hypoxia, ischemia, brain injury, diabetic neuropathy, peripheral neuropathy, nerve transplantation, multiple sclerosis, peripheral nerve injury, and hair loss.

The present crystalline form can be used to treat neural degeneration, including preventing neurodegeneration such as, for example, neurodegeneration caused by chemotherapy and/or neurodegenerative disorders, as well as other conditions such as inducing hair follicle cell survival caused by, for example, chemotherapy.

The present invention further provides for novel methods of facilitating cell survival. Representative cells include, but are not limited to, septal, hippocampal, cortical, sensory, sympathetic, motor neurons, hair follicle cells, progenitor, and stem cells. Generally, such cells include neurons, oligodendrocytes and hair follicle cells. Specifically, the methods comprise treating a cell with the present crystalline form, whereby the compound induces survival signaling and inhibits proNGF-induced cell death.

The present invention also discloses a method of administering the present crystalline $P75^{NTR}$ form in order to ameliorate a condition mediated by binding in a subject. The method can comprise the step of administering to a subject an effective amount of a crystalline form of the present invention.

As used herein, administering can be effected or performed using any of the various methods known to those skilled in the art. The crystalline form can be administered, for example, subcutaneously, intravenously, parenterally, intraperitoneally, intradermally, intramuscularly, topically, enteral (e.g., orally), rectally, nasally, buccally, sublingually, vaginally, by inhalation spray, by drug pump or via an implanted reservoir in dosage formulations containing conventional non-toxic, physiologically acceptable carriers or vehicles.

Further, the presently disclosed crystalline forms can be administered to a localized area in need of treatment. This can be achieved by, for example, and not by way of limitation, local infusion during surgery, topical application, transdermal patches, by injection, by catheter, by suppository, or by implant (the implant can optionally be of a porous, non-porous, or gelatinous material), including membranes, such as sialastic membranes or fibers.

The form in which the crystalline form is administered (e.g., syrup, elixir, capsule, tablet, foams, emulsion, gel, etc.) will depend in part on the route by which it is administered. For example, for mucosal (e.g., oral mucosa, rectal, intestinal mucosa, bronchial mucosa) administration, nose drops, aerosols, inhalants, nebulizers, eye drops or suppositories can be used. The crystalline form can also be used to coat bioimplantable materials to enhance neurite outgrowth, neural survival, or cellular interaction with the implant surface. The crystalline forms and agents disclosed herein can be administered together with other biologically active agents, such as analgesics, anti-inflammatory agents, anesthetics and other agents which can control one or more symptoms or causes of a $p75^{NTR}$-mediated condition.

Additionally, administration can comprise administering to the subject a plurality of dosages over a suitable period of time. Such administration regimens can be determined according to routine methods, upon a review of the instant disclosure.

The crystalline forms of the present application can be employed as the sole active agent in a pharmaceutical or can be used in combination (e.g., administered proximate in time to each other or even in the same formulation) with other active ingredients, e.g., neurotrophins, or other factors or drugs which can facilitate neural survival or axonal growth in neurodegenerative diseases, including but not limited to amyloid-β inhibitors, acetylcholinesterase inhibitors, butyrylcholinesterase inhibitors, and N-methyl-D-aspartate subtype of glutamate receptor antagonists.

Crystalline forms of the invention are generally administered in a dose of about 0.01 mg/kg/dose to about 100 mg/kg/dose. Alternately the dose can be from about 0.1 mg/kg/dose to about 10 mg/kg/dose; or about 1 mg/kg/dose to 10 mg/kg/dose. In some dosages, the crystalline forms disclosed herein are administered at about 5 mg/kg/dose. Time release preparations may be employed or the dose may be administered in as many divided doses as is convenient. When other methods are used (e.g. intravenous administration), crystalline forms are administered to the affected tissue at a rate from about 0.05 to about 10 mg/kg/hour, alternately from about 0.1 to about 1 mg/kg/hour. Such rates are easily maintained when these crystalline forms are intravenously administered as discussed herein. Generally, topically administered formulations are administered in a dose of about 0.5 mg/kg/dose to about 10 mg/kg/dose range. Alternately, topical formulations are administered at a dose of about 1 mg/kg/dose to about 7.5 mg/kg/dose or even about 1 mg/kg/dose to about 5 mg/kg/dose.

A range of from about 0.1 to about 100 mg/kg is appropriate for a single dose. Continuous administration is appropriate in the range of about 0.05 to about 10 mg/kg. Topical administration is appropriate for conditions such as hair loss or wound revascularization.

Drug doses can also be given in milligrams per square meter of body surface area rather than body weight, as this method achieves a good correlation to certain metabolic and excretionary functions. Moreover, body surface area can be used as a common denominator for drug dosage in adults and children as well as in different animal species (Freireich et al., (1966) Cancer Chemother Rep. 50, 219-244). Briefly, to express a mg/kg dose in any given species as the equivalent mg/sq m dose, the dosage is multiplied by the appropriate km factor. In an adult human, 100 mg/kg is equivalent to 100 mg/kg×37 kg/sq m=3700 mg/m$^2$.

Insofar as the crystalline forms disclosed herein can take the form of a mimetic or fragment thereof, it is to be appreciated that the potency, and therefore dosage of an effective amount can vary. However, one skilled in the art can readily assess the potency of a crystalline form of the type presently envisioned by the present application.

In settings of a gradually progressive nervous system disorder, crystalline forms of the present application are generally administered on an ongoing basis. In certain settings administration of a crystalline form disclosed herein can commence prior to the development of disease symptoms as part of a strategy to delay or prevent the disease. In other settings a crystalline form disclosed herein is administered after the onset of disease symptoms as part of a strategy to slow or reverse the disease process and/or part of a strategy to improve cellular function and reduce symptoms. Crystalline forms have been developed that cross the blood brain barrier and hence would be delivered by oral administration or by other peripheral routes. Crystalline forms that do not cross the blood brain barrier are applied for targets outside of the central nervous system. For targets and tissues outside of the nervous system, crystalline forms are applied in either acute or chronic settings by other oral or directed target administration such as by topical application.

It will be appreciated by one of skill in the art that dosage range will depend on the particular crystalline form, and its potency. The dosage range is understood to be large enough to produce the desired effect in which the neurodegenerative or other disorder and the symptoms associated therewith are ameliorated and/or survival of the cells is achieved, but not be so large as to cause unmanageable adverse side effects. It will be understood, however, that the specific dose level for any particular patient will depend on a variety of factors including the activity of the specific crystalline form employed; the age, body weight, general health, sex and diet of the individual being treated; the time and route of administration; the rate of excretion; other drugs which have previously been administered; and the severity of the particular disease undergoing therapy, as is well understood by those skilled in the art. The dosage can also be adjusted by the individual physician in the event of any complication. No unacceptable toxicological effects are expected when crystalline forms disclosed herein are used in accordance with the present application.

An effective amount of the crystalline forms disclosed herein comprise amounts sufficient to produce a measurable biological response. Actual dosage levels of active ingredients in a therapeutic crystalline form of the present application can be varied so as to administer an amount of the active crystalline form that is effective to achieve the desired therapeutic response for a particular subject and/or application. Preferably, a minimal dose is administered, and the dose is escalated in the absence of dose-limiting toxicity to a minimally effective amount. Determination and adjustment of a therapeutically effective dose, as well as evaluation of when and how to make such adjustments, are known to those of ordinary skill in the art.

Further with respect to the methods of the present application, a preferred subject is a vertebrate subject. A preferred vertebrate is warm-blooded; a preferred warm-blooded vertebrate is a mammal. The subject treated by the presently disclosed methods is desirably a human, although it is to be understood that the principles of the present application indicate effectiveness with respect to all vertebrate species which are to be included in the term "subject." In this context, a vertebrate is understood to be any vertebrate species in which treatment of a neurodegenerative disorder is desirable. As used herein, the term "subject" includes both human and animal subjects. Thus, veterinary therapeutic uses are provided in accordance with the present application.

As such, the present application provides for the treatment of mammals such as humans, as well as those mammals of importance due to being endangered, such as Siberian tigers; of economic importance, such as animals raised on farms for consumption by humans; and/or animals of social importance to humans, such as animals kept as pets or in zoos or farms. Examples of such animals include but are not limited to: carnivores such as cats and dogs; swine, including pigs, hogs, and wild boars; ruminants and/or ungulates such as cattle, oxen, sheep, giraffes, deer, goats, bison, and camels; and horses. Also provided is the treatment of birds, including the treatment of those kinds of birds that are endangered and/or kept in zoos, as well as fowl, and more particularly domesticated fowl, i.e., poultry, such as turkeys, chickens, ducks, geese, guinea fowl, and the like, as they are also of economical importance to humans. Thus, also provided is the treatment of livestock, including, but not limited to, domesticated swine, ruminants, ungulates, horses (including race horses), poultry, and the like.

The following examples further illustrate the present invention but should not be construed as in any way limiting its scope.

EXAMPLES

Analytical Methods—
various analytical methods, as described below, were applied to the present crystalline forms and their precursors to characterize their physiochemical properties.

Microscopy:

A Zeiss Universal microscope configured with a polarized visible light source and polarizable analyzer was used to evaluate the optical properties of the samples. Specimens were typically mounted on a microscope slide with a drop of immersion oil and a cover glass. Magnification was typically 100×. Observations of particle/crystal size and shape were recorded. The presence of birefringence was also noted.

Molecular Spectroscopy—$^1$H-NMR:

Samples were prepared by dissolving 1-10 mg in dimethylsulfoxide (DMSO)-$d_6$ with 0.05% (v/v) tetramethylsilane (TMS). Spectra were collected at ambient temperature on a Bruker Avance III 400 MHz FT-NMR spectrometer and Bruker Topspin software (version 2.1). Prior to each sample analysis, the magnetic field surrounding the sample was optimized by an automated shimming program.

Differential Scanning Calorimetry (DSC):

DSC data were collected on a TA Instruments DSC. In general, samples in the mass range of 1 to 10 mg were crimped in aluminum sample pans and scanned from 25 to about 250° C. or 300° C. at 10° C./minute using a nitrogen purge of 50 mL/min.

Thermogravimetric Analysis (TGA):

TGA data were collected on a TA Instruments 2950 TGA. In general, samples in the mass range of 2 to 10 mg were placed in an open, pre-tared platinum sample pan and scanned from 25 to about 150° C. at 10° C./minute using a nitrogen purge at 100 mL/min.

Hot Stage Microscopy (HSM):

A Zeiss Universal microscope configured with a polarized visible light source and a Linkam hot stage accessory was used. Specimens were mounted on a microscope slide with a cover glass. Magnification was typically 6.3×. Samples were heated from 25° C. to about 250° C. at 10 or 2° C./minute. Linksys 32 temperature control and data capture software system (Linkam Scientific Instruments Ltd, Waterfield, Tadworth, Surrey KT20 SLR, UK). Observations of phase change, recrystallization, evolution of bubbles, etc. were recorded.

Raman Spectroscopy:

Raman spectra were obtained with a Thermo DXR dispersive Raman spectrometer using laser excitation at 780 nm. Spectra were acquired from 3300 to 300 cm$^{-1}$ (Raman shift) using a 400 line/mm wide-range dispersive grating and from 1850 to 300 cm$^{-1}$ (Raman shift) using an 830 line/mm high resolution dispersive grating. Each scan was 5 sec, and 64 scans were collected for each analysis. Samples were analyzed as bulk powders and from 96-well plate experiments.

X-Ray Powder Diffraction (XRD):

X-ray powder diffraction patterns were obtained using a Bruker D8 Discovery diffractometer equipped with an XYZ stage, laser video microscope for positioning, and a two dimensional HiStar area Detector. Collection times were nominally 60 seconds. A Cu Kα radiation 1.5406 angstrom source operating at 40 kV and 40 mA was used to irradiate samples. The X-ray optics consists of a Gobel mirror coupled with a pinhole collimator of 0.5 mm. Theta-theta continuous scans were employed with a sample-detector distance of approximately 15 cm, which gives an effective 2θ range of 4-40° C. Samples were mounted in low background quartz plates.

Solubility:

Milligram size quantities of each sample were placed into a vial. Water was added and the vials were stirred for a few minutes, followed by visual observation for remaining solids. The solvent was incrementally added until the solids were dissolved, or a maximum volume of solvent was added and the experiment was terminated. It turned out that all the salts tested were highly water soluble.

Hygroscopicity—Dynamic Vapor Sorption (DVS):

Samples were analyzed using an automated dynamic vapor sorption analyzer. The sample (about 1-10 mg) was dried in the instrument 0% RH for 6 hours. The samples were subjected to 0 to 95% RH back to 5% RH at 25° C. in 5% RH steps.

Stability:

The scaled up salts and free base were challenged by heat (solids stored at 25 and 60° C. for 1 week), oxidation (solids stored in oxygen headspace at 25° C. for 1 week), light (solids exposed to ≥1×ICH UV confirmatory conditions), and solutions (HPLC diluent) at 25 and 40° C. for 1 week. These samples were analyzed, along with unstressed controls, by HPLC to characterize their stability.

HPLC Analysis:

Crystalline forms (i.e., salts and free base) of the present invention were analyzed by total area normalization (TAN). The samples were dissolved in 1:1 Acetonitrile (ACN): Water ($H_2O$) at a concentration of 0.5 mg/mL.

HPLC Conditions:

HPLC Column: XBridge Shield RP18, 3.5 um, 4.6×100 mm
  Column Temp: 30° C.
  Auto sampler Flush: Water:CAN (1:1)
  Flow Rate: 1 mL/min
  Injection Volume: 15 mL
  UV Detection: 205 nm w/ spectral acquisition
  Mobile Phase: A—$H_2O$ pH 10 with $NH_4OH$
  B—ACN Gradient Pump Program:

| Step Time (minutes) | % A (pH 10 aq) | % B (CAN) | Curve |
| --- | --- | --- | --- |
| 0.5 | 90.0 | 10.0 | 0.0 |
| 5.0 | 90.0 | 10.0 | 0.0 |
| 10.0 | 10.0 | 90.0 | 1.0 |
| 3.0 | 10.0 | 90.0 | 0.0 |
| 6.0 | 90.0 | 10.0 | 0.0 |

Example 1. Characterization of the Amorphous Dihydrochloride Salt of (2S,3S)-2-amino-3-methyl-N-(2-morpholinoethyl)-pentanamide The free base compound of (2S,3S)-2-amino-3-methyl-N-(2-morpholinoethyl)-pentanamide can be prepared from isoleucine by synthetic methods known to one skilled in the art. Standard procedures and chemical transformation and related methods are well known to one skilled in the art, and such methods and procedures have been described, for example, in standard references such as Fiesers' Reagents for Organic Synthesis, John Wiley and Sons, New York, N.Y., 2002; Organic Reactions, vols. 1-83, John Wiley and Sons, New York, N.Y., 2006; March J. and Smith M., Advanced Organic Chemistry, 6th ed., John Wiley and Sons, New York, N.Y.; and Larock R. C., Comprehensive Organic Transformations, Wiley-VCH Publishers, New York, 1999. All texts and references cited herein are incorporated by reference in their entirety. Other related synthetic methods can be found in U.S. Patent Application Publication Nos. 2006/024072 and 2007/0060526, the contents of which are herein incorporated by reference in their entirety for all purposes. The amorphous dihydrochloride (di-HCl) salt of (2S,3S)-2-amino-3-methyl-N-(2-morpholinoethyl)-pentanamide can be prepared by mixing two molar equivalents of HCl with one molar equivalent of (2S,3S)-2-amino-3-methyl-N-(2-morpholinoethyl)-pentanamide in appropriate solvent(s) and then separating the di-HCl salt from the solvent(s) mixture.

Figure 2:
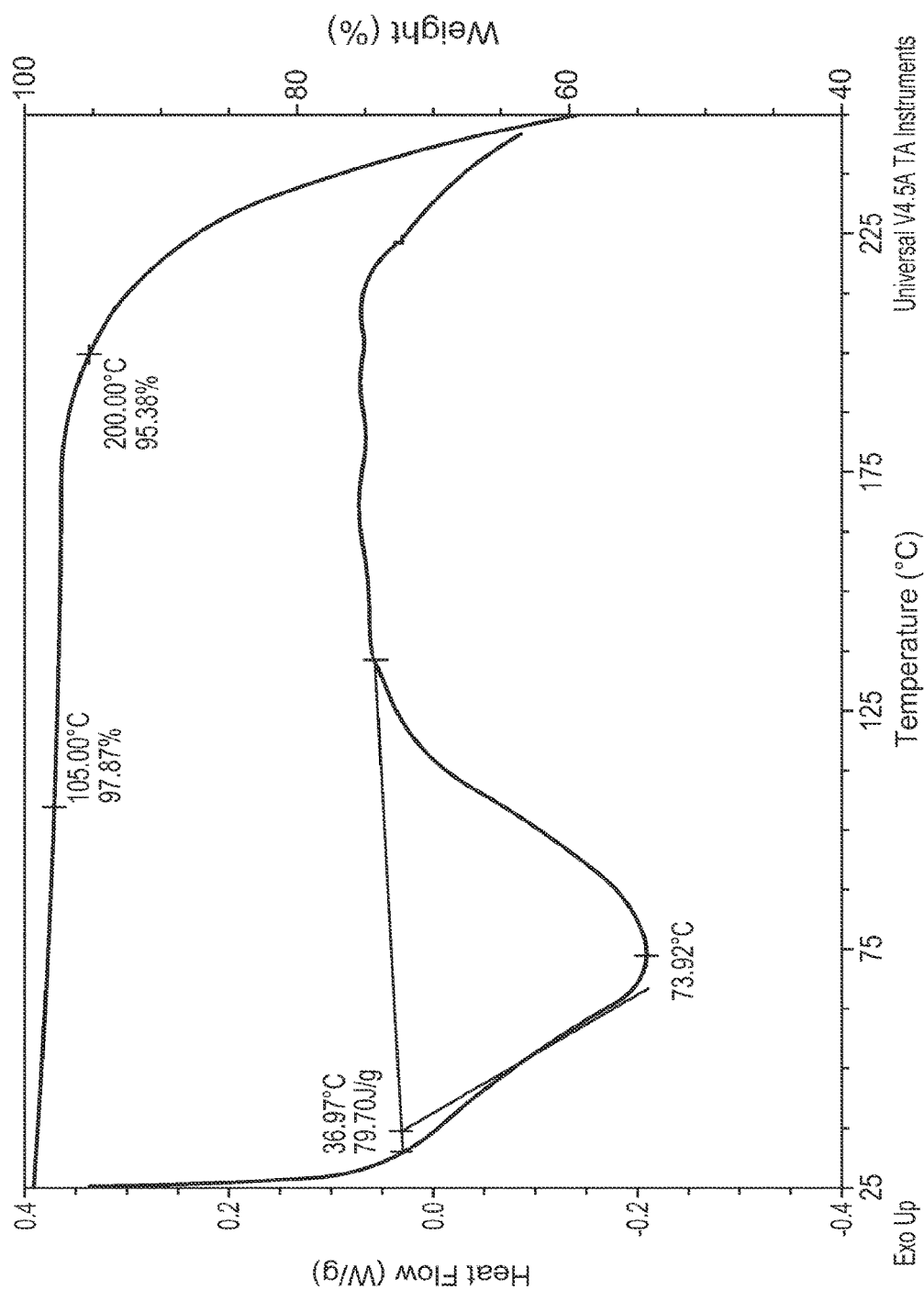
FIG. 2 is an overlay of DSC and TGA thermograms of the amorphous di-HCl salt of (2S,3S)-2-amino-3-methyl-N-(2-morpholinoethyl)-pentanamide.
Figure 3A:
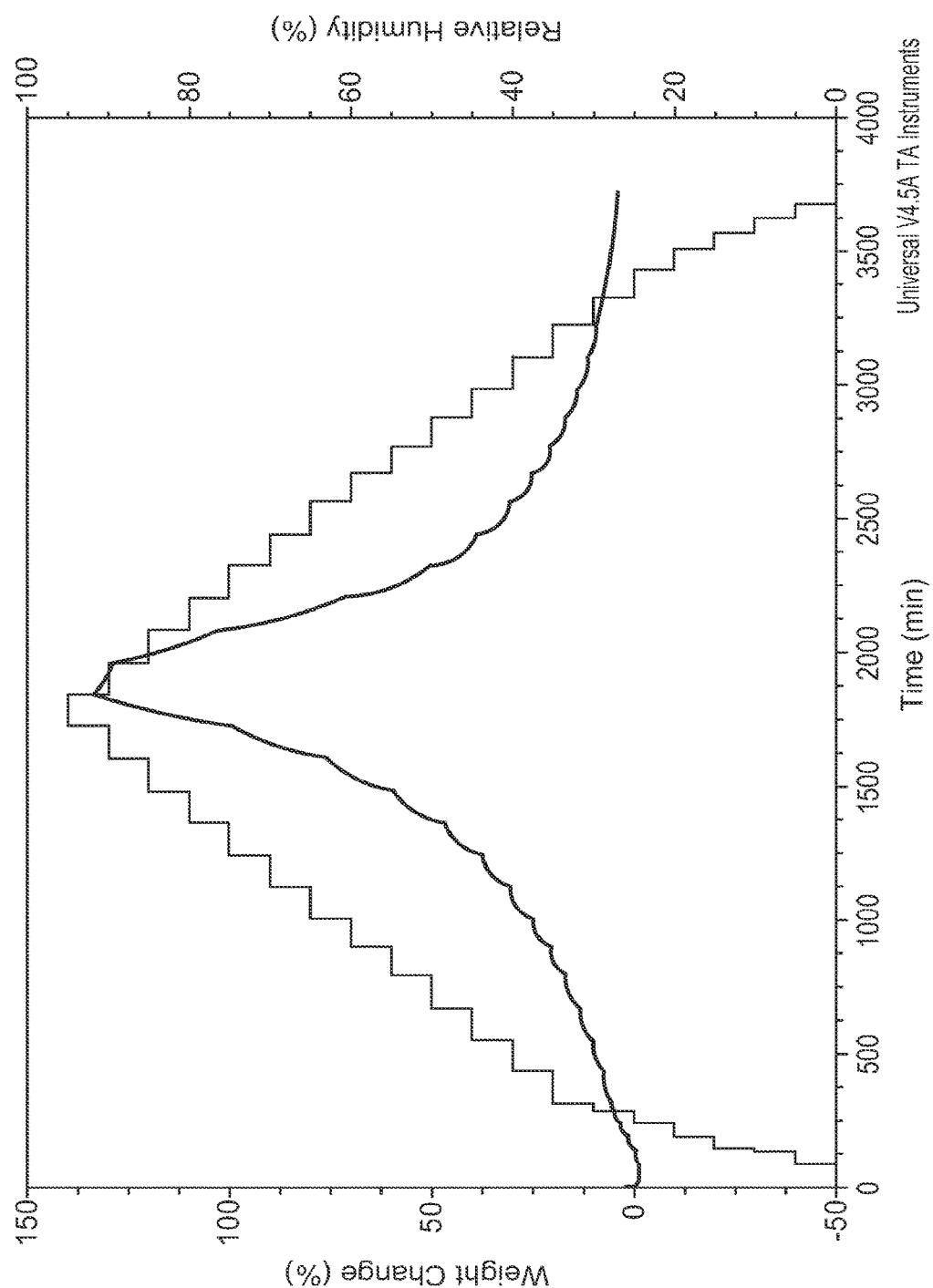
FIGS. 3A and 3B are DVS plots of the amorphous di-HCl salt of (2S,3S)-2-amino-3-methyl-N-(2-morpholinoethyl)-pentanamide.
Figure 3B:
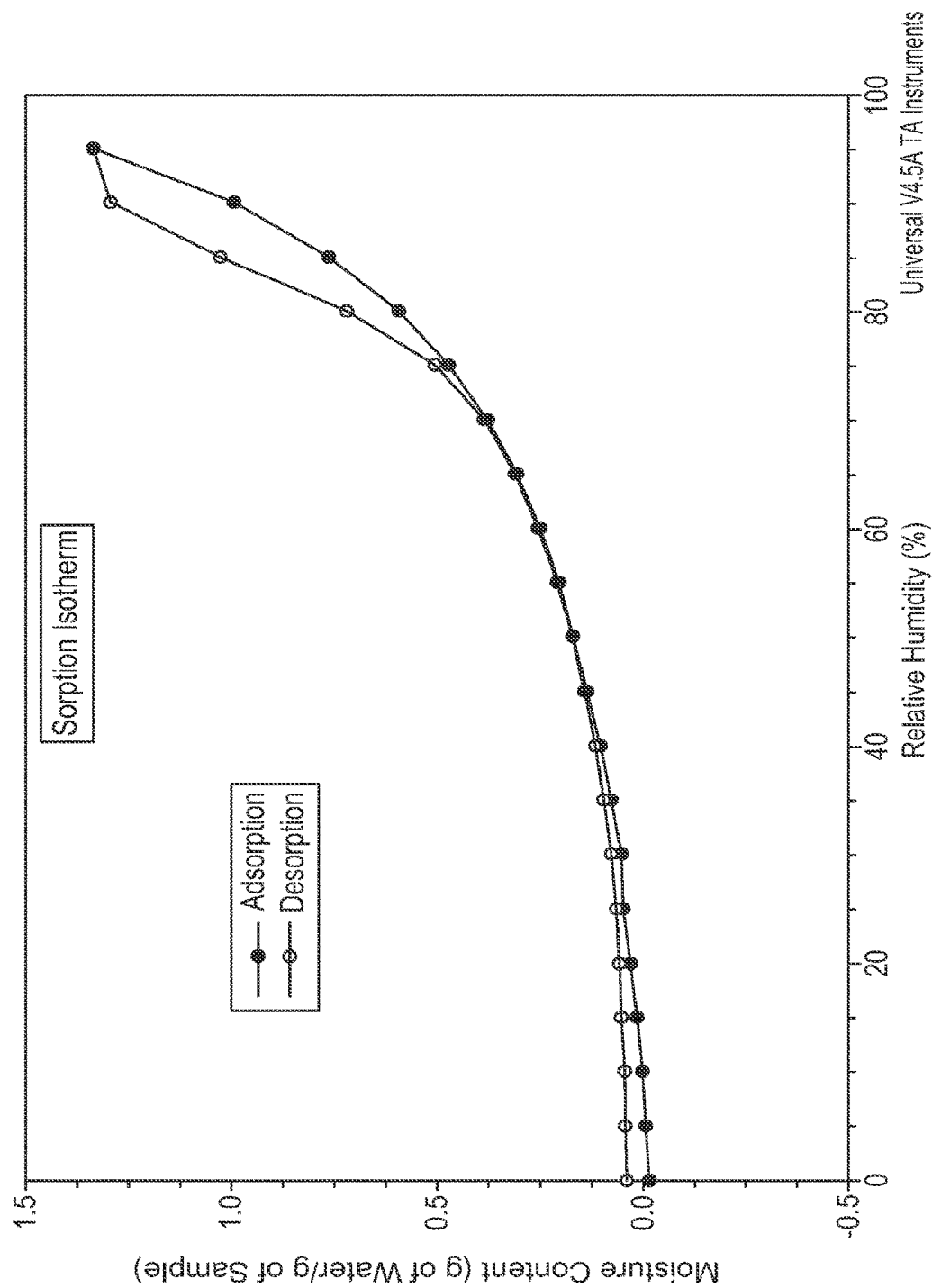
Figure 4:
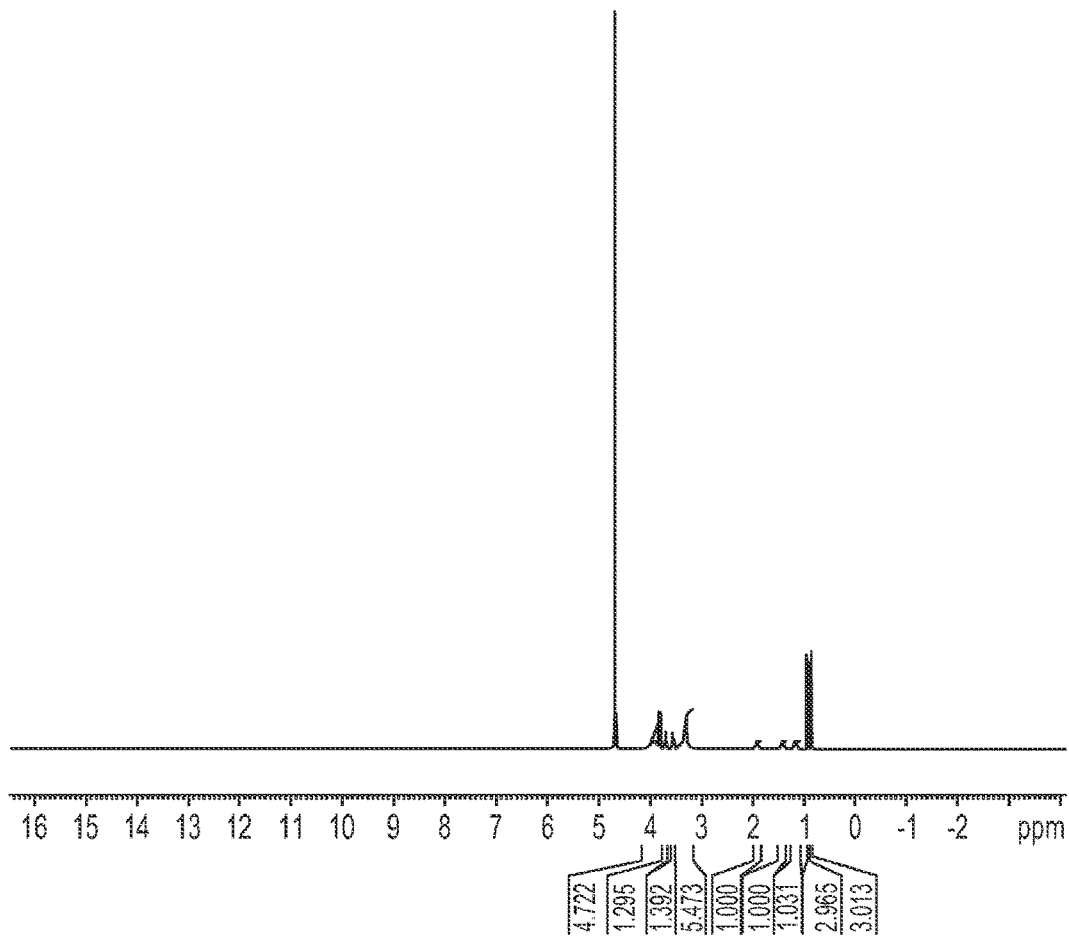
FIG. 4 is a H-NMR, i.e., proton NMR, spectrum of the amorphous di-HCl salt of (2S,3S)-2-amino-3-methyl-N-(2-morpholinoethyl)-pentanamide.

The amorphous di-HCl salt of (2S,3S)-2-amino-3-methyl-N-(2-morpholinoethyl)-pentanamide was analyzed via the methods as described above. The XRD analysis indicated it was amorphous/low ordered as shown in FIG. 1. The DSC thermogram exhibited a broad endotherm with onset temperature 37° C. and peak temperature 74° C. and an enthalpy value of $\Delta H=80$ J/g. The TGA thermogram indicated the di-HCl salt is anhydrous and starts to decompose after about 200° C. An overlay of DSC and TGA thermograms are shown in FIG. 2. The moisture sorption-desorption isotherm of the di-HCl salt (FIGS. 3A and 3B) was collected using dynamic vapor sorption (DVS) analysis. The material did not adsorb much moisture from 0% to 20% RH, then it showed steady sorption up to 140 wt % moisture at 95% RH (likely deliquescence). This sample showed rapid desorption from 95% to 70% RH and then continues desorbing at a relatively slower pace to a mass about 5 wt % greater than the original value at 0% RH. This sample shows a small hysteresis between the sorption and desorption phase. Overall this material is quite hygroscopic. The crude solubility of the di-HCl salt in water was >30 mg/mL. The proton NMR spectrum of the amorphous di-HCl salt is shown in FIG. 4.

Example 2. Preparation of (2S,3S)-2-amino-3-methyl-N-(2-morpholinoethyl)-pentanamide (Free Base)

Five grams of (2S,3S)-2-amino-3-methyl-N-(2-morpholinoethyl)-pentanamide di-HCl salt was dissolved in 150 mL of ethanol. Sodium bicarbonate (5.3 g), dissolved in 100 mL of HPLC water, was added to this solution. The mixed solution was sonicated for ~10 minutes. This solution was concentrated using a rotovap, and the residue was dissolved in 300 mL of methylene chloride. This solution was passed through a short plug of carbonate bonded silica gel. This solution was concentrated using rotovap and the residue was lyophilized to dry, resulting in 3.6 g of the free base as a white solid. Proton NMR, C-13 NMR and LC/MS confirmed the structure of this material as the free base of (2S,3S)-2-amino-3-methyl-N-(2-morpholinoethyl)-pentanamide.

Figure 7:
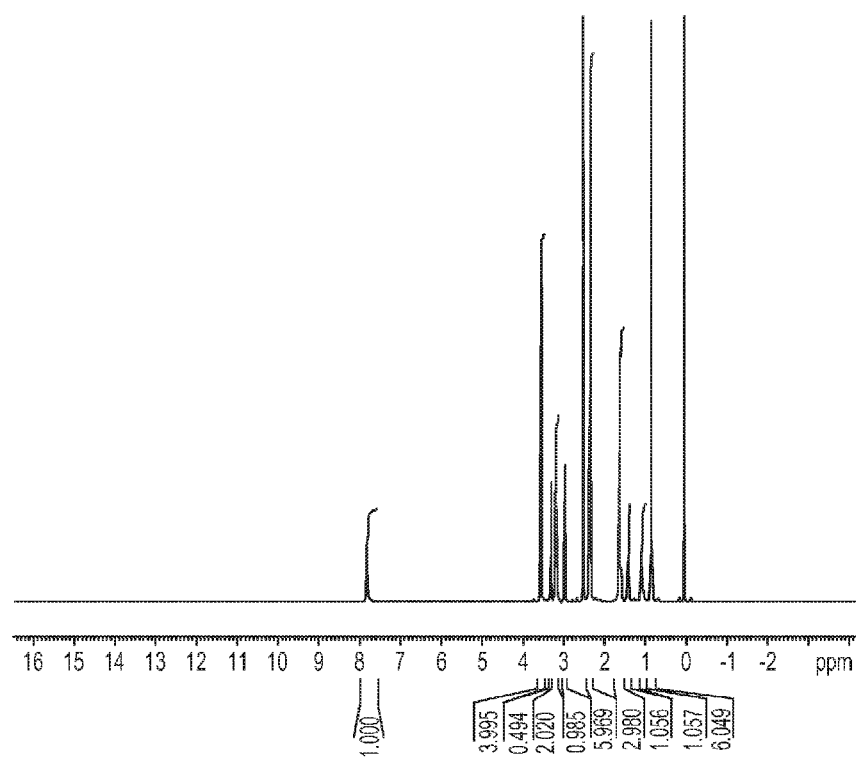
FIG. 7 is a H-NMR spectrum of (2S,3S)-2-amino-3-methyl-N-(2-morpholinoethyl)-pentanamide (free base).
Figure 8A:
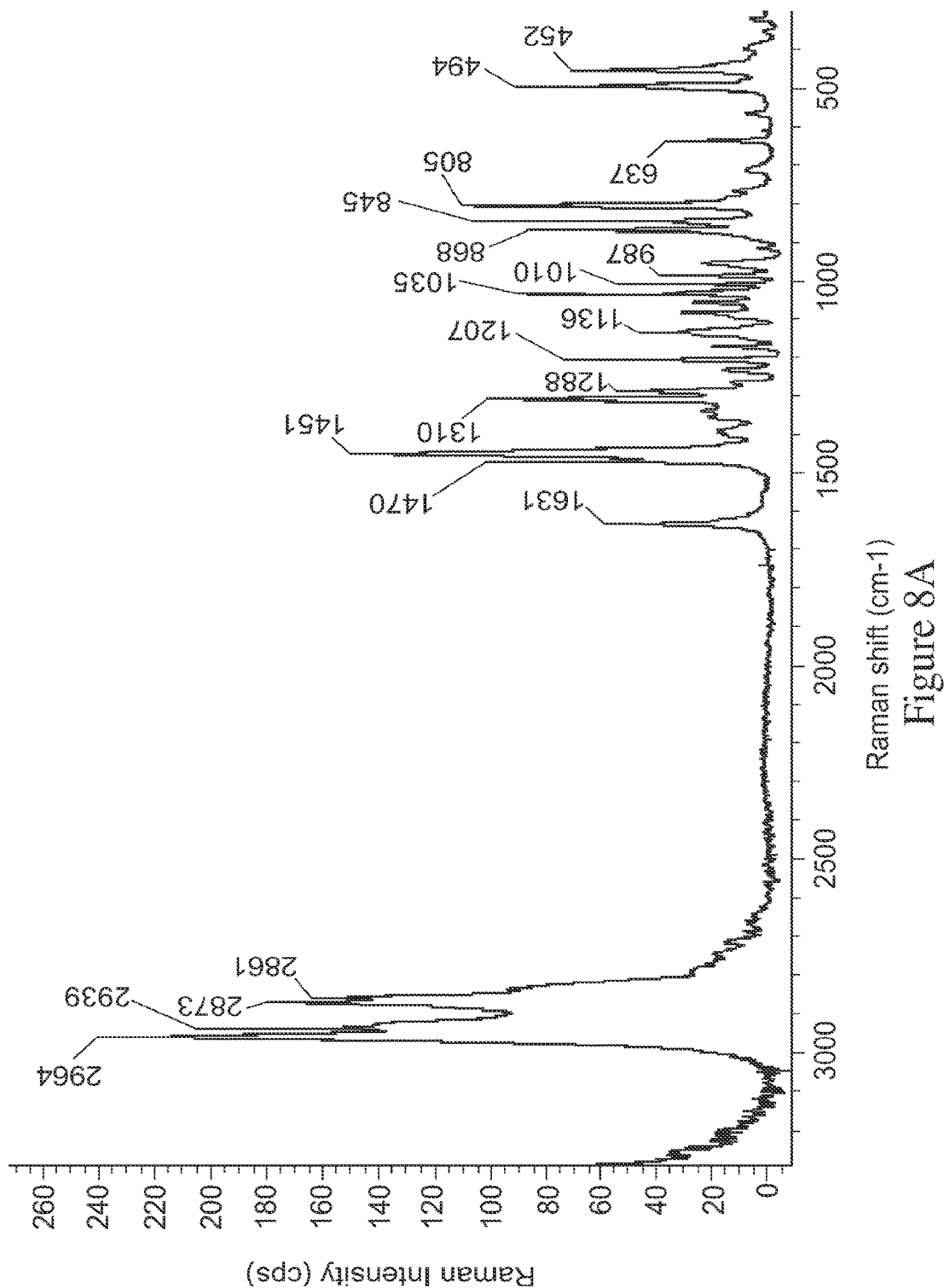
FIGS. 8A and 8B are Raman spectrum of (2S,3S)-2-amino-3-methyl-N-(2-morpholinoethyl)-pentanamide (free base).
Figure 8B:
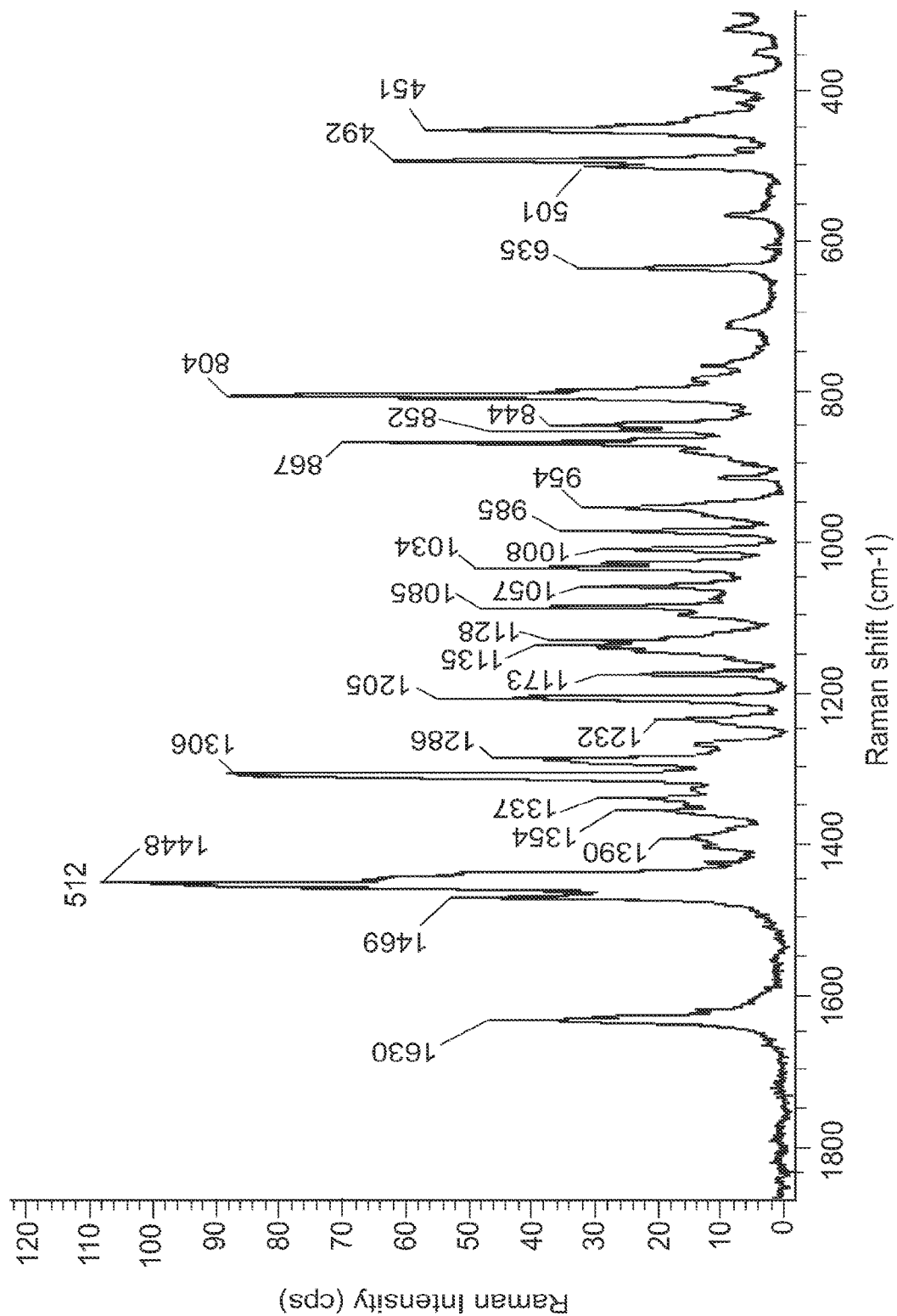
Figure 9A:
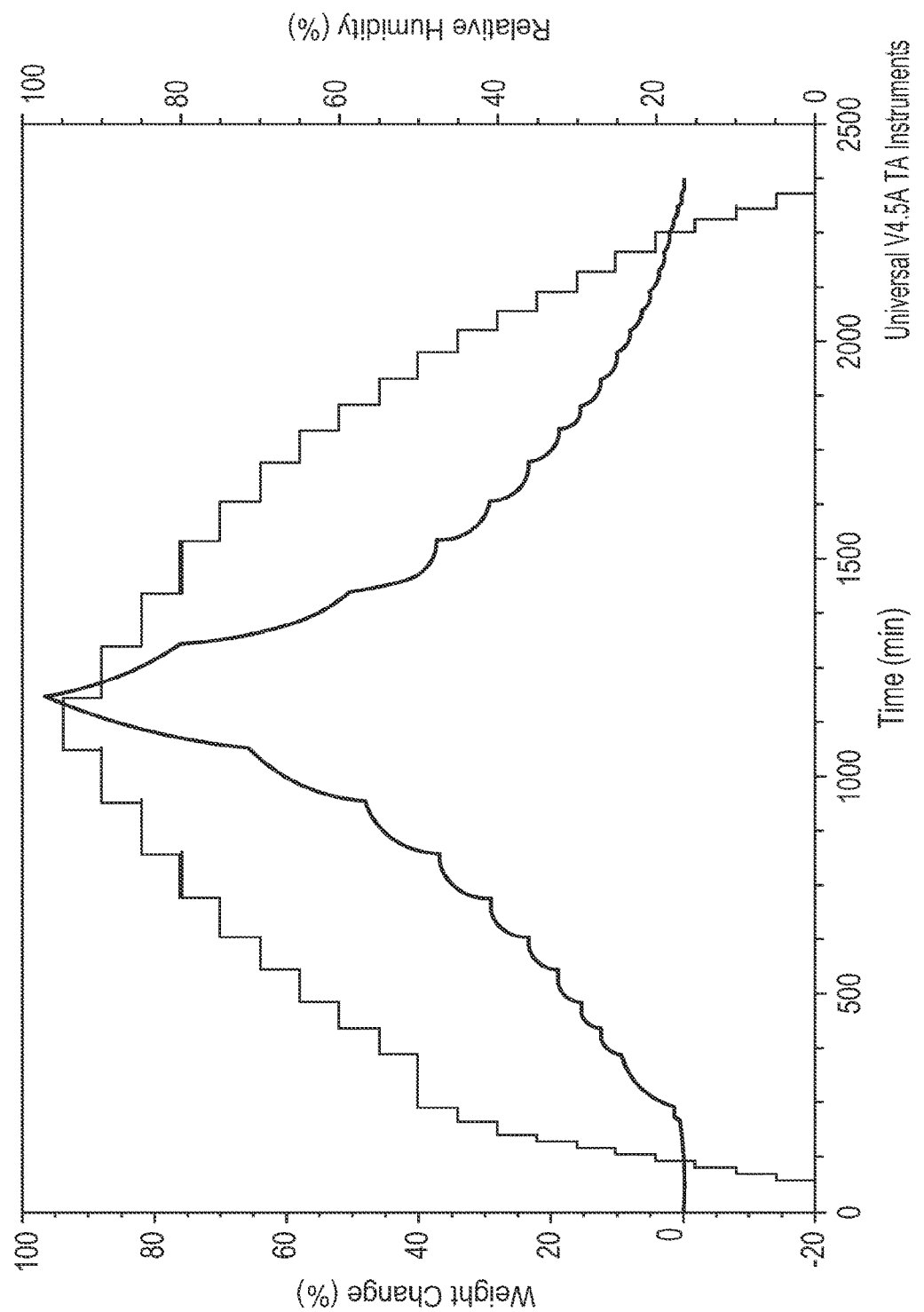
FIGS. 9A and 9B are DVS plots of (2S,3S)-2-amino-3-methyl-N-(2-morpholinoethyl)-pentanamide (free base).
Figure 9B:
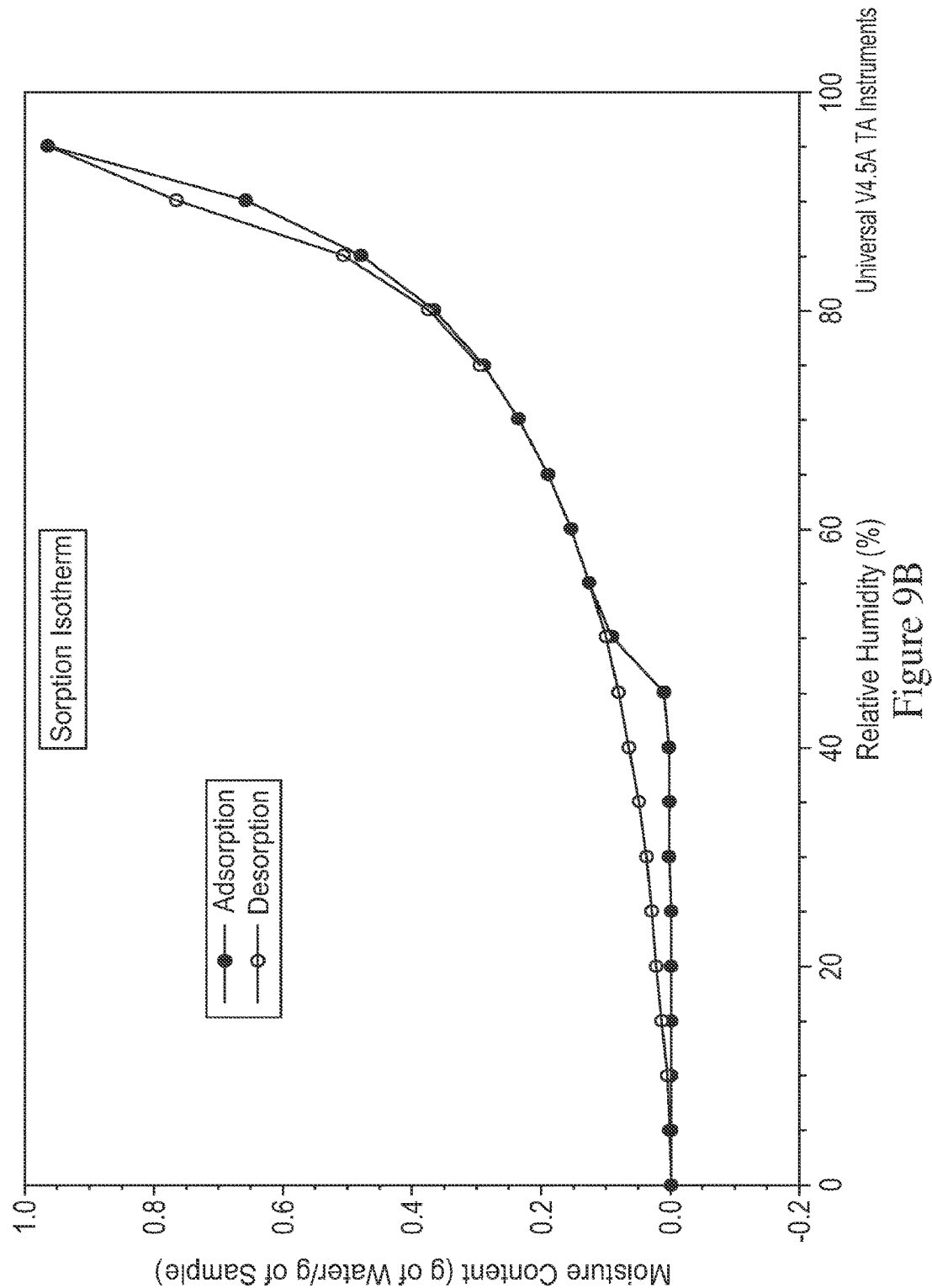

In the process of converting the di-HCl salt to free base, the sample was lyophilized to avoid formation of oil. XRD analysis of the lyophilized free base surprisingly revealed it was crystalline, as shown in FIG. 5. The DSC thermogram exhibited an endotherm with extrapolated onset temperature 51° C. and peak temperature 53° C. and an enthalpy value of $\Delta H_f=104$ J/g. The TGA thermogram shows less than 0.6 wt % loss at 105° C., suggesting it was solvent free. An overlay of the DSC and TGA thermograms can be seen in FIG. 6. The crude solubility of free base in water was >30 mg/mL. The proton NMR was consistent with the free base. The NMR and Raman spectra are shown in FIGS. 7 and 8A and 8B, respectively. The moisture sorption-desorption isotherm (FIGS. 9A and 9B) was collected using dynamic vapor sorption (DVS) analysis. The sample did not adsorb much moisture content from 0% to 45% RH under the experimental conditions. Above 45% RH the sample appears to adsorb moisture of ~10 wt % from 45% to 50% RH followed by rapid sorption up to 96 wt % moisture at 95% RH. In the desorption phase, the free base shows a rapid desorption from 95% to 80% RH, then the sample desorbs at a relatively slow pace to the original weight at 0% RH. The sample may form a hydrate near 45% RH. The putative hydrate appears to deliquesce resulting in an amorphous glass by the end of the scan.

Example 3. Preparation of (2S,3S)-2-amino-3-methyl-N-(2-morpholinoethyl)-pentanamide Monosulfate The free base as prepared in Example 2 was dissolved in methanol, and a portion of this solution was transferred to provide 2 mg equivalent of free base. Sulfuric acid was dissolved in THF or methanol. Equal molar portions of the free base and acid solutions were mixed, and the resulting mixture solutions were dried under nitrogen purge at ambient temperature to provide the desired monosulfate salts as dry solids. The product was slurried in 2-propanol to increase the crystallinity.

XRD indicated the solids are crystalline (FIG. 10) and exhibited a different pattern from the free base. The DSC (FIG. 11) shows a small broad endotherm with peak temperature 76° C., then the broad exotherm with peak temperature 176° C. The hot stage microscopy data suggest the material decomposes near 165° C. The Raman spectrum of this sample is given in FIGS. 12A and 12B.

Example 4. Preparation of (2S,3S)-2-amino-3-methyl-N-(2-morpholinoethyl)-pentanamide tetra (monohydrogensulfate), monosulfate The free base as prepared in Example 2 was dissolved in methanol, and a portion of this solution was transferred to provide 25 mg equivalent of free base. Sulfuric acid was dissolved or suspended in water, methanol, or acetonitrile. The free base and sulfuric acid solutions/suspensions (providing 1:2 molar ratio of free base and sulfuric acid) were mixed. The resulting mixture solutions/suspensions were slurried in 2-propanol at ambient temperature to obtain clear solutions. The clear solutions were evaporated under nitrogen at ~1.5 psi to provide suspensions which were subsequently filtered to provide the tetra(monohydrogensulfate), monosulfate salts as solids.

Figure 15:
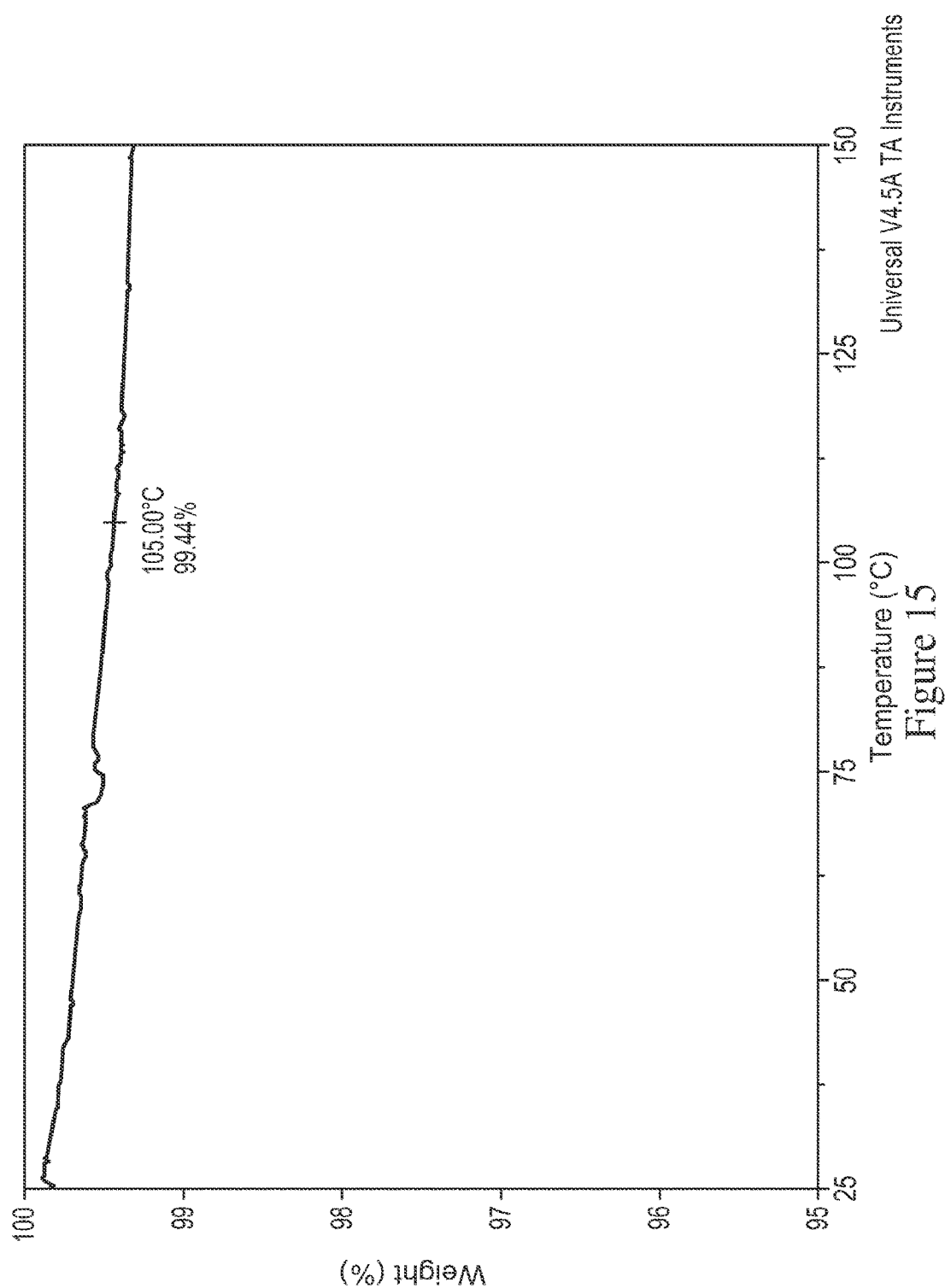
FIG. 15 is a TGA thermogram of (2S,3S)-2-amino-3-methyl-N-(2-morpholinoethyl)-pentanamide tetra(monohydrogensulfate), monosulfate.
Figure 16A:
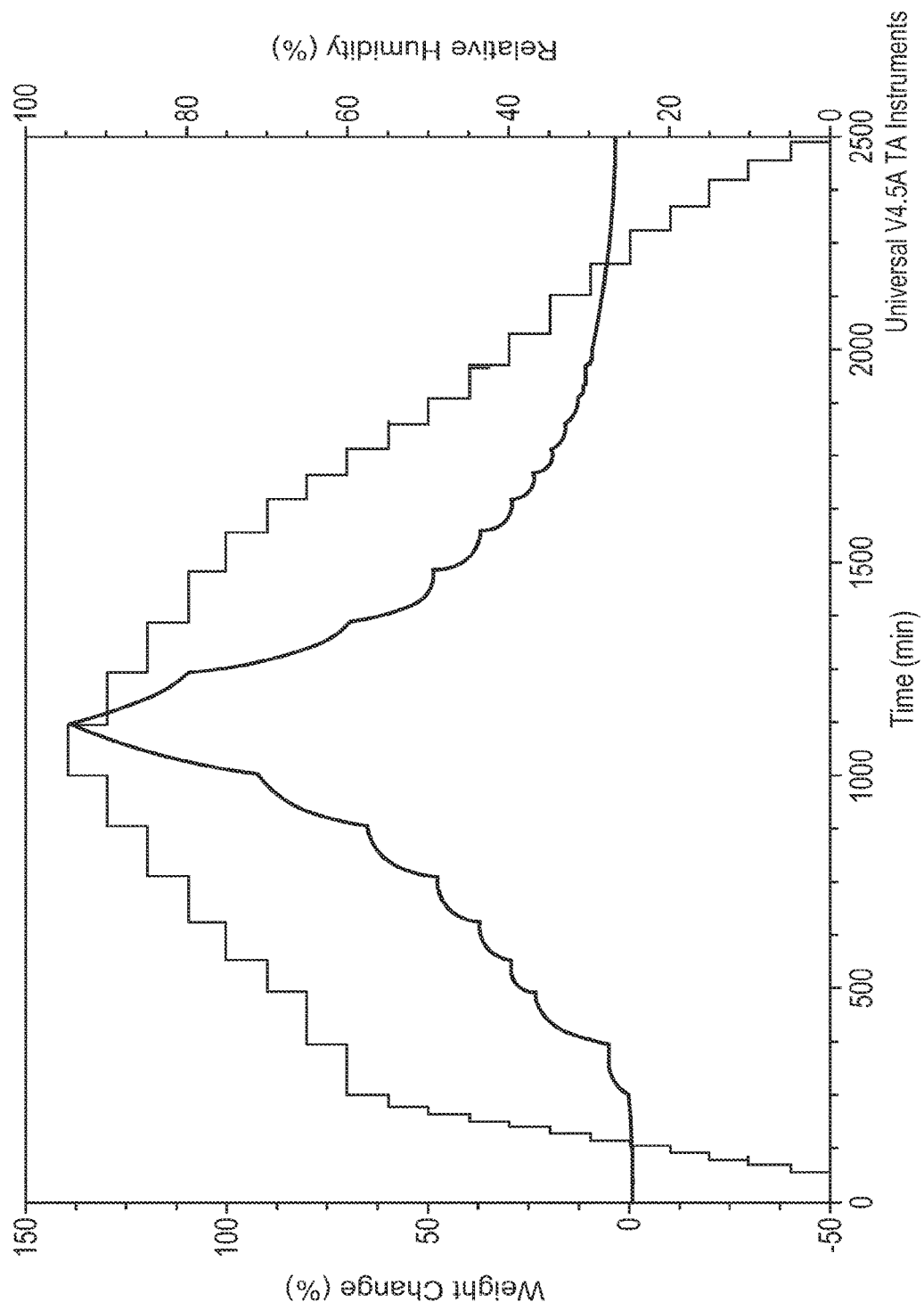
FIGS. 16A and 16B are DVS plots of (2S,3S)-2-amino-3-methyl-N-(2-morpholinoethyl)-pentanamide tetra(monohydrogensulfate), monosulfate.
Figure 16B:
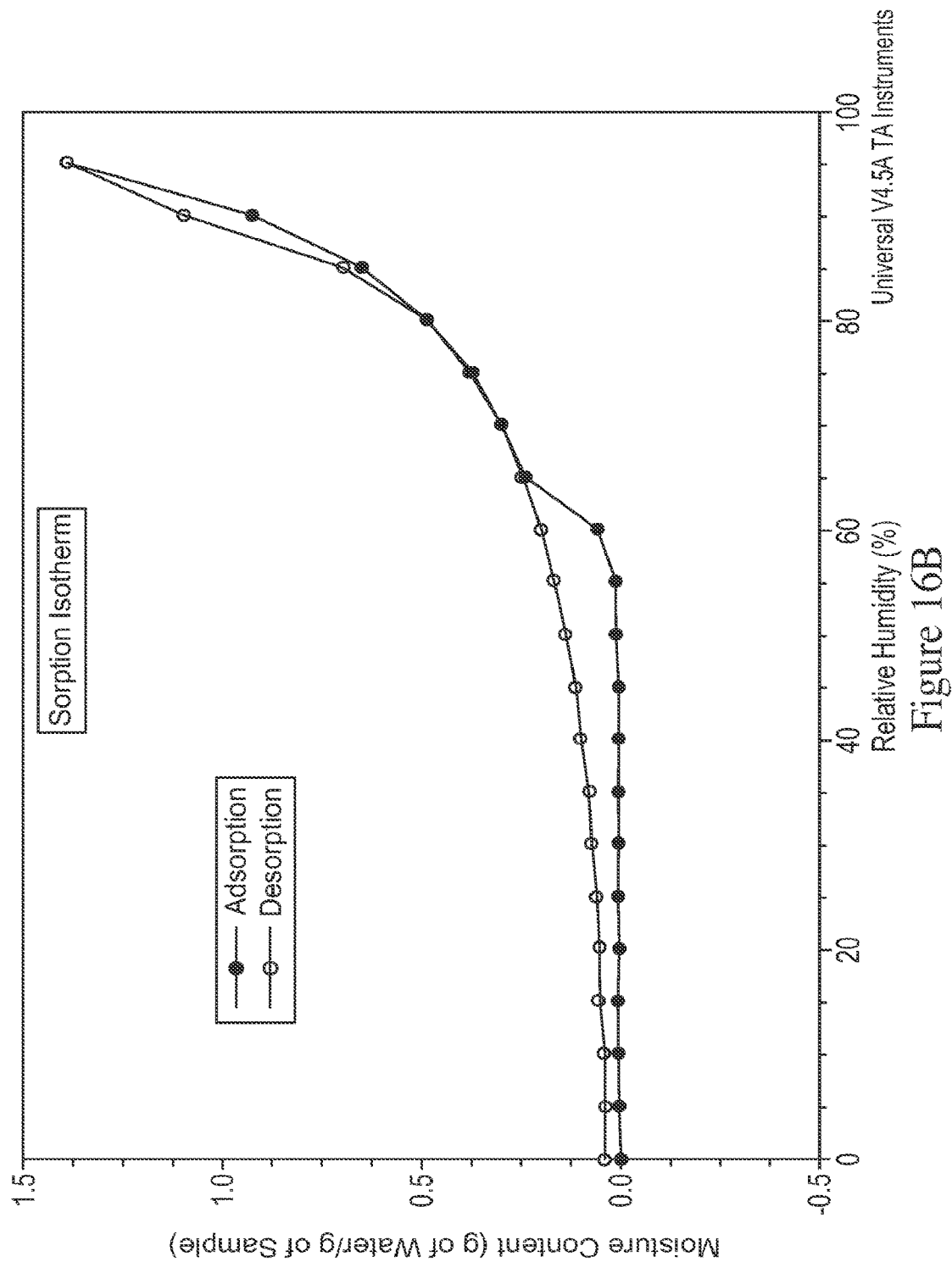
Figure 17:
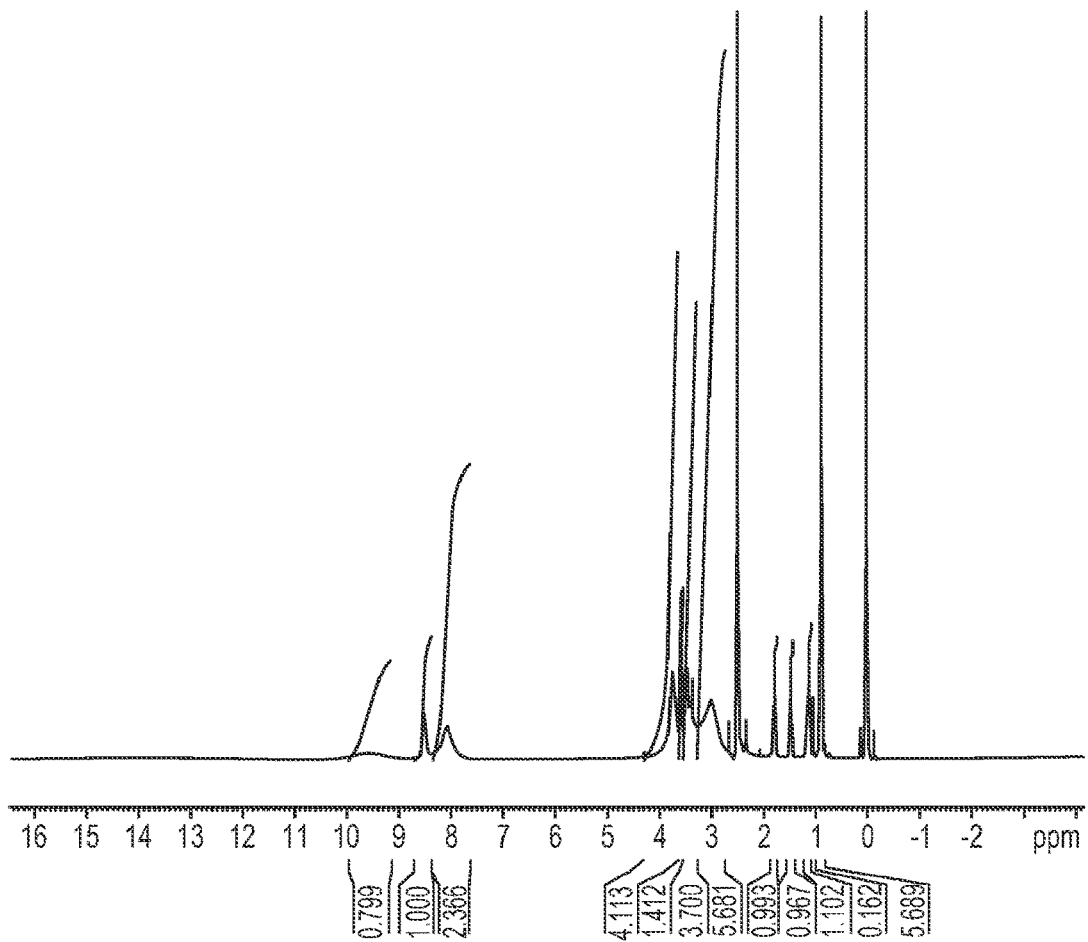
FIG. 17 is a H-NMR spectrum of (2S,3S)-2-amino-3-methyl-N-(2-morpholinoethyl)-pentanamide tetra(monohydrogensulfate), monosulfate.

XRD indicated the tetra(monohydrogensulfate), monosulfate material is crystalline as shown in FIG. 13 and is different from free base. The DSC (FIG. 14) shows a broad endotherm with extrapolated onset temperature of 210° C., peak temperature of 228° C., which appears to be accompanied by decomposition. The TGA (FIG. 15) shows tetra (monohydrogensulfate), monosulfate material has less than 0.7 wt % loss at 105° C., indicating the isolated sample was dry. Hot stage microscopy data revealed the material completely melted near 220° C. followed by immediate discoloration and the formation of bubbles, confirming the material is decomposing upon melting. The moisture sorption-desorption isotherm (FIGS. 16A and 16B) was collected using dynamic vapor sorption (DVS) analysis. The tetra (monohydrogensulfate), monosulfate does not sorbs much water from 0% to 60% RH under the experimental conditions, then it shows rapid sorption up to 140 wt % water at 95% RH. In the desorption phase, the tetra(monohydrogensulfate), monosulfate material shows a rapid desorption from 95% to 80% RH, then the sample desorbs at a relatively slow pace to a mass about 4 wt % greater than the original value at 0% RH. The behavior of this sample was similar to all the other samples. Apparent deliquescence at high humidity followed by glass formation upon evaporation. A hydrate may also form near 60% RH. Some additional scans stopping at humidifies before deliquescence may yield some additional insight into the behavior of the putative hydrate. Proton NMR and Raman spectra of this sample are given in FIGS. 17 and 18A and 18B, respectively. The tetra(monohydrogensulfate), monosulfate was found to have high solubility in water (>3M/mL) at ambient temperature.

Example 5. Preparation of (2S,3S)-2-amino-3-methyl-N-(2-morpholinoethyl)-pentanamide Digluconate The digluconate salt was prepared by using the same procedure described in Example 3 except that sulfuric acid was replaced by gluconic acid and the molar ratio of the free base to gluconic acid is 1:2.

Alternatively, the free base as prepared in Example 2 was dissolved in methanol, and a portion of this solution was transferred to provide 2 mg equivalent of free base. Gluconic acid was dissolved or suspended in EtOH/Heptane or THF/Heptane. The free base and gluconic acid solutions/suspensions (providing 1:2 molar ratio of free base and gluconic acid) were mixed, and the resulting mixture solutions were dried under nitrogen purge at ambient temperature to provide the desired digluconate salts as dry powdery solids.

Figure 21:
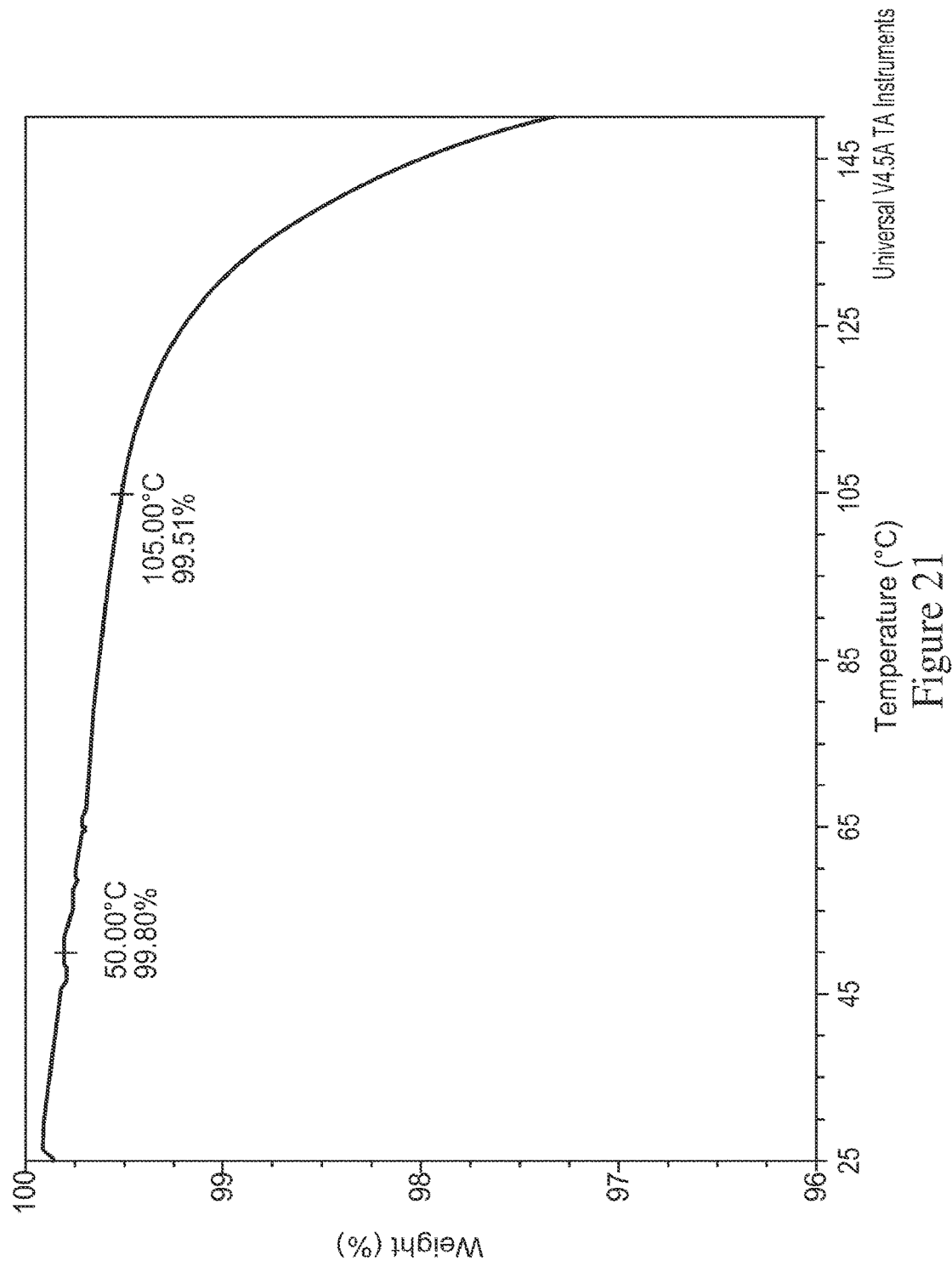
FIG. 21 is a TGA thermogram of (2S,3S)-2-amino-3-methyl-N-(2-morpholinoethyl)-pentanamide digluconate.
Figure 22A:
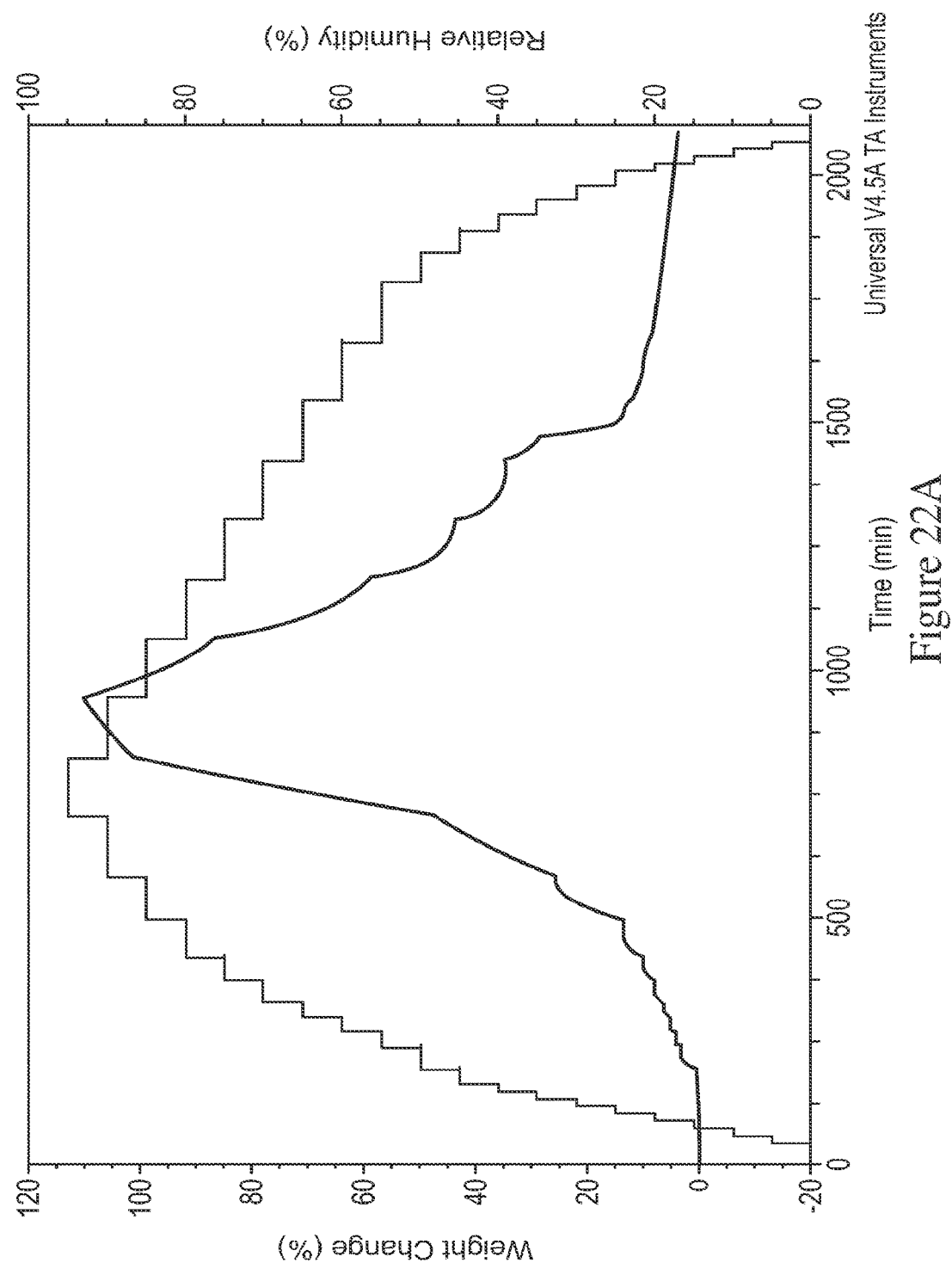
FIGS. 22A and 22B are DVS plots of (2S,3S)-2-amino-3-methyl-N-(2-morpholinoethyl)-pentanamide digluconate.
Figure 22B:
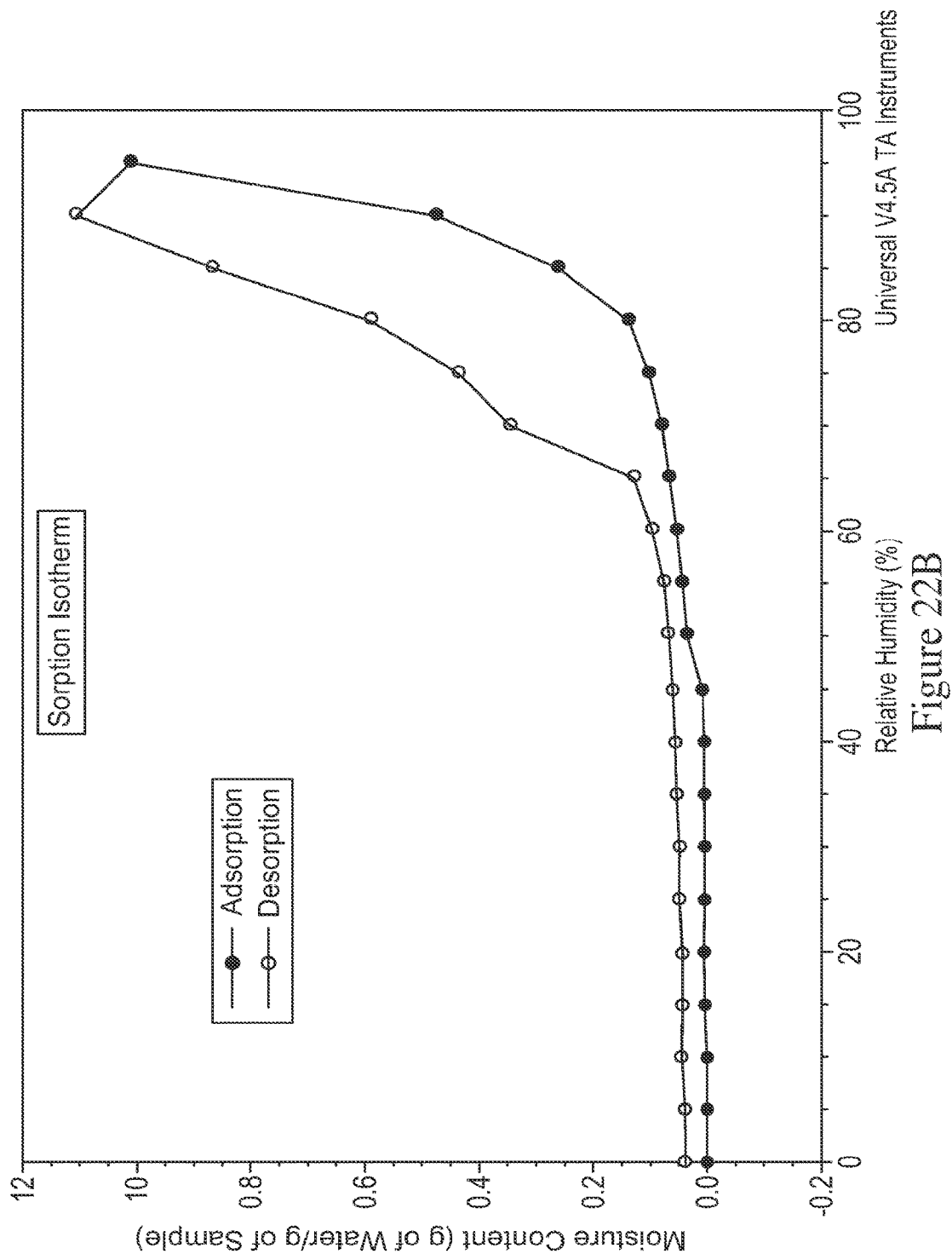
Figure 23:
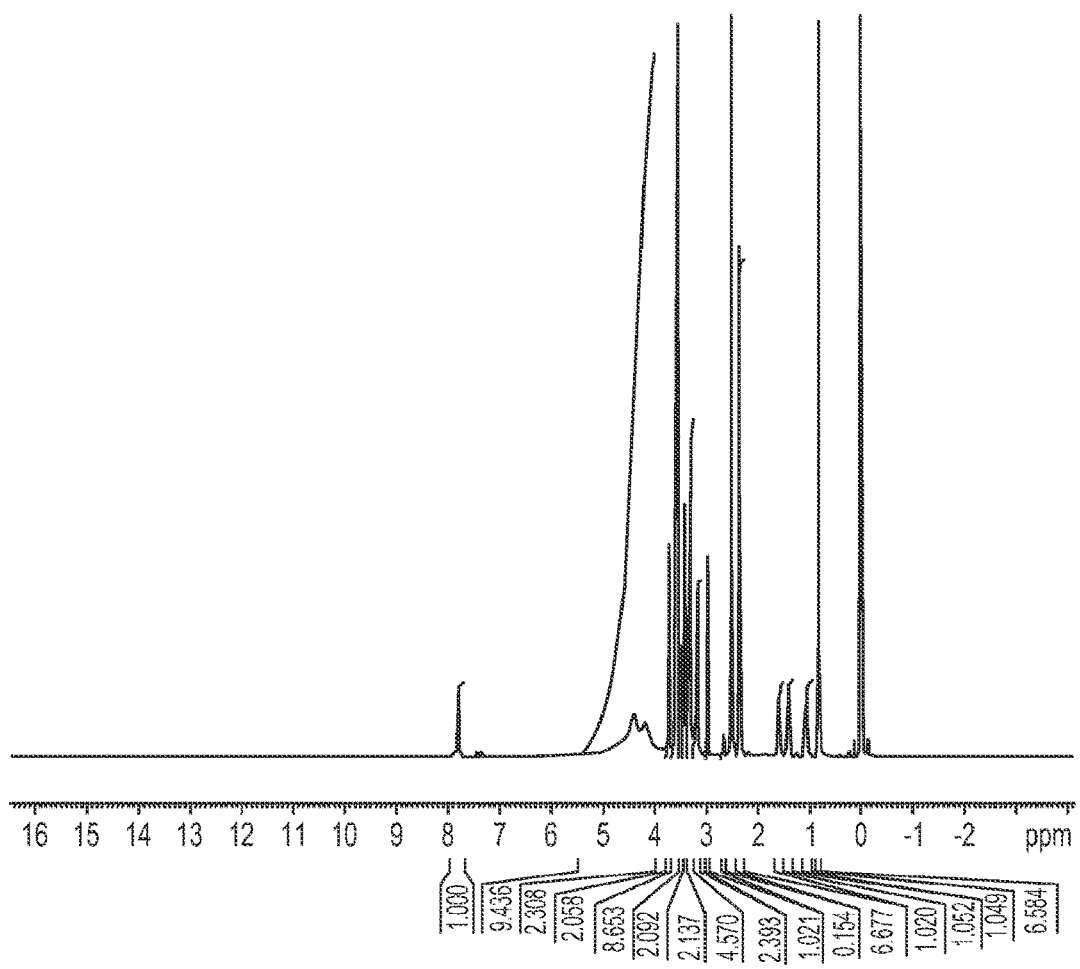
FIG. 23 is a H-NMR spectrum of (2S,3S)-2-amino-3-methyl-N-(2-morpholinoethyl)-pentanamide digluconate.
Figure 24A:
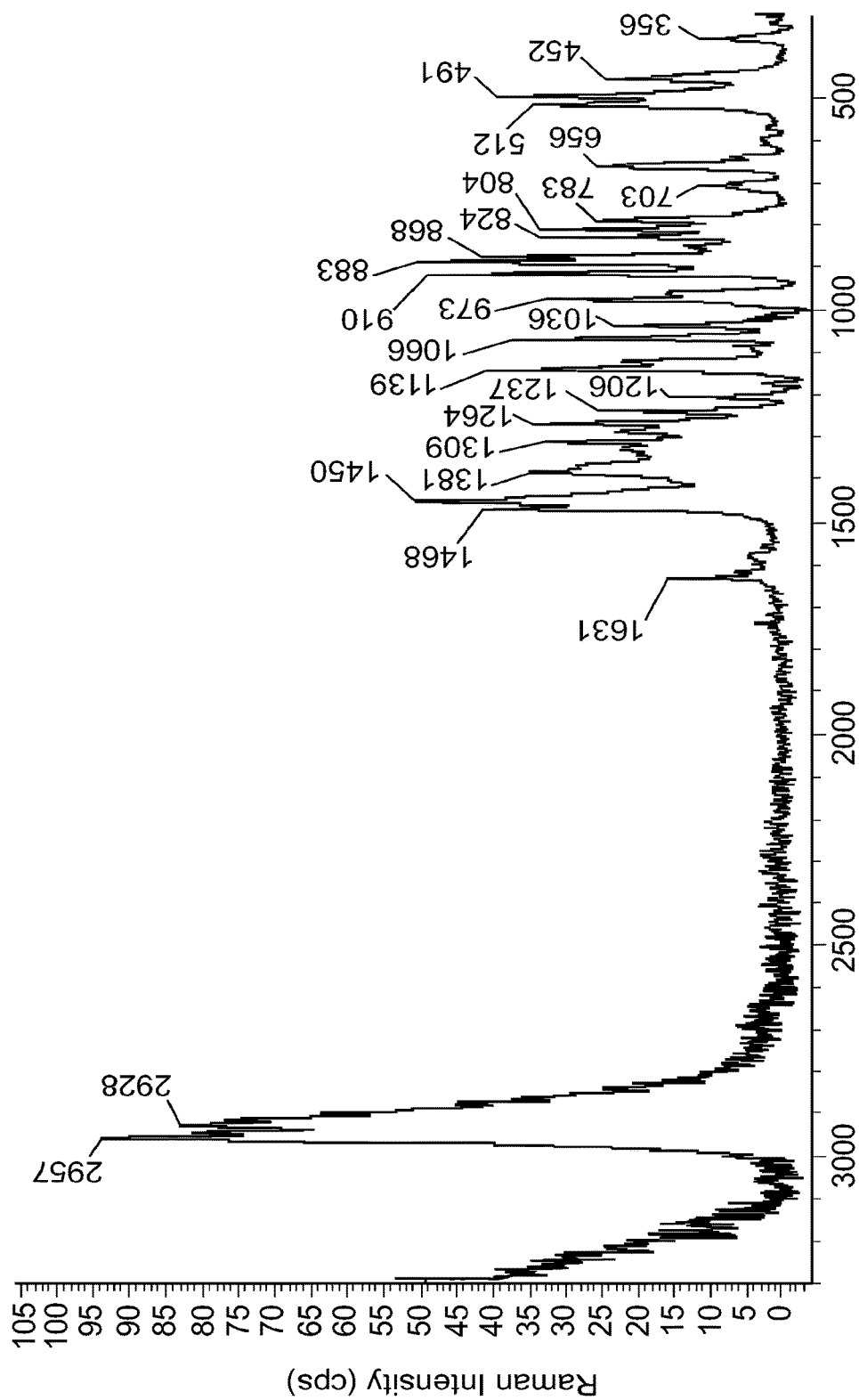
FIGS. 24A and 24B are Raman spectrum of (2S,3S)-2-amino-3-methyl-N-(2-morpholinoethyl)-pentanamide digluconate.
Figure 24B:
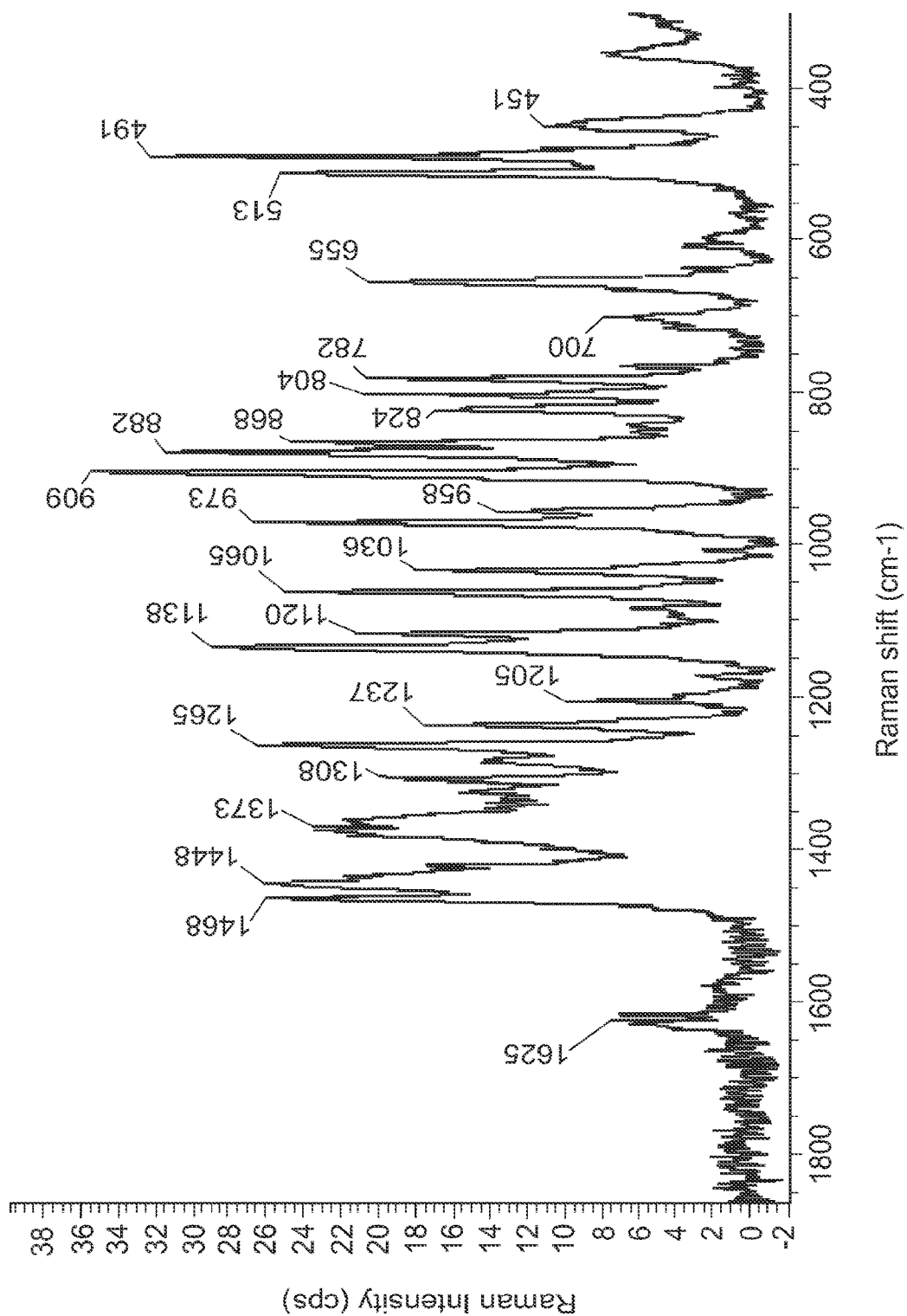

XRD indicated the material is crystalline and exhibits a different pattern from the free base as shown in FIG. 19. The DSC (FIG. 20) shows a small but sharp endotherm with an extrapolated onset of 50° C., followed by a sharp melting endotherm with an extrapolated onset of 180° C. which was followed by decomposition. The TGA (FIG. 21) shows a 0.5 wt % loss at about 105° C., suggesting the salt specimen was relatively dry. Hot stage microscopy data suggest a possible phase transformation at about 50° C. The material was observed to melt at about 178° C. Additional studies to confirm that the 50° C. endotherm is a solid transformation and not simply melting of residual free base should be considered. The moisture sorption-desorption isotherm (FIGS. 22A and 22B) was collected using dynamic vapor sorption (DVS) analysis. The digluconate salt did not adsorb much moisture from 0% to 45% RH under the experimental conditions, then it shows rapid sorption behavior up to 110 wt % moisture at 95% RH. In the desorption phase, the digluconate salt shows two distinct phases: rapid desorption from 95% to 65% RH, then the sample desorbs at a relatively slow pace to a mass about 4 wt % greater than the original value at 0% RH. This material appears to have deliquesced and then evaporated to a glassy substance during the desorption segment. The proton NMR and Raman spectra of the digluconate salt sample are shown in FIGS. 23 and 24A and 24B respectively. The digluconate salt was found to have high solubility in water (>30 mg/mL) like all of the specimens examined during the current study.

Example 6. Preparation of (2S,3S)-2-amino-3-methyl-N-(2-morpholinoethyl)-pentanamide Dimesylate The dimesylate salt was prepared by using the same procedure described in Example 3 except that sulfuric acid was replaced by methanesulfonic acid and the molar ratio of the free base to methanesulfonic acid is 1:2.

Alternatively, the free base as prepared in Example 2 was dissolved in methanol, and a portion of this solution was transferred to provide 2 mg equivalent of free base. Methanesulfonic acid was dissolved or suspended in EtOH/Heptane or THF/Heptane. The free base and methanesulfonic acid solutions/suspensions (providing 1:2 molar ratio of free base and methanesulfonic acid) were mixed, and the resulting mixture solutions were dried under nitrogen purge at ambient temperature to provide the desired dimesylate salts as dry powdery solids.

Figure 26B:
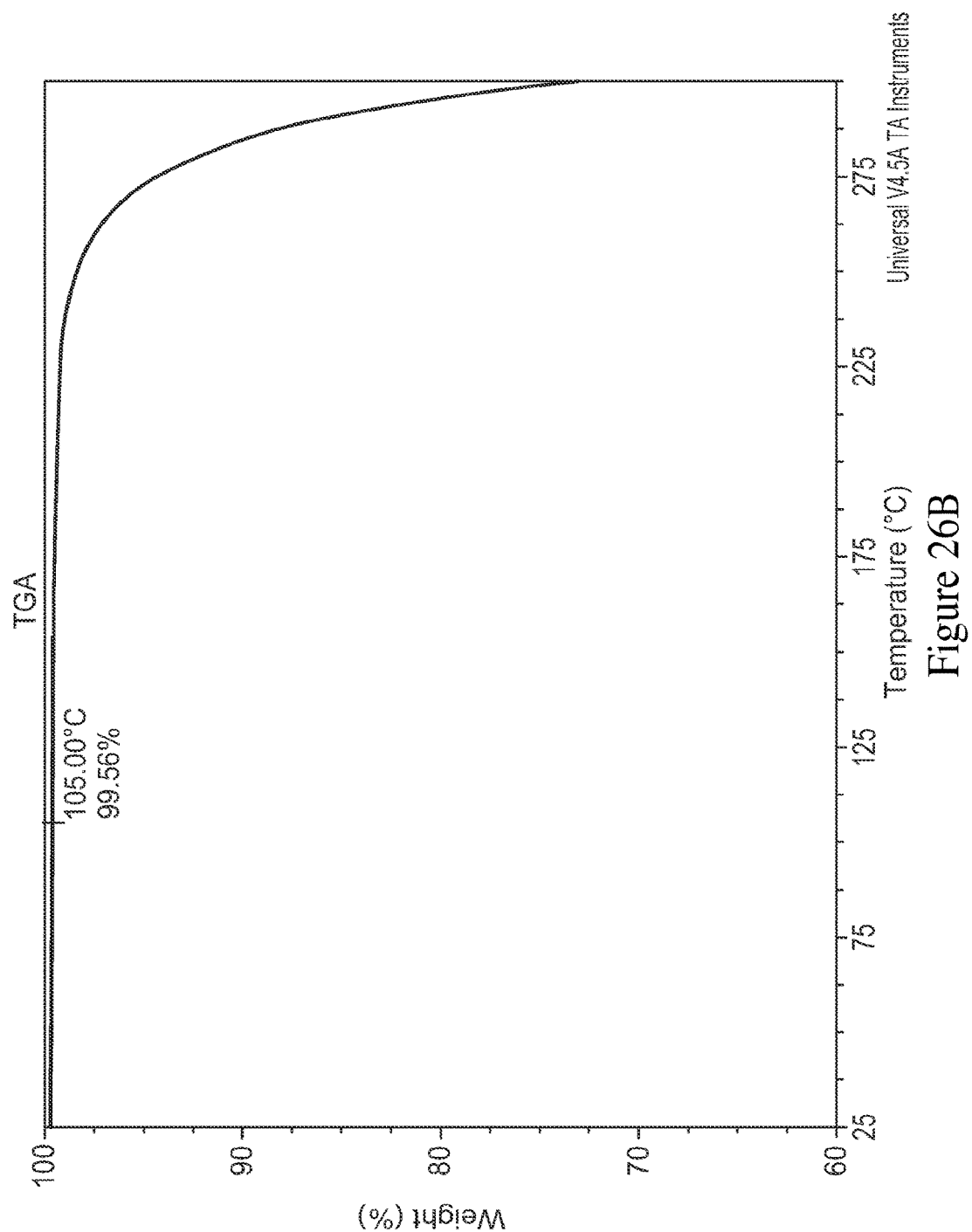
FIG. 26B is a TGA thermogram of (2S,3S)-2-amino-3-methyl-N-(2-morpholinoethyl)-pentanamide dimesylate.
Figure 27A:
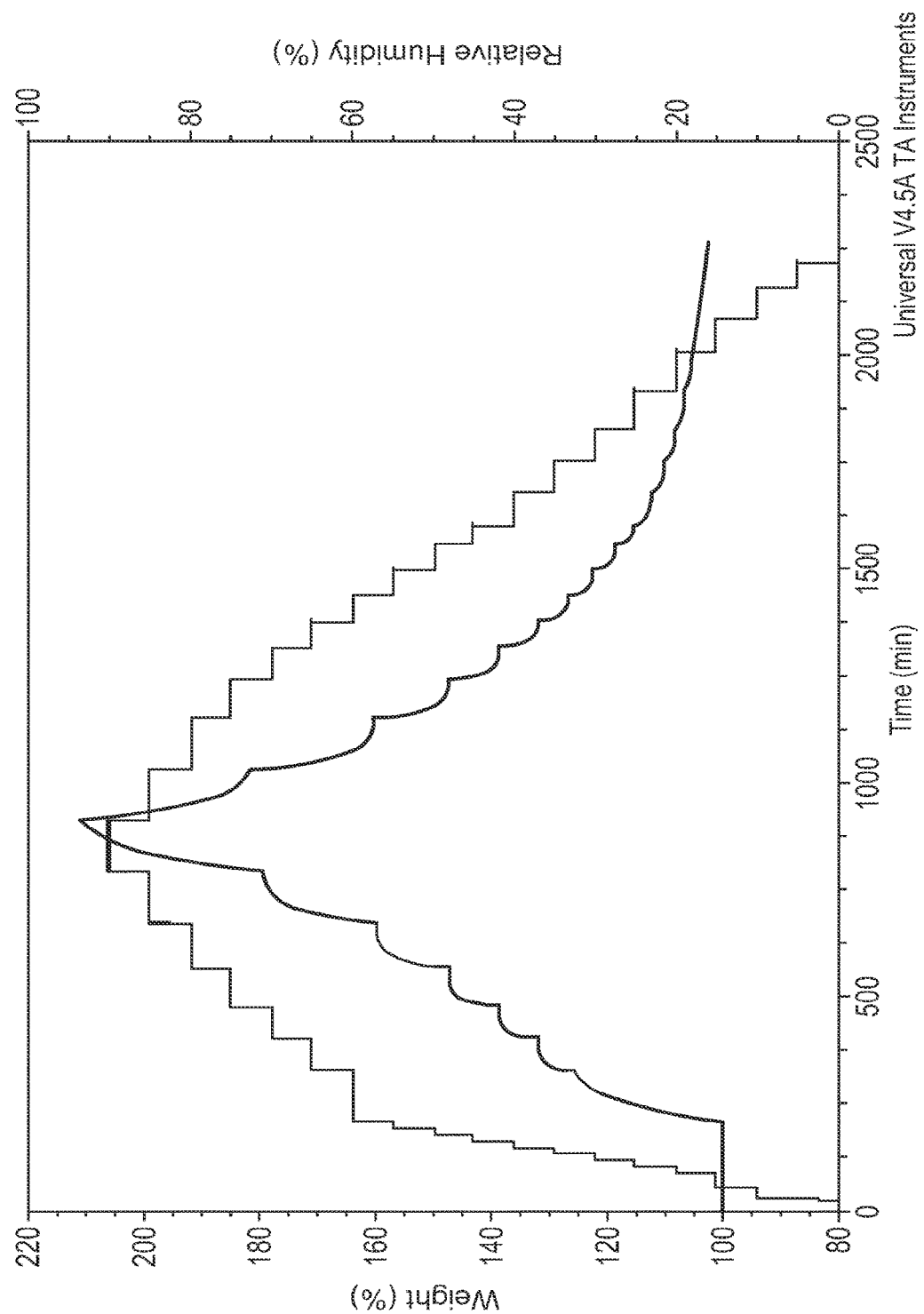
FIGS. 27A and 27B are DVS plots of (2S,3S)-2-amino-3-methyl-N-(2-morpholinoethyl)-pentanamide dimesylate.
Figure 27B:
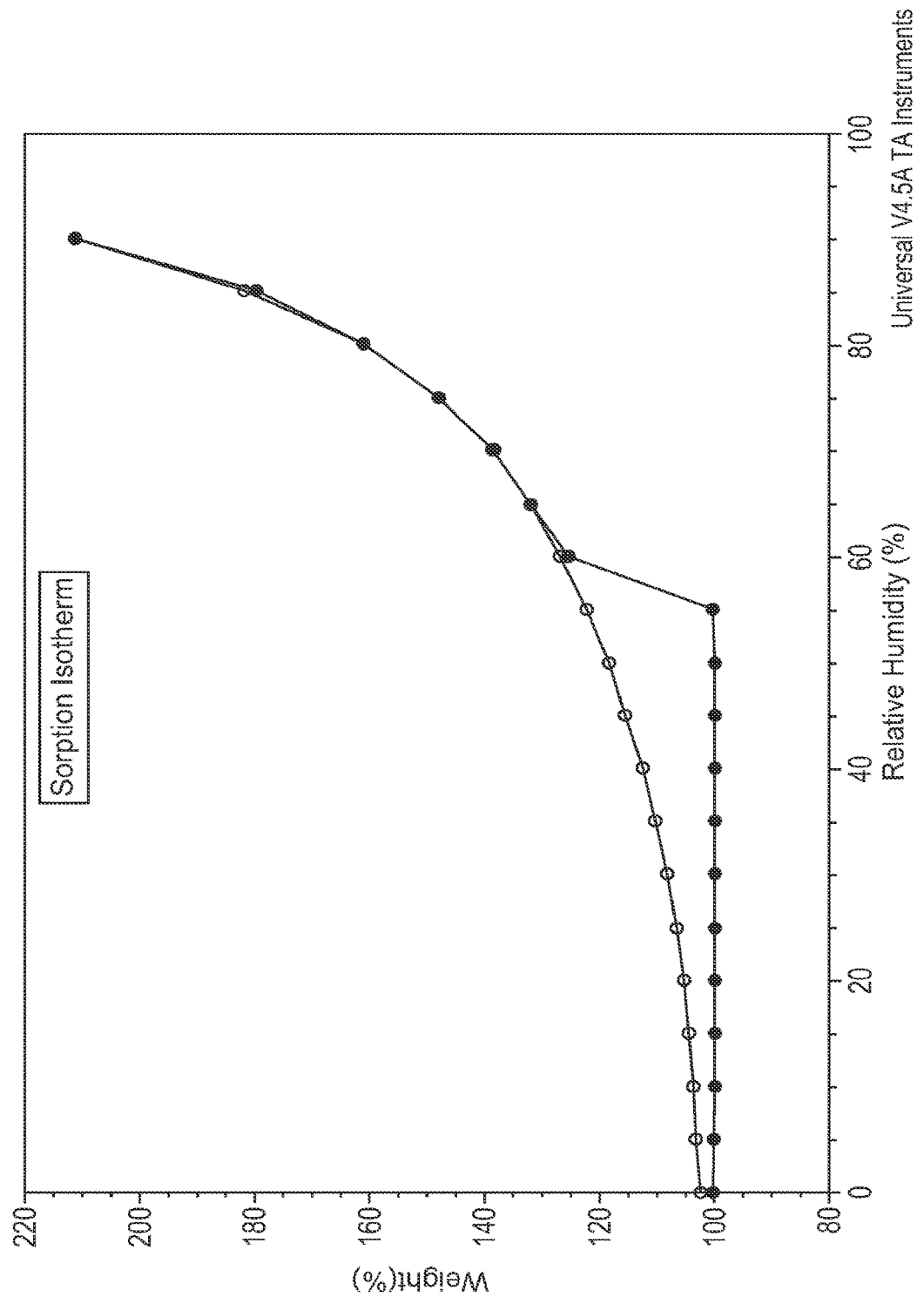
Figure 28:
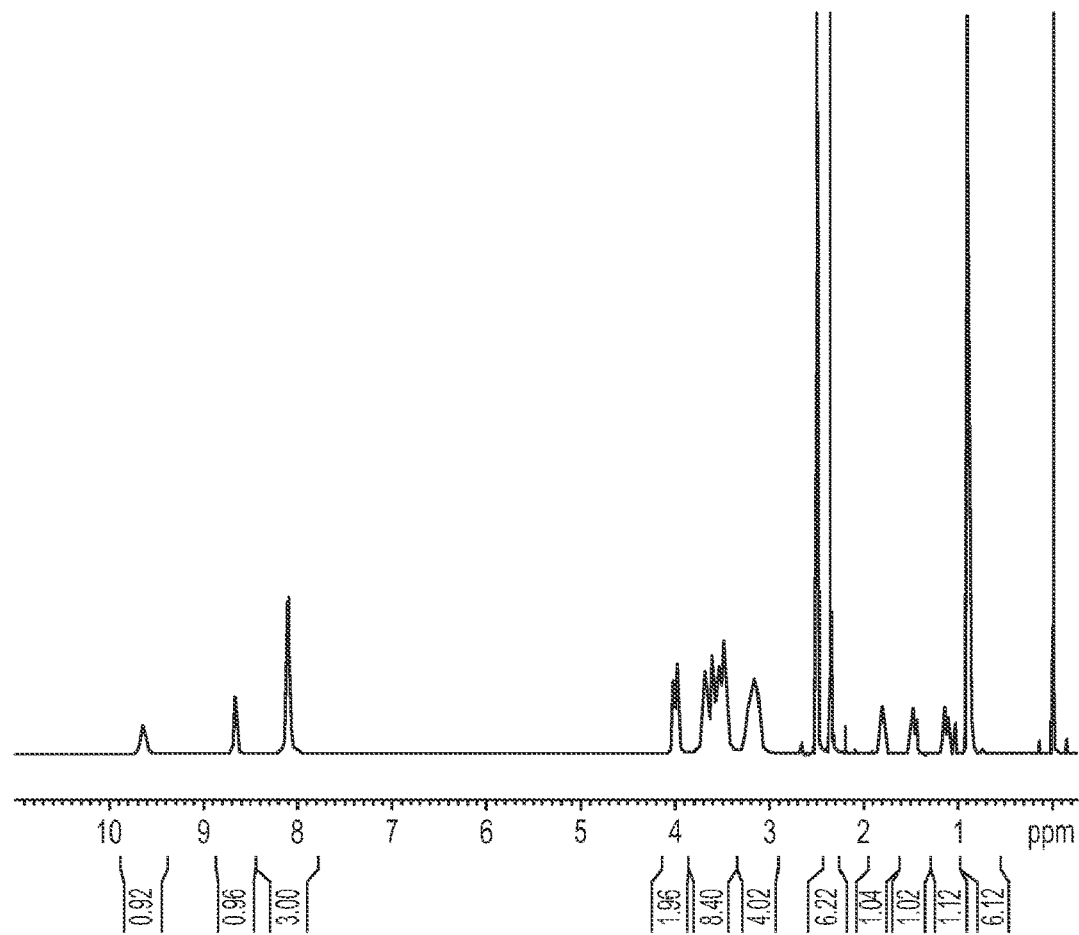
FIG. 28 is a H-NMR spectrum of (2S,3S)-2-amino-3-methyl-N-(2-morpholinoethyl)-pentanamide dimesylate.
Figure 29:
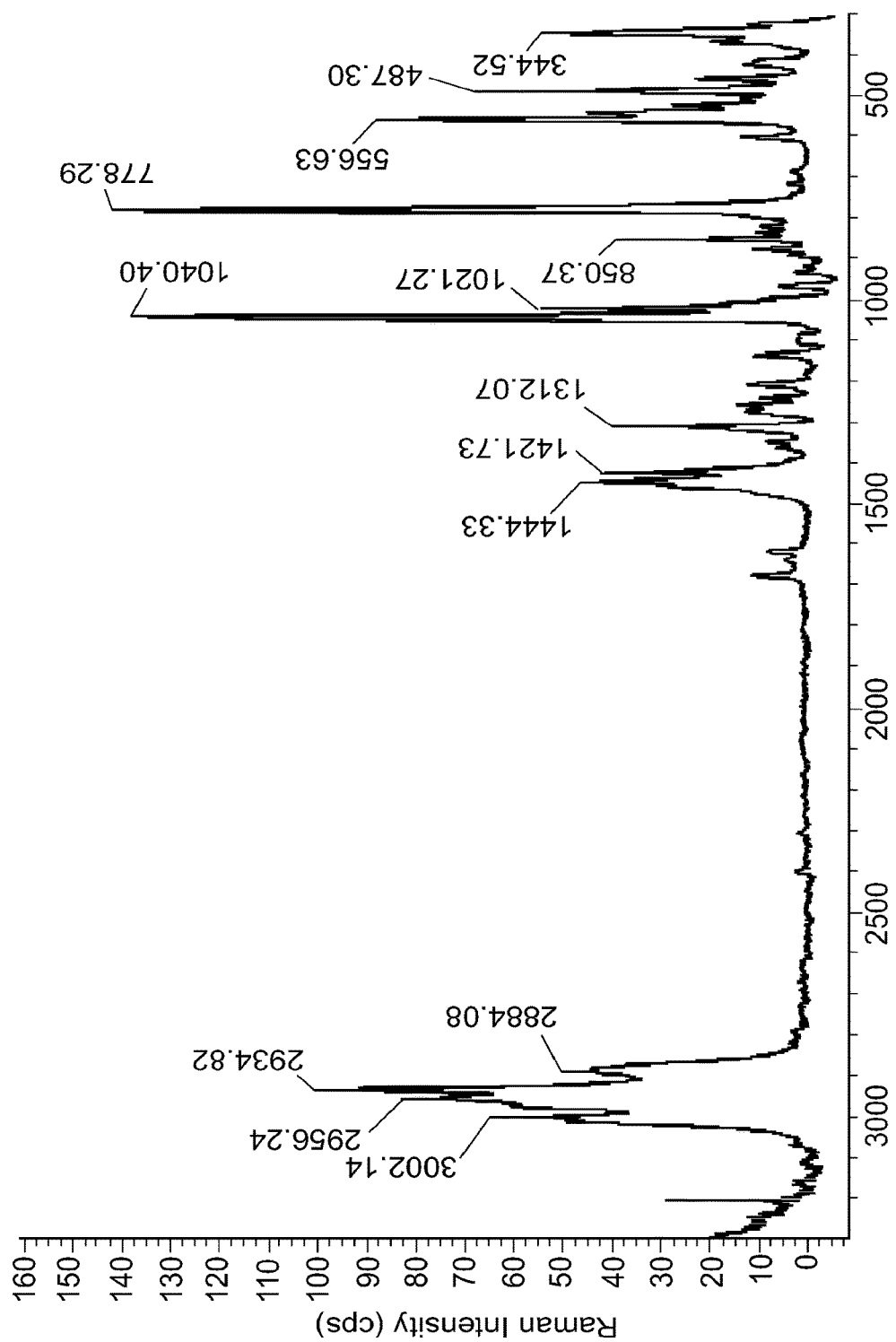
FIG. 29 is Raman spectrum of (2S,3S)-2-amino-3-methyl-N-(2-morpholinoethyl)-pentanamide dimesylate.

XRD indicated the material is nicely crystalline and exhibits a different pattern from the free base, as shown in FIG. 25. The DSC (FIG. 26A) shows a sharp melting endotherm with an extrapolated onset of 180° C. which was followed by decomposition at approximately 250° C. The TGA (FIG. 26B) shows a 0.5 wt % loss at about 105° C., suggesting the salt specimen was relatively dry. Hot stage microscopy data suggest the material was observed to melt at about 178° C. The moisture sorption-desorption isotherm (FIGS. 27A and 27B) was collected using dynamic vapor sorption analysis. The dimesylate salt did not adsorb much moisture from 0% to 55% RH under the experimental conditions, then it shows rapid sorption behavior up to 110 wt % moisture at 95% RH. In the desorption phase, the dimesylate salt shows two distinct phases: rapid desorption from 95% to 65% RH, then the sample desorbs at a relatively slow pace to a mass about 3 wt % greater than the original value at 0% RH. The proton NMR and Raman spectra of the dimesylate salt sample are shown in FIGS. 28 and 29, respectively. The dimesylate salt was found to have high solubility in water (≥28 mg/mL).

Example 7. Preparation of (2S,3S)-2-amino-3-methyl-N-(2-morpholinoethyl)-pentanamide Ditosylate The ditosylate salt was prepared by using the same procedure described in Example 3 except that sulfuric acid was replaced by p-toluenesulfonic acid and the molar ratio of the free base to p-toluenesulfonic acid is 1:2.

Alternatively, the free base as prepared in Example 2 was dissolved in methanol, and a portion of this solution was transferred to provide 2 mg equivalent of free base. Toluenesulfonic acid was dissolved or suspended in EtOH/Heptane or THF/Heptane. The free base and p-toluenesulfonic acid solutions/suspensions (providing 1:2 molar ratio of free base and p-toluenesulfonic acid) were mixed, and the resulting mixture solutions were dried under nitrogen purge at ambient temperature to provide the desired ditosylate salts as dry powdery solids.

Figure 31B:
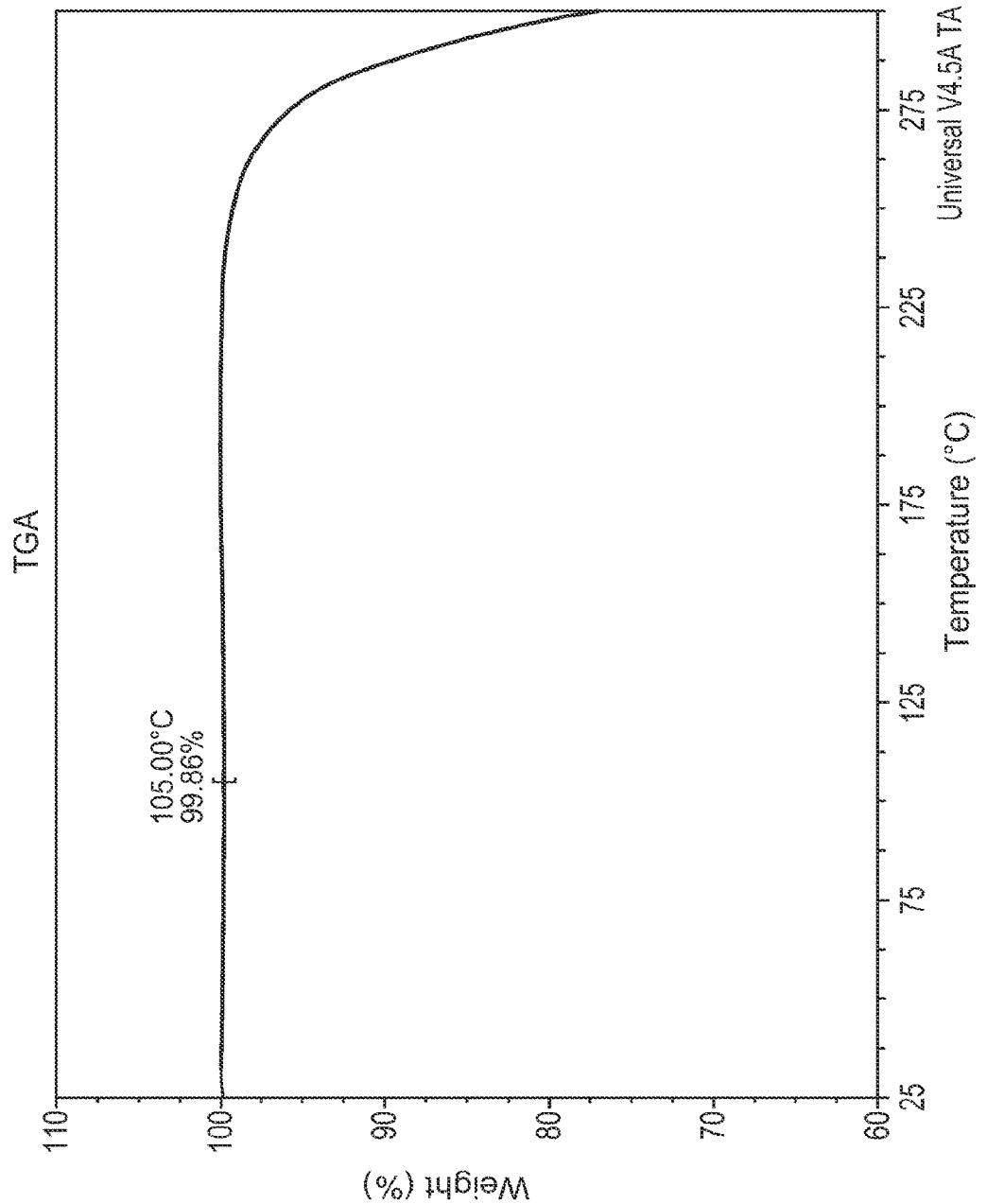
FIG. 31B is a TGA thermogram of (2S,3S)-2-amino-3-methyl-N-(2-morpholinoethyl)-pentanamide ditosylate.
Figure 32A:
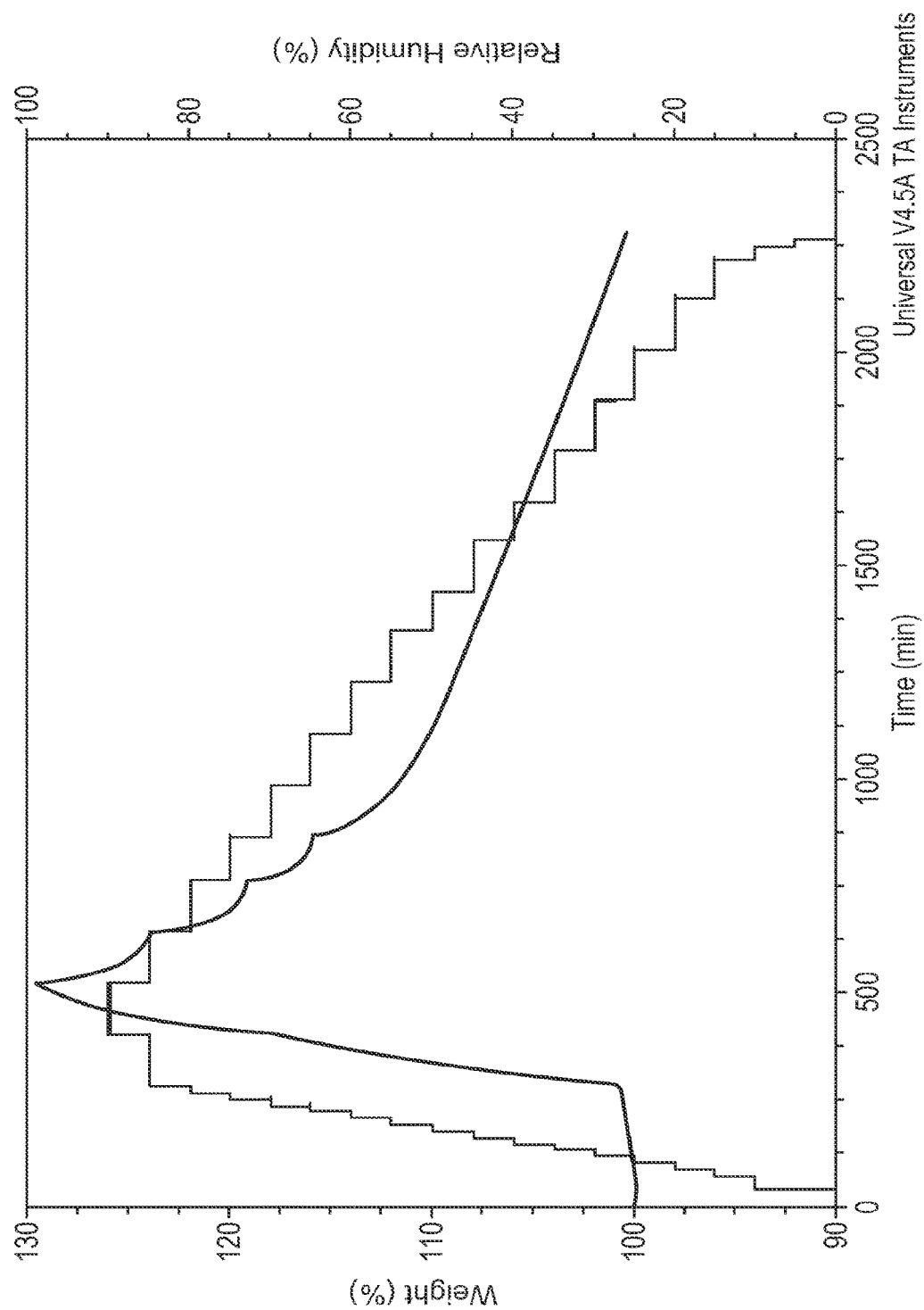
FIGS. 32A and 32B are DVS plots of (2S,3S)-2-amino-3-methyl-N-(2-morpholinoethyl)-pentanamide ditosylate.
Figure 32B:
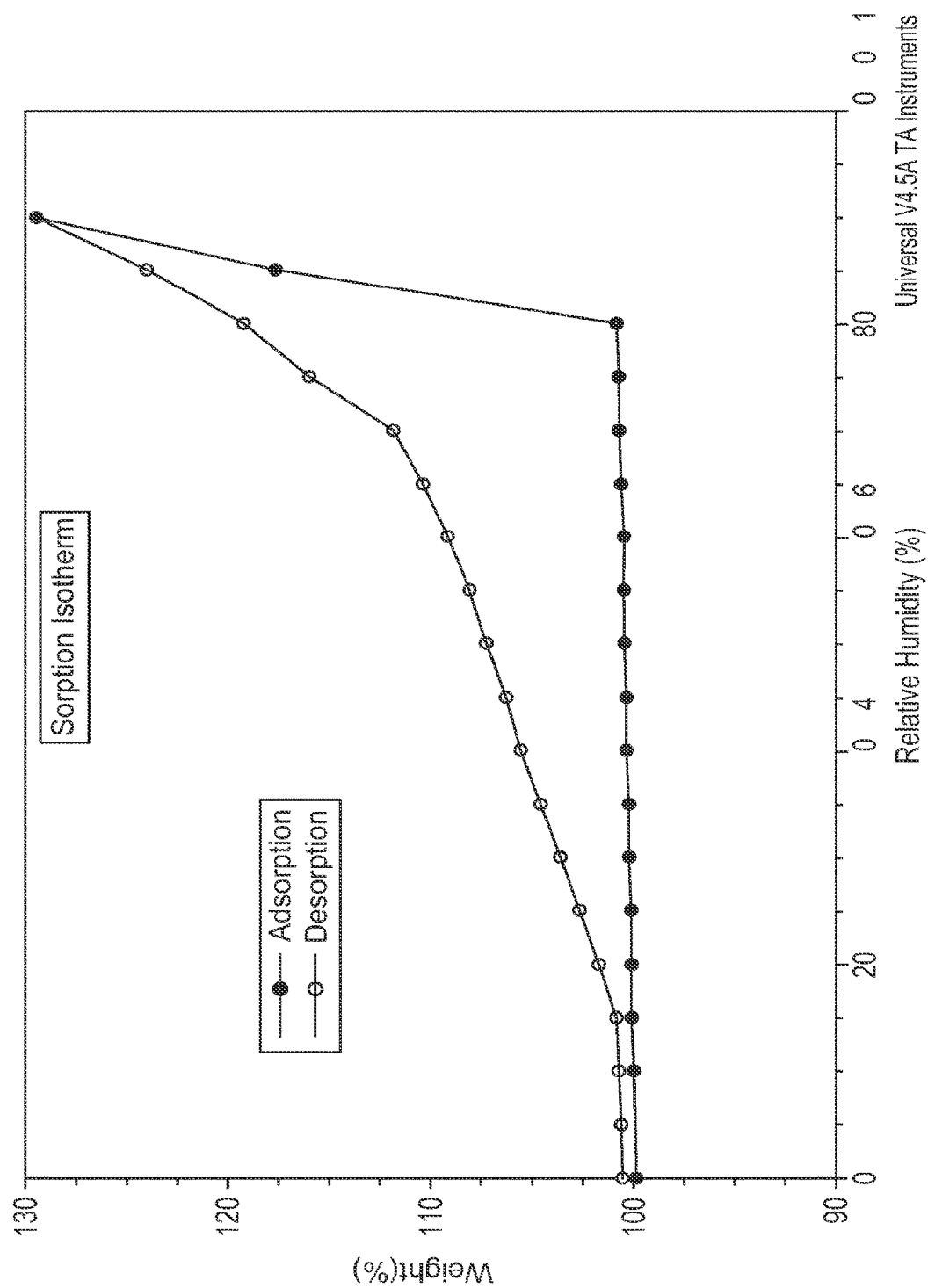
Figure 33:
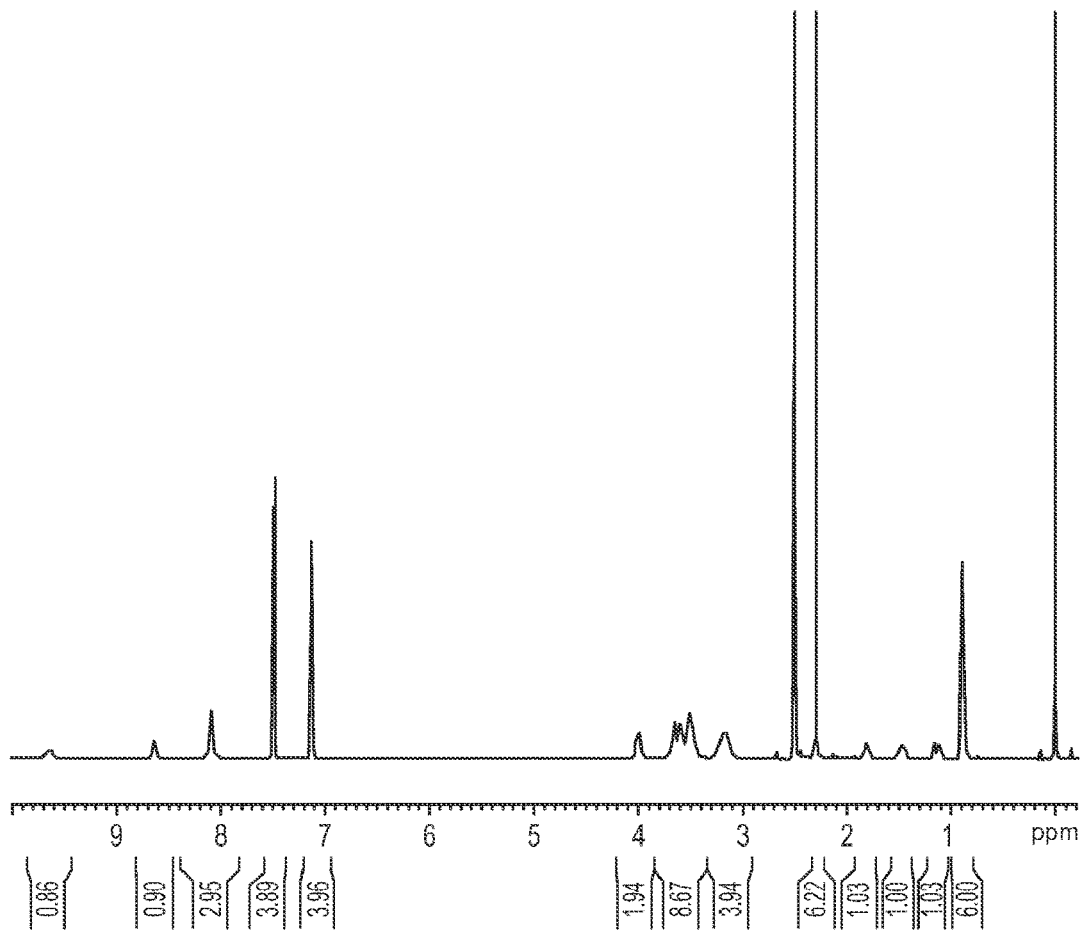
FIG. 33 is a H-NMR spectrum of (2S,3S)-2-amino-3-methyl-N-(2-morpholinoethyl)-pentanamide ditosylate.
Figure 34:
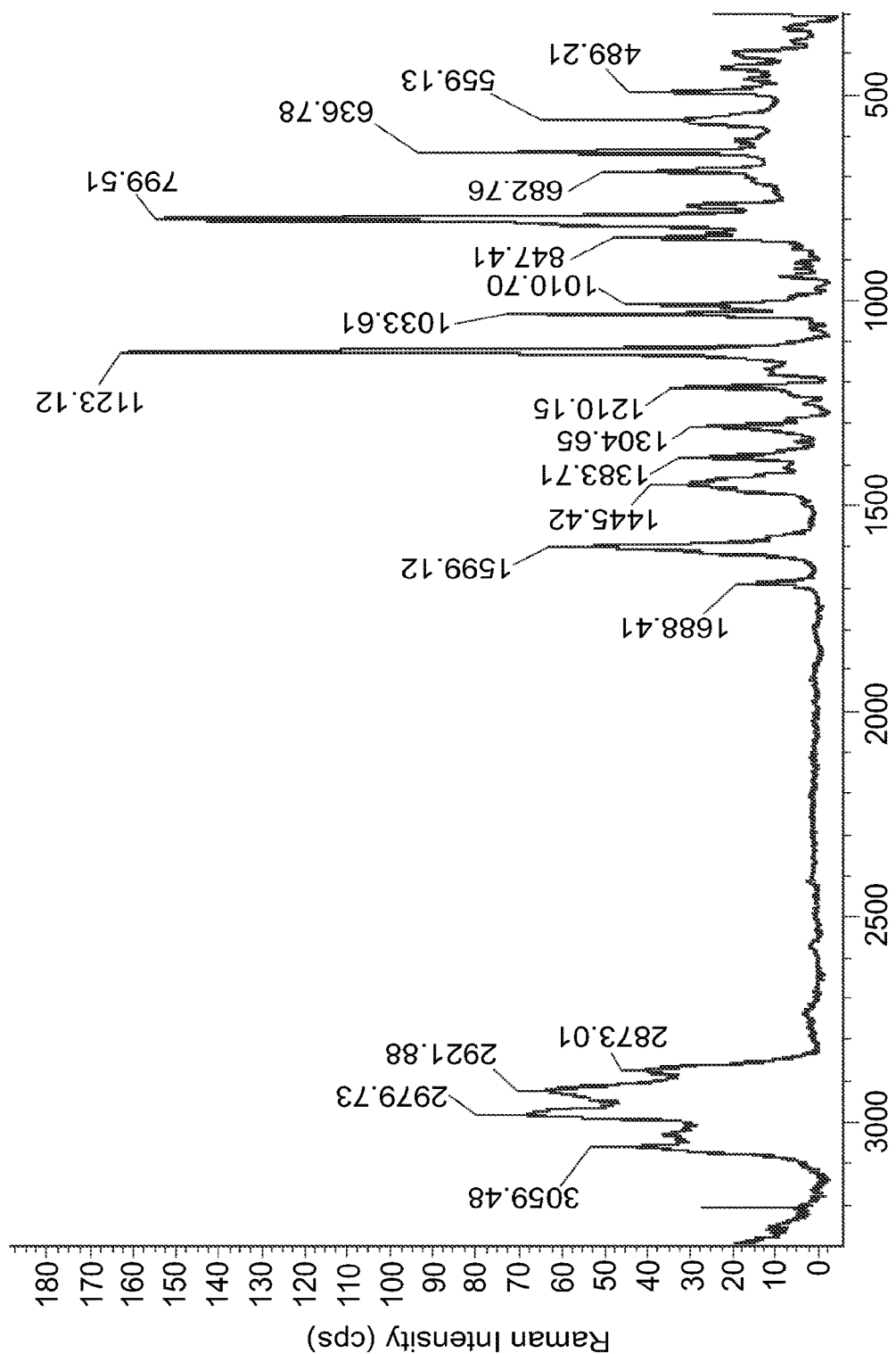
FIG. 34 is Raman spectrum of (2S,3S)-2-amino-3-methyl-N-(2-morpholinoethyl)-pentanamide ditosylate.

XRD indicated the material is nicely crystalline and exhibits a different pattern from the free base, as shown in FIG. 30. The DSC (FIG. 31A) shows a sharp melting endotherm with an extrapolated onset of 191° C. with a stable baseline. The TGA (FIG. 31B) shows approximately 0.2 wt % loss at about 105° C., suggesting the salt specimen was relatively dry. Hot stage microscopy data revealed the material melted at about 189° C. The moisture sorption-desorption isotherm (FIGS. 32A and 32B) collected using dynamic vapor sorption (DVS) analysis, did not adsorb much moisture from 0% to 80% RH under the experimental conditions, followed by a rapid sorption behavior up to 30 wt % moisture at 90% RH. In the desorption phase, this salt lost water rapidly at first then slowed down over the 70 to 20% RH range. This sample may form hydrates at high humidity. Additional studies should be done to examine the nature of this salt form. The proton NMR and Raman spectra of the ditosylate salt sample are shown in FIGS. 33 and 34, respectively. The ditosylate salt was found to have a low solubility in water (0.5-0.7 mg/mL) relative to the free base.

Example 8. Preparation of 2-amino-3-methyl-N-(2-morpholinoethyl)-pentanamide Dinapsylate The dinapsylate salt was prepared by using the same procedure described in Example 3 except that sulfuric acid was replaced by 2-naphthalenesulfonic acid and the molar ratio of the free base to 2-naphthalenesulfonic acid is 1:2.

Alternatively, the free base as prepared in Example 2 was dissolved in methanol, and a portion of this solution was transferred to provide 2 mg equivalent of free base. 2-Naphthalenesulfonic acid was dissolved or suspended in EtOH/Heptane or THF/Heptane. The free base and 2-naphthalenesulfonic acid solutions/suspensions (providing 1:2 molar ratio of free base and 2-naphthalenesulfonic acid) were mixed, and the resulting mixture solutions were dried under nitrogen purge at ambient temperature to provide the desired dinapsylate salts as dry powdery solids.

Figure 36B:
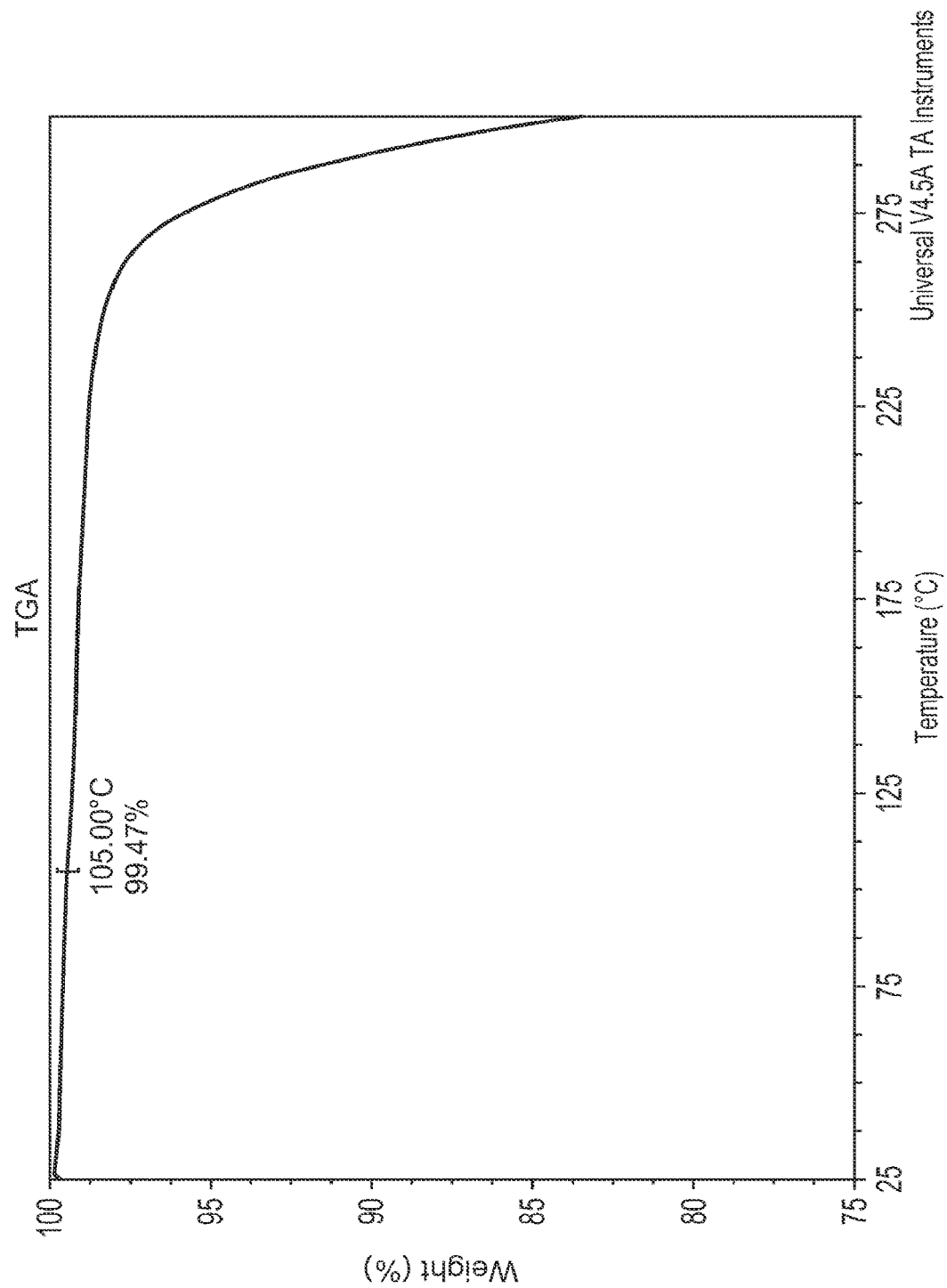
FIG. 36B is a TGA thermogram of (2S,3S)-2-amino-3-methyl-N-(2-morpholinoethyl)-pentanamide dinapsylate.
Figure 37A:
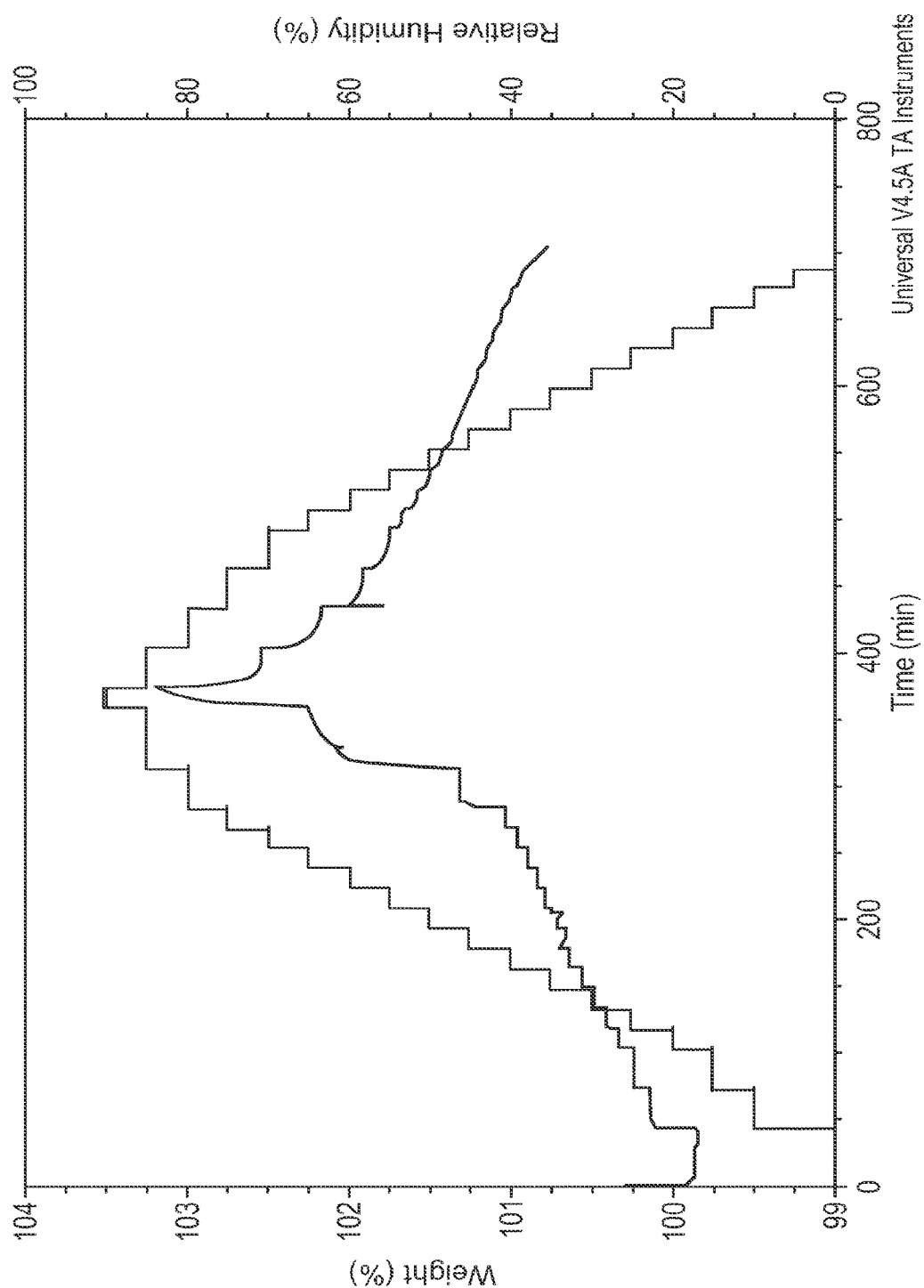
FIGS. 37A and 37B are DVS plots of (2S,3S)-2-amino-3-methyl-N-(2-morpholinoethyl)-pentanamide dinapsylate.
Figure 37B:
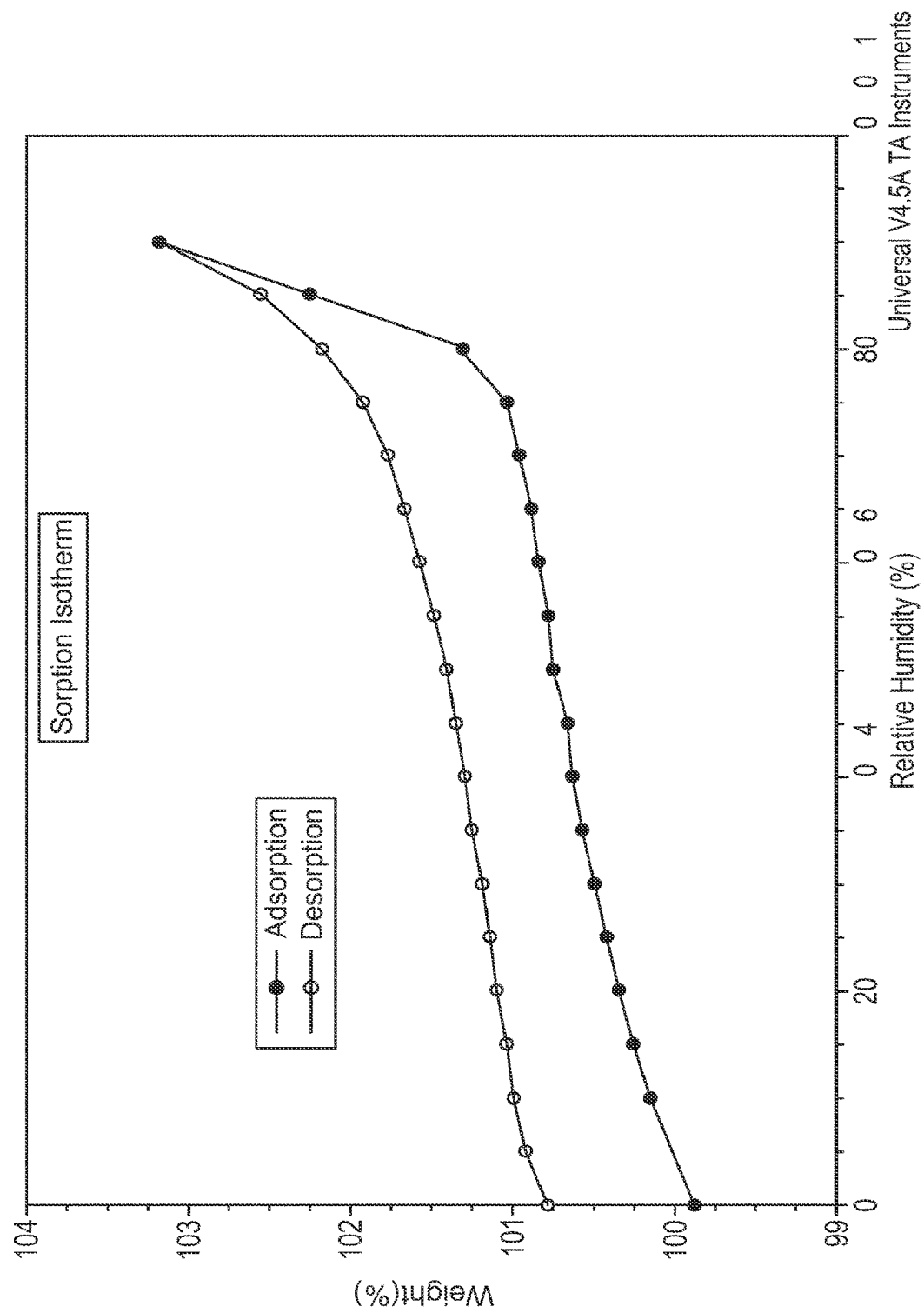
Figure 38:
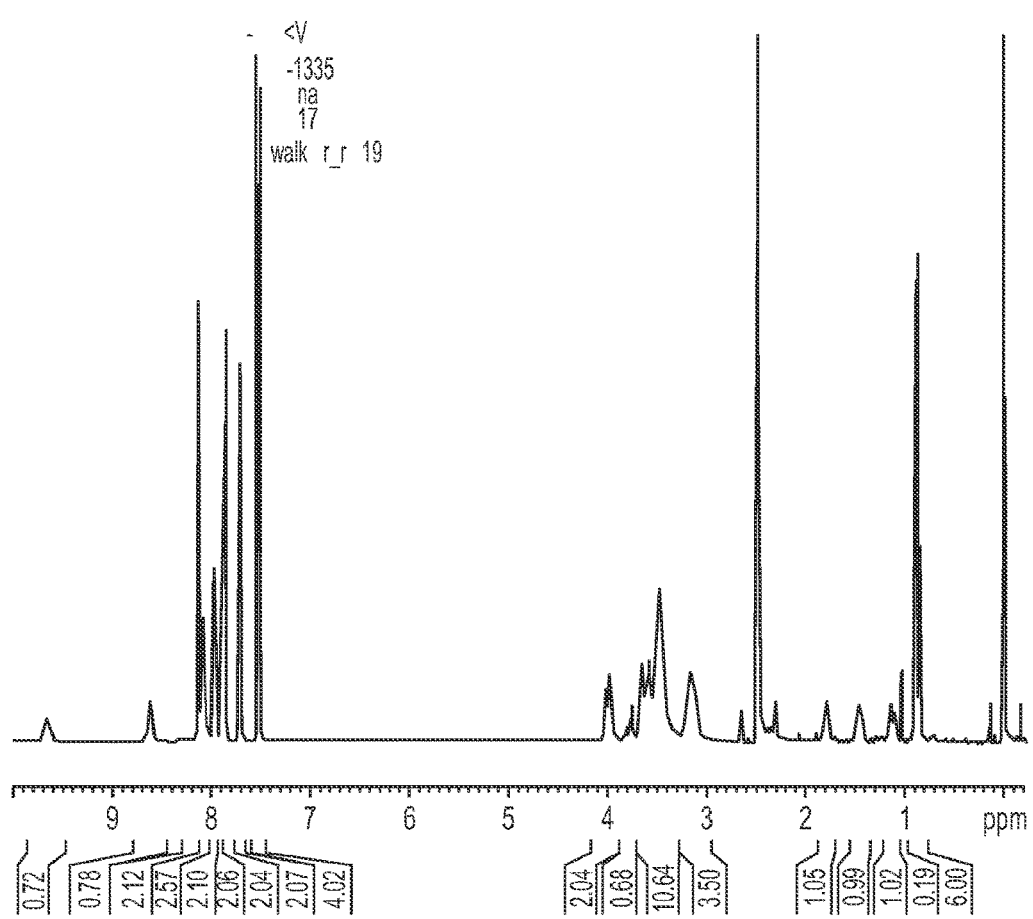
FIG. 38 is a H-NMR spectrum of (2S,3S)-2-amino-3-methyl-N-(2-morpholinoethyl)-pentanamide dinapsylate.
Figure 39:
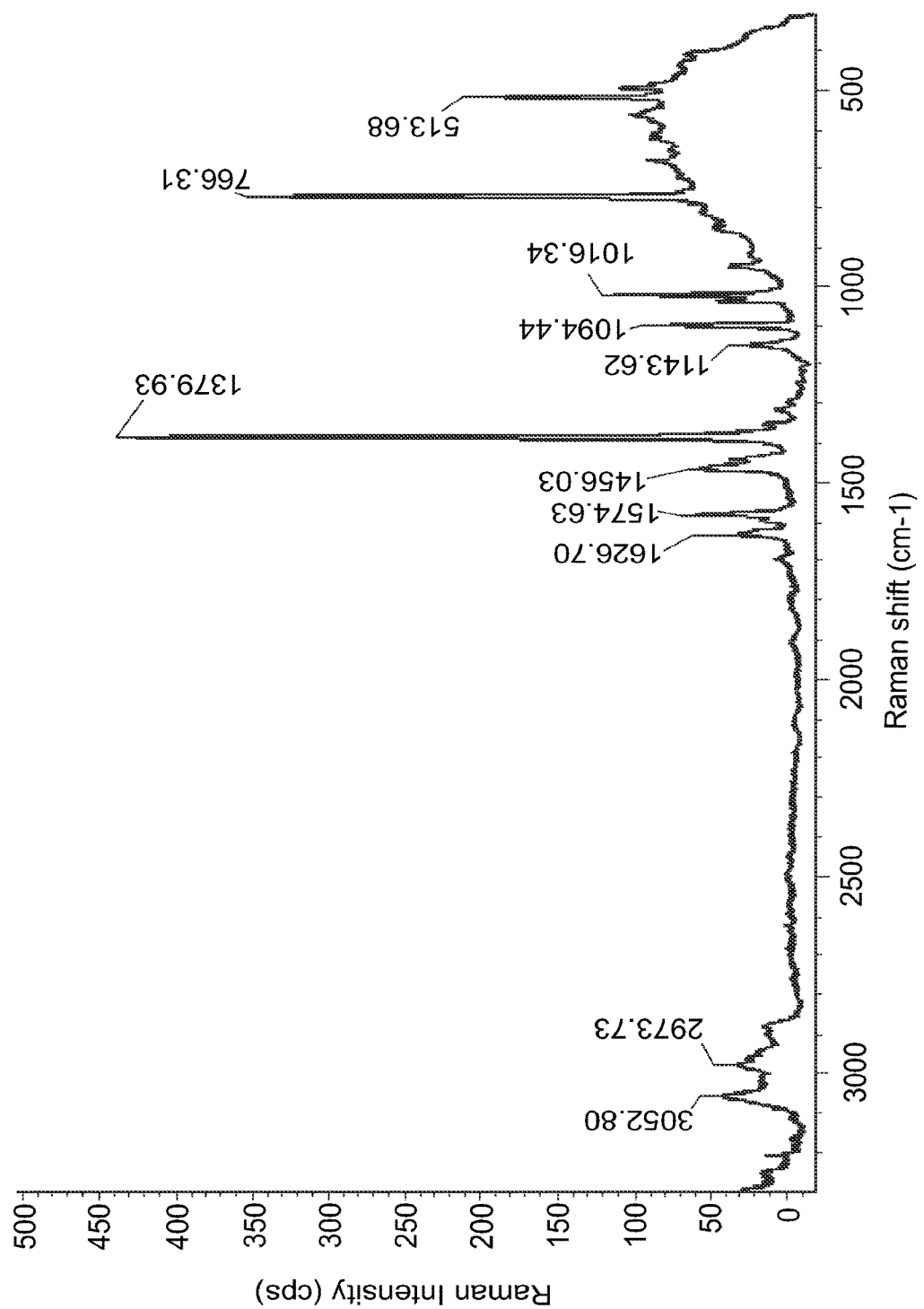
FIG. 39 is Raman spectrum of (2S,3S)-2-amino-3-methyl-N-(2-morpholinoethyl)-pentanamide dinapsylate.

XRD indicated the material is nicely crystalline and exhibits a different pattern from the free base, as shown in FIG. 35. The DSC (FIG. 36A) shows a small endotherm with an extrapolated onset of 180° C. which was followed by decomposition at approximately 225° C. The TGA (FIG. 36B) shows a 0.5 wt % loss at about 105° C., suggesting the salt specimen was relatively dry. The DVS isotherm is shown in FIGS. 37A and 37B. This salt form only took up about 3 to 4 wt % water at high humidity. The sample sorbed surface water until about 80% RH where rapid uptake began. The sample did not reach equilibrium at the highest humidity. Hysteresis was observed between the sorption and desorption segments of the experiment. This sample did not appear deliquescent, but may form a stable hydrate at high water activity levels. Additional work needs to be done to understand the hydration profile of this salt form. The proton NMR spectrum (FIG. 38) confirmed the material was a dinapsylate salt. The Raman spectrum of the dinapsylate salt sample is shown in FIG. 39. The dinapsylate salt was found to have a low solubility in water (0.2-0.4 mg/mL) relative to the free base.

Example 9. Preparation of (2S,3S)-2-amino-3-methyl-N-(2-morpholinoethyl)-pentanamide Mono-edisylate The monoedisylate salt was prepared by using the same procedure described in Example 3 except that sulfuric acid was replaced by 1,2-ethanedisulfonic acid and the molar ratio of the free base to 1,2-ethanedisulfonic acid is 1:1.

Alternatively, the free base as prepared in Example 2 was dissolved in methanol, and a portion of this solution was transferred to provide 2 mg equivalent of free base. 1,2-Ethanedisulfonic acid was dissolved or suspended in EtOH/Heptane or THF/Heptane. The free base and 1,2-ethanedisulfonic acid solutions/suspensions (providing 1:1 molar ratio of free base and 1,2-ethanedisulfonic acid) were mixed, and the resulting mixture solutions were dried under nitrogen purge at ambient temperature to provide the desired monoedisylate salts as dry powdery solids.

Figure 41B:
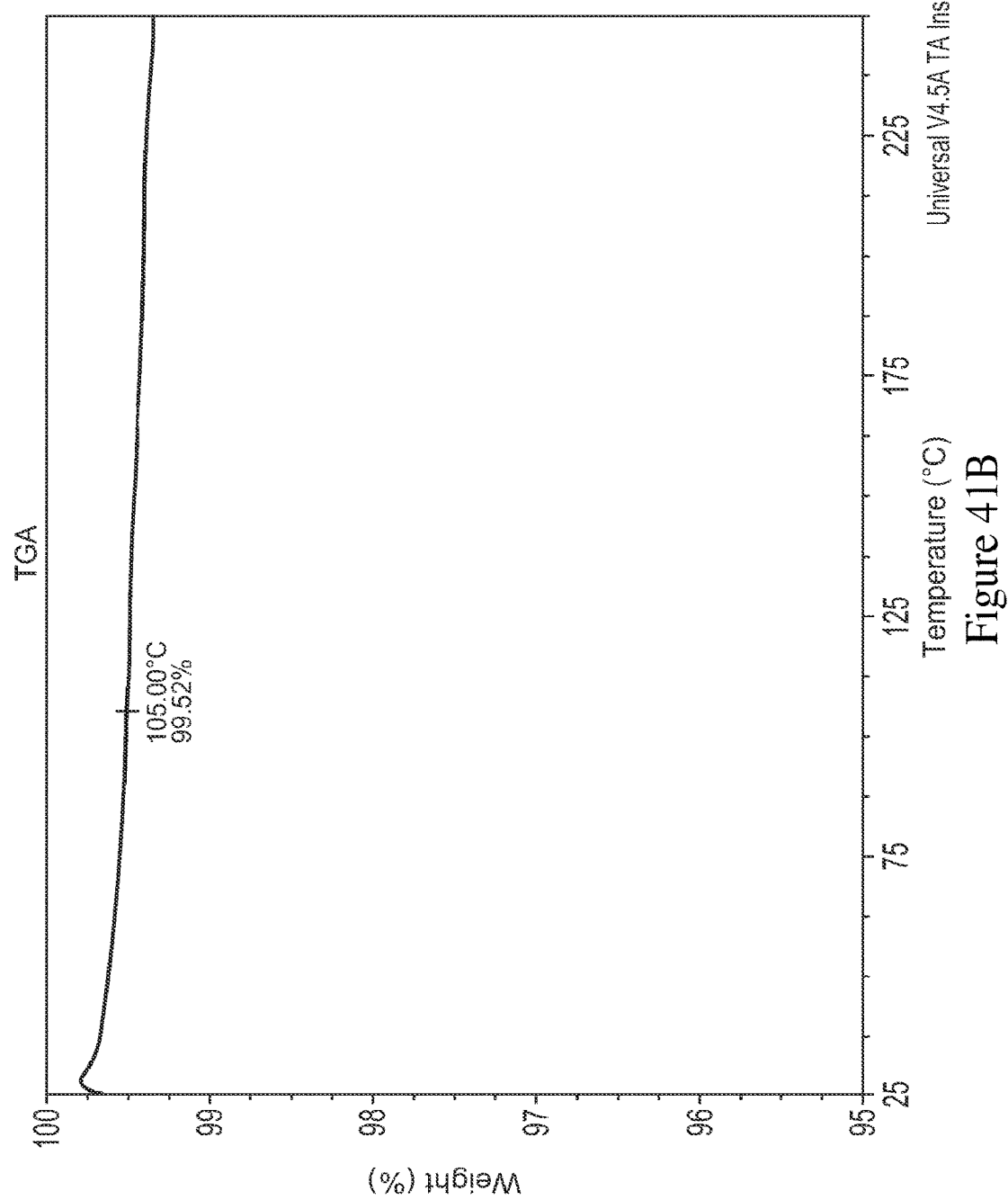
FIG. 41B is a TGA thermogram of (2S,3S)-2-amino-3-methyl-N-(2-morpholinoethyl)-pentanamide monoedisylate.
Figure 42A:
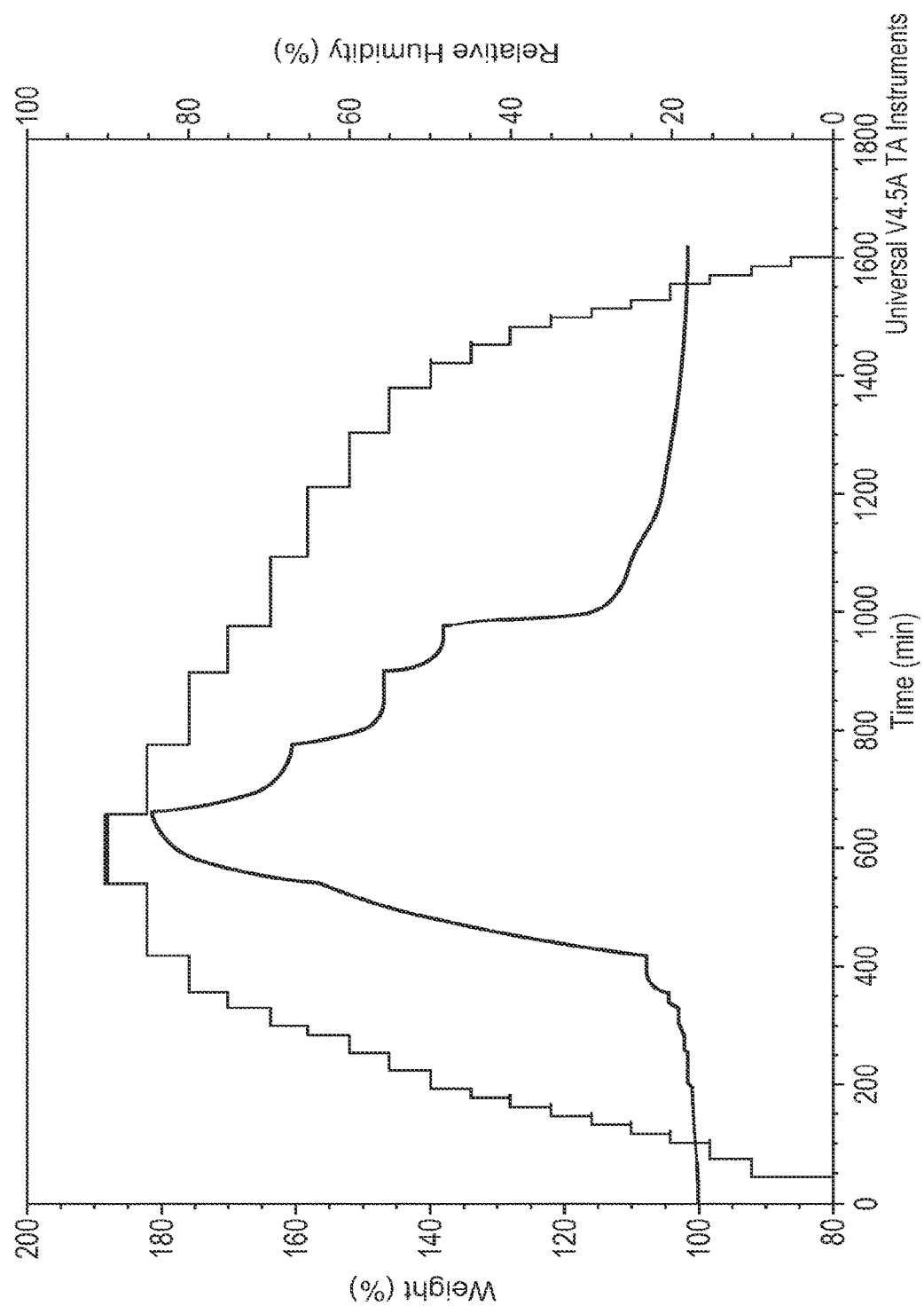
FIGS. 42A and 42B are DVS plots of (2S,3S)-2-amino-3-methyl-N-(2-morpholinoethyl)-pentanamide monoedisylate.
Figure 42B:
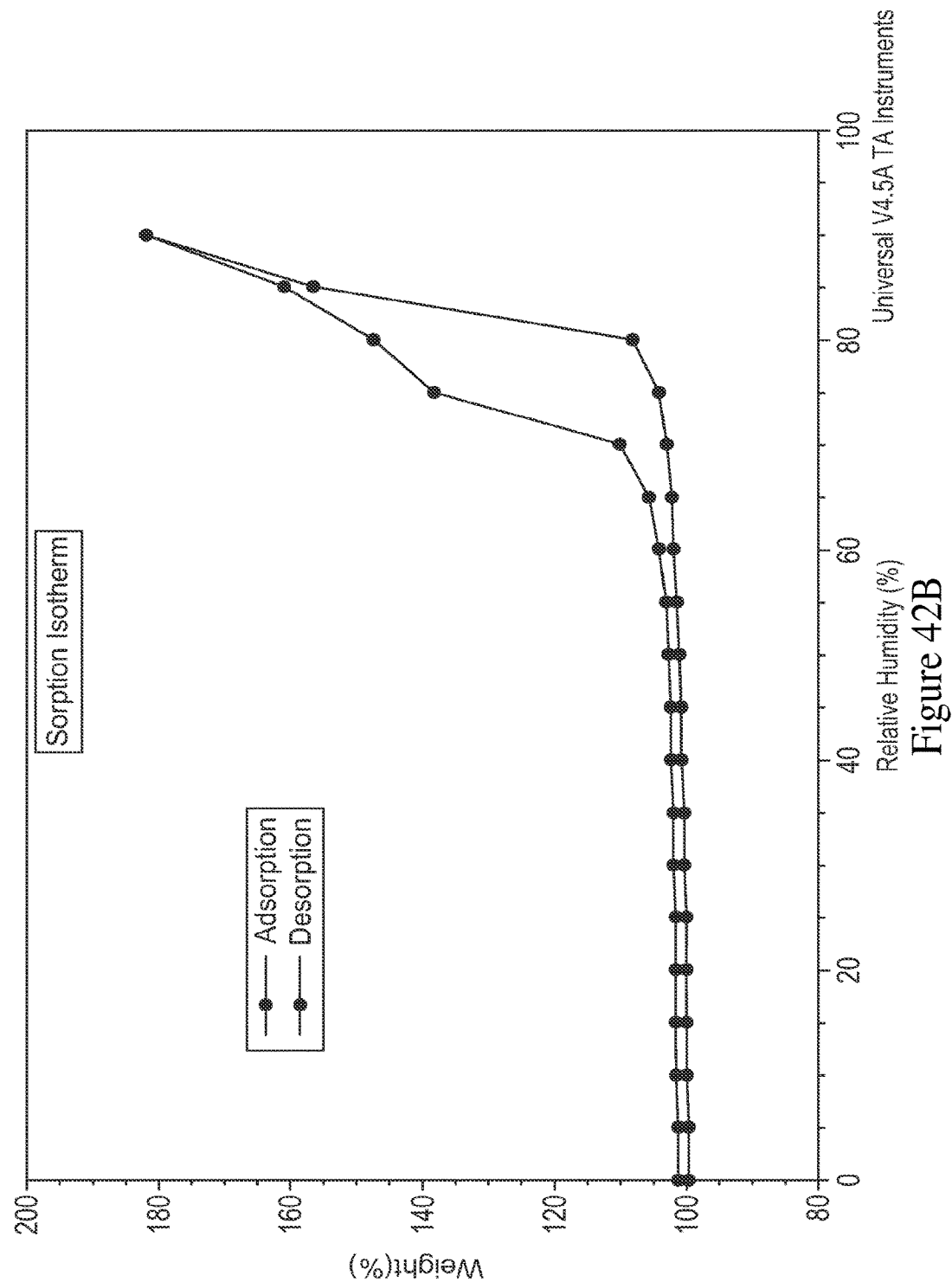
Figure 43:
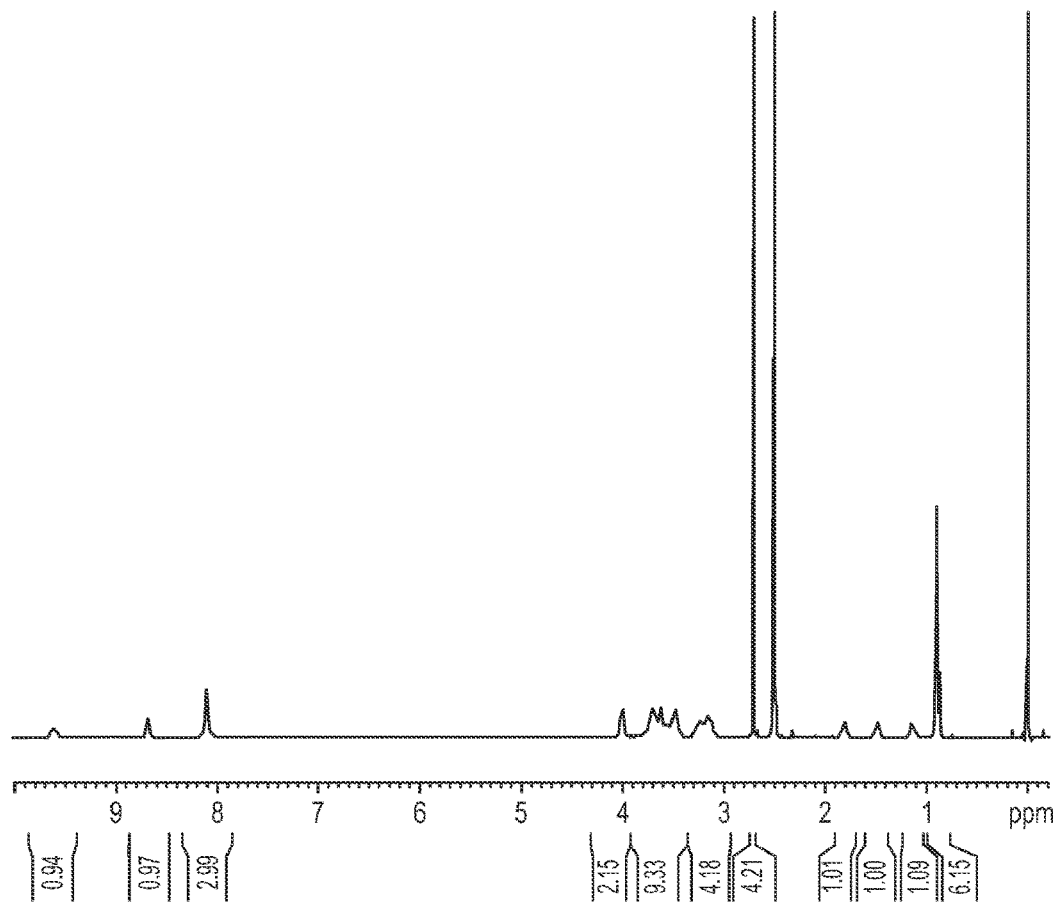
FIG. 43 is a H-NMR spectrum of (2S,3S)-2-amino-3-methyl-N-(2-morpholinoethyl)-pentanamide monoedisylate.
Figure 44:
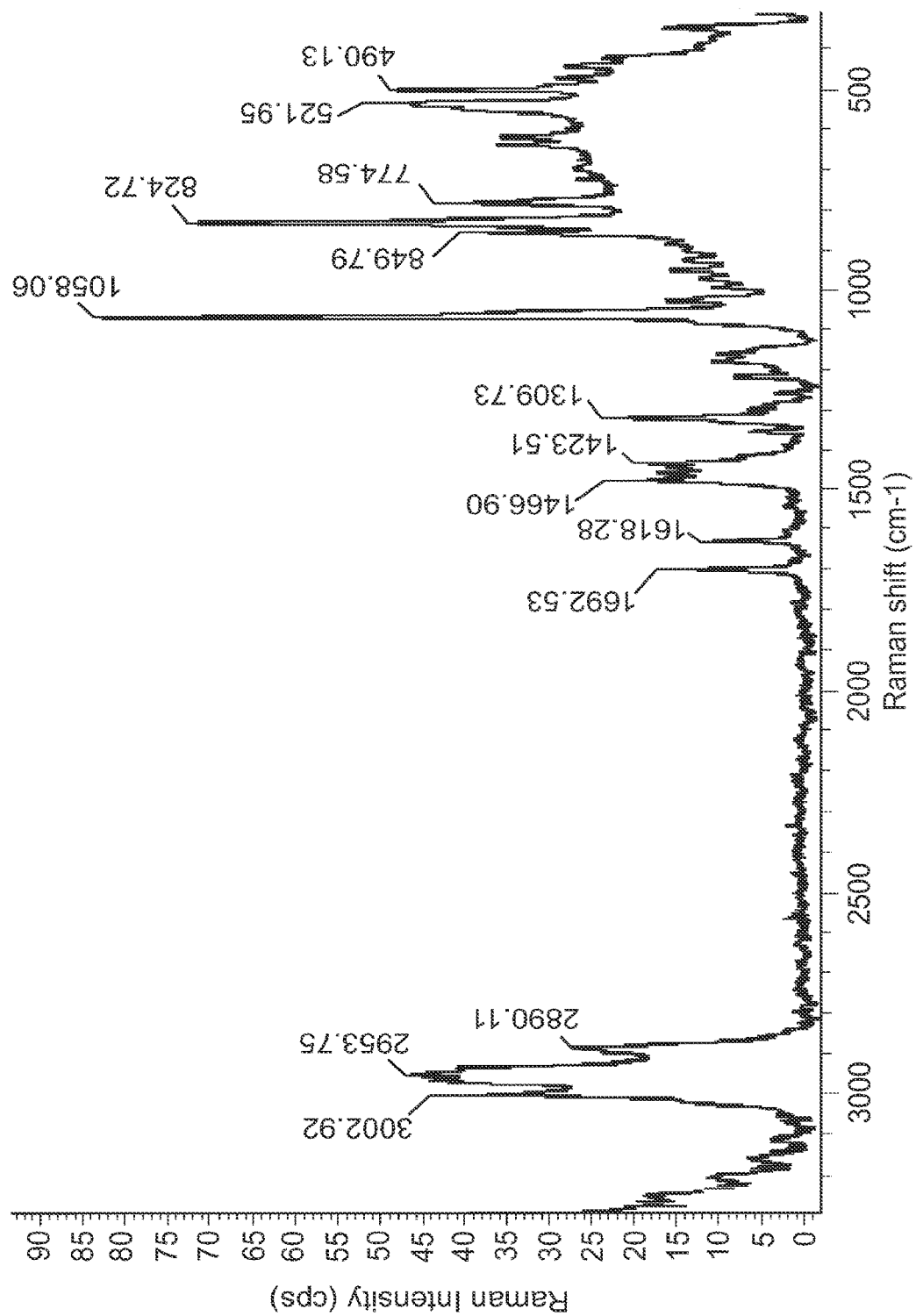
FIG. 44 is Raman spectrum of (2S,3S)-2-amino-3-methyl-N-(2-morpholinoethyl)-pentanamide monoedisylate.

XRD indicated the material is nicely crystalline and exhibits a different pattern from the free base, as shown in FIG. 40. The DSC (FIG. 41A) shows a melting endotherm with an extrapolated onset of 317° C. which decomposes while melting. The TGA (FIG. 41B) shows a 0.5 wt % loss at about 105° C., suggesting the salt specimen was relatively dry. Hot stage microscopy data suggest the material was observed to melt and decompose at about 315° C. The moisture sorption-desorption isotherm (FIGS. 42A and 42B) was collected using dynamic vapor sorption analysis. The monedisylate salt did not show much water uptake up to 80% RH under the experimental conditions, then it shows rapid sorption behavior up to 85 wt % moisture at 90% RH. In the desorption phase, the monoedisylate salt quickly dries by about 70% RH at which time it follows the sorption curve back to 0% RH. This isotherm indicate the material may form a hydrate at high humidity as well as deliquesce. The hydrate may only be stable at high humidities given the observation that the material readily dries by 70% RH on the desorption segment. The proton NMR spectrum (FIG. 43) confirmed the material was a mono edisylate salt. Raman spectrum of the monoedisylate salt sample is shown in FIG. 44. The monoedisylate salt was found to have moderate solubility in water (<14 mg/mL).

Example 10. Preparation of (2S,3S)-2-amino-3-methyl-N-(2-morpholinoethyl)-pentanamide Monooxalate The monooxalate salt was prepared by using the same procedure described in Example 3 except that sulfuric acid was replaced by gluconic acid and the molar ratio of the free base to oxalic acid is 1:2.

Alternatively, the free base as prepared in Example 2 was dissolved in methanol, and a portion of this solution was transferred to provide 2 mg equivalent of free base. Oxalic acid was dissolved or suspended in EtOH/Heptane or THF/Heptane. The free base and gluconic acid solutions/suspensions (providing 1:2 molar ratio of free base and gluconic acid) were mixed, and the resulting mixture solutions were dried under nitrogen purge at ambient temperature to provide the desired monooxalate salts as dry powdery solids.

Figure 46B:
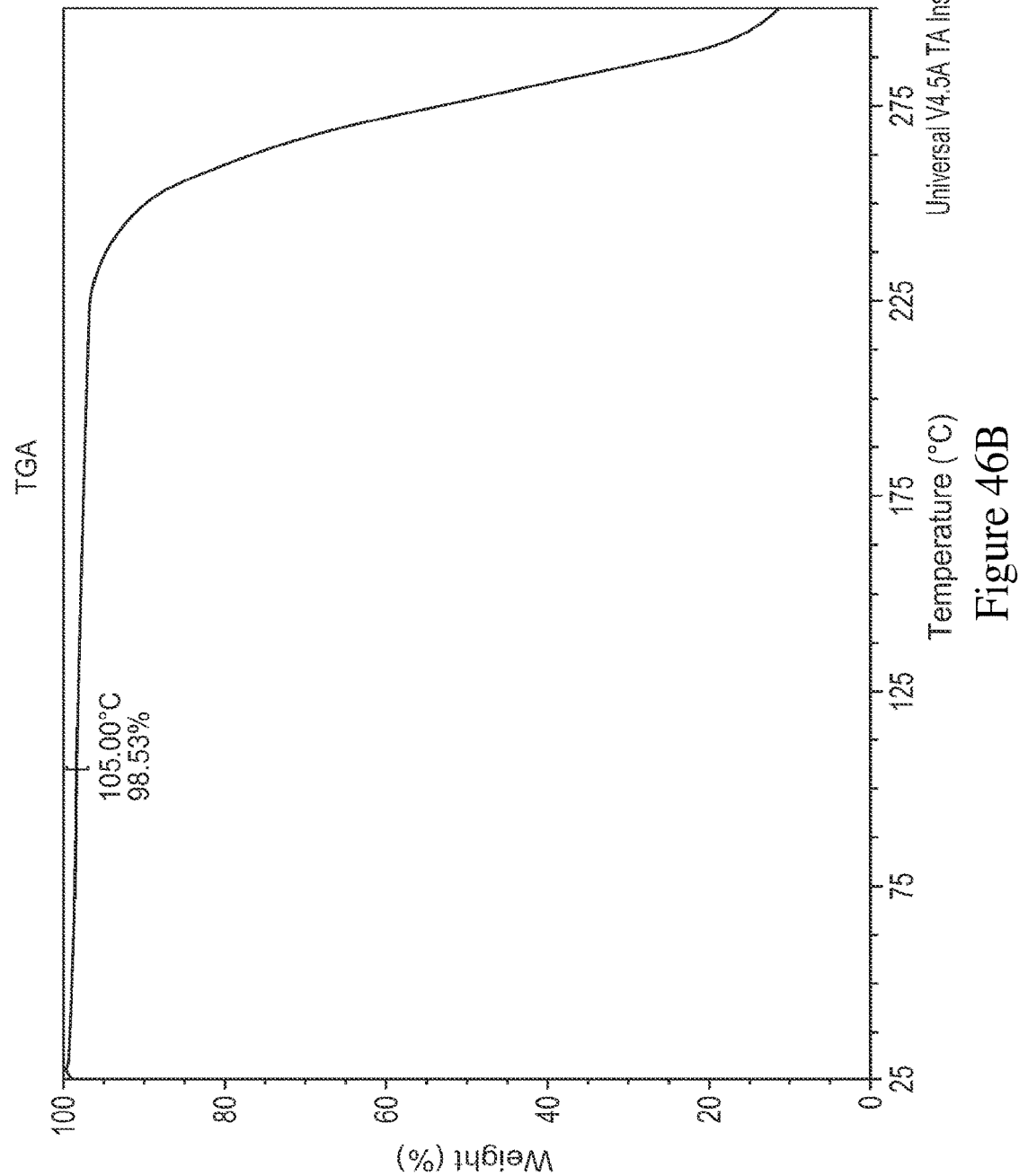
FIG. 46B is a TGA thermogram of (2S,3S)-2-amino-3-methyl-N-(2-morpholinoethyl)-pentanamide monooxalate.
Figure 47A:
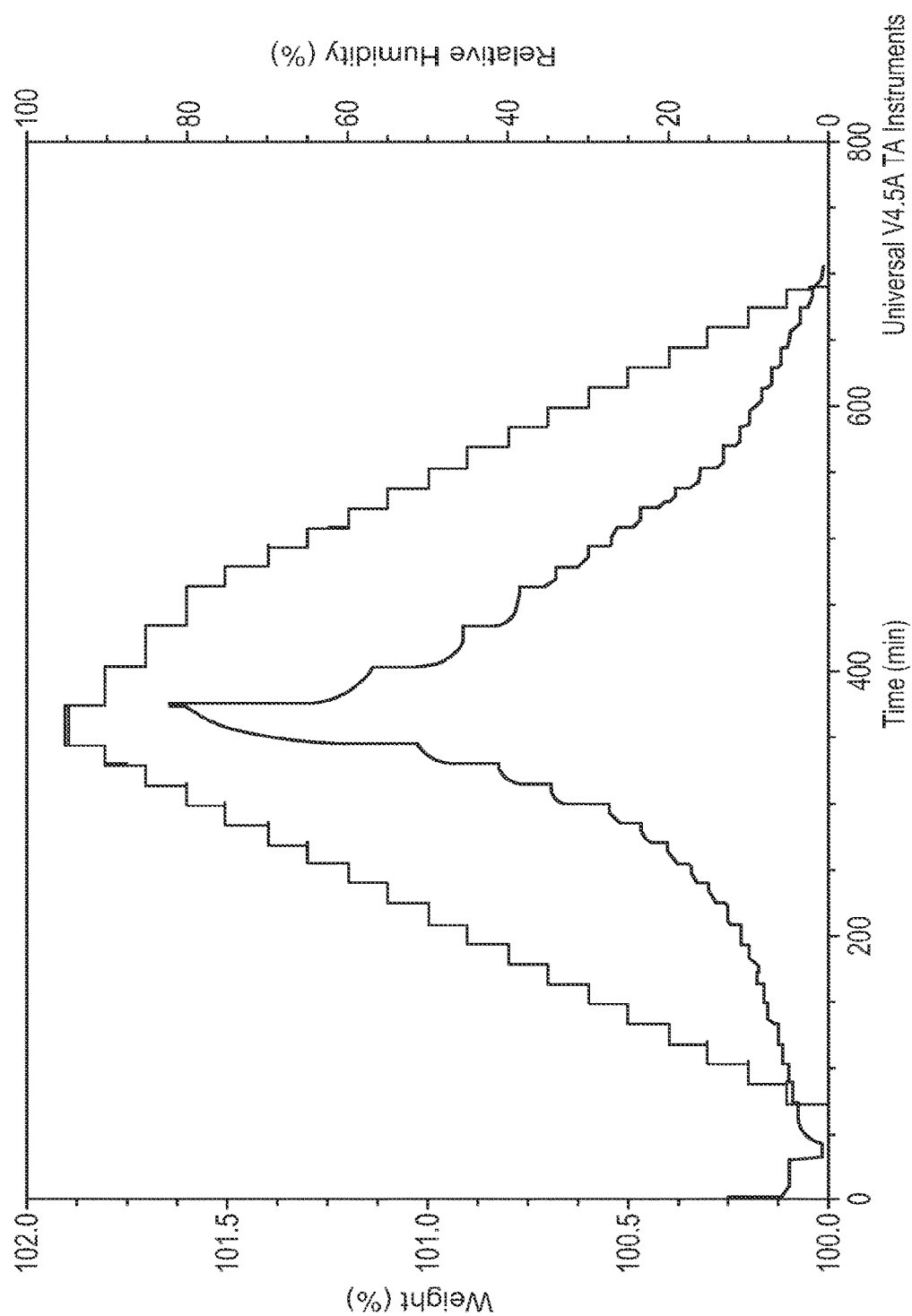
FIGS. 47A and 47B are DVS plots of (2S,3S)-2-amino-3-methyl-N-(2-morpholinoethyl)-pentanamide monooxalate.
Figure 47B:
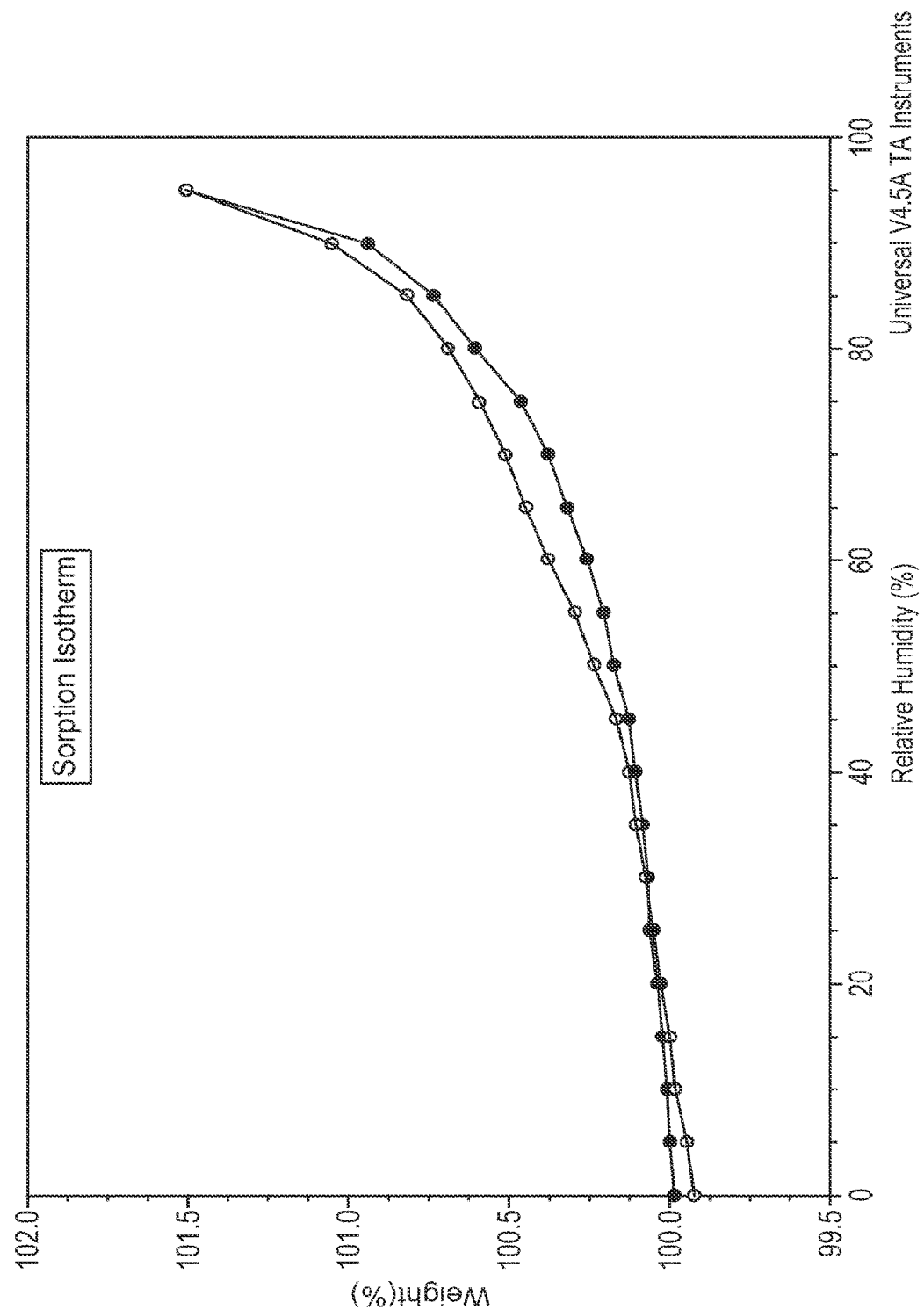
Figure 48:
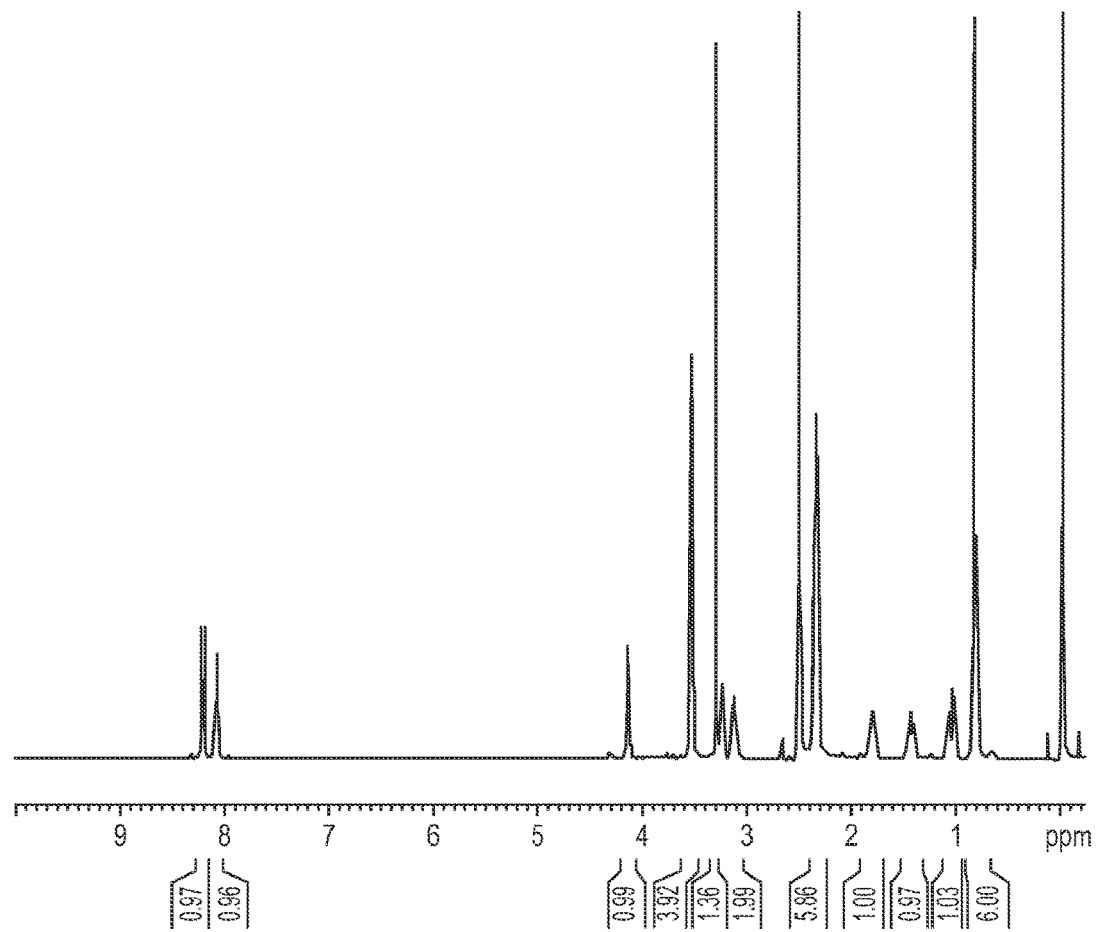
FIG. 48 is a H-NMR spectrum of (2S,3S)-2-amino-3-methyl-N-(2-morpholinoethyl)-pentanamide monooxalate.
Figure 49:
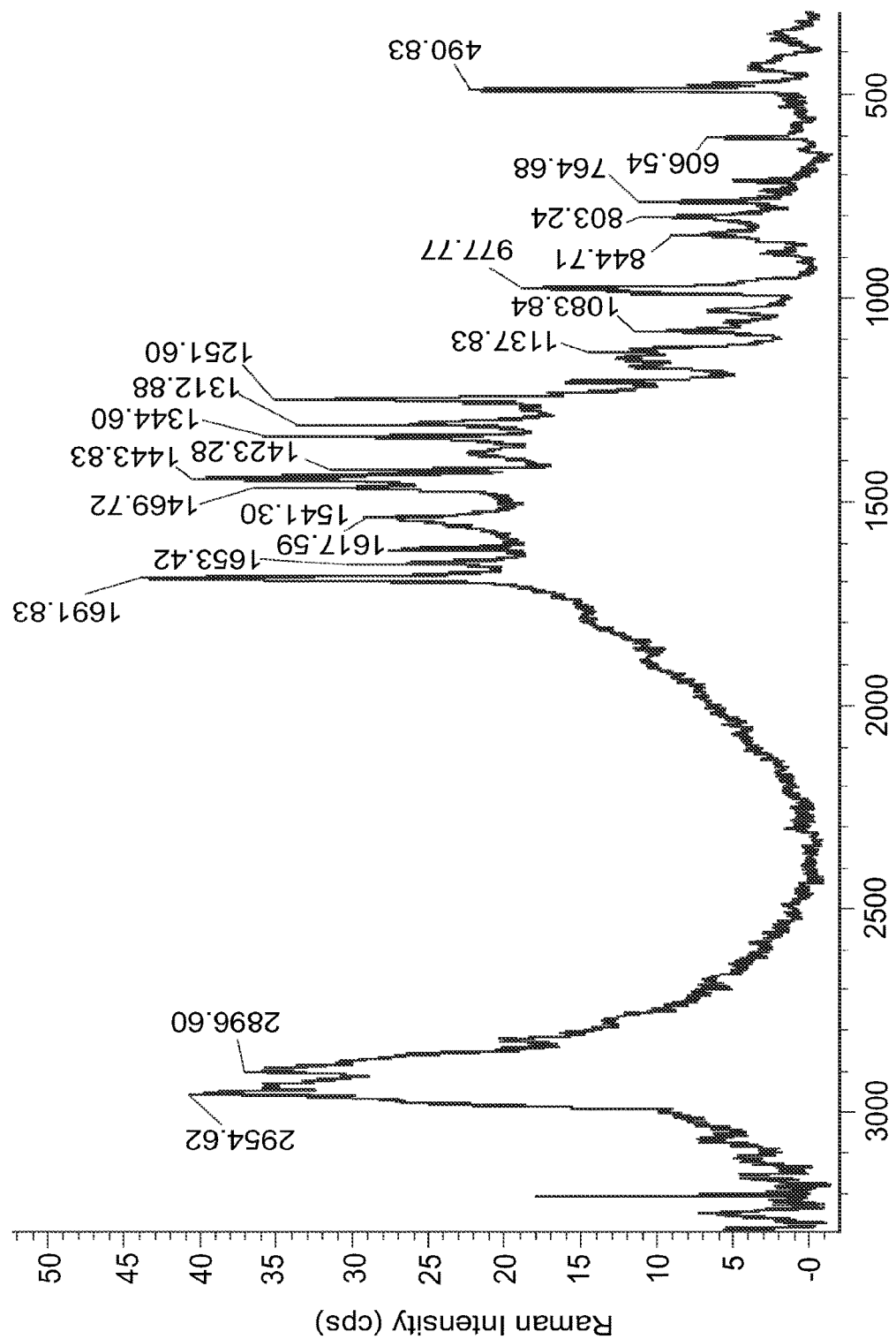
FIG. 49 is Raman spectrum of (2S,3S)-2-amino-3-methyl-N-(2-morpholinoethyl)-pentanamide monooxalate.
Figure 50:
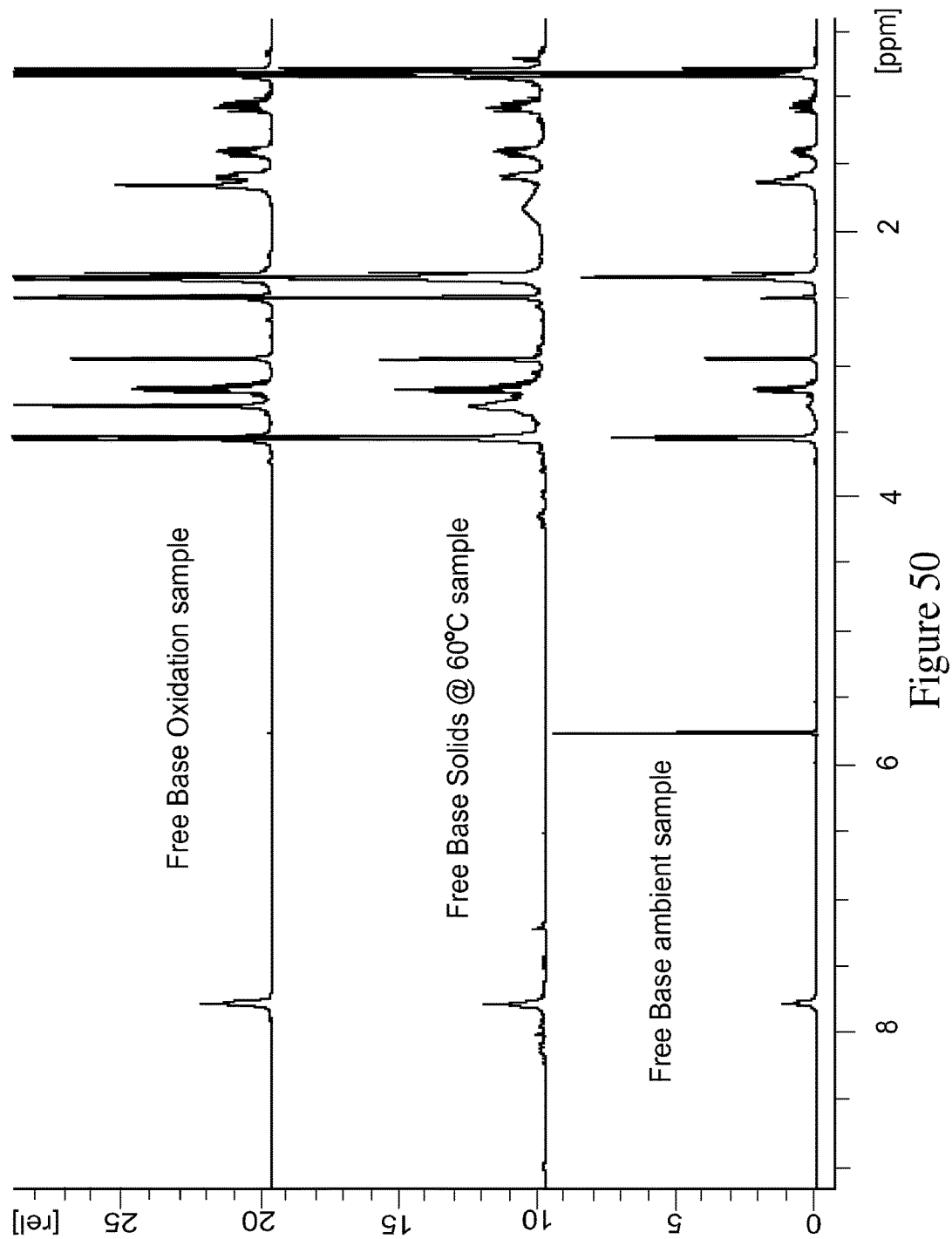
FIG. 50 is a graph of H-NMR spectrum of stability study of (2S,3S)-2-amino-3-methyl-N-(2-morpholinoethyl)-pentanamide free base.
Figure 51:
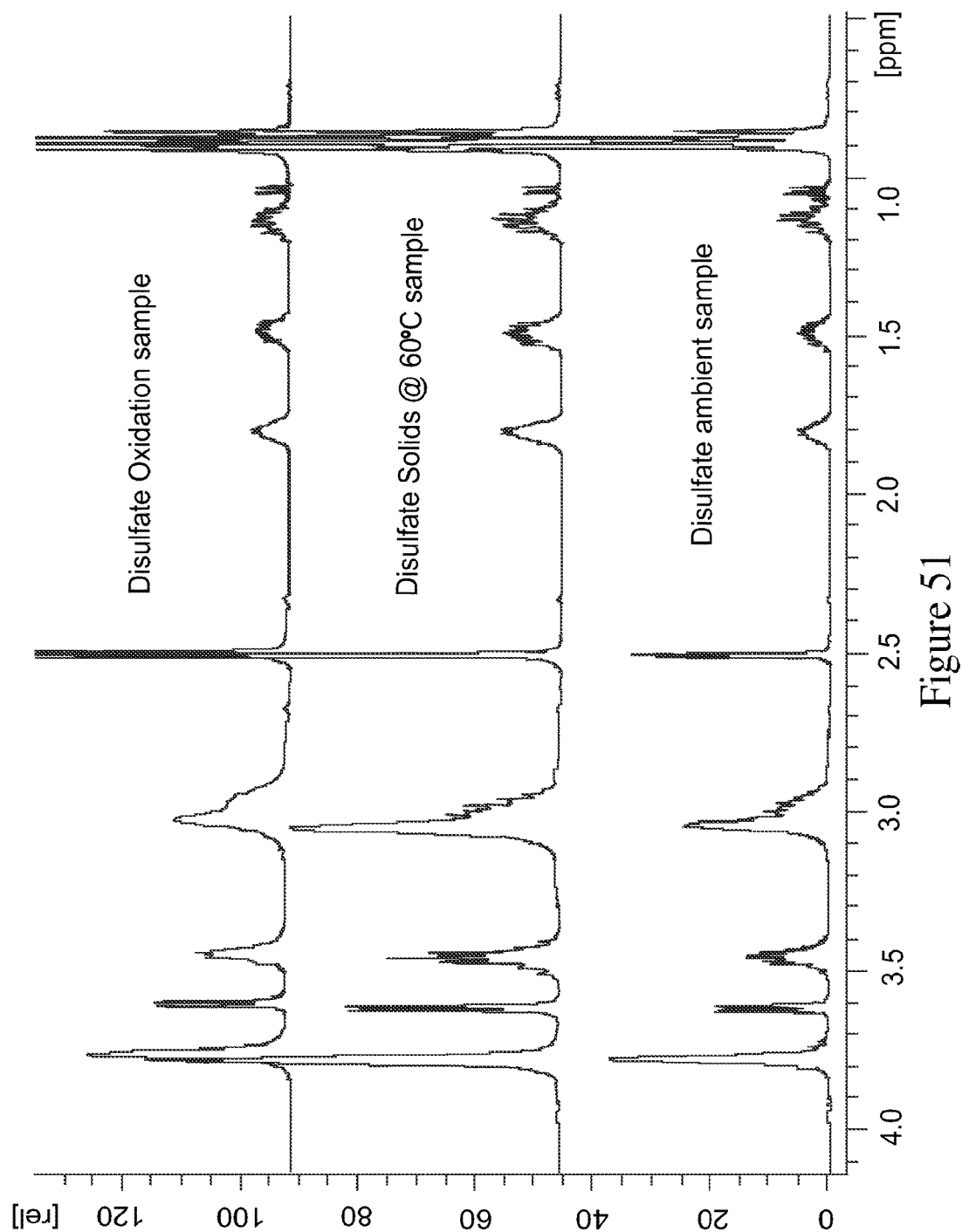
FIG. 51 is a graph of H-NMR spectrum of stability study of (2S,3S)-2-amino-3-methyl-N-(2-morpholinoethyl)-pentanamide tetra(monohydrogensulfate), monosulfate.
Figure 52:
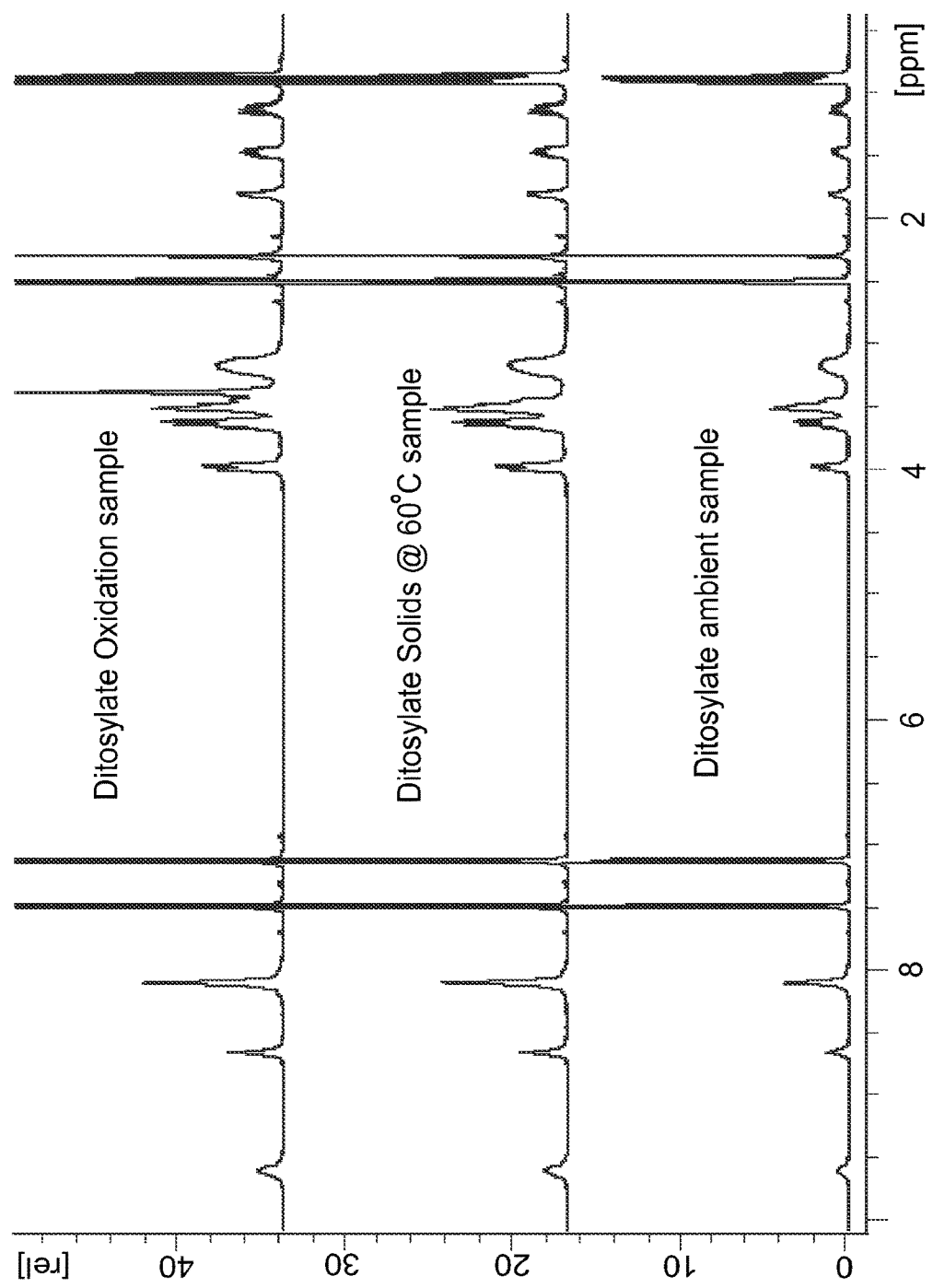
FIG. 52 is a graph of H-NMR spectrum of stability study of (2S,3S)-2-amino-3-methyl-N-(2-morpholinoethyl)-pentanamide ditosylate.
Figure 53:
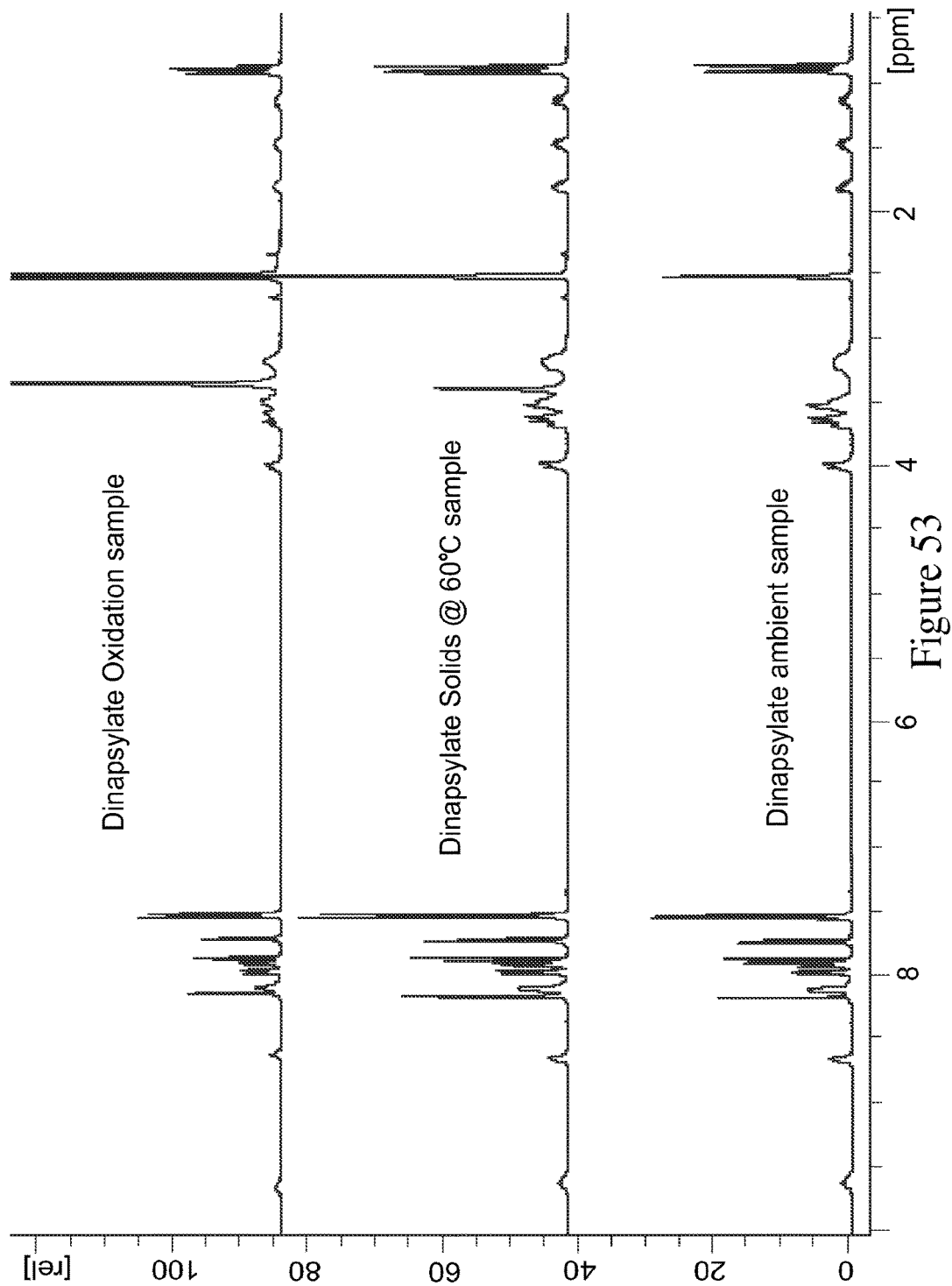
FIG. 53 is a graph of H-NMR spectrum of stability study of (2S,3S)-2-amino-3-methyl-N-(2-morpholinoethyl)-pentanamide dinapsylate.
Figure 54:
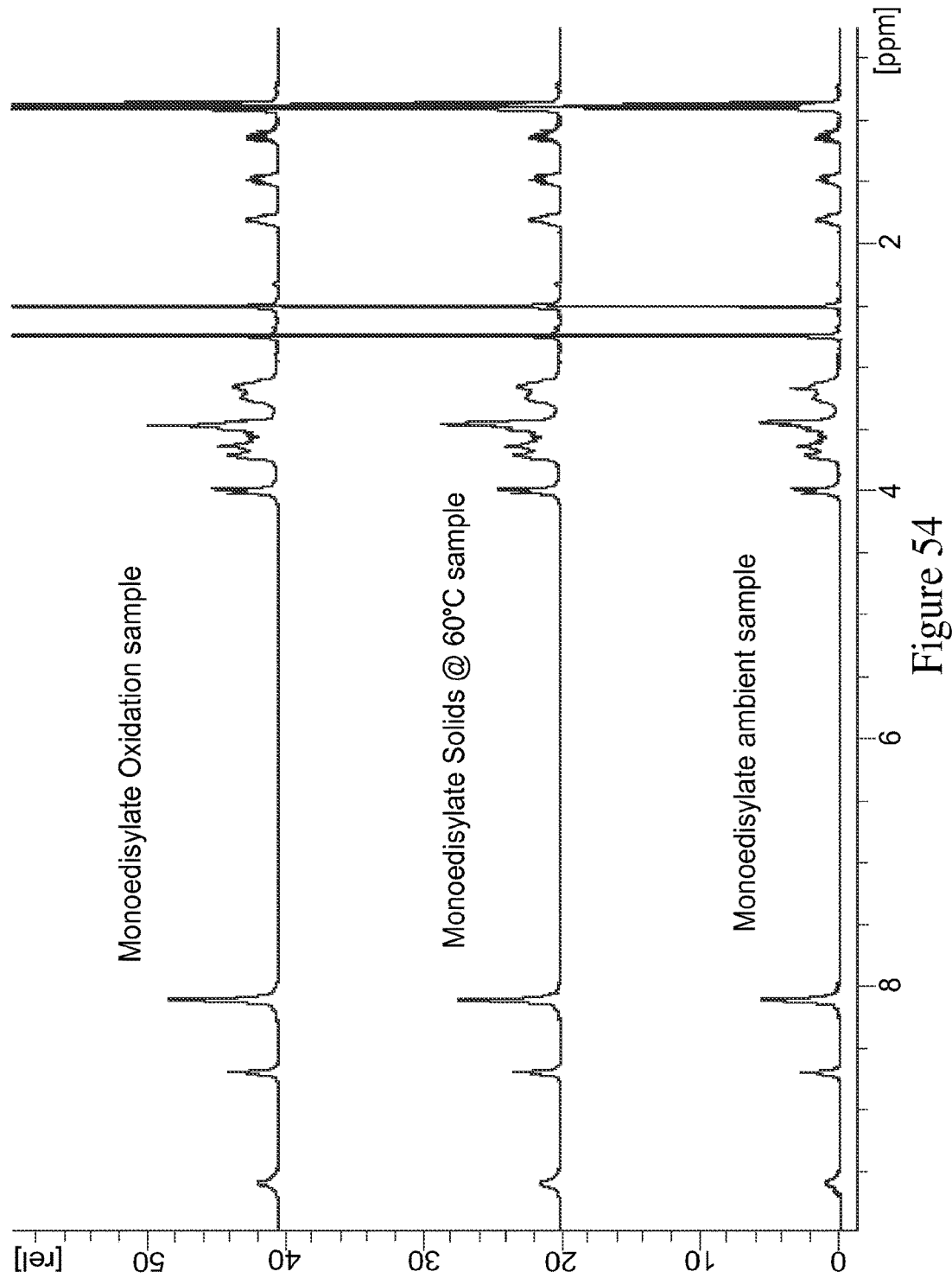
FIG. 54 is a graph of H-NMR spectrum of stability study of (2S,3S)-2-amino-3-methyl-N-(2-morpholinoethyl)-pentanamide monoedisylate.

XRD indicated the material is crystalline and exhibits a different pattern from the free base, as shown in FIG. 45. The DSC (FIG. 46A) shows a small but sharp endotherm with onset of 207° C. followed by a sharp melting endotherm with an extrapolated onset of 233° C. The TGA (FIG. 46B) shows a 1.5 wt % loss at about 105° C., suggesting the salt specimen was dry. The moisture sorption-desorption isotherm (FIGS. 47A and 47B) was collected using dynamic vapor sorption analysis. The monooxalate sample did not absorb much water over most of the scan. The sample began taking up water more rapidly above 50% RH, but even at 95% RH the sample had only gained 1.5 wt % water. In the desorption phase, the salt showed little hysteresis, with the desorption curve being very similar to the sorption curve. Overall, the sorption characteristics indicate this salt form did not take up much water. The proton NMR and Raman spectra of the monooxalate salt sample are shown in FIGS. 48 and 49, respectively.

Example 11. Large Scale Preparation of (2S,3S)-2-amino-3-methyl-N-(2-morpholinoethyl)-pentanamide (Free Base)

A 5 L flask was charged with LM11A31 diHCl salt (148 g, 0.468 mol) and DCM (3 L, 20 vol). A solution of aqueous sodium hydroxide (35.6 g, 0.889 mol, 1.9 eq) in deionized water (148 mL, 1 vol) was slowly added to the heterogeneous mixture eventually forming a clear solution. The mixture was transferred to a separatory funnel and the lower organic layer was drained. The upper aqueous layer was extracted with DCM (3×100 mL) and the organic layers were combined and dried over sodium sulfate. The solution was concentrated to an oil which crystallized to a waxy white solid upon standing. The solids were dried under high vacuum to afford 105 g (95% yield) of (2S,3S)-2-amino-3-methyl-N-(2-morpholinoethyl)-pentanamide Free Base. ¹HNMR, LC-MS confirmed the identity and XRD pattern matched the small scale screen sample pattern.

Example 12. Large Scale Preparation of (2S,3S)-2-amino-3-methyl-N-(2-morpholinoethyl)-pentanamide tetra(monohydrogensulfate), monosulfate To a solution of (2S,3S)-2-amino-3-methyl-N-(2-morpholinoethyl)-pentanamide free base (25 g, 0.103 mol) dissolved in absolute, anhydrous ethanol (250 mL, 10 vol) cooled in an ice-water bath was slowly added concentrated sulfuric acid (4 mL, 75 mmol) by dropwise addition. Precipitation immediately occurred causing stirring to stop. The ice-water bath was removed and the addition of ethanol (200 mL) and isopropanol (225 mL) was necessary to restart stirring. The remaining required sulfuric acid (7 mL, 131 mmol) was slowly added in an ethanol:isopropanol solution (2:1, 75 mL). An exotherm (20.8° C.-24.0° C.) was observed. The white slurry was allowed to stir overnight under positive nitrogen pressure. The mixture was then filtered washing with isopropanol (150 mL) and dried under high vacuum (35° C.-40° C.) to afford 33.6 g (75% yield) of (2S,3S)-2-amino-3-methyl-N-(2-morpholinoethyl)-pentanamide tetra(monohydrogensulfate), monosulfate as a white solid. ¹HNMR, LC-MS confirmed the identity and XRD pattern matches the small scale screen sample pattern.

Example 13. Large Scale Preparation of (2S,3S)-2-amino-3-methyl-N-(2-morpholinoethyl)-pentanamide Ditosylate To a solution of (2S,3S)-2-amino-3-methyl-N-(2-morpholinoethyl)-pentanamide free base (15 g, 0.062 mol) dissolved in anhydrous tetrahydrofuran (300 mL, 20 vol) was added p-toluenesulfonic acid monohydrate (23.4 g, 0.123 mol, 2 eq) in one portion. The initially clear mixture becomes cloudy and produces a mild exotherm. After about 15 min, crystals begin to precipitate from solution and the mixture continued to stir for 1.5 h. The solids were collected by vacuum filtration, and the wet cake was dried in a 40° C. vacuum oven to afford 32.5 g (90% yield) of (2S,3S)-2-amino-3-methyl-N-(2-morpholinoethyl)-pentanamide Ditosylate as a white solid. ¹H NMR confirmed the identity and XRD pattern matches the small scale screen sample pattern.

Example 14. Large Scale Preparation of (2S,3S)-2-amino-3-methyl-N-(2-morpholinoethyl)-pentanamide Dinapsylate To a solution of (2S,3S)-2-amino-3-methyl-N-(2-morpholinoethyl)-pentanamide free base (15 g, 0.062 mol) dissolved in anhydrous tetrahydrofuran (300 mL, 20 vol) was added 2-naphthalene sulfonic acid hydrate (25.7 g, 0.123 mol, 2 eq) in one portion. Solids rapidly precipitate from the initially cloudy mixture. The mixture was stirred at ambient temperature for about 30 min, and then the solids were collected by vacuum filtration. The wet cake was dried in a 40° C. vacuum oven to afford 33.9 g (83% yield) of (2S,3S)-2-amino-3-methyl-N-(2-morpholinoethyl)-pentanamide Dinapsylate as a white solid. ¹H NMR confirmed the identity and XRD pattern matches the small scale screen sample pattern.

Example 15. Large Scale Preparation of (2S,3S)-2-amino-3-methyl-N-(2-morpholinoethyl)-pentanamide Monoedisylate To a solution of (2S,3S)-2-amino-3-methyl-N-(2-morpholinoethyl)-pentanamide free base (20 g, 0.082 mol) dissolved in methanol (400 mL, 20 vol) was added 1,2-ethanedisulfonic acid dihydrate (18.6 g, 0.082 mol, 1 eq) in one portion. The homogeneous mixture quickly becomes cloudy, and after about 5 min, solids precipitate. Agitation became difficult and an additional 200 mL methanol was added to facilitate stirring. The mixture was stirred at ambient temperature for about 30 min, and then the solids were collected by vacuum filtration. The wet cake was dried in a 40° C. vacuum oven to afford 33.4 g (93% yield) of (2S,3S)-2-amino-3-methyl-N-(2-morpholinoethyl)-pentanamide edisylate as a white solid. ¹H NMR confirmed the identity and XRD pattern matches the small scale screen sample pattern.

Example 16. Stability Study of Representative Salts

Four representative salts, i.e., monoedisylate, ditosylate, dinapsylate and tetra(monohydrogensulfate), monosulfate, prepared at the 30 plus gram scale were challenged using heat (solids stored at 25 and 60° C. for 1 week), oxidation (solids stored in oxygen headspace at 25° C. for 1 week), light (UV source under ICH confirmatory conditions >200 Whr/m²), and solutions (in HPLC diluent) at 25 and 40° C. for 1 week. Stressed samples were analyzed using HPLC to determine their impurity profiles.

TABLE 10

Summary of HPLC Stability Data on Representative Salts.

| Test Conditions of the Salts | HPLC Total Area Normalization - Area % Purity | | | | |
|---|---|---|---|---|---|
| | Free Base | tetra(monohydrogensulfate), monosulfate | Ditosylate | Dinapsylate | Monoedisylate |
| Solid State - Ambient | 100 | 99.98 | 99.82 | 99.90 | 99.79 |
| Solid State - 60 C. | N/a | 99.98 | 99.94 | 99.87 | 99.95 |
| Solution* - Ambient | N/a | 99.90 | 99.89 | 99.87 | 999.81 |
| Solution* - 40 C. | 99.89 | 99.75 | 99.91 | 99.96 | 99.90 |
| Oxidation Ambient | 99.97 | 99.97 | 99.92 | 99.81 | 99.95 |
| Photo Stability - Dark Control | 99.97 | 99.97 | 99.94 | 99.85 | 99.97 |
| Photo Stability - Exposed | 99.98 | 99.94 | 99.93 | 99.82 | 99.86 |

*Solution of water and acetonitrile (1:1).

** N/a = Data not available.

The stability results shown in Table 10 represent the averages of two injections of duplicate sample preparations. The HPLC stability data showed that the salts exhibited little to no degradation with the conditions used.

To confirm the little or no degradation observed in the HPLC stability study, some samples (solids stored at 60° C. and oxidation) of four of the salts and free base were further analyzed by proton NMR (i.e., HNMR). The analysis was qualitative.

FIGS. 50 to 54 showed the proton NMR overlay spectra for samples analyzed during the stability portion of the study. The NMR stability data showed that the salts exhibited high stability with little or no degradation under stress. The NMR stability data also showed that the salts are slightly more stable than the free base. Specifically, slight degradation of free base after heat stress can be seen in the NMR spectra.

Example 17. Pharmacokinetic Study of Representative Salts

The objective of this study was to provide preliminary pharmacokinetic information regarding the exposure of different salt forms of LM11A-31 in rat plasma and brain when dosed by oral gavage. Groups consisting of nine male rats received single doses of 25 mg/kg free base by oral gavage. Plasma samples were obtained from three rats per timepoint after administration (0.5, 1, 2, 3, 4, and 8 hours) and brain samples were collected at 1-, 3-, and 8-hour terminations (three rats per time point).

The samples were analyzed by LC-MS/MS to determine the plasma and brain concentrations of the test article. Pharmacokinetic analysis of the plasma concentration data was conducted using noncompartmental analysis with Win-Nonlin Version 4.1. Plasma pharmacokinetic parameters are summarized in Table 11 and Table 12 below:

TABLE 11

| Salt (dosed) | Rsq | $T_{1/2}$ (h) | $T_{max}$ (h) | $C_{max}$ (ng/mL) | $AUC_{all}$ (h * ng/mL) | $AUC_{INF}$ (h * ng/mL) | $AUC_{\%Extrap}$ (%) |
|---|---|---|---|---|---|---|---|
| Free base | 0.987 | 1.05 | 0.5 | 371 | 321 | 316 | 4.81 |
| Ditosylate | 0.944 | 0.63 | 0.5 | 296 | 295 | 290 | 1.45 |
| tetra(monohydrogensulfate), monosulfate | 1.000 | 1.10 | 0.5 | 413 | 416 | 410 | 5.26 |
| Dinapsylate | 0.890 | 1.90 | 0.5 | 335 | 270 | 280 | 3.44 |
| Edisylate | 0.973 | 0.708 | 0.5 | 284 | 247 | 243 | 1.52 |

TABLE 12

| Salt (dosed) | Brain:Plasma Ratio | Maximum Brain Level (ng/g tissue) |
|---|---|---|
| Free base | 2.0-3.5 | 105 |
| Ditosylate | 1.0-5.7 | 120 |
| tetra(monohydrogensulfate), monosulfate | 0.6-1.8 | 77 |
| Dinapsylate | 3.5-4.4 | 123 |
| Edisylate | 1.4-3.3 | 98 |

In general, the tetra(monohydrogensulfate), monosulfate salt resulted in higher exposure (AUC and Cmax) than the free base and the dinapsylate salt has a longer terminal plasma half-life and higher brain-to-plasma ratio than the free base. Overall the tetra(monohydrogensulfate), monosulfate and dinapsylate salts demonstrate better PK properties than the free base.

The patents and publications listed herein describe the general skill in the art and are hereby incorporated by reference in their entireties for all purposes and to the same extent as if each was specifically and individually indicated to be incorporated by reference. In the case of any conflict between a cited reference and this specification, the specification shall control. In describing embodiments of the present application, specific terminology is employed for the sake of clarity. However, the invention is not intended to be limited to the specific terminology so selected. Nothing in this specification should be considered as limiting the scope of the present invention. All examples presented are representative and non-limiting. The above-described embodiments may be modified or varied, without departing from the invention, as appreciated by those skilled in the art in light of the above teachings. It is therefore to be understood that, within the scope of the claims and their equivalents, the invention may be practiced otherwise than as specifically described.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A crystalline form of the compound represented by the formula:

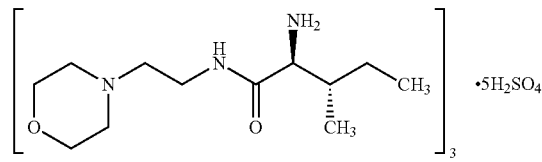

that exhibits an X-ray powder diffraction pattern comprising peaks at about 8.01±0.3; 9.85±0.3; 21.30±0.3; and 21.99±0.3 degrees two-theta.

2. The crystalline form of claim 1, wherein the X-ray powder diffraction pattern further comprises peaks at about 15.01±0.3; 18.06±0.3; 18.88±0.3; 24.27±0.3 and 15.499±0.3 degrees two-theta.

3. A pharmaceutical composition comprising a crystalline form of claim 1 or 2 and a pharmaceutically acceptable excipient.

\* \* \* \* \*